US012622917B2

(12) United States Patent
Chen et al.

(10) Patent No.: US 12,622,917 B2
(45) Date of Patent: *May 12, 2026

(54) HIGH-ACTIVITY WNT PATHWAY INHIBITOR COMPOUND

(71) Applicant: ADLAI NORTYE BIOPHARMA CO., LTD., Hangzhou (CN)

(72) Inventors: Yufeng Chen, Hangzhou (CN); Peng Wu, Hangzhou (CN); Meng Lv, Hangzhou (CN); Canfeng Liu, Hangzhou (CN); Han Yang, Hangzhou (CN); Kaixuan Chen, Hangzhou (CN); Wanli Cheng, Hangzhou (CN); Feifan Li, Hangzhou (CN); Youping Wang, Hangzhou (CN); Keke Chen, Hangzhou (CN); Pingping Lu, Hangzhou (CN); Nanhai He, Hangzhou (CN)

(73) Assignee: ADLAI NORTYE BIOPHARMA CO., LTD., Hangzhou (CN)

( * ) Notice: Subject to any disclaimer, the term of this patent is extended or adjusted under 35 U.S.C. 154(b) by 434 days.

This patent is subject to a terminal disclaimer.

(21) Appl. No.: 18/034,200

(22) PCT Filed: Oct. 27, 2021

(86) PCT No.: PCT/CN2021/126539
§ 371 (c)(1),
(2) Date: Apr. 27, 2023

(87) PCT Pub. No.: WO2022/089454
PCT Pub. Date: May 5, 2022

(65) Prior Publication Data
US 2023/0390301 A1     Dec. 7, 2023

(30) Foreign Application Priority Data
Oct. 28, 2020    (CN) .......................... 202011175894.X

(51) Int. Cl.
*A61K 31/551*     (2006.01)
*A61K 31/519*     (2006.01)
*A61K 31/527*     (2006.01)
*A61K 31/5383*    (2006.01)
*A61P 35/00*      (2006.01)

(52) U.S. Cl.
CPC .......... *A61K 31/551* (2013.01); *A61K 31/519* (2013.01); *A61K 31/527* (2013.01); *A61K 31/5383* (2013.01); *A61P 35/00* (2018.01)

(58) Field of Classification Search
CPC .. A61K 31/551; A61K 31/519; A61K 31/527; A61K 31/5383; A61K 31/55; A61P 35/00; A61P 29/00; A61P 37/02; A61P 37/06; Y02P 20/55; C07D 487/16; C07D 487/20; C07D 491/22; C07D 471/14; C07D 471/16; C07D 487/22; C07B 2200/07
See application file for complete search history.

(56) References Cited

U.S. PATENT DOCUMENTS

2015/0119387 A1     4/2015  An
2017/0313682 A1     11/2017  Kc et al.

FOREIGN PATENT DOCUMENTS

CN      104379583  A      2/2015
CN      109310690  A      2/2019
WO      2014145909 A2     9/2014
WO      2014165232 A1     10/2014
WO      2020125759 A1     6/2020

OTHER PUBLICATIONS

CAS Registry No. 2379576-32-4 (which entered the STN database on Nov. 14, 2019). (Year: 2019).*
The European Search Report was issued on Sep. 19, 2024 for this European counterpart application No. 21885181.4.
International Search Report for PCT/CN2021/126539 mailed Jan. 26, 2022, ISA/CN.

* cited by examiner

*Primary Examiner* — Kamal A Saeed
*Assistant Examiner* — Meghan C Heasley
(74) *Attorney, Agent, or Firm* — Yue (Robert) Xu; Apex Attorneys at Law, LLP

(57)     ABSTRACT

Provided are a compound having the structure of formula (I) for inhibiting Wnt pathway activity, a pharmaceutical composition comprising the compound, and use of the compound in prevention and/or treatment of cancers, tumors, inflammatory diseases, autoimmune diseases, or immune-mediated diseases.

(I)

10 Claims, 1 Drawing Sheet

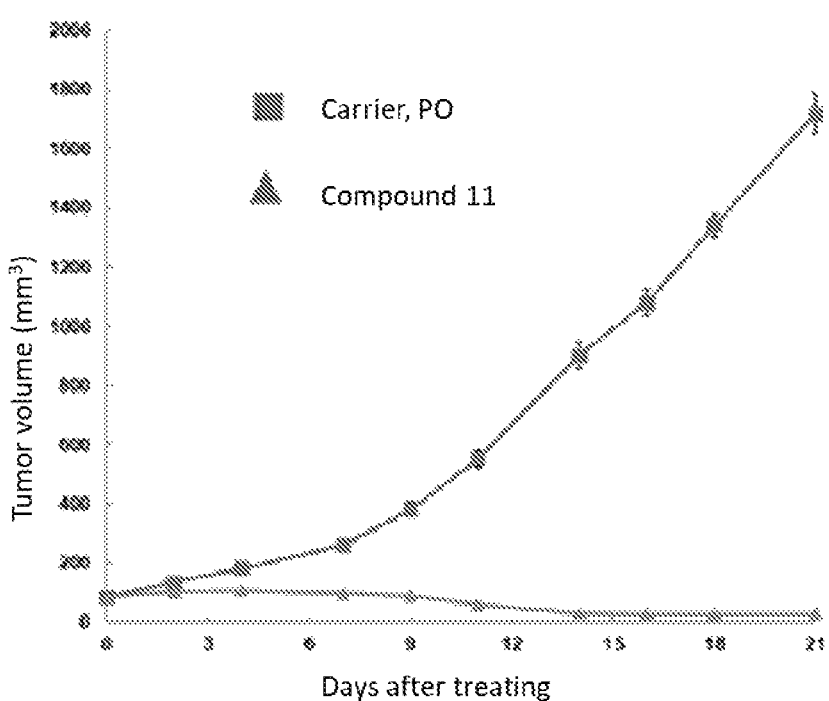
Tumor volume of NCI-H929 xenograft model in female SCID mice (mm$^3$)
(Mean $\pm$ SEM)

1

HIGH-ACTIVITY WNT PATHWAY INHIBITOR COMPOUND

CROSS REFERENCE TO RELATED APPLICATIONS

This application is the national phase of International Application No. PCT/CN2021/126539, titled "HIGH-AC-TIVITY WNT PATHWAY INHIBITOR COMPOUND", filed on Oct. 27, 2021, which claims the priority to Chinese Patent Application No. 202011175894.X, titled "HIGH-ACTIVITY WNT PATHWAY INHIBITOR COMPOUND", filed on Oct. 28, 2020 with the China National Intellectual Property Administration, which is incorporated herein by reference in entirety.

TECHNICAL FIELD

The invention relates to a heterocyclic compound, in particular to a highly active Wnt pathway inhibitor and its application.

BACKGROUND

Wnt/β-catenin signal transduction pathway is a pathway conserved in biological evolution. In normal somatic cells, β-catenin is only a cytoskeleton protein that forms a complex with E-cadherin at the cell membrane to maintain the adhesion of the same type of cells and prevent cell movement. When the Wnt signaling pathway is not activated, the β-catenin in the cytoplasm is phosphorylated to form a β-catenin degradation complex with APC, Axin, and GSK3β, and the ubiquitin system is activated to degrade β-catenin through the proteasome pathway, so that the cytoplasmic β-catenin was maintained at a low level. When cells are stimulated by Wnt signal, Wnt protein binds to the specific receptor Frizzled protein on the cell membrane, and the activated Frizzled receptor recruits intracellular Dishev-eled protein, which inhibits the degradation activity of the β-Catenin degradation complex formed by GSK3β and other proteins, stabilizing β-Catenin protein in free state in cyto-plasm. The stable accumulated β-Catenin in the cytoplasm enters the nucleus and binds to the LEF/TCF transcription factor family to initiate the transcription of downstream target genes (such as c-myc, c-jun, Cyclin D1, etc.). Tran-sitional activation of the Wnt/β-catenin signaling pathway is closely related to the occurrence of various cancers (includ-ing colon cancer, gastric cancer, breast cancer, etc.). For example, abnormal activation of Wnt signaling pathway and nuclear accumulation of β-catenin protein widely exist in colorectal cancer, and the proliferation of colon cancer can be inhibited by inhibiting the activity of Wnt signaling pathway. APC mutations exist in more than 85% of colorec-tal cancers, and the mutated APC blocks the phosphorylation and degradation of β-catenin and induces the occurrence of colorectal cancer. In addition, mutations of Axin and β-catenin itself can also cause the intracellular accumulation of β-catenin and activate the Wnt/β-catenin pathway.

CONTENTS OF THE INVENTION

The present invention provides a compound having a structure of formula (I) for inhibiting Wnt pathway activity and pharmaceutically acceptable salts, isotopic derivatives, and stereoisomers:

2

(I)

wherein: ▬ ▬ ▬ means existence or non-existence;

$R_1$ represents $C_1$-$C_6$ alkyl, $C_3$-$C_6$ cycloalkyl, $C_6$-$C_{10}$ aryl, 5-10 membered heteroaryl, and said $R_1$ can be option-ally substituted by 0, 1, 2, 3 substituents selected from: hydrogen, halogen, $OR_a$, halogenated ($C_1$-$C_6$) alkyl, ($C_3$-$C_6$) cycloalkyl, halogenated ($C_3$-$C_6$) cycloalkyl, cyano, $SR_a$, halogenated ($C_1$-$C_6$) alkoxy, halo ($C_3$-$C_6$) cycloalkoxy, halo ($C_1$-$C_6$) alkylthio, ($C_3$-$C_6$) cycloal-kyloxy, ($C_3$-$C_6$) cycloalkylthio, halo ($C_3$-$C_6$) cycloal-kylthio;

X represents —$(CR^aR^{a'})_m$—, —$(CR^aR^{a'})_m$ $O(CR^aR^{a'})$—, —$(CR^aR^{a'})_m$ $S(R^aR^a)_n$;

$C_y$ represents $C_6$-$C_{10}$ aryl or 5-10 membered heteroaryl, and it can be optionally substituted by 0, 1, 2, 3 substituents selected from: hydrogen, halogen, —$OR_a$, ($C_1$-$C_6$) alkyl, halo ($C_1$-$C_6$) alkyl, ($C_3$-$C_6$) cycloalkyl, cyano, hydroxyl ($C_1$-$C_6$) alkyl;

$R_2$ represents hydrogen, ($C_1$-$C_6$) alkyl, halo ($C_1$-$C_6$) alkyl, ($C_3$-$C_6$) cycloalkyl, hydroxyl ($C_1$-$C_6$) alkyl;

$R_3$ and $R_{3'}$ independently represent hydrogen, halogen, $OR_a$, ($C_1$-$C_6$) alkyl, ($C_3$-$C_6$) cycloalkyl, hydroxyl ($C_1$-$C_6$ alkyl), ($C_1$-$C_6$) alkoxy ($C_1$-$C_6$) alkyl;

alternatively, $R_3$ and $R_{3'}$ form a 3-6 membered saturated or unsaturated ring together with the carbon atom connected to them, and the ring can also optionally contain 1 or 2 heteroatoms selected from O, S, and N; and the ring can also be optionally substituted by 0, 1, 2 halogens, hydroxyl, $C_1$-$C_6$ alkyl;

alternatively, $R_2$, $R_3$ or $R_{2'}$, $R_3$ form a 4-6 membered saturated or unsaturated ring together with the atoms connected to them, the ring may optionally contain 1 or 2 heteroatoms selected from O, S, and N; and the ring can also be optionally substituted by 0, 1, 2 halogens, hydroxyl, $C_1$-$C_6$ alkyl;

$R_4$ and $R_{4'}$ independently represent hydrogen, $C_1$-$C_6$ alkyl, $C_3$-$C_6$ cycloalkyl, hydroxyl ($C_1$-$C_6$ alkyl), halo-genated ($C_1$-$C_6$ alkyl), ($C_1$-$C_6$) alkoxy ($C_1$-$C_6$) alkyl;

alternatively, $R_4$ and $R_{4'}$ together form =O;

$R^T$ and $R^{T'}$ each independently represent hydrogen, $C_1$-$C_6$ alkyl, halogenated ($C_1$-$C_6$ alkyl), hydroxyl $C_1$-$C_6$ alkyl, $C_3$-$C_6$ cycloalkyl, halogen, $OR_a$;

alternatively, $R^T$ and $R^{T'}$ together form a 3-6 membered ring with the atom connected to them;

wherein, when ▬ ▬ ▬ represents absence, A represents $(CR^LR^{L'})_p$, wherein $R^L$ and $R^{L'}$ each independently represent hydrogen, $C_1$-$C_6$ alkyl, halo ($C_1$-$C_6$ alkyl), hydroxyl ($C_1$-$C_6$ alkyl), $C_3$-$C_6$ cycloalkyl, halogen, $OR_a$, or $R^L$ and $R^{L'}$ together form a 3-6 membered ring with the carbon atom connected to them, and the ring can optionally contain 0, 1, 2 heteroatoms selected from O, S, N, and the ring can also be optionally substituted by 0, 1, 2 halogens, hydroxyl;

wherein, when ▬ ▬ ▬ represents existence, A rep-resents $CR^H$, wherein $R^H$ means hydrogen, $C_1$-$C_6$ alkyl, halogenated ($C_1$-$C_6$ alkyl), hydroxyl ($C_1$-$C_6$ alkyl), $C_3$-$C_6$ cycloalkyl, halogen, $OR_a$;

wherein, $R_a$, $R_{a'}$ independently represent hydrogen and $C_1$-$C_6$ alkyl;

wherein, m, n, and p each independently represent 0, 1, 2.

In one embodiment, wherein X represents —O—, —CH$_2$—, —OCH$_2$ or —CH$_2$CH$_2$—.

In one embodiment, wherein $C_v$ represents 0, 1, 2 substituents selected from ($C_1$-$C_6$) alkyl, ($C_3$-$C_6$) cycloalkyl, halogenated ($C_1$-$C_6$ alkyl), —OR$^a$, halogen, cyano, NR$^a$R$^{a'}$, hydroxyl ($C_1$-$C_6$) alkyl substituted pyrazolyl, pyridyl, pyrazinyl, pyrimidinyl, imidazolyl, phenyl; wherein, R$^a$, R$^{a'}$ each independently represent hydrogen and $C_1$-$C_6$ alkyl.

In one embodiment, wherein $R_1$ represents ($C_1$-$C_6$) alkyl, ($C_3$-$C_6$) cycloalkyl, ($C_6$-$C_{10}$) aryl, (5-10) membered heteroaryl, which is optionally substituted by 0, 1, 2 substituents selected from halogen, OR$^a$, ($C_1$-$C_6$) alkyl, halo($C_1$-$C_6$ alkyl); wherein, R$^a$ represents hydrogen and $C_1$-$C_6$ alkyl.

In one embodiment, wherein $R_2$ represents hydrogen or ($C_1$-$C_6$) alkyl.

In one embodiment, wherein $R_3$ and $R_{3'}$ each independently represent hydrogen or ($C_1$-$C_6$)alkyl.

In one embodiment, wherein $R_4$ and $R_{4'}$ together form =O.

Preferably, the compounds of the invention have the following structures:

| serial number | Compound Structure |
| --- | --- |
| 1 (W164) | |
| 2 (W179) | |
| 3 (W166) | |
| 4 (W169) | |
| 5 (W171) | |

-continued

| serial number | Compound Structure |
|---|---|
| 6 (W172) | |
| 7 (W174) | |
| 8 (W175) | |
| 9 (W176) | |
| 10 (W177) | |
| 11 (W178) | |

-continued

| serial number | Compound Structure |
|---|---|
| 12 (W180) | |
| 13 (W181) | |
| 14 (W182) | |
| 15 (W183) | |
| 16 (W184) | |
| 17 (W185) | |

-continued

| serial number | Compound Structure |
| --- | --- |
| 18 (W186) | |
| 19 (W75) | |
| 20 (W159) | |
| 21 (W155) | |
| 22 (W154) | |
| 23 (W153) | |

-continued

| serial number | Compound Structure |
| --- | --- |
| 24 (W150) | |
| 25 (W148) | |
| 26 (W110) | |
| 27 (W64) | |
| 28 (W94) | |

-continued

| serial number | Compound Structure |
| --- | --- |
| 29 | |
| 30 | |
| 31 | |
| 32 | |
| 33 | |

-continued

| serial number | Compound Structure |
| --- | --- |
| 34 | |
| 35 | |
| 36 | |
| 37 | |
| 38 | |

-continued

| serial number | Compound Structure |
| --- | --- |
| 39 | |
| 40 | |
| 41 | |
| 42 | |
| 43 | |

-continued

| serial number | Compound Structure |
| --- | --- |
| 44 | |
| 45 | |
| 46 | |
| 47 | |
| 48 | |

-continued

| serial number | Compound Structure |
| --- | --- |
| 49 | |
| 50 | |
| 51 | |
| 52 | |
| 53 | |

-continued

| serial number | Compound Structure |
| --- | --- |
| 54 | |
| 55 | |
| 56 | |
| 57 | |
| 58 | |

-continued

| serial number | Compound Structure |
| --- | --- |
| 59 | |
| 60 | |
| 61 (W2) | |
| 62 (W13) | |
| 63 (W22) | |

-continued

| serial number | Compound Structure |
| --- | --- |
| 64 (W23) | |
| 65 (W32) | |
| 66 (W43) | |
| 67 (W46) | |
| 68 (W49) | |

-continued

| serial number | Compound Structure |
| --- | --- |
| 69 (W50) | |
| 70 (W55) | |
| 71 (W56) | |
| 72 (W57) | |
| 73 (W85) | |

-continued

| serial number | Compound Structure |
| --- | --- |
| 74 (W69) | |
| 75 (W77) | |
| 76 (W83) | |
| 77 (W86) | |
| 78 (W87) | |
| 79 (W95) | |

-continued

| serial number | Compound Structure |
|---|---|
| 80 (W104) | |
| 81 (W105) | |
| 82 (W107) | |
| 83 (W116) | |
| 84 (W123) | |
| 85 (W132) | |

-continued

| serial number | Compound Structure |
| --- | --- |
| 86 (W135) | |
| 87 (W136) | |
| 88 (W140) | |
| 89 (W150) | |
| 90 (W152) | |

-continued

| serial number | Compound Structure |
|---|---|
| 91 (W212) | |
| 92 (W232) | |
| 93 (W223) | |
| 94 (W252) | |
| 95 (W253) | |
| 96 (W256) | |
| 97 (W312) | |

-continued

| serial number | Compound Structure |
| --- | --- |
| 98 (W188) | |
| 99 (W193) | |
| 100 (W239) | |
| 101 (W213) | |
| 102 (W214) | |
| 103 (W195) | |
| 104 (W198) | |

-continued

| serial number | Compound Structure |
| --- | --- |
| 105 (W199) | |
| 106 (W190) | |
| 107 (W192) | |
| 108 (W207) | |
| 109 (W220) | |
| 110 (W231) | |

-continued

| serial number | Compound Structure |
| --- | --- |
| 111 (W241) | |
| 112 (W242) | |
| 113 (W247) | |
| 114 (W243) | |
| 115 (W244) | |
| 116 (W249) | |

-continued

| serial number | Compound Structure |
| --- | --- |
| 117 (W237) | |
| 118 (W279) | |
| 119 (W255) | |
| 120 (W265) | |
| 121 (W266) | |
| 122 (W272) | |

-continued

| serial number | Compound Structure |
| --- | --- |
| 123 (W276) | |
| 124 (W278) | |
| 125 (W281) | |
| 126 (W308) | |
| 127 (W280) | |
| 128 (W263) | |

-continued

| serial number | Compound Structure |
|---|---|
| 129 (W369) | |
| 130 (W354) | |
| 131 (W366) | |
| 132 (W383) | |
| 133 (W377) | |
| 134 (W380) | |

-continued

| serial number | Compound Structure |
| --- | --- |
| 135 (W382) | |
| 136 (W381) | |
| 137 (W335) | |
| 138 (W271) | |
| 139 (W268) | |
| 140 (W376) | |

-continued

| serial number | Compound Structure |
|---|---|
| 141 (W261) | |
| 142 (W257) | |
| 143 (W277) | |
| 144 (W290) | |
| 145 (W331) | |
| 146 (W273) | |

-continued

| serial number | Compound Structure |
|---|---|
| 147 (W274) | |
| 148 (W250) | |
| 149 (W285) | |
| 150 (W301) | |
| 151 (W332) | |
| 152 (W336) | |

-continued

| serial number | Compound Structure |
|---|---|
| 153 (W293) | |
| 154 (W258) | |
| 155 (W347) | |
| 156 (W264) | |
| 157 (W262) | |
| 158 (W275) | |

-continued

| serial number | Compound Structure |
| --- | --- |
| 159 (W259) | |
| 160 (W362) | |
| 161 (W269) | |
| 162 (W270) | |
| 163 (W325) | |
| 164 (W326) | |

-continued

| serial number | Compound Structure |
| --- | --- |
| 165 (W286) | |
| 166 (W287) | |
| 167 (W289) | |
| 168 (W298) | |
| 169 (W294) | |
| 170 (W368) | |

-continued

| serial number | Compound Structure |
| --- | --- |
| 171 (W367) | |
| 172 (W305) | |
| 173 (W313) | |
| 174 (W314) | |
| 175 (W327) | |

-continued

| serial number | Compound Structure |
| --- | --- |
| 176 (W296) | |
| 177 (W297) | |
| 178 (W333) | |
| 179 (W375) | |
| 180 (W386) | |
| 181 (W396) | |

-continued

| serial number | Compound Structure |
| --- | --- |
| 182 (W395) | |
| 183 (W309) | |
| 184 (W282) | |
| 185 (W310) | |
| 186 (W311) | |
| 187 (W315) | |

-continued

| serial number | Compound Structure |
| --- | --- |
| 188 (W316) | |
| 189 (W306) | |
| 190 (W317) | |
| 191 (W318) | |
| 192 (W324) | |
| 193 (W342) | |

-continued

| serial number | Compound Structure |
|---|---|
| 194 (W341) | |
| 195 (W323) | |
| 196 (W344) | |
| 197 (W343) | |
| 198 (W307) | |
| 199 (W319) | |

-continued

| serial number | Compound Structure |
|---|---|
| 200 (W320) | |
| 201 (W360) | |
| 202 (W361) | |
| 203 (W372) | |
| 204 (W374) | |

-continued

| serial number | Compound Structure |
| --- | --- |
| 205 (W379) | |
| 206 (W388) | |
| 207 (W357) | |
| 208 (W) | |
| 209 (W) | |
| 210 (W371) | |

-continued

| serial number | Compound Structure |
| --- | --- |
| 211 (W390) | |
| 212 (W389) | |
| 213 (W355) | |
| 214 (W392) | |
| 215 (W391) | |

-continued

| serial number | Compound Structure |
| --- | --- |

216 (W352)

217 (W359)

218 (W339)

219 (W338)

220 (W398)

-continued

| serial number | Compound Structure |
|---|---|
| 221 (W399) | |
| 222 (W402) | |
| 223 (W403) | |
| 224 (W406) | |
| 225 (W407) | |
| 226 (W411) | |

-continued

| serial number | Compound Structure |
| --- | --- |
| 227 (W412) | |
| 228 (W413) | |
| 229 (W414) | |
| 230 (W415) | |
| 231 (W417) | |
| 232 (W418) | |

-continued

| serial number | Compound Structure |
| --- | --- |
| 233 (W419) | |
| 234 (W420) | |
| 235 (W422) | |
| 236 (W424) | |
| 237 (W425) | |

-continued

| serial number | Compound Structure |
|---|---|
| 238 (W426) | |
| 239 (W427) | |
| 240 (W428) | |
| 241 (W431) | |
| 242 | |
| 243 | |

| serial number | Compound Structure |
|---|---|
| 244 | |
| 245 | |
| 246 | |
| 247 | |
| 248 | |

-continued

| serial number | Compound Structure |
| --- | --- |
| 249 | |
| 250 | |
| 251 | |
| 252 | |
| 253 | |

-continued

| serial number | Compound Structure |
|---|---|
| 254 | |
| 255 | |
| 256 | |
| 257 | |
| 258 | |

-continued

| serial number | Compound Structure |
|---|---|
| 259 | |
| 260 | |
| 261 | |
| 262 | |
| 263 | |

-continued

| serial number | Compound Structure |
| --- | --- |
| 264 | |
| 265 | |
| 266 | |
| 267 | |
| 268 | |

-continued

| serial number | Compound Structure |
| --- | --- |
| 269 | |

It is particularly noted that, herein, when referring to a "compound" having a specific structural formula, generally also encompassing its stereoisomers, diastereomers, enantiomers, racemic mixtures and isotopes derivative.

It is well known to those skilled in the art that a compound's salt, solvate, and hydrate are alternative forms of the compound, and they can all be converted into the compound under certain conditions. When referring to a compound, it generally includes its pharmaceutically acceptable salt, and further includes its solvate and hydrate.

Similarly, when referring to a compound herein, its prodrugs, metabolites and nitroxides are also generally included.

The pharmaceutically acceptable salts of the present invention may be formed using, for example, the following inorganic or organic acids: "Pharmaceutically acceptable salt" means a salt which, within the scope of reasonable medical judgment, is suitable for use in contact with tissues of humans and lower animals, without undue toxicity, irritation, allergic reaction, etc., can be called a reasonable benefit/risk ratio. The salts can be prepared in situ during the final isolation and purification of the compounds of the invention, or alone by reacting the free base or acid with a suitable reagent, as outlined below. For example, a free base function can be reacted with a suitable acid. In addition, when the compound of the present invention bears an acidic moiety, suitable pharmaceutically acceptable salts thereof may include metal salts, such as alkali metal salts (such as sodium or potassium salts); and alkaline earth metal salts (such as calcium or magnesium salts). Examples of pharmaceutically acceptable non-toxic acid addition salts are salts formed by amino acids with inorganic acids (e.g., hydrochloric, hydrobromic, phosphoric, sulfuric, and perchloric) or organic acids (e.g., acetic, oxalic, maleic, tartaric, citric acid, succinic acid or malonic acid), or salts formed by using other methods known in the art such as ion exchange. Other pharmaceutically acceptable salts include adipate, sodium alginate, ascorbate, aspartate, benzenesulfonate, benzoate, bisulfate, borate, butyrate, camphorate, camphorsulfonate, citrate, cyclopentanepropionate, digluconate, lauryl sulfate, ethylate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate Salt, maleate, malonate, methanesulfonate, 2-naphthalenesulfonate, nicotinate, nitrate, oleate, oxalate, palmitate, pamoate, pectate Salt, persulfate, 3-phenylpropionate, phosphate, bitter salt, pivalate, propionate, stearate, succinate, sulfate, tartrate, thiocyanate, p-toluene sulfonate, undecanoate, valerate, etc.

Representative alkali or alkaline earth metal salts include those of sodium, lithium, potassium, calcium, magnesium, and the like. Other pharmaceutically acceptable salts include, where appropriate, nontoxic ammonium salts, quaternary ammonium salts, and amine cations formed with counterions, for example, halides, hydroxides, carboxylates, sulfates, phosphates, nitrates, lower alkylsulfonates and arylsulfonates.

The pharmaceutically acceptable salts of the present invention can be prepared by conventional methods, for example, by dissolving the compound of the present invention in a water-miscible organic solvent (such as acetone, methanol, ethanol and acetonitrile), adding an excess of aqueous solution of organic acid or inorganic acid aqueous solution, so that the salt is precipitated from the resulting mixture, the solvent and remaining free acid are removed therefrom, and the precipitated salt is isolated.

The precursors or metabolites described in the present invention may be precursors or metabolites known in the art, as long as the precursors or metabolites are transformed into compounds through in vivo metabolism. For example, "prodrugs" refer to those prodrugs of the compounds of the present invention which, within the scope of sound medical judgment, are suitable for use in contact with tissues of humans and lower animals without undue toxicity, irritation, allergic response, etc., and qualified as having a reasonable benefit/risk ratio and valid for its intended use. The term "prodrug" refers to a compound that is rapidly transformed in vivo to yield the parent compound of the above formula, for example by in vivo metabolism, or N-demethylation of a compound of the invention.

"Solvate" as used herein means a physical association of a compound of the present invention with one or more solvent molecules, whether organic or inorganic. This physical association includes hydrogen bonding. In some cases, for example, when one or more solvent molecules are incorporated into the crystal lattice of a crystalline solid, solvates will be able to be isolated. Solvent molecules in solvates may exist in regular and/or disordered arrangements. Solvates may contain stoichiometric or non-stoichiometric amounts of solvent molecules. "Solvate" encompasses both solution-phase and isolatable solvates. Exemplary solvates include, but are not limited to, hydrates, ethanolates, methanolates, and isopropanolates. Solvation methods are well known in the art.

The "stereoisomerism" described in the present invention is divided into conformational isomerism and configurational isomerism, and configurational isomerism can also be divided into cis-trans isomerism and optical isomerism (that is, optical isomerism). Due to the rotation or twisting of carbon and carbon single bonds in organic molecules of a certain configuration, a stereoisomerism phenomenon in which each atom or atomic group of the molecule has a different arrangement in space, the common structures are alkanes and cycloalkanes. Such as the chair conformation and boat conformation that appear in the structure of cyclohexane. "Stereoisomer" means when a compound of the present invention contains one or more asymmetric centers and is thus available as racemates and racemic mixtures, single enantiomers, diastereomeric mixtures and single diastereomers. The compound of the present invention has an asymmetric center, and each asymmetric center can produce two optical isomers, and the scope of the present invention includes all possible optical isomers and diastereoisomer mixtures and pure or partially pure compounds. The compounds described herein may exist in tautomeric forms having different points of attachment of hydrogens by displacement of one or more double bonds. For example, a ketone and its enol form are keto-enol tautomers. Each tautomer and mixtures thereof are included in the compounds of the present invention. Enantiomers, diastereoisomers, racemates, mesoisomers, cis-trans isomers, tautomers, geometric isomers, epimers of all compounds of formula (I) Conformants and their mixtures, etc., are included in the scope of the present invention.

The "isotopic derivatives" of the present invention refer to molecules that are labeled with isotopes of the compounds in this patent. Isotopes commonly used for isotopic labeling are: hydrogen isotopes, $^2$H and $^3$H; carbon isotopes: $^{11}$C, $^{13}$C and $^{14}$C; chlorine isotopes: $^{35}$Cl and $^{37}$Cl; fluorine isotopes: $^{18}$F; iodine isotopes: $^{123}$I and $^{125}$I; nitrogen isotopes: $^{13}$N and $^{15}$N; Oxygen isotopes: $^{15}$O, $^{17}$O and $^{18}$O and sulfur isotope $^{35}$S. These isotope-labeled compounds can be used to study the distribution of pharmaceutical molecules in tissues. Especially deuterium $^3$H and carbon $^{13}$C are more widely used due to their easy labeling and convenient detection. Substitution of certain heavy isotopes, such as deuterium (2H), can enhance metabolic stability, prolong half-life and thus provide therapeutic advantages for dose reduction. Isotopically labeled compounds are generally synthesized starting from labeled starting materials and carried out in the same way as non-isotopically labeled compounds using known synthetic techniques.

The present invention also provides the use of the compound of the present invention in the preparation of medicaments for preventing and/or treating cancer, tumor, inflammatory disease, autoimmune disease or immune-mediated disease.

In addition, the present invention provides a pharmaceutical composition for preventing and/or treating cancer, tumor, inflammatory disease, autoimmune disease, neurodegenerative disease, attention-related disease or immune-mediated disease, which comprises the compounds of present invention as active ingredients.

In addition, the present invention provides a method for preventing and/or treating cancer, tumor, inflammatory disease, autoimmune disease, neurodegenerative disease, attention-related disease or immune-mediated disease, which comprises administering a compound of the present invention tot a mammal in need thereof.

Representative examples of inflammatory, autoimmune, and immune-mediated diseases may include, but are not limited to, arthritis, rheumatoid arthritis, spondyloarthritis, gouty arthritis, osteoarthritis, juvenile arthritis, Other Arthritis Conditions, Lupus, Systemic Lupus Erythematosus (SLE), Skin Related Disorders, Psoriasis, Eczema, Dermatitis, Atopic Dermatitis, Pain, Pulmonary Disease, Lung Inflammation, Adult Respiratory Distress Syndrome (ARDS), pulmonary sarcoidosis, chronic pulmonary inflammatory disease, chronic obstructive pulmonary disease (COPD), cardiovascular disease, atherosclerosis, myocardial infarction, congestive heart failure, myocardial ischemia-reperfusion injury, inflammatory bowel disease, Crohn's disease, ulcerative colitis, irritable bowel syndrome, asthma, Sjogren's syndrome, autoimmune thyroid disease, urticaria (rubella), multiple sclerosis, scleroderma, organ transplant rejection, xenograft, idiopathic thrombocytopenic purpura (ITP), Parkinson's disease, Alzheimer's disease, diabetes-related diseases, inflammation, pelvic inflammatory disease, allergic rhinitis, allergic bronchitis, allergic sinusitis, leukemia, lymphoma, B Cell Lymphoma, T Cell Lymphoma, Myeloma, Acute Lymphocytic Leukemia (ALL), Chronic Lymphocytic Leukemia (CLL), Acute Myeloid Leukemia (AML), Chronic Myelogenous Leukemia (CML), Hairy Cell Leukemia, He Jie King's disease, non-Hodgkin's lymphoma, multiple myeloma, myelodysplastic syndrome (MDS), myeloproliferative neoplasm (MPN), diffuse large B-cell lymphoma, and follicular lymphoma.

Representative examples of cancer or tumor may include, but are not limited to, skin cancer, bladder cancer, ovarian cancer, breast cancer, stomach cancer, pancreatic cancer, prostate cancer, colon cancer, lung cancer, bone cancer, brain cancer, neuroblastoma, rectal cancer, colon cancer, familial adenomatous polyposis carcinoma, hereditary non-polyposis colorectal cancer, esophagus cancer, lip cancer, larynx cancer, hypopharyngeal cancer, tongue cancer, salivary gland cancer, stomach cancer, adenocarcinoma, medullary thyroid cancer, Papillary thyroid cancer, renal cancer, renal parenchymal cancer, ovarian cancer, cervical cancer, uterine body cancer, endometrial cancer, choriocarcinoma, pancreatic cancer, prostate cancer, testicular cancer, urinary cancer, melanoma, brain tumors such as Glioblastoma, astrocytoma, meningioma, medulloblastoma and peripheral neuroectodermal tumor, Hodgkin lymphoma, non-Hodgkin lymphoma, Burkitt lymphoma, acute lymphoblastic leukemia (ALL), chronic lymphocytic leukemia (CLL), acute myeloid leukemia (AML), chronic myelogenous leukemia (CML), adult T-cell leukemia lymphoma, diffuse large B-cell lymphoma (DLBCL), hepatocellular carcinoma, gallbladder Carcinoma, bronchial carcinoma, small cell lung cancer, non-small cell lung cancer, multiple myeloma, basal cell tumor, teratoma, retinoblastoma, choroidal melanoma, seminoma, rhabdomyosarcoma, craniopharyngioma, osteosarcoma, chondrosarcoma, sarcoma, liposarcoma, fibrosarcoma, Ewing sarcoma, or plasmacytoma.

When the compound of the present invention or a pharmaceutically acceptable salt thereof is administered in combination with another anticancer agent or immune checkpoint inhibitor for the treatment of cancer or tumors, the compound of the present invention or a pharmaceutically acceptable salt thereof can provide enhanced anticancer effects.

Representative examples of anticancer agents useful in the treatment of cancer or tumors may include, but are not limited to, cell signal transduction inhibitors, chlorambucil, melphalan, cyclophosphamide, ifosfamide, busulfan, carbamate, Mustin, lomustine, streptozotocin, cisplatin, carboplatin, oxaliplatin, dacarbazine, temozolomide, procarbazine, methotrexate, fluorouracil, cytarabine, gemcitabine, Mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin C, ixabepilone, tamoxifen, flutamide, gonadorelin analogs, methadone Progesterone, prednisone, dexamethasone, methylprednisolone, thalidomide, interferon alpha, leucovorin, sirolimus, sirolimus ester, everolimus, afatinib, alisertib, amuvatinib, apatinib, axitinib, bortezomib, bosutinib, britinib, cabozantinib, cediranib, crenolanib, kezhuotinib, dabrafenib, dabrafenib, Cotinib, danucitinib, dasatinib, dovitinib, erlotinib, foretinib, ganetespib, gefitinib, ibrutinib, icotinib, imatinib, iniparib, la Patinib, lenvatinib, linifanib, linsitinib, masitinib, momelotinib, motisanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tiratinib, tivantinib, tivozanib, tofacitinib, Trametinib, vandetanib, veliparib, vemurafenib, vimodegib, volasertib, alemtuzumab, bevacizumab, berentuzumab vedotin, catumaxumab Antibodies, cetuximab, denosumab, gemtuzumab, ipilimumab, nimotuzumab, ofatumumab, panitumumab, rituximab, tositumumab Monoclonal antibody, trastuzumab, PI3K inhibitor, CSF1R inhibitor, A2A and/or A2B receptor antagonist, IDO inhibitor, anti-PD-1 antibody, anti-PD-L1 antibody, LAG3 antibody, TIM-3 antibody and an anti-CTLA-4 antibody or any combination thereof.

Compounds of the present invention, or pharmaceutically acceptable salts thereof, provide enhanced therapeutic effect.

Representative examples of therapeutic agents useful in the treatment of inflammatory, autoimmune, and immune-mediated diseases can include, but are not limited to, steroidal agents (e.g., prednisone, prednisone, prednisone, methylphenidate, cortisone, cortisone, hydroxycortisone, betamethasone, dexamethasone, etc.), methotrexate, leflunomide, anti-TNFα agents (e.g., etanercept, infliximab, adalib monoclonal antibody, etc.), calcineurin inhibitors (eg, tacrolimus, pimecrolimus, etc.), and antihistamines (eg, diphenhydramine, hydroxyzine, loratadine, ebazan Tin, ketotifen, cetirizine, levocetirizine, fexofenadine, etc.), and at least one therapeutic agent selected from them can be included in the pharmaceutical composition of the present invention.

The compound of the present invention or a pharmaceutically acceptable salt thereof can be administered orally or parenterally as an active ingredient, and its effective amount ranges from 0.1 to 2,000 mg/kg body weight/day in mammals including humans (about 70 kg in body weight), Preferably 1 to 1,000 mg/kg body weight/day, and administered in single or 4 divided doses per day, or with or without a scheduled time. The dose of the active ingredient can be adjusted according to a number of relevant factors such as the condition of the subject to be treated, the type and severity of the disease, the rate of administration and the doctor's opinion. In some cases, amounts less than the above dosages may be appropriate. Amounts greater than the above doses may be used if no deleterious side effects are caused and such amounts may be administered in divided doses daily.

In addition, the present invention also provides a method for preventing and/or treating tumors, cancers, viral infections, organ transplant rejection, neurodegenerative diseases, attention-related diseases or autoimmune diseases, which comprises administering a compound of the present invention or a pharmaceutical composition of the present invention to a mammal in need thereof.

The pharmaceutical composition of the present invention can be formulated into dosage forms for oral administration or parenteral administration (including intramuscular, intravenous and subcutaneous routes, intratumoral injection) according to any of the conventional methods, such as tablets, granules, powders, capsules, syrups, emulsions, microemulsions, solutions or suspensions.

Pharmaceutical compositions of the present invention for oral administration can be prepared by mixing the active ingredient with carriers such as cellulose, calcium silicate, corn starch, lactose, sucrose, dextrose, calcium phosphate, stearic acid, magnesium stearate, calcium stearate, gelatin, talc, surfactant, suspending agent, emulsifier and diluent. Examples of carriers employed in the injectable compositions of the present invention are water, saline solution, glucose solution, glucose-like solution, alcohol, glycol, ether (e.g., polyethylene glycol 400), oil, fatty acids, fatty acid esters, glycerides, surfactants, suspending and emulsifying agents.

Other features of the invention will become apparent in the course of the description of exemplary embodiments of the invention which are given to illustrate the invention and are not intended to be limiting thereof, the following examples were prepared, separated and characterized using the methods disclosed in the invention.

The compounds of the present invention can be prepared in a variety of ways known to those skilled in the art of organic synthesis, using the methods described below as well as synthetic methods known in the art of synthetic organic chemistry or by variations thereof known to those skilled in the art to synthesize compounds of the invention. Preferred methods include, but are not limited to, those described below. Reactions are performed in solvents or solvent mixtures appropriate to the kit materials used and to the transformations effected. Those skilled in the art of organic synthesis will appreciate that the functionality present on the molecule is consistent with the proposed transitions. This sometimes requires judgment to alter the order of synthetic steps or starting materials to obtain the desired compound of the invention.

DESCRIPTION OF DRAWINGS

FIG. 1 shows the effect of compound 11 on the tumor volume of human myeloma cell NCI-H929 SCID xenografts.

DETAILED DESCRIPTION

Terms

Unless otherwise stated, the terms used in the present application, including the specification and claims, are defined as follows. It must be noted that in the specification and appended claims, the singular form "a" and "an" includes plural references unless the context clearly dictates otherwise. If not stated otherwise, conventional methods of mass spectrometry, NMR, HPLC, protein chemistry, biochemistry, recombinant DNA techniques and pharmacology are used. In this application, the use of "or" or "and" means "and/or" if not stated otherwise.

In the description and claims, a given chemical formula or name shall cover all stereo and optical isomers and racemates in which such isomers exist. Unless otherwise indicated, all chiral (enantiomers and diastereoisomers) and racemic forms are within the scope of the invention. Many geometric isomers of C=C double bonds, C=N double bonds, ring systems, etc. may also exist in the compounds, and all such stable isomers are encompassed within the present invention. The present invention describes cis- and trans-(or E- and Z-) geometric isomers of the compounds of the invention and which may be isolated as a mixture of isomers or as separated isomeric forms. The compounds of the invention may be isolated in optically active or racemic forms. All methods used to prepare the compounds of the invention and intermediates prepared therein are considered part of the invention. When preparing enantiomeric or diastereomeric products, they may be separated by customary methods, for example by chromatography or fractional crystallization. Depending on the process conditions, the end products of the invention are obtained in free (neutral) or salt form. The free forms and salts of these end products are within the scope of the present invention. A compound can be converted from one form to another, if desired. A free base or acid can be converted into a salt; a salt can be converted into the free compound or another salt; a mixture of isomeric compounds of the invention can be separated into the individual isomers. The compounds of the invention, their free forms and salts, may exist in various tautomeric forms in which the hydrogen atoms are transposed to other parts of the molecule and thus the chemical bonds between the atoms of the molecule are rearranged. It is to be understood that all tautomeric forms which may exist are included within the present invention.

Unless otherwise defined, the definitions of the substituents in the present invention are independent and not interrelated, for example, for $R^a$ (or $R^{a'}$) in the substituents, they are independent in the definitions of different substituents. Specifically, when one definition is selected for $R^a$ (or $R^{a'}$) in one substituent, it does not mean that $R^a$ (or $R^{a'}$) has the same definition in other substituents. More specifically, for example (but not exhaustively) for $NR^a R^{a'}$, when $R^a$ (or $R^{a'}$) is defined from hydrogen, it does not mean that in —C(O)—$NR^a R^{a'}$, $R^a$ (or $R^{a'}$) must be hydrogen.

Unless otherwise defined, when a substituent is noted as "optionally substituted", the substituent is selected from, for example, the following substituents, such as alkyl, cycloalkyl, aryl, heterocyclyl, halogen, hydroxy, alkoxy, oxo, alkanoyl, aryloxy, alkanoyloxy, amino, alkylamino, arylamino, arylalkylamino, disubstituted amine groups (wherein 2 amino substituents are selected from alkyl, aryl or arylalkyl), alkanoylamino, aroylamino, aralkanoylamino, substituted alkanoylamino, substituted arylamino, substituted aralkanoylamino, thio, alkylthio, arylthio, arylalkylthio, arylthiocarbonyl, arylalkylthiocarbonyl, alkylsulfonyl, arylsulfonyl, arylalkylsulfonyl, sulfonylamino such as —SO$_2$NH$_2$, substituted sulfonylamino, nitro, cyano, carboxyl, carbamoyl such as —CONH$_2$, substituted carbamoyl such as —CONH alkyl, —CONH aryl, —CONH arylalkyl or with two In the case of one substituent selected from alkyl, aryl or arylalkyl, alkoxycarbonyl, aryl, substituted aryl, guanidino, heterocyclyl such as indolyl, imidazolyl, furyl, Thienyl, thiazolyl, pyrrolidinyl, pyridyl, pyrimidinyl, pyrrolidinyl, piperidinyl, morpholinyl, piperazinyl, homopiperazinyl, etc. and substituted heterocyclic groups.

The term "alkyl" or "alkylene" as used herein is intended to include both branched and straight chain saturated aliphatic hydrocarbon groups having the indicated number of carbon atoms. For example, "C$_1$-C$_6$ alkyl" means an alkyl group having 1 to 6 carbon atoms. Examples of alkyl groups include, but are not limited to, methyl (Me), ethyl (Et), propyl (such as n-propyl and isopropyl), butyl (such as n-butyl, isobutyl, t-butyl), and pentyl (eg n-pentyl, isopentyl, neopentyl).

The term "alkenyl" denotes a straight or branched chain hydrocarbon group containing one or more double bonds and generally having a length of 2 to 20 carbon atoms. For example, "C$_2$-C$_6$ alkenyl" contains two to six carbon atoms. Alkenyl groups include, but are not limited to, e.g. vinyl, propenyl, butenyl, 1-methyl-2-buten-1-yl, and the like.

The term "alkynyl" denotes a straight or branched chain hydrocarbon group containing one or more triple bonds and generally having a length of 2 to 20 carbon atoms. For example, "C$_2$-C$_6$ alkynyl" contains two to six carbon atoms. Representative alkynyl groups include, but are not limited to, for example, ethynyl, 1-propynyl, 1-butynyl, and the like.

The term "alkoxy" or "alkyloxy" refers to —O-alkyl. "C$_1$-C$_6$ alkoxy" (or alkyloxy) is intended to include C$_1$, C$_2$, C$_3$, C$_4$, C$_5$, C$_6$ alkoxy. Examples of alkoxy include, but are not limited to, methoxy, ethoxy, propoxy (e.g., n-propoxy and isopropoxy), and tert-butoxy. Similarly, "alkylthio" or "thioalkoxy" denotes an alkyl group as defined above having the indicated number of carbon atoms attached through a sulfur bridge; e.g. methyl-S— and ethyl-S—.

The term "carbonyl" refers to an organic functional group (C=O) consisting of two atoms, carbon and oxygen, linked by a double bond.

The term "aryl", alone or as part of a larger moiety such as "aralkyl", "aralkoxy" or "aryloxyalkyl", refers to a single ring having a total of 5 to 12 ring members, a bicyclic or tricyclic ring system, wherein at least one ring in the system is aromatic and wherein each ring in the system contains 3 to 7 ring members. In certain embodiments of the invention, "aryl" refers to an aromatic ring system which includes, but is not limited to, phenyl, biphenyl, indanyl, 1-naphthyl, 2-naphthyl, and tetrahydronaphthyl. The term "aralkyl" or "arylalkyl" refers to an alkyl residue attached to an aryl ring. Non-limiting examples include benzyl, phenethyl, and the like. A fused aryl group can be attached to another group at a suitable position on the cycloalkyl ring or aromatic ring. For example dashed lines drawn from ring systems indicate that bonds may be attached to any suitable ring atom.

The term "cycloalkyl" refers to a monocyclic or bicyclic cyclic alkyl group. Monocyclic cyclic alkyl refers to C$_3$-C$_5$ cyclic alkyl, including but not limited to cyclopropyl, cyclobutyl, cyclopentyl, cyclohexyl and norbornyl. Branched cycloalkyl groups such as 1-methylcyclopropyl and 2-methylcyclopropyl are included within the definition of "cycloalkyl". Bicyclic cyclic alkyl groups include bridged, spiro, or fused ring cycloalkyls.

The term "cycloalkenyl" refers to a monocyclic or bicyclic cyclic alkenyl group. Monocyclic cyclic alkenyl refers to C$_3$-C$_5$ cyclic alkenyl, including but not limited to cyclopropenyl, cyclobutenyl, cyclopentenyl, cyclohexenyl and norbornenyl. Branched cycloalkenyl groups such as 1-methylcyclopropenyl and 2-methylcyclopropenyl are included within the definition of "cycloalkenyl". Bicyclic cyclic alkenyl groups include bridged, spiro, or fused ring cyclic alkenyl groups.

"Halo" or "halogen" includes fluoro, chloro, bromo and iodo. "Haloalkyl" is intended to include branched and straight chain saturated aliphatic hydrocarbon groups having the indicated number of carbon atoms substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl and heptachloropropyl. Examples of haloalkyl also include "fluoroalkyl" intended to include branched and straight-chain saturated aliphatic hydrocarbon groups having the specified number of carbon atoms and substituted with 1 or more fluorine atoms.

"Haloalkoxy" or "haloalkyloxy" means a haloalkyl group as defined above having the indicated number of carbon atoms attached through an oxygen bridge. For example, "haloC$_1$-C$_6$ alkoxy" is intended to include C$_1$, C$_2$, C$_3$, C$_4$, C$_5$, C$_6$ haloalkoxy. Examples of haloalkoxy include, but are not limited to, trifluoromethoxy, 2,2,2-trifluoroethoxy, and pentafluoroethoxy. Similarly, "haloalkylthio" or "thiohaloalkoxy" denotes a haloalkyl group as defined above having the indicated number of carbon atoms attached through a sulfur bridge; for example trifluoromethyl-S— and pentafluoroethyl —S—.

In the present disclosure, the expression C$_{x1}$-C$_{x2}$ is used when referring to some substituent groups, which means that the number of carbon atoms in the substituent groups may be x1 to x2. For example, C$_0$-C$_8$ means that the group contains 0, 1, 2, 3, 4, 5, 6, 7 or 8 carbon atoms, C$_1$-C$_8$ means that the group contains 1, 2, 3, 4, 5, 6, 7 or 8 carbon atoms, C$_2$-C$_8$ means that the group contains 2, 3, 4, 5, 6, 7 or 8 carbon atoms, C$_3$-C$_8$ means that the group contains 3, 4, 5, 6, 7 or 8 carbon atoms, C$_4$-C$_8$ means that the group contains 4, 5, 6, 7 or 8 carbon atoms, C$_0$-C$_6$ means that the group contains 0, 1, 2, 3, 4, 5 or 6 carbon atoms, C$_1$-C$_6$ means that the group contains 1, 2, 3, 4, 5 or 6 carbon atoms, C$_2$-C$_6$ means that the group contains 2, 3, 4, 5 or 6 carbon atoms, C$_3$-C$_6$ means that the group contains 3, 4, 5 or 6 carbon atoms.

In this disclosure, the expression "x1-x2 membered ring" is used when referring to cyclic groups such as aryl, heteroaryl, cycloalkyl, and heterocycloalkyl, which means that the number of the ring atoms of the group can be x1 to x2. For example, the 3-12 membered cyclic group may be a 3, 4, 5, 6, 7, 8, 9, 10, 11 or 12 membered ring, and the number of ring atoms may be 3, 4, 5, 6, 7, 8, 9, 10, 11 or 12; 3-6-membered ring means that the cyclic group can be 3, 4, 5 or 6-membered ring, and the number of ring atoms can be 3, 4, 5 or 6; 3-8 membered ring means that the cyclic group can be 3, 4, 5, 6, 7 or 8 membered ring, and the number of ring atoms can be 3, 4, 5, 6, 7 or 8; 3-9 A membered ring means that the cyclic group can be a 3, 4, 5, 6, 7, 8 or 9-membered ring, and the number of ring atoms can be 3, 4, 5, 6, 7, 8 or 9; 4-7 membered ring means that the cyclic group can be a 4, 5, 6 or 7-membered ring, and the number of ring atoms can be 4, 5, 6 or 7; 5-8-membered ring means that the cyclic group can be 5, 6, 7 or 8-membered ring, the number of ring atoms can be 5, 6, 7 or 8; 5-12 membered ring means that the ring group can be 5, 6, 7, 8, 9, 10, 11 or 12-membered ring, the number of ring atoms can be 5, 6, 7, 8, 9, 10, 11 or 12; 6-12 membered ring means that the ring group can be 6, 7, 8, 9, 10, 11- or 12-membered rings may have 6, 7, 8, 9, 10, 11 or 12 ring atoms. The ring atoms may be carbon atoms or heteroatoms, for example selected from N, O and S. When the ring is heterocyclic, the heterocyclic ring may contain 1, 2, 3, 4, 5, 6, 7, 8, 9, 10 or more ring heteroatoms, for example selected from N, O and S of heteroatoms.

In the present disclosure, the one or more halogens may each be independently selected from fluorine, chlorine, bromine and iodine.

The term "heteroaryl" means a stable 3-membered, 4-membered, 5-membered, 6-membered, or 7-membered aromatic monocyclic or aromatic bicyclic ring or 7-, 8-, 9-, 10-, 11-, 12-membered aromatic polycyclic heterocycles that are fully unsaturated, partially unsaturated, and contain carbon atoms and 1, 2, 3, or 4 heteroatoms independently selected from N, O, and S; and include any of the following polycyclic groups in which any heterocyclic ring as defined above is fused to a benzene ring. Nitrogen and sulfur heteroatoms can be optionally oxidized. The nitrogen atom is substituted or unsubstituted (i.e. N or NR, where R is H or another substituent if defined). A heterocycle can be attached to its pendant group at any heteroatom or carbon atom that results in a stable structure. The heterocyclyl groups described herein may be substituted on carbon or nitrogen atoms if the resulting compound is stable. The nitrogen in the heterocycle can optionally be quaternized. Preferably, when the total number of S and O atoms in the heterocycle exceeds 1, then these heteroatoms are not adjacent to each other. Preferably, the total number of S and O atoms in the heterocycle is not greater than one. When the term "heterocycle" is used, it is intended to include heteroaryl. Examples of heteroaryl groups include, but are not limited to, acridinyl, azetidinyl, aziocinyl, benzimidazolyl, benzofuryl, benzothiofuranyl, benzothienyl, benzoxazolyl, benzoxazolinyl, benzothiazolyl, benzotriazolyl, benzotetrazolyl, benzisoxazolyl, benzisothiazolyl, benzimidazolyl, carbazolyl, 4aH-carbazolyl, carbolinyl, chromanyl, chromenyl, cinnolinyl, decahydroquinolyl, 2H,6H-1,5,2-dithiazinyl, dihydrofuro[2, 3-b] Tetrahydrofuryl, furyl, furanyl, imidazolidinyl, imidazolinyl, imidazolyl, 1H-indazolyl, imidazopyridyl, indolenyl, indolinyl, Indolazinyl, indolyl, 3H-indolyl, isatinoyl, isobenzofuryl, isochromanyl, isoindazolyl, isoindolinyl, isoindolyl, isoindolyl Quinolinyl, isothiazolyl, isothiazolopyridyl, isoxazolyl, isoxazolopyridyl, methylenedioxyphenyl, morpholinyl, diazanaphthyl, octahydroisoquinoline oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridyl, oxazolidinyl, diazaphenyl, oxindolyl, pyrimidinyl, phenanthridinyl, phenanthrolinyl, phenazinyl, phenothiazinyl, phenoxathiyl, phenoxazinyl, phthalazinyl, piperazinyl, piperidinyl, piperidinyl, 4-piperidinyl, piperonyl, pteridinyl, purinyl, Pyranyl, pyrazinyl, pyrazolidinyl, pyrazolinyl, pyrazolopyridyl, pyrazolyl, pyridazinyl, pyridoxazolyl, pyridimidazolyl, pyridothiazolyl, pyridyl, pyrimidinyl, pyrrolidinyl, pyrrolinyl, 2-pyrrolidonyl, 2H-pyrrolyl, pyrrolyl, quinazolinyl, quinolinyl, 4H-quinazinyl, quinoxalinyl, quinuclidinyl, Tetrazolyl, tetrahydrofuryl, tetrahydroisoquinolyl, tetrahydroquinolyl, 6H-1,2,5-thiadiazinyl, 1,2,3-thiadiazolyl, 1,2,4-Thiadiazolyl, 1,2,5-thiadiazolyl, 1,3,4-thiadiazolyl, thianthryl, thiazolyl, thienyl, thiazolopyridyl, thienothiazolyl, thienooxa Azolyl, thienoimidazolyl, thienyl, triazinyl, 1,2,3-triazolyl, 1,2,4-triazolyl, 1,2,5-triazolyl, 1,3,4-Triazolyl and xanthenyl, quinolinyl, isoquinolyl, phthalazinyl, quinazolinyl, indolyl, isoindolyl, indolinyl, 1H-indazolyl, benzo Imidazolyl, 1,2,3,4-tetrahydroquinolinyl, 1,2,3,4-tetrahydroisoquinolinyl, 5,6,7,8-tetrahydro-quinolinyl, 2,3-dihydro-benzofuryl, chromanyl, 1,2,3,4-tetrahydro-quinoxalinyl and 1,2,3,4-tetrahydro-quinazolinyl. The term "heteroaryl" may also include biaryl structures formed by the above-defined "aryl" and a monocyclic "heteroaryl", such as but not limited to "-phenylbipyridyl-", "-"phenyl bipyrimidyl", "-pyridyl biphenyl", "-pyridyl bipyrimidyl-", "-pyrimidyl biphenyl-"; wherein the present invention also includes condensed rings containing, for example, the above-mentioned heterocycles and spiro compounds.

As used herein, the term "heterocycloalkyl" refers to a monocyclic heterocycloalkyl system, or a bicyclic heterocycloalkyl system, and also includes spiroheterocycle or bridged heterocycloalkyl. Monocyclic heterocycloalkyl refers to a 3-8 membered, saturated or unsaturated but non-aromatic cyclic alkyl system containing at least one selected from O, N, S, and P. A bicyclic heterocycloalkyl system refers to a heterocycloalkyl fused to a phenyl, or a cycloalkyl, or a cycloalkenyl, or a heterocycloalkyl, or a heteroaryl.

The term "bridged cycloalkyl" as used herein refers to polycyclic compounds sharing two or more carbon atoms.

Such "bridged cycloalkyl" can be divided into bicyclic bridged ring hydrocarbons and polycyclic bridged ring hydrocarbons. The former is composed of two alicyclic rings sharing more than two carbon atoms; the latter is a bridged ring hydrocarbon composed of more than three rings.

The term "spirocycloalkyl" as used herein refers to polycyclic hydrocarbons in which the monocyclic rings share one carbon atom (called the spiro atom).

The term "bridged ring heterogroup" used herein refers to a polycyclic compound sharing two or more carbon atoms, and the ring contains at least one atom selected from O, N, and S. It can be divided into bicyclic bridged heterocycles and polycyclic bridged heterocycles.

The term "heterospirocyclyl" used herein refers to a polycyclic hydrocarbon that shares one carbon atom (called a spiro atom) between monocyclic rings, and the ring contains at least one atom selected from O, N, and S.

The term "substituted" as used herein means that at least one hydrogen atom is replaced by a non-hydrogen group, provided that normal valences are maintained and that the substitution results in a stable compound. A ring double bond, as used herein, is a double bond formed between two adjacent ring atoms (e.g., $C=C$, $C=N$ or $N=N$).

Where nitrogen atoms (e.g. amines) are present on compounds of the invention, these nitrogen atoms can be converted to N-oxides by treatment with oxidizing agents (e.g. mCPBA and/or hydrogen peroxide) to obtain other compounds of the invention. Accordingly, both shown and claimed nitrogen atoms are considered to cover both the shown nitrogen and its N-oxides to obtain the derivatives of the present invention.

When any variable occurs more than one time in any composition or formula of a compound, its definition on each occurrence is independent of its definition at every other occurrence. Thus, for example, if a group is shown to be substituted with 0-3 R, then said group may be optionally substituted with up to three R groups, and R at each occurrence is independently selected from the definition of R. Also, combinations of substituents and/or variables are permissible only if such combinations result in stable compounds.

The term "patient" as used herein refers to an organism being treated by the methods of the present invention. Such organisms preferably include, but are not limited to, mammals (e.g., murine, simian, equine, bovine, porcine, canine, feline, etc.) and most preferably refer to humans.

As used herein, the term "effective amount" means the amount of a drug or agent (i.e., a compound of the invention) that will elicit the biological or medical response of a tissue, system, animal or human being sought, e.g., by a researcher or clinician. Furthermore, the term "therapeutically effective amount" means an amount that results in improved treatment, cure, prevention or alleviation of a disease, disorder or side effect, or a reduction in or the rate of disease progression. An effective amount may be given in one or more administrations, applications or doses and is not intended to be limited by a particular formulation or route of administration. The term also includes within its scope amounts effective to enhance normal physiological function.

As used herein, the term "treating" includes any effect that results in amelioration of a condition, disease, disorder, etc., such as alleviation, reduction, regulation, amelioration or elimination, or amelioration of the symptoms thereof.

The term "pharmaceutically acceptable" is used herein to refer to those compounds, substances, compositions and/or dosage forms: within the scope of sound medical judgment, they are suitable for use in contact with human and animal tissues without excessive toxicity, irritation, allergic reactions, and/or other problems or complications, commensurate with a reasonable benefit/risk ratio.

The phrase "pharmaceutically acceptable carrier" as used herein means a pharmaceutical substance, composition or vehicle, such as a liquid or solid filler, diluent, excipient, manufacturing aid (e.g. lubricant, talc, magnesium stearate, calcium stearate or zinc stearate or stearic acid) or solvent-encapsulated substances involved in the carrying or transport of a subject compound from one organ or body part to another. Each carrier must be "acceptable" in the sense of being compatible with the other ingredients of the formulation and not injurious to the patient.

The term "pharmaceutical composition" means a composition comprising a compound of the present invention together with at least one other pharmaceutically acceptable carrier. "Pharmaceutically acceptable carrier" means a medium generally accepted in the art for the delivery of biologically active agents to animals, particularly mammals, including (i.e.) adjuvants, excipients or vehicles, such as diluents, preservatives, fillers, flow regulators, disintegrants, wetting agents, emulsifiers, suspending agents, sweeteners, flavoring agents, fragrances, antibacterial agents, antifungal agents, lubricants and dispersants, depending on mode of administration and nature of dosage form.

Certain Pharmaceutical and Medical Terms

The term "acceptable", as used herein, means that a formulation ingredient or active ingredient does not have an undue adverse effect on health for the general purpose of treatment.

The term "cancer", as used herein, refers to an abnormal growth of cells that cannot be controlled and, under certain conditions, is capable of metastasizing (spreading). Cancers of this type include, but are not limited to, solid tumors (e.g., bladder, bowel, brain, chest, uterus, heart, kidney, lung, lymphoid tissue (lymphoma), ovary, pancreas or other endocrine organs (eg, thyroid), prostate, skin (melanoma), or blood cancer (such as non-leukemic leukemia).

The term "administration in combination" or similar terms, as used herein, refers to the administration of several selected therapeutic agents to a patient, in the same or different modes of administration at the same or different times.

The term "enhancing" or "capable of enhancing", as used herein, means that the desired result can be increased or prolonged, either in potency or duration. Thus, in relation to enhancing the therapeutic effect of a drug, the term "capable of potentiating" refers to the ability of the drug to increase or prolong its potency or duration in the system. As used herein, "potency value" refers to the ability to maximize the enhancement of another therapeutic drug in an ideal system.

The term "immune disease" refers to a disease or condition of an adverse or deleterious reaction to an endogenous or exogenous antigen. The result is usually dysfunction of the cells, or destruction thereof and dysfunction, or destruction of organs or tissues that may produce immune symptoms.

The terms "kit" and "product packaging" are synonymous.

The term "subject" or "patient" includes mammals and non-mammals. Mammals include, but are not limited to, mammals: humans, non-human primates such as orangutans, apes, and monkeys; agricultural animals such as cattle, horses, goats, sheep, and pigs; domestic animals such as rabbits and dogs; experimental animals include rodents, such as rats, mice and guinea pigs. Non-mammalian animals include, but are not limited to, birds, fish, and the like. In a preferred embodiment, the selected mammal is a human.

The term "treatment", "course of treatment" or "therapy" as used herein includes alleviating, suppressing or improving the symptoms or conditions of a disease; inhibiting the development of complications; improving or preventing the underlying metabolic syndrome; inhibiting the development of diseases or symptoms, Such as controlling the development of a disease or condition; alleviating a disease or a symptom; causing a disease or a symptom to regress; alleviating a complication caused by a disease or a symptom, or preventing and/or treating a sign caused by a disease or a symptom.

As used herein, a certain compound or pharmaceutical composition, after administration, can improve a certain disease, symptom or situation, especially improve its severity, delay the onset, slow down the progression of the disease, or reduce the duration of the disease. Circumstances that may be attributable to or related to the administration, whether fixed or episodic, continuous or intermittent.

Route of Administration

Suitable routes of administration include, but are not limited to, oral, intravenous, rectal, aerosol, parenteral, ocular, pulmonary, transdermal, vaginal, ear canal, nasal administration and topical administration. In addition, by way of example only, parenteral administration includes intramuscular injection, subcutaneous injection, intravenous injection, intramedullary injection, intraventricular injection, intraperitoneal injection, intralymphatic injection, and intranasal injection.

In one aspect, the compounds described herein are administered locally rather than systemically. In certain embodiments, the depot formulation is administered by implantation (e.g., subcutaneously or intramuscularly) or by intramuscular injection. Additionally, in another embodiment, the drug is administered via a targeted drug delivery system. For example, liposomes coated with organ-specific antibodies. In such embodiments, the liposomes are selectively directed to and taken up by specific organs.

Pharmaceutical Composition and Dosage

The present invention also provides pharmaceutical compositions comprising a therapeutically effective amount of one or more compounds of the present invention formulated together with one or more pharmaceutically acceptable carriers (additives) and/or diluents, and optionally one or more of the other therapeutic agents described above. The compounds of the present invention may be administered for any of the above uses by any suitable means, for example orally, such as tablets, pills, powders, granules, elixirs, tinctures, suspensions (including nanosuspensions, micro-suspensions, spray-dried dispersions), syrups and emulsions; sublingually; buccally; parenterally, such as by subcutaneous, intravenous, intramuscular or intrasternal injection or infusion techniques (e.g., as sterile injectable aqueous or nonaqueous solutions or suspensions liquid form); nasally, including to the nasal membranes, such as by inhalation spray; topically, such as in the form of a cream or ointment; or rectally, such as in the form of a suppository; or by intratumoral injection. They can be administered alone, but generally will be administered using a pharmaceutical carrier selected on the basis of the chosen route of administration and standard pharmaceutical practice.

Pharmaceutical carriers are formulated according to a number of factors within the purview of those skilled in the art. These factors include, but are not limited to: the type and nature of the active agent being formulated; the subject to whom the composition containing the active agent is to be administered; the intended route of administration of the composition; and the therapeutic indication being targeted. Pharmaceutical carriers include aqueous and non-aqueous liquid media and various solid and semisolid dosage forms.

Such carriers may include many different ingredients and additives other than the active agent, which are included in the formulation for various reasons known to those skilled in the art, such as to stabilize the active agent, binders, and the like. A description of suitable pharmaceutical carriers and the factors involved in the selection of the carrier can be found in several readily available sources, such as Allen L. V. Jr. et al. Remington: The Science and Practice of Pharmacy (2 Volumes), 22nd Edition (2012), Pharmaceutical Press.

Dosage regimens for the compounds of the present invention will of course vary depending on known factors such as the pharmacodynamic properties of the particular agent and its mode and route of administration; the species, age, sex, health, medical condition and weight of the recipient; nature and extent of symptoms; type of concomitant therapy; frequency of therapy; route of administration, patient's renal and hepatic function, and desired effects. As a general guide, the daily oral dosage of each active ingredient should be from about 0.001 mg/day to about 10-5000 mg/day, preferably from about 0.01 mg/day to about 1000 mg/day, and most preferably From about 0.1 mg/day to about 250 mg/day. The most preferred dose intravenously will be about 0.01 mg/kg/minute to about 10 mg/kg/minute during a constant rate infusion. The compounds of the present invention may be administered in a single daily dose, or the total daily dose may be administered in divided doses of two, three or four times daily.

The compounds are usually formulated with a suitable pharmaceutical diluent, excipient or carrier (herein collectively referred to as drug carriers) in the form of mixtures for administration.

Dosage forms (pharmaceutical compositions) suitable for administration may contain from about 1 milligram to about 2000 milligrams of active ingredient per dosage unit. In these pharmaceutical compositions, the active ingredient will generally be present in an amount of about 0.1-95% by weight, based on the total weight of the composition.

A typical capsule for oral administration contains at least one compound of the invention (250 mg), lactose (75 mg) and magnesium stearate (15 mg). The mixture was passed through a 60 mesh screen and packed into size 1 gelatin capsules.

A typical injectable formulation can be prepared by aseptically placing at least one compound of the present invention (250 mg) in a vial, lyophilizing in a sterile manner and sealing. For use, the vial contents are mixed with 2 mL of normal saline to produce an injectable formulation.

Included within the scope of the present invention are pharmaceutical compositions comprising (alone or in combination with a pharmaceutical carrier) a therapeutically effective amount of at least one compound of the present invention as an active ingredient. Optionally, compounds of the invention may be used alone, in combination with other compounds of the invention, or in combination with one or more other therapeutic agents (eg, anticancer agents or other pharmaceutically active substances).

Irrespective of the chosen route of administration, the compounds of the invention (which may be used in suitably hydrated form) and/or the pharmaceutical compositions of the invention are formulated into pharmaceutical dosage forms by conventional methods known to those skilled in the art.

Actual dosage levels of the active ingredients in the pharmaceutical compositions of the invention can be varied to obtain an amount of active ingredient that is effective to achieve the desired therapeutic response, composition, and mode of administration for a particular patient without being toxic to the patient.

The selected dosage level will depend on a variety of factors, including the activity of the particular compound of the invention employed, or its ester, salt or amide; the route of administration; the time of administration; the rate of excretion of the particular compound employed; and the rate and extent of absorption; duration of treatment; other drugs, compounds and/or substances used in combination with the particular compound used; factors well known in the medical art such as age, sex, weight, condition, general health and prior medical history of the patient being treated.

A physician or veterinarian having ordinary skill in the art can readily determine and prescribe the effective amount of the pharmaceutical composition required. For example, the physician or veterinarian can start the doses of the compounds of the invention employed in the pharmaceutical composition at levels lower than required to achieve the desired therapeutic effect and gradually increase the dosage until the desired effect is achieved. In general, a suitable daily dose of a compound of the invention will be that amount of the compound at the lowest dose effective to produce a therapeutic effect. Such effective dosage will generally depend on the factors mentioned above. Typically, oral, intravenous, intracerebroventricular and subcutaneous doses of the compounds of this invention to patients range from about 0.01 to about 50 mg/kg body weight/day. If desired, an effective daily dose of the active compound may be administered in two, three, four, five, six or more sub-doses at appropriate intervals throughout the day, optionally in unit dosage form. In certain aspects of the invention, the administration is once daily.

Although the compounds of the present invention may be administered alone, it is preferred to administer the compounds in the form of pharmaceutical formulations (compositions).

Kit/Product Packaging

Kits/product packaging are also described herein for use in the treatment of the above indications. These kits may consist of transporters, packs, or container boxes, which may be divided into compartments to accommodate one or more types of containers, such as vials, test tubes, and the like, each container containing a separate component in the method described above. Suitable containers include bottles, vials, syringes, test tubes and the like. Containers are made of acceptable materials such as glass or plastic.

For example, a container may contain one or more compounds described herein, either as a pharmaceutical composition or in admixture with other ingredients described herein. The container can have a sterile outlet (eg, the container can be an IV bag or bottle, the stopper of which can be pierced by a hypodermic needle). Such a kit may contain a compound, and instructions for use, labels or instructions for use described herein.

A typical kit may include one or more containers, each containing one or more materials (such as reagents, concentrated stock solutions, and/or or equipment). These materials include, but are not limited to, buffers, diluents, filters, needles, syringes, transporters, bags, containers, bottles and/or test tubes, accompanied by a list of contents and/or instructions for use, and inner packaging also accompanied by instructions. Instructions for the entire set are to be included.

Labels can be displayed on or closely associated with the container. The appearance of the label on the container means that the label letters, numbers or other features are pasted, molded, or engraved on the container; the label can also appear in the container box or shipping box containing various containers, such as in the product insert. A label may be used to indicate a specific therapeutic use of the contents. The label may also bear instructions for use of the contents, such as described in the methods above.

All features described in this specification (including any stated claims, abstract and drawings), and/or all steps involved in any method or process, may exist in any combination, unless certain features or steps are mutually exclusive in the same combination.

The above-mentioned features mentioned in the present invention, or the features mentioned in the embodiments can be combined arbitrarily. All the features disclosed in the specification of this case can be used in combination with any combination, and each feature disclosed in the specification can be replaced by any alternative feature that can provide the same, equivalent or similar purpose. Therefore, unless otherwise specified, the disclosed features are only general examples of equivalent or similar features.

Below in conjunction with specific embodiment, further illustrate the present invention. It should be understood that these examples are only used to illustrate the present invention and are not intended to limit the scope of the present invention. For the experimental methods without specific conditions indicated in the following examples, usually follow the conventional conditions or the conditions suggested by the manufacturer. All percentages, ratios, ratios, or parts are by weight unless otherwise indicated.

The unit of weight volume percentage in the present invention is well known to those skilled in the art, for example, it refers to the weight of solute in 100 ml of solution. Unless otherwise defined, all professional and scientific terms used herein have the same meanings as commonly understood by those skilled in the art. In addition, any methods and materials similar or equivalent to those described can be applied to the method of the present invention. The preferred implementation methods and materials described herein are for demonstration purposes only.

EXAMPLE

General Process

When the preparation route is not included, the raw materials and reagents used in the present invention are known products, which can be synthesized according to methods known in the art, or can be obtained by purchasing commercially available products. All commercially available reagents were used without further purification.

Room temperature means 20-30° C.

If here is no special description in the reaction examples, the reactions are all carried out under a nitrogen atmosphere. The nitrogen atmosphere refers to a nitrogen balloon of about 1 L connected to the reaction flask.

The hydrogenation reaction is usually vacuumized and filled with hydrogen, and the operation is repeated 3 times. The hydrogen atmosphere means that the reaction bottle is connected with a hydrogen balloon of about 1 L.

Microwave reactions use the Biotage® Initiator$^+$ Microwave Reactor.

The structures of the compounds of the present invention were determined by nuclear magnetic resonance (NMR) and mass spectroscopy (MS). NMR shifts ($\delta$) are given in units of $10^{-6}$ (ppm). The determination of NMR is to use (Bruker Ascend™ 500 type) nuclear magnetic analyzer, the measurement solvent is deuterated dimethyl sulfoxide (DMSO-d6), deuterated chloroform (CDCl3), deuterated methanol (CD30D), and the internal standard is tetramethylsilane (TMS). The following abbreviations are used for the multiplicity of NMR signals: s=singlet, brs=broad, d=doublet, t=triplet, m=multiplet. Coupling constants are listed as J values, measured in Hz.

For LC-MS determination, a Thermo liquid mass spectrometer (UltiMate 3000+MSQ PLUS) was used. For HPLC measurement, a Thermo high pressure liquid chromatograph (UltiMate 3000) was used. For Reverse-Phase Preparative Chromatography a Thermo (UltiMate 3000) reverse-phase preparative chromatograph was used. The flash column chromatography uses Agela (FS-9200T) automatic column passing machine, and the silica gel prepacked column uses Santai SEPAFLASH® prepacked column. Yantai Huanghai HSGF254 or Qingdao GF254 silica gel plates are used for thin-layer chromatography silica gel plates, and the specifications of thin-layer chromatography separation and purification products are 0.4 mm to 0.5 mm.

Example 1

(S)-4,5-dimethyl-2-((((1-((6-(trifluoromethyl)pyridine-3-yl)methyl)-1H-pyrazol-4-yl)methyl)amino)-4,5,9,10-tetrahydro-6H,8H-pyrido[3,2,1-de]pteridin-6-one Compound 1 was prepared by the following steps:

-continued

-continued

1

Step 1: Dissolve 6-trifluoromethyl-3-pyridinemethanol 1a (4.0 g, 22.58 mmol) in dichloromethane (20 mL), add thionyl chloride (26.87 g, 225.83 mmol, 16.38 mL), after the addition, the reaction was warmed to room temperature and stirred overnight at 55° C. The reaction solution was concentrated to obtain crude yellow oil 1b (4.4 g, yield 99%). ESI-MS (m/z): 196.5 [M+H]⁺.

Step 2: Dissolve compound 1b (4.4 g, 22.48 mmol), compound 1c (1.8 g, 18.73 mmol) in N, N-dimethylformamide (10 mL), and add potassium carbonate (6.47 g, 46.83 mmol). The reaction solution was stirred overnight at room temperature. The reaction solution was diluted with ethyl acetate, washed with water and saturated brine successively, the organic phase was dried over anhydrous sodium sulfate, filtered and concentrated to obtain a yellow solid 1d (4.5 g, yield 94%). ESI-MS (m/z): 256.4 [M+H]⁺.

Step 3: Compound 1d (4.5 g, 17.63 mmol) and hydroxylamine hydrochloride (1.73 g, 26.45 mmol) were dissolved in ethanol (20 mL), and stirred overnight at room temperature. Zinc powder (4.58 g, 70.53 mmol) and acetic acid (50 mL) were added to the reaction solution and heated to 70° C. overnight. After the reaction, most of the solvent was distilled off under reduced pressure, the residue was adjusted to pH 11-12 with 2N sodium hydroxide, and filtered. The filtrate was extracted three times with dichloromethane, the organic phases were combined, dried over anhydrous sodium sulfate, filtered and concentrated to obtain yellow oil 1e (3.5 g, yield 77%). ESI-MS (m/z): 257.6 [M+H]⁺.

Step 4: 2,4-dichloropyrido[3,2-d]pyrimidine 1f (1.7 g, 8.50 mmol) and (S)-2-(methylamino)propionic acid methyl ester hydrochloride 1g (1.70 g, 11.05 mmol) was dissolved in tetrahydrofuran (40 mL), triethylamine (2.58 g, 25.50 mmol, 3.53 mL) was added, and stirred overnight at room temperature. The completion of the reaction was monitored by LCMS, the reaction solution was concentrated, and the residue was purified by silica gel column chromatography to obtain a yellow oil 1h (1.1 g, yield 46%). ESI-MS (m/z): 281 [M+H]⁺.

Step 5: Dissolve compound 1h (1.1 g, 3.92 mmol) in tetrahydrofuran (20 mL), add aqueous hydrochloric acid (6N, 0.65 mL) and platinum dioxide (88 mg, 0.39 mmol), and replace the reaction system with hydrogen by a hydrogen balloon, stirred at room temperature under hydrogen balloon pressure for 48 hours, and LCMS monitored the completion of the reaction. The reaction solution was diluted with methanol, filtered, and the filtrate was concentrated and purified by silica gel column chromatography to obtain white solid 1i (900 mg, yield 90%). ESI-MS (m/z): 253 [M+H]⁺.

Step 6: Compound 1i (300 mg, 1.19 mmol), Compound 1e (395 mg, 1.54 mmol), Pd₂(dba)₃ (217 mg, 0.23 mmol), t-BuONa (342 mg, 3.56 mmol) and X-Phos (113 mg, 0.23 mmol) was dispersed in toluene (10 mL). The reaction system was replaced with nitrogen and heated to 100° C. to react for 16 hours. LCMS monitored that the reaction was complete. The reaction solution was concentrated, and the residue was purified by silica gel column chromatography, and the obtained crude product was purified by preparative HPLC to obtain white solid 1 (143 mg, yield 25%). ESI-MS (m/z): 473.2 [M+H]⁺; ¹HNMR (500 MHz, DMSO-d6) δ 8.61 (s, 1H), 8.13 (s, 1H), 7.86 (d, J=8.0 Hz, 1H), 7.82 (dd, J=8.0, 1.5 Hz, 1H), 7.74 (s, 1H), 7.41 (s, 1H), 6.67 (t, J=5.5 Hz 1H), 5.43 (s, 2H), 4.28-4.16 (m, 2H), 4.10 (q, J=7.0 Hz, 1H), 4.04-3.96 (m, 1H), 3.30-3.20 (m, 1H), 2.93 (s, 3H), 2.54-2.50 (m, 2H), 1.95-1.85 (m, 1H), 1.84-1.70 (m, 1H), 1.21 (d, J=7.0 Hz, 3H).

Example 2

(R)-4,5-dimethyl-2-(((1-((6-(trifluoromethyl)pyridin-3-yl)methyl)-1H-pyrazol-4-yl)methyl)amino)-4,5,9, 10-tetrahydro-6H,8H-pyrido[3,2,1-de]pteridin-6-one Replace (R)-2-(methylamino)methyl propionate hydrochloride 1g in the fourth step in Example 1 with (S)-2-(methylamino)methyl propionate hydrochloride, use similar methods and reaction steps, compound 2 can be obtained. ESI-MS (m/z): 473.5 [M+H]⁺; ¹HNMR (500 MHz, DMSO-d6) δ 8.63 (s, 1H), 8.17 (s, 1H), 7.89 (d, J=8.0 Hz, 1H), 7.85 (d, J=8.5 Hz, 1H), 7.77 (s, 1H), 7.44 (s, 1H), 6.69 (t, J=5.0 Hz, 1H), 5.46 (s, 2H), 4.33-4.18 (m, 2H), 4.12 (q, J=7.0 Hz, 1H), 4.07-4.00 (m, 1H), 3.31-3.24 (m, 1H), 2.95 (s, 3H), 2.56-2.52 (m, 2H), 1.98-1.90 (m, 1H), 1.85-1.75 (m, 1H), 1.23 (d, J=6.5 Hz, 3H).

Example 3

6-methyl-4-(((1-((6-(trifluoromethyl)pyridin-3-yl) methyl)-1H-pyrazol-4-yl)methyl)amino)-7,8-di-hydro-3,5,6,9a-tetraazabenzo[cd]azulene-9(6H)-one Compound 3 was prepare by the following steps:

Step 1: Dissolve compound 3a (5.0 g, 26.59 mmol), triethylamine (5.38 g, 53.19 mmol) and 4-dimethylamino-pyridine (324 mg, 2.66 mmol) in dichloromethane (50 mL), at room temperature Di-tert-butyl dicarbonate (6.38 g, 29.25 mmol) was added dropwise and the reaction solution was stirred overnight, and the completion of the reaction was monitored by LCMS. The reaction solution was concentrated, and the residue was purified by silica gel column chromatography to obtain compound 3b (5.3 g, yield 69%). ESI-MS (m/z): 288.4 [M+H]⁺.

Step 2: Compound 3b (1.0 g, 3.48 mmol), ethyl 3-(meth-ylamino)propionate 3c (0.55 g, 4.2 mmol) and N,N-diiso-propylethylamine (1.35 g, 10.4 mmol) were dissolved in tetrahydrofuran (10 mL), stirred overnight at 50° C., and the reaction was monitored by TLC. The reaction solution was concentrated, and the residue was purified by silica gel column chromatography to obtain a colorless oily substance 3d (1.33 g, yield 100%). ESI-MS (m/z): 383.2 [M+H]⁺.

Step 3: Dissolve compound 3d (1.3 g, 3.40 mmol), compound 1e (1.04 g, 4.07 mmol) in n-butanol (5 mL), add trifluoroacetic acid (0.13 mL, 1.7 mmol). The reaction solution was heated to 150° C. by microwave to react for 5 hours, and LCMS monitored the end of the reaction. The reaction solution was concentrated, and the residue was purified by silica gel column chromatography to obtain a mixture (0.8 g) of brown solid 3e and 3f, which was directly used in the next reaction. ESI-MS (m/z): 503.3 [M+H]⁺, 531.3 [M+H]⁺.

Step 4: Dissolve the product from the previous step (300 mg) in tetrahydrofuran (5 mL), add 1,8-diazabicyclo[5.4.0] undec-7-ene (0.18 mL, 1.2 mmol). Under nitrogen protection, the reaction was carried out at 70° C. for 16 hours, and LCMS monitored the end of the reaction. The reaction solution was concentrated, and the residue was prepared by preparative HPLC to obtain a white solid 3 (4 mg). ESI-LCMS (m/z): 457.2 [M+H]⁺; ¹HNMR (500 MHz, DMSO-d6) δ 8.63 (s, 1H), 7.90-7.82 (m, 3H), 7.78 (s, 1H), 7.44 (s, 1H), 6.64 (t, J=6.1 Hz, 1H), 6.47 (d, J=3.7 Hz, 1H), 5.45 (s, 2H), 4.32 (d, J=6.1 Hz, 2H), 3.68-3.61 (m, 2H), 3.16 (s, 3H), 3.14-3.09 (m, 2H).

Examples 4, 5 and 6

6,7-dimethyl-4-(((1-((6-(trifluoromethyl)pyridin-3-yl)methyl)-1H-pyrazol-4-yl) methyl)amino)-7,8-dihydro-3,5,6,9a-tetraazabenzo[cd]azulene-9(6H)-one (R)-6,7-dimethyl-4-(((1-((6-(trifluoromethyl)pyridin-3-yl)methyl)-1H-pyrazol-4-yl)methyl)amino)-7,8-dihydro-3,5,6,9a-tetraazabenzo[cd]azulene-9(6H)-one (S)-6,7-dimethyl-4-(((1-((6-(trifluoromethyl)pyridin-3-yl)methyl)-1H-pyrazol-4-yl)methyl)amino)-7,8-dihydro-3,5,6,9a-tetraazabenzo[cd]azulene-9(6H)-one Compounds 4, 5 and 6 were prepared by the following steps:

4c (R = Et)
4d (R = n-Bu)

-continued

4

5

+

6

Step 1: Dissolve compound 3b (1.0 g, 3.5 mmol) and ethyl 3-(methylamino)butyrate 4a (0.6 g, 4.2 mmol) in tetrahydrofuran (10 mL), add N,N-diisopropyl Ethylamine (1.35 g, 10.4 mmol). The reaction was carried out overnight at 50° C., and the reaction was complete as monitored by TLC. The reaction solution was concentrated, and the residue was purified by silica gel column chromatography to obtain yellow solid 4b (1.22 g, yield 89%). ESI-MS (m/z): 397.3 [M+H]$^+$.

Step 2: Dissolve compound 4b (1.17 g, 2.9 mmol) in n-butanol (5 mL), add trifluoroacetic acid (0.2 mL, 2.9 mmol), heat the system to 150° C. by microwave to react for 5 h, and LCMS monitored that the reaction was complete. The reaction solution was concentrated, and the residue was purified by silica gel column chromatography to obtain a brown solid mixture of 4c and 4d (1.1 g), which was directly used in the next reaction. ESI-MS (m/z): 517.2 [M+H]$^+$, 545.5 [M+H]$^+$.

Step 3: Dissolve the mixture of 4c and 4d (320 mg) obtained in the previous step in tetrahydrofuran (5 mL), add 1,8-diazabicyclo[5.4.0]undec-7-ene (0.18 mL, 1.2 mmol). The reaction solution was stirred overnight at 70° C., and the reaction was complete as monitored by LC-MS. The reaction solution was concentrated, and the residue was purified by silica gel column chromatography to obtain white solid 4 (110 mg, yield 38%). ESI-MS (m/z): 471.0 [M+H]$^+$; $^1$HNMR (500 MHz, DMSO-d6) δ 8.61 (s, 1H), 7.88-7.81 (m, 3H), 7.76 (s, 1H), 7.43 (s, 1H), 6.64 (br s, 1H), 6.44 (d, J=3.6 Hz, 1H), 5.43 (s, 2H), 4.30 (d, J=5.9 Hz, 2H), 3.96-3.88 (m, 1H), 3.37 (d, J=16.1 Hz, 1H), 3.16 (s, 3H), 3.00 (dd, J=16.0, 6.7 Hz, 1H), 1.10 (d, J=6.8 Hz, 3H).

Step 4: Racemate compound 4 (102 mg) was resolved by chiral column to obtain compound 5 (P1, 50 mg) and compound 6 (P2, 40 mg).

Compound 5: chiral column retention time=5.62 min (ICH column, HEP:IPA (0.1% DEA)=60:40); ESI-MS (m/z): 471.3 [M+H]$^+$; $^1$HNMR (500 MHz, DMSO-d6) S 8.63 (s, 1H), 7.89-7.83 (m, 3H), 7.78 (s, 1H), 7.44 (s, 1H), 6.64 (t, J=6.1 Hz, 1H), 6.45 (d, J=3.6 Hz, 1H), 5.45 (s, 2H), 4.31 (d, J=6.0 Hz, 2H), 3.98-3.89 (m, 1H), 3.38 (d, J=15.9 Hz, 1H), 3.18 (s, 3H), 3.02 (dd, J=16.0, 6.7 Hz, 1H), 1.12 (d, J=6.8 Hz, 3H).

Compound 6: chiral column retention time=6.24 min (ICH column, HEP:IPA (0.1% DEA)=60:40); ESI-MS (m/z): 471.3 [M+H]$^+$; $^1$HNMR (500 MHz, DMSO-d6) S 8.63 (s, 1H), 7.89-7.83 (m, 3H), 7.78 (s, 1H), 7.45 (s, 1H), 6.64 (t, J=5.7 Hz, 1H), 6.46 (d, J=3.6 Hz, 1H), 5.45 (s, 2H), 4.32 (d, J=6.0 Hz, 2H), 3.98-3.87 (m, 1H), 3.38 (d, J=16.0 Hz, 1H), 3.18 (s, 3H), 3.02 (dd, J=16.0, 6.7 Hz, 1H), 1.12 (d, J=6.8 Hz, 3H).

Example 7

(S)-4,5-dimethyl-2-(((1-(2,2,2-trifluoroethyl)-1H-pyrazol-4-yl)methyl)amino)-4,5,9,10-tetrahydro-6H,8H-pyrido[3,2,1-de]pteridin-6-one Compound 7 was prepared by the following steps:

1c

7a

-continued

1i

Pd₂(dba)₃, X—Phos,
t-BuONa, Toluene

7b

7

J=7.0 Hz, 1H), 4.04-3.96 (m, 1H), 3.29-3.21 (m, 1H), 2.94 (s, 3H), 2.53-2.50 (m, 2H), 1.96-1.88 (m, 1H), 1.86-1.75 (m, 1H), 1.21 (d, J=7.0 Hz, 3H).

Example 8

(S)-4,5-dimethyl-2-(((6-(trifluoromethoxy)pyridin-3-yl)methyl)amino)-4,5,9,10-tetrahydro-6H,8H-pyrido[3,2,1-de]pteridin-6-one

8

Compound 8 was prepared by the following steps:

8a

1i

Pd₂(dba)₃, X-Phos,
t-BuONa, Toluene

8

Step 1: Dissolve 1H-pyrazole-4-carbaldehyde 1c (5 g, 52.04 mmol) in N, N-dimethylformamide (20 mL), and add successively $Cs_2CO_3$ (33.91 g, 104.07 mmol) and 2, 2,2-Trifluoroethyl trifluoromethanesulfonate (18.12 g, 78.05 mmol). After reacting at room temperature for 4 hours, TLC showed that the conversion of the starting material was complete. The reaction solution was diluted with ethyl acetate and washed with saturated brine. The organic phase was dried over anhydrous sodium sulfate, filtered and concentrated to obtain compound 7a (8.0 g), which was directly used in the next reaction.

Step 2: Dissolve compound 7a (8.0 g) obtained in the previous step in ethanol (20 mL), add hydroxylamine hydrochloride (6.24 g, 89.83 mmol), and stir the reaction solution at room temperature overnight. The reaction solution was concentrated to obtain the crude oxime, which was redissolved in acetic acid (50 mL), and zinc powder (17.47 g, 267.18 mmol) was added. The reaction solution was reacted at 60° C. for 2 hours, and the conversion was complete as monitored by LC-MS. The reaction solution was cooled to room temperature, diluted with ethyl acetate, and basified to pH=10 with NaOH solution (2N). The mixture was filtered, and the filtrate was concentrated to obtain compound 7b (4.5 g), which was directly used in the next reaction.

Step 3: Compound 1i (200 mg, 0.79 mmol), compound 7b (212 mg, 1.19 mmol), Pd₂(dba)₃ (144 mg, 0.15 mmol), t-BuONa (228 mg, 2.37 mmol) and X-Phos (75 mg, 0.15 mmol) was dispersed in toluene (10 mL), and the reaction system was replaced with nitrogen and heated to 100° C. for 16 hours. The completion of the reaction was monitored by LCMS, the reaction solution was concentrated, and the residue was purified by silica gel column chromatography, and the obtained crude product was purified by preparative HPLC to obtain a white solid 7 (71 mg, yield 22%). ESI-MS (m/z): 396.3 [M+H]⁺; ¹HNMR (500 MHz, DMSO-d6) δ 8.13 (s, 2H), 7.67 (s, 1H), 7.46 (s, 1H), 6.74 (t, J=5.0 Hz, 1H), 5.03 (q, J=9.0 Hz, 2H), 4.30-4.17 (m, 2H), 4.11 (q, Step 1: Compound 1i (80 mg, 0.31 mmol), 6-(trifluoromethoxy)pyridine-3-methylamine hydrochloride 8a (94 mg, 0.41 mmol), Pd₂(dba)₃ (57 mg, 0.063 mmol), X-Phos (30 mg, 0.063 mmol) and t-BuONa (91 mg, 0.094 mmol) were dispersed in toluene (5 mL). The system was replaced with nitrogen and heated to 100° C. to react for 16 hours. LCMS monitored that the reaction was complete. The reaction solution was concentrated, and the residue was purified by preparative HPLC to obtain a white solid 8 (28 mg, yield 22%). ESI-MS (m/z): 409.3 [M+H]⁺; ¹HNMR (500 MHz, DMSO-d6) δ 8.31 (d, J=2.5 Hz, 1H), 8.20 (s, 1H), 7.95 (dd, J=8.5, 2.5 Hz, 1H), 7.24 (d, J=8.5 Hz, 1H), 7.12 (t, J=6.0 Hz, 1H), 4.48-4.36 (m, 2H), 4.12 (q, J=7.0 Hz, 1H), 4.08-3.97 (m, 1H), 3.33-3.23 (m, 1H), 2.92 (s, 3H), 1.99-1.88 (m, 1H), 1.86-1.73 (m, 1H), 1.23 (d, J=7.0 Hz, 3H).

Example 9

6,7-dimethyl-4-(((1-(2,2,2-trifluoroethyl)-1H-pyra-zol-4-yl)methyl)amino)-7,8-dihydro-3,5,6,9a-tetraaz-abenzo[cd]azulene-9(6H)-one Compound 9 was prepared by the following steps:

9a (R=Et)
9b (R=n-Bu)

9

Step 1: Dissolve compound 4b (1.2 g, 3.0 mmol) and compound 7b (0.65 g, 3.63 mmol) in n-butanol (5 mL), add trifluoroacetic acid (0.2 mL, 2.9 mmol), and use microwave to heat the reaction solution to 150° C. to react for 5 hours.

LC-MS monitored that the reaction was complete. The reaction solution was concentrated, and the residue was purified by silica gel column chromatography to obtain a brown solid mixture of 9a and 9b (0.95 g), which was directly used in the next reaction. ESI-MS (m/z): 440.3 [M+H]$^+$, 468.2 [M+H]$^+$.

Step 2: 9a and 9b (300 mg) were dissolved in THF (5 mL), and 1,8-diazabicyclo[5.4.0]undec-7-ene (0.20 mL, 1.4 mmol) was added. The reaction solution was stirred overnight at 70° C., and the reaction was complete as monitored by LC-MS. The reaction solution was concentrated, and the residue was purified by silica gel column chromatography to obtain 9 (130 mg) as a white solid. ESI-MS (m/z): 394.3 [M+H]$^+$; $^1$HNMR (500 MHz, DMSO-d6) δ 7.87 (d, J=3.7 Hz, 1H), 7.70 (s, 1H), 7.50 (s, 1H), 6.72 (br s, 1H), 6.46 (d, J=3.6 Hz, 1H), 5.05 (q, J=9.2 Hz, 2H), 4.33 (d, J=6.1 Hz, 2H), 3.97-3.93 (m, 1H), 3.39 (d, J=15.9 Hz, 1H), 3.20 (s, 3H), 3.02 (dd, J=16.1, 6.7 Hz, 1H), 1.12 (d, J=6.9 Hz, 3H).

Example 10

6-methyl-4-(((1-(2,2,2-trifluoroethyl)-1H-pyrazol-4-yl)methyl)amino)-7,8-dihydro-3,5,6,9a-tetraaz-abenzo[cd]azulene-9(6H)-one Compound 10 was prepared by the following steps:

3b 10a (R=Et)
10b (R=n-Bu)

-continued

10

Step 1: Dissolve compounds 3d (500 mg, 1.3 mmol) and 7b (0.28 g, 1.57 mmol) in n-butanol (4 mL), add trifluoro-acetic acid (0.1 mL, 1.3 mmol), and use microwave to heat the reaction solution to 150° C. to react for 5 hours. LC-MS monitored that the reaction was complete. The reaction solution was concentrated, and the residue was purified by silica gel column chromatography to obtain a brown solid mixture of 10a and 10b (420 mg), which was directly used in the next reaction. ESI-MS (m/z): 426.3 [M+H]+, 454.2 [M+H]+.

Step 2: 10a and 10b (420 mg) were dissolved in tetrahy-drofuran (5 mL), and 1,8-diazabicyclo[5.4.0]undec-7-ene (0.29 mL, 2.0 mmol) was added. The reaction solution was stirred overnight at 70° C., and the reaction was complete as monitored by LC-MS. The reaction solution was concen-trated, and the residue was purified by silica gel column chromatography to obtain a white solid 10 (50 mg, yield 10% in two steps). ESI-MS (m/z): 380.3 [M+H]+; 1HNMR (500 MHz, DMSO-d6) δ 7.87 (d, J=3.7 Hz, 1H), 7.70 (s, 1H), 7.50 (s, 1H), 6.71 (br s, 1H), 6.48 (d, J=3.7 Hz, 1H), 5.05 (q, J=9.2 Hz, 2H), 4.33 (d, J=6.1 Hz, 2H), 3.73-3.62 (m, 2H), 3.18 (s, 3H), 3.16-3.08 (m, 2H).

Example 11

(S)-4,5-dimethyl-2-(((6-((6-(trifluoromethyl)pyridin-3-yl)oxy)pyridin-3-yl)methyl)amino)-4,5,9,10-tetra-hydro-6H,8H-pyrido[3,2,1-de]pteridin-6-one Compound 11 was prepared by the following steps:

Step 1: Dissolve 6-(trifluoromethyl)pyridin-3-ol 11a (1.0 g, 6.13 mmol) in dimethyl sulfoxide (10 mL), and add cesium carbonate (2.0 g, 6.13 mmol). At room temperature the reaction mixture was stirred for 30 minutes, and then 2-fluoropyridine-5-carbaldehyde 11b (1.53 g, 12.26 mmol) was added, and the reaction mixture was stirred for another 2 hours and the reaction. was terminated. The reaction solution was diluted with ethyl acetate, washed with water and saturated brine successively, the organic phase was dried over anhydrous sodium sulfate, concentrated by filtration, and the residue was purified by silica gel column chroma-tography to obtain product 11c (1.5 g, yield 91%). 1HNMR (500 MHz, DMSO-d6) δ 10.04 (s, 1H), 8.79-8.70 (m, 2H), 8.37 (dd, J=8.6, 2.3 Hz, 1H), 8.05 (d, J=1.0 Hz, 2H), 7.42 (d, J=8.6 Hz, 1H).

Step 2: Dissolve compound 11c (1.53 g, 5.70 mmol) in ethanol (5 mL), add hydroxylamine hydrochloride (792 mg, 11.41 mmol), and stir overnight at room temperature. The reaction solution was concentrated to obtain the crude oxime, which was redissolved in acetic acid (5 mL), added zinc powder (1.94 g, 29.66 mmol), and stirred at room temperature for 2 hours. The reaction was complete by LCMS detection. The reaction mixture was filtered, and the filtrate was concentrated to remove most of the acetic acid, diluted with ethyl acetate, and then basified to pH=11 with NaOH solution (2N). The mixture was filtered, and the filtrate was concentrated to obtain compound 11d (1.3 g), which was directly used in the next reaction. ESI-MS (m/z): 270.5 [M+H]+.

The second step: compound 11d (383 mg), compound 1i (300 mg, 1.19 mmol), Pd2(dba)3 (217 mg, 0.23 mmol), t-BuONa (342 mg, 3.56 mmol) and X-Phos (113 mg, 0.23 mmol) were dispersed in toluene (10 mL), the system was replaced with nitrogen and then heated to 100° C. for 16 hours. LCMS monitored the end of the reaction, and the reaction solution was concentrated. The residue was purified by silica gel column chromatography to obtain the crude product, which was then passed through preparative HPLC purification to obtain compound 11 (20 mg, yield 3%). ESI-MS (m/z): 486.4 [M+H]$^+$; $^1$HNMR (500 MHz, DMSO-d6) δ 8.64 (d, J=2.6 Hz, 1H), 8.17 (s, 1H), 8.14 (d, J=2.2 Hz, 1H), 7.98 (d, J=8.6 Hz, 1H), 7.92-7.86 (m, 2H), 7.18 (d, J=8.4 Hz, 1H), 7.06 (br s, 1H), 4.40-4.30 (m, 2H), 4.12 (q, J=6.8 Hz, 1H), 4.05-3.99 (m, 1H), 3.26 (d, J=3.2 Hz, 1H), 2.94 (s, 3H), 1.96-1.88 (m, 1H), 1.85-1.76 (m, 1H), 1.24 (d, J=6.8 Hz, 3H).

Example 12

(S)-2-(((6-(3,3-difluorocyclobutoxy)pyridin-3-yl)methyl)amino)-4,5-dimethyl-4, 5,9,10-Tetrahydro-6H,8H-pyrido[3,2,1-de]pteridin-6-one Compound 12 was prepared by the following steps:

12a

12b

12c

-continued

12

Step 1: Dissolve 3,3-difluorocyclobutanol 12a (572 mg, 5.30 mmol) in N,N-dimethylformamide (20 mL), add cesium carbonate (3.98 g, 12.23 mmol) and 2-fluoropyridine-5-carbaldehyde 11b (0.51 g, 4.08 mmol), the reaction was quenched after stirring for 3 hours. The reaction solution was diluted with ethyl acetate, washed with saturated brine, and the organic phase was dried over anhydrous sodium sulfate, filtered and concentrated. The residue was subjected to silica gel column chromatography to obtain compound 12b (0.55 g, yield 63%).

Step 2: Dissolve compound 12b (0.55 g, 2.58 mmol) in ethanol (20 mL), add hydroxylamine hydrochloride (358 mg, 5.16 mmol), and stir overnight at room temperature. The reaction solution was concentrated to obtain the crude oxime, which was redissolved in acetic acid (10 mL), and zinc powder (997 mg, 15.25 mmol) was added. After being stirred at 60° C. for 3 hours, LCMS monitored that the reaction was complete. The reaction mixture was filtered, and the filtrate was concentrated to remove most of the acetic acid, diluted with ethyl acetate, and basified to pH=11 with NaOH solution (2N) under ice bath. The mixture was filtered, and the filtrate was concentrated to obtain compound 12c (0.3 g), which was directly used in the next reaction.

Step 3: Compound 12c (135 mg), compound 1i (80 mg, 0.31 mmol), Pd$_2$(dba)$_3$ (57 mg, 0.063 mmol), t-BuONa (91 mg, 0.94 mmol) and X-Phos (30 mg, 0.063 mmol) were dispersed in toluene (10 mL), and the reaction system was heated to 100° C. to react for 5 hours after being replacing with nitrogen. The completion of the reaction was monitored by LCMS, the reaction solution was concentrated, and the residue was purified by preparative thin-layer chromatography to obtain a crude product, which was then purified by preparative HPLC to obtain compound 12 (8 mg, yield 5%). ESI-MS (m/z): 431.2 [M+H]$^+$; $^1$HNMR (500 MHz, DMSO-d6) δ 8.23 (br s, 1H), 8.10 (s, 1H), 7.70 (dd, J=8.4, 2.0 Hz, 1H), 7.00 (br s, 1H), 6.80 (d, J=8.4 Hz, 1H), 5.12-5.03 (m, 1H), 4.40-4.25 (m, 2H), 4.15-4.10 (m, 1H), 4.05-4.00 (m, 1H), 3.31-3.25 (m, 1H), 3.20-3.07 (m, 2H), 2.94 (s, 3H), 2.70-2.60 (m, 2H), 1.97-1.88 (in, 1H), 1.84-1.76 (m, 1H), 1.23 (d, J=6.7 Hz, 3H).

Example 13

(S)-4,5-dimethyl-2-(((1-(3-(trifluoromethyl)benzyl)-1H-pyrazol-4-yl)methyl)amino)-4,5,9,10-tetrahydro-6H,8H-pyrido[3,2,1-de]pteridin-6-one Compound 13 was prepared by the following steps:

Step 1: Dissolve 4-(Boc-aminomethyl)pyrazole 13b (0.3 g, 1.52 mmol) in N,N-dimethylformamide (10 mL) and add 3-trifluoromethylbenzyl chloride 13a (443 mg, 2.28 mmol) and cesium carbonate (1.49 g, 4.56 mmol), the reaction was terminated after stirring at room temperature for 4 hours. The reaction solution was diluted with ethyl acetate, washed with saturated brine, the organic phase was dried over anhydrous sodium sulfate, filtered and concentrated to obtain compound 13c (0.51 g, yield 94%). ESI-MS (m/z): 356.5 [M+H]+.

Step 2: Dissolve compound 13c (0.51 g, 1.44 mmol) in dioxane (5 mL), add 4N dioxane hydrochloride solution (1 mL), and stir the reaction solution at room temperature overnight, and LCMS monitored that the reaction was complete. The reaction solution was concentrated to obtain compound 13d (0.36 g).

Step 3: compound 13d (393 mg), compound 1i (300 mg, 1.19 mmol), Pd₂(dba)₃ (217 mg, 0.23 mmol), t-BuONa (342 mg, 3.56 mmol) and S-Phos (97 mg, 0.23 mmol) were dispersed in toluene (20 mL), and the reaction system was heated to 100° C. and reacted for 16 hours after replacing nitrogen. The completion of the reaction was monitored by LCMS, the reaction solution was concentrated, and the residue was purified by preparative thin-layer chromatography to obtain a crude product, which was then purified by preparative HPLC to obtain compound 13 (200 mg, yield 35%). ESI-MS (m/z): 472.5 [M+H]+; ¹HNMR (500 MHz, DMSO-d6) δ 8.17 (s, 1H), 7.73 (s, 1H), 7.65 (d, J=7.6 Hz, 1H), 7.61-7.55 (m, 2H), 7.50 (d, J=7.7 Hz, 1H), 7.42 (s, 1H), 6.69 (br s, 1H), 5.38 (s, 2H), 4.30-4.18 (in, 2H), 4.12 (q, J=6.7 Hz, 1H), 4.07-4.00 (m, 1H), 3.31-3.24 (m, 1H), 2.95 (s, 3H), 2.57-2.52 (m, 2H), 1.97-1.89 (m, 1H), 1.86-1.75 (m, 1H), 1.23 (d, J=6.7 Hz, 3H).

Example 14

(S)-2-(((1-(4-fluorophenethyl)-1H-pyrazol-4-yl)methyl)amino)-4,5-dimethyl-4,5, 9,10-Tetrahydro-6H,8H-pyrido[3,2,1-de]pteridin-6-one Compound 14 can be obtained by replacing 3-trifluoromethylbenzyl chloride 13a in the first step in Example 13 with 4-fluorobromoethylbenzene by using similar methods and reaction steps. ESI-MS (m/z): 436.5 [M+H]+; ¹HNMR (500 MHz, DMSO-d6) δ 8.13 (s, 1H), 7.43 (s, 1H), 7.33 (s, 1H), 7.14-7.09 (m, 2H), 7.04-6.98 (m, 2H), 6.59 (br s, 1H), 4.22 (t, J=7.2 Hz, 2H), 4.17 (dd, J=11.7, 6.1 Hz, 2H), 4.14-4.08 (m, 1H), 4.03-3.98 (m, 1H), 3.29-3.22 (m, 1H), 3.01 (t, J=7.2 Hz, 2H), 2.92 (s, 3H), 2.55-2.50 (m, 2H), 1.95-1.87 (m, 1H), 1.83-1.74 (m, 1H), 1.21 (d, J=6.8 Hz, 3H).

Example 15

(S)-2-(((1-(4-fluorobenzyl)-1H-pyrazol-4-yl)methyl)
amino)-4,5-dimethyl-4,5,9,10-tetrahydro-6H,8H-
pyrido[3,2,1-de]pteridin-6-one Compound 15 can be obtained by replacing 3-trifluorom-
ethylbenzyl chloride 13a in the first step in Example 13 with
4-fluorobenzyl chloride by using similar methods and reac-
tion steps. ESI-MS (m/z): 422.5 [M+H]$^+$; $^1$HNMR (500
MHz, DMSO-d6) δ 8.12 (s, 1H), 7.63 (s, 1H), 7.36 (s, 1H),
7.27-7.22 (m, 2H), 7.15-7.10 (m, 2H), 6.66 (br s, 1H), 5.22
(s, 2H), 4.25-4.16 (m, 2H), 4.10 (q, J=6.7 Hz, 1H), 4.03-3.97
(m, 1H), 3.29-3.22 (m, 1H), 2.93 (s, 3H), 2.53-2.49 (m, 2H),
1.95-1.86 (m, 1H), 1.83-1.72 (m, 1H), 1.21 (d, J=6.8 Hz,
3H).

Example 16

(S)-4,5-dimethyl-2-(((6-((4-(trifluoromethyl)benzyl)
oxy)pyridin-3-yl)methyl)amino)-4,5,9,10-tetrahydro-
6H,8H-pyrido[3,2,1-de]pteridin-6-one Compound 16 was prepared by the following steps:

136

-continued

Step 1: Dissolve 2-hydroxy-5-pyridinecarbaldehyde 16a
(0.5 g, 4.06 mmol) in N,N-dimethylformamide (30 mL), add
cesium carbonate (3.97 g, 12.18 mmol) and 4-(trifluorom-
ethyl)benzyl chloride 16b (1.03 g, 5.28 mmol). The reaction
solution was stirred overnight at room temperature. The
reaction solution was diluted with ethyl acetate, washed with
saturated brine, and the organic phase was dried over
anhydrous sodium sulfate, filtered and concentrated. The
residue was purified by silica gel column chromatography to
obtain compound 16c (0.91 g, yield 79%). ESI-MS (m/z):
282.3 [M+H]$^+$; $^1$HNMR (500 MHz, DMSO-d6) δ 9.62 (s,
1H), 8.80 (d, J=2.4 Hz, 1H), 7.83 (dd, J=9.5, 2.4 Hz, 1H),
7.74 (d, J=8.2 Hz, 2H), 7.55 (d, J=8.1 Hz, 2H), 6.56 (d, J=9.5
Hz, 1H), 5.30 (s, 2H).

Step 2: Dissolve compound 16c (0.91 g, 3.24 mmol) in
ethanol (20 mL), add hydroxylamine hydrochloride (449
mg, 6.47 mmol), and stir overnight at room temperature.
Zinc powder (993 mg, 15.19 mmol) and concentrated hydro-
chloric acid (0.5 mL) were added to the reaction mixture,
and the reaction was terminated after 0.5 hours at room
temperature. The reaction solution was basified with aque-
ous ammonia to pH=11, diluted with ethyl acetate, and
washed with saturated brine. The organic phase was dried
over anhydrous sodium sulfate, filtered and concentrated to
obtain compound 16d (0.72 g), which was directly used in
the next reaction. ESI-MS (m/z): 282.3 [M+H]$^+$.

Step 3: compound 16d (290 mg), compound 1i (200 mg,
0.79 mmol), Pd$_2$(dba)$_3$ (144 mg, 0.15 mmol), t-BuONa (228
mg, 2.37 mmol) and S-Phos (64 mg, 0.15 mmol) were
dispersed in toluene (20 mL), and the reaction system was
heated to 100° C. to react for 16 hours after replacing
nitrogen. The completion of the reaction was monitored by LCMS, the reaction solution was concentrated, and the residue was purified by preparative thin-layer chromatography to obtain a crude product, which was then purified by preparative HPLC to obtain compound 16 (175 mg, yield 44%). ESI-MS (m/z): 499.5 [M+H]⁺; ¹HNMR (500 MHz, DMSO-d6) δ 8.24 (s, 1H), 7.82 (d, J=1.8 Hz, 1H), 7.75-7.71 (in, 2H), 7.66-7.62 (t, 2H), 7.57 (dd, J=9.3, 2.3 Hz, 1H), 7.02 (br s, 1H), 6.51 (d, J=9.3 Hz, 1H), 5.26 (s, 2H), 4.26-4.15 (m, 3H), 4.13-4.07 (m, 1H), 3.37-3.30 (m, 1H), 2.97 (s, 3H), 2.57-2.50 (m, 2H), 2.02-1.94 (m, 1H), 1.90-1.81 (m, 1H), 1.29 (d, J=6.8 Hz, 3H).

Example 17

(S)-4,5-dimethyl-2-(((6-((3-(trifluoromethyl)benzyl) oxy)pyridin-3-yl)methyl)amino)-4,5,9,10-tetrahydro-6H,8H-pyrido[3,2,1-de]pteridin-6-one Compound 17 can be obtained by using 3-(trifluoromethyl)benzyl chloride 13a instead of 4-(trifluoromethyl)benzyl chloride 16b in the first step in Example 16 by using similar methods and reaction steps. ESI-MS (m/z): 499.5 [M+H]⁺; ¹HNMR (500 MHz, DMSO-d6) δ 8.25 (s, 1H), 7.82 (d, J=1.8 Hz, 1H), 7.75-7.71 (in, 2H), 7.66-7.62 (m, 2H), 7.57 (dd, J=9.3, 2.3 Hz, 1H), 7.02 (br s, 1H), 6.51 (d, J=9.3 Hz, 1H), 5.26 (s, 2H), 4.26-4.15 (m, 3H), 4.13-4.07 (m, 1H), 3.37-3.30 (m, 1H), 2.97 (s, 3H), 2.57-2.50 (m, 2H), 2.02-1.94 (m, 1H), 1.90-1.81 (m, 1H), 1.29 (d, J=6.8 Hz, 3H).

Example 18

(S)-2-(((2-(cyclopropylmethyl)pyrimidin-5-yl) methyl)amino)-4,5-dimethyl-4,5,9, 10-tetrahydro-6H,8H-Pyrido[3,2,1-de]pteridin-6-one Compound 18 was prepared by the following steps:

Step 1: Compound 18a (65 mg, 0.40 mmol), compound 1i (100 mg, 0.40 mmol), Pd₂(dba)₃ (36 mg, 0.04 mmol), t-BuONa (114 mg, 1.19 mmol) and S-Phos (32 mg, 0.079 mmol) was dispersed in toluene (10 mL), and the reaction system was replaced with nitrogen and heated to 100° C. to react for 16 hours. The completion of the reaction was monitored by LCMS, the reaction solution was concentrated, and the residue was subjected to preparative thin-layer chromatography to obtain a crude product, which was then prepared by Prep-HPLC to obtain a white solid 18 (52 mg, yield 34%). ESI-MS (m/z): 380.5 [M+H]⁺; ¹HNMR (500 MHz, DMSO-d6) δ 8.66 (s, 2H), 8.14 (s, 1H), 7.09 (br s, 1H), 4.42-4.29 (m, 2H), 4.12 (q, J=6.7 Hz, 1H), 4.05-3.96 (m, 1H), 3.31-3.23 (m, 1H), 2.93 (s, 3H), 2.71 (d, J=7.0 Hz, 2H), 2.55-2.51 (m, 2H), 1.96-1.88 (m, 1H), 1.84-1.74 (m, 1H), 1.22 (d, J=6.8 Hz, 3H), 1.19-1.09 (m, 1H), 0.47-0.38 (m, 2H), 0.24-0.14 (m, 2H).

Example 19

(S)-4,6-dimethyl-N-((1-((6-(trifluoromethyl)pyridin-3-yl)methyl)-1H-pyrazol-4-yl)methyl)-5,6-dihydro-4H-pyrrolo[3,2,1-de]pteridin-2-amine Compound 19 was prepared by the following steps:

19a

19b
Cs₂CO₃, DMF

19c
HCl

19d
NaH, MeI 19e
1e
TFA

19

Step 1: Dissolve compounds 19a (200 mg, 1.06 mmol) and 19b (808 mg, 3.19 mmol) in N, N-dimethylformamide (5 mL), add Cs₂CO₃ (1.39 g, 4.26 mmol). The temperature of the reaction solution was raised to 100° C. to react for 2 hours, and the reaction was complete as monitored by LCMS. The reaction solution was diluted with water and extracted with ethyl acetate. The organic phase was washed with saturated brine, dried over anhydrous sodium sulfate, filtered and concentrated. The residue was purified by silica gel column chromatography to obtain white solid 19c (200 mg, yield 60%). ESI-MS (m/z): 253.5 [M−55]⁺.

Step 2: Dissolve compound 19c (200 mg, 0.64 mmol) in dioxane (5 mL), add concentrated hydrochloric acid (118 mg, 0.098 mL), and stir the reaction solution at room temperature for 1 hour, and monitor the completion of the reaction by LCMS. The reaction solution was concentrated under reduced pressure to obtain compound 19d (135 mg, yield 99%). ESI-MS (m/z): 209.7 [M+1]⁺.

Step 3: Dissolve compound 19d (135 mg, 0.64 mmol) in THF (3 mL), add NaH (77 mg, 1.92 mmol) under ice bath, stir the reaction solution for 5 minutes and add iodomethane (137 mg, 0.97 mmol). Stirring was continued for half an hour, and LCMS monitored that the reaction was complete. The reaction solution was diluted with water and extracted with ethyl acetate. The organic phase was washed with saturated brine, dried over anhydrous sodium sulfate, filtered and concentrated. The residue was purified by silica gel column chromatography to obtain compound 19e (60 mg, yield 41%). ESI-MS (m/z): 223.6 [M+H]⁺.

Step 4: Dissolve compound 19e (60 mg, 0.26 mmol) and 1e (103 mg, 0.40 mmol) in n-butanol (5 mL), add trifluoroacetic acid (153 mg, 1.35 mmol). The reaction solution was heated by microwave to 150° C. to react for 4 hours. LCMS monitored that the reaction was complete. The reaction solution was concentrated, and the residue was purified by preparative HPLC to obtain compound 19 (20 mg, yield 16%). ESI-MS (m/z): 443.6 [M+H]⁺; ¹HNMR (500 MHz, DMSO-d6) δ 8.64 (s, 1H), 8.18 (s, 1H), 7.92-7.81 (m, 3H), 7.49 (s, 1H), 7.28 (s, 1H), 6.09 (s, 1H), 5.47 (s, 2H), 4.36 (d, J=5.4 Hz, 2H), 4.18 (dd, J=12.3, 3.9 Hz, 1H), 4.07 (dd, J=12.4, 2.9 Hz, 1H), 3.99 (s, 1H), 3.11 (s, 3H), 1.24 (d, J=6.5 Hz, 3H).

Example 20

(S)-4,6-dimethyl-N-((6-(3,3,3-trifluoropropyl)pyridin-3-yl)methyl)-5,6-dihydro-4H-pyrrole And[3,2,1-de]pteridin-2-amine Compound 20 was prepared by the following steps:

19e
20a

20

Step 1: Dissolve compounds 19e (81 mg, 0.36 mmol) and 20a (112 mg, 0.55 mmol) in n-butanol (3 mL), add trifluoroacetic acid (41 mg, 0.36 mmol). The reaction solution was heated to 150° C. by microwave to react for 3 hours. LCMS monitored that the reaction was complete. The reaction solution was concentrated, and the residue was purified by preparative HPLC to obtain compound 20 (101 mg, yield 70%). ESI-MS (m/z): 391.4 [M+H]⁺; ¹HNMR (500 MHz, DMSO-d6) δ 8.54 (d, J=1.8 Hz, 1H), 8.21 (s, 1H), 7.73 (dd, J=8.0, 2.2 Hz, 1H), 7.51 (d, J=2.4 Hz, 1H), 7.32 (d, J=8.0 Hz, 1H), 6.18 (d, J=2.7 Hz, 1H), 4.57 (d, J=5.8 Hz, 2H), 4.43-4.35 (m, 1H), 3.81 (dd, J=12.9, 4.1 Hz, 1H), 3.50 (dd, J=12.9, 8.6 Hz, 1H), 3.17 (s, 3H), 2.95 (dd, J=9.2, 6.7 Hz, 2H), 2.75-2.63 (m, 2H), 1.45 (d, J=6.4 Hz, 3H).

Example 21

(S)-8-(difluoromethyl)-4,6-dimethyl-N-((1-((6-(trifluoromethyl)pyridin-3-yl)methyl)-1H-pyridine Azol-4-yl) methyl)-5,6-dihydro-4H-pyrrolo[3,2,1-de]pteridin-2-amine Compound 21 was prepared by the following steps:

19e n-BuLi, DMF

21a

DAST

21b

1e

21

Step 1: Under nitrogen protection, compound 19e (0.6 g, 2.69 mmol) was dissolved in anhydrous THF (10 mL), cooled to −70° C., and n-butyllithium (6.7 mL, 1.6 M, 10.78 mmol), and N, N-dimethylformamide (787 mg, 10.78 mmol) was added after stirring for 15 minutes. The reaction solution was reacted at −70° C. for 2 hours, and then saturated aqueous ammonium chloride solution (2 mL) was added to terminate the reaction. The reaction mixture was diluted with ethyl acetate and washed with saturated brine. The organic phase was dried over anhydrous sodium sulfate, filtered and concentrated. The residue was purified by silica gel column chromatography to obtain compound 21a (0.3 g, yield 44%). ESI-MS (m/z): 251.5 [M+H]$^+$.

Step 2: Dissolve compound 21a (0.45 g, 1.80 mmol) in dichloromethane (10 mL), add diethylaminosulfur trifluoride DAST (1.2 mL) dropwise under ice-cooling, then warm to room temperature and stir for 3 hours. The reaction solution was quenched by adding saturated aqueous sodium bicarbonate (2 mL), diluted with dichloromethane, and washed with saturated brine. The organic phase was dried over anhydrous sodium sulfate, filtered and concentrated. The residue was purified by silica gel column chromatography to obtain compound 21b (0.25 g, yield 51%). ESI-MS (m/z): 273.4 [M+H]$^+$.

Step 3: Compound 21b (100 mg, 0.36 mmol), compound 1e (122 mg, 0.47 mmol), Pd2(dba)3 (67 mg, 0.073 mmol), t-BuONa (105 mg, 1.10 mmol) and X-Phos (34 mg, 0.073 mmol) were dispersed in toluene (3 mL), the reaction system was replaced with nitrogen and then heated to 100° C. to react for 16 hours. The completion of the reaction was monitored by LCMS, the reaction solution was concentrated, and the residue was first subjected to silica gel column chromatography to obtain a crude product which was then purified by Prep-HPLC to obtain compound 21 (55 mg, yield 30%). ESI-MS (m/z): 493.3 [M+H]$^+$; $^1$HNMR (500 MHz, DMSO-d6) δ 8.64 (s, 1H), 8.21 (s, 1H), 7.87-7.83 (m, 2H), 7.80 (s, 1H), 7.47 (s, 1H), 7.26 (t, J=53.7 Hz, 1H), 6.39 (s, 1H), 5.45 (s, 2H), 4.74-4.68 (m, 1H), 4.31 (d, J=5.8 Hz, 2H), 3.76 (dd, J=12.6, 3.7 Hz, 1H), 3.46 (dd, J=12.6, 2.2 Hz, 1H), 3.09 (s, 3H), 1.29 (d, J=6.5 Hz, 3H).

Example 22

(S)-8-(difluoromethyl)-4,5-dimethyl-N-((1-((6-(trifluoromethyl)pyridin-3-yl)methyl)-1H-pyridine Azol-4-yl) methyl)-5,6-dihydro-4H-pyrrolo[3,2,1-de]pteridin-2-amine Compound 22 was prepared by the following steps:

-continued

Step 1: Dissolve compound 19a (5.0 g, 26.59 mmol), 22a (7.57 g, 31.91 mmol) and 18-crown-6 (2.11 g, 7.98 mmol) in dioxane (50 mL), add potassium carbonate (11.03 g, 79.78 mmol). The reaction system was heated to 50° C. to react for 16 hours. LCMS monitored the completion of the reaction. The reaction solution was diluted with ethyl acetate, washed with water and saturated brine, and the organic phase was dried over anhydrous sodium sulfate, filtered and concentrated. The residue was slurried with ethyl acetate/petroleum ether (1/1) to obtain gray solid 22b (8 g, crude product), which was directly used in the next reaction. ESI-MS (m/z): 345.4 [M+H]$^+$.

Step 2: Compound 22b (5.0 g, crude product) was dissolved in dichloromethane (30 mL), and dioxane hydrochloride solution (4N, 18.1 mL) was added, and the reaction solution was stirred at room temperature for 16 hours, and the reaction was complete as monitored by LCMS. The reaction solution was filtered, the filter cake was collected, and dried under reduced pressure to obtain the hydrochloride salt of compound 22c (4.0 g, crude product), which was directly used in the next reaction. ESI-MS (m/z): 245.6 [M+H]$^+$.

Step 3: Dissolve the hydrochloride salt of compound 22c (4.0 g, crude product) in a mixture of dioxane (50 mL) and N, N-dimethylformamide (5 mL), add N,N-diisopropylethylamine (1.84 g, 14.21 mmol), the reaction solution was heated to 100° C. to react for 16 hours, and the reaction was complete as monitored by LCMS. The reaction solution was concentrated, and the residue was diluted with ethyl acetate, and washed successively with saturated ammonium chloride solution and saturated brine. The organic phase was dried over anhydrous sodium sulfate, filtered and concentrated. The residue was purified by silica gel column chromatography to give 22d (1.6 g) as a yellow solid. ESI-MS (m/z): 209.6 [M+H]$^+$.

Step 4: Dissolve compound 22d (2.1 g, 10.06 mmol) in anhydrous N, N-dimethylformamide (15 mL), add NaH (401 mg, content 60%, 10.06 mmol) in batches under ice-cooling). The reaction mixture was stirred for 30 minutes and iodomethane (1.43 g, 10.06 mmol, 0.93 mL) was added. The reaction solution was raised to room temperature, and after stirring for 16 hours, the reaction was complete as monitored by LCMS. The reaction solution was diluted with ethyl acetate, washed with water and saturated brine successively, the organic phase was dried over anhydrous sodium sulfate, filtered and concentrated to obtain a yellow solid 22e (2.0 g, yield 89%). ESI-MS (m/z): 223.5 [M+H]$^+$.

Step 5: Under nitrogen protection, compound 22e (200 mg, 0.89 mmol) was dissolved in anhydrous tetrahydrofuran (8 mL). The reaction solution was cooled to −70° C., and n-butyl lithium solution (2.5M, 1.8 mL) was added drop-wise. After stirring for 30 minutes, N,N-dimethylformamide (262 mg, 3.59 mmol) was added. The reaction mixture was stirred at −70° C. for 3 hours and then slowly warmed to room temperature. The reaction solution was quenched with dilute hydrochloric acid (1N), diluted with ethyl acetate, and washed with water and saturated brine in sequence. The organic phase was dried over anhydrous sodium sulfate, filtered and concentrated. The residue was purified by silica gel column chromatography to obtain compound 22f (150 mg, yield 66%). ESI-MS (m/z): 251.5 [M+H]$^+$.

Step 6: Dissolve compound 22f (150 mg, 0.59 mmol) in dichloromethane (5 mL), add diethylaminosulfur trifluoride DAST (192 mg, 1.20 mmol, 0.16 mL) dropwise under ice-cooling, Then warm to room temperature and stir for 5 hours. The reaction solution was quenched by adding satu-rated aqueous sodium bicarbonate (2 mL), diluted with dichloromethane, and washed with saturated brine. The organic phase was dried over anhydrous sodium sulfate, filtered and concentrated. The residue was purified by silica gel column chromatography to obtain 22 g (150 mg, yield 73%) of white solid. ESI-MS (m/z): 273.4 [M+H]$^+$.

Step 7: Compound 22g (110 mg, 0.40 mmol), compound 1e (134 mg, 0.52 mmol), Pd$_2$(dba)$_3$ (73 mg, 0.08 mmol), t-BuONa (116 mg, 1.21 mmol) and X-Phos (38 mg, 0.08 mmol) was dispersed in toluene (4 mL), and the reaction system was replaced with nitrogen and heated to 100° C. to react for 16 hours. The completion of the reaction was monitored by LCMS, the reaction solution was concen-trated, and the residue was purified by Prep-HPLC to obtain compound 22 (35 mg, yield 17%). ESI-MS (m/z): 493.2 [M+H]$^+$; $^1$HNMR (500 MHz, DMSO-d6) δ 8.64 (s, 1H), 7.91-7.82 (m, 2H), 7.79 (s, 1H), 7.46 (s, 1H), 7.22 (t, J=53.5 Hz, 1H), 6.45-6.29 (m, 2H), 5.45 (s, 2H), 4.30 (d, J=6.0 Hz, 2H), 4.20 (dd, J=12.5, 3.5 Hz, 1H), 4.09 (dd, J=12.5, 3.5 Hz, 1H), 3.99-3.88 (m, 1H), 3.05 (s, 3H), 1.23 (d, J=6.5 Hz, 3H).

Example 23

(S)-4-isopropyl-6-methyl-N-((1-((6-(trifluoromethyl) pyridin-3-yl)methyl)-1H-pyrazol-4-yl) methyl)-5,6-dihydro-4H-pyrrolo[3,2,1-de]pteridin-2-amine Compound 23 was prepared by the following steps:

Step 1: Dissolve compound 19e (0.2 g, 0.95 mmol) in anhydrous N, N-dimethylformamide (5 mL), add NaH (115 mg, content 60%, 2.87 mmol) in batches under ice-cooling. The reaction mixture was stirred for 5 minutes and then iodoisopropane (211 mg, 1.25 mmol, 0.12 mL) was added. The reaction solution was raised to room temperature, and after stirring for 3 hours, the reaction was complete as monitored by LCMS. The reaction solution was diluted with ethyl acetate, washed with saturated brine, and the organic phase was dried over anhydrous sodium sulfate, filtered and concentrated. The residue was purified by silica gel column chromatography to obtain compound 23a (185 mg, yield 76%). ESI-MS (m/z): 251.5 [M+H]$^+$.

Step 2: Compound 23a (100 mg, 0.39 mmol), compound 1e (132 mg, 0.51 mmol), Pd$_2$(dba)$_3$ (73 mg, 0.08 mmol), t-BuONa (115 mg, 1.20 mmol) and X-Phos (38 mg, 0.08 mmol) were dispersed in toluene (5 mL). The reaction system was replaced with nitrogen and heated to 100° C. to react for 16 hours. The completion of the reaction was monitored by LCMS, the reaction solution was concen-trated, and the residue was purified by Prep-HPLC to obtain compound 23 (31 mg, yield 16%). ESI-MS (m/z): 471.2 [M+H]$^+$; $^1$HNMR (500 MHz, DMSO-d6) δ 8.63 (s, 1H), 8.26 (s, 1H), 7.88-7.80 (m, 2H), 7.77 (s, 1H), 7.45 (s, 1H), 7.29 (d, J=2.7 Hz, 1H), 6.51 (br s, 1H), 6.03 (d, J=2.7 Hz, 1H), 5.44 (s, 2H), 4.85-4.79 (m, 1H), 4.29 (d, J=5.8 Hz, 2H), 4.25-4.20 (m, 1H), 3.66 (dd, J=12.6, 3.5 Hz, 11H), 3.25-3.20 (m, 1H), 1.41 (d, J=6.4 Hz, 3H), 1.19-1.14 (m, 6H).

Example 24

(R)-5-(methoxymethyl)-4-methyl-N-((1-((6-(trifluo-romethyl)pyridin-3-yl)methyl)-1H-pyrazole-4-yl)methyl)-5,6-dihydro-4H-pyrrolo[3,2,1-de]pteridin-6,6-d2-2-amine Compound 24 was prepared by the following steps:

-continued

Step 1: under nitrogen protection, SOCl$_2$ (1.72 g, 14.47 mmol, 1.05 mL) was dissolved in anhydrous dichloromethane (100 mL). After the reaction solution was cooled to −70° C., a solution of imidazole (2.63 g, 38.60 mmol) and triethylamine (2.93 g, 28.95 mmol, 4.01 mL) in anhydrous dichloromethane (10 mL) was added dropwise. The reaction is violently exothermic, and the internal temperature of the reaction solution is controlled below −40° C. After the dropwise addition, the reaction solution was re-cooled to −70° C. and stirred for 10 minutes, and then a solution of compound 24a (2.0 g, 9.65 mmol) in anhydrous dichloromethane (10 mL) was added dropwise. The reaction mixture was slowly warmed to room temperature and stirred overnight. The reaction solution was diluted with dichloromethane, 0.5M aqueous citric acid solution was added, and the organic phase was separated. The obtained organic phase was washed successively with saturated sodium bicarbonate solution and saturated brine, dried over anhydrous sodium sulfate, filtered and concentrated to obtain compound 24b (2.43 g, crude product), which was directly used in the next reaction.

Step 2: Compound 24b (2.43 g) obtained in the previous step was dissolved in a mixed solution of acetonitrile (55 mL) and water (25 mL), and ruthenium trichloride (99 mg, 0.47 mmol) and sodium periodate (4.10 g, 19.19 mmol) were added successively under ice bath. The reaction mixture was stirred at room temperature for 3 hours and then quenched. The reaction solution was diluted with ethyl acetate, washed with saturated brine, and the organic phase was dried over anhydrous sodium sulfate, filtered and concentrated to obtain compound 24c (2.2 g, crude product), which was directly used in the next reaction.

Step 3: Dissolve compound 19a (1.3 g, 6.91 mmol), 22a (2.23 g) and 18-crown-6 (91 mg, 0.34 mmol) in dioxane (20 mL), add potassium carbonate (2.87 g, 20.74 mmol). The reaction system was heated to 60° C. to react for 16 hours, and the reaction was monitored by LCMS. The reaction solution was diluted with ethyl acetate, washed with water and saturated brine respectively, the organic phase was dried over anhydrous sodium sulfate, filtered and concentrated to obtain compound 24d (2.6 g, crude product), which was directly used in the next reaction. ESI-MS (m/z): 377.5 [M+H]+.

Step 4: Compound 24d (1.65 g, crude product) was dissolved in dioxane (10 mL), concentrated hydrochloric acid (1.33 mL) was added, and the reaction solution was stirred at room temperature for 3 hours, and the reaction was complete as monitored by LCMS. The reaction solution was concentrated to obtain the hydrochloride salt of compound 24e (1.2 g, crude product), which was directly used in the next reaction. ESI-MS (m/z): 277.4 [M+H]+.

Step 5: Dissolve the hydrochloride salt of compound 24e (1.3 g, crude product) in a mixture of dioxane (20 mL) and N, N-dimethylformamide (2 mL), add N,N-diisopropylethylamine (2.68 g, 20.73 mmol, 3.43 mL), the reaction solution was heated to 100° C. to react for 16 hours, and the reaction was complete by LCMS monitoring. The reaction solution was concentrated, and the residue was diluted with ethyl acetate, and washed successively with saturated ammonium chloride solution and saturated brine. The organic phase was dried over anhydrous sodium sulfate, filtered and concentrated. The residue was purified by silica gel column chromatography to obtain compound 24f (0.56 g). ESI-MS (m/z): 241.5 [M+H]+.

Step 6: Dissolve compound 24f (0.1 g, 0.41 mmol) in anhydrous N, N-dimethylformamide (5 mL), add NaH (49 mg, content 60%, 1.22 mmol) under ice-cooling, The reaction mixture was stirred for 5 minutes and then iodomethane (70 mg, 0.49 mmol) was added. The reaction solution was raised to room temperature, and after stirring for 3 hours, the reaction was complete as monitored by LCMS. The reaction solution was diluted with ethyl acetate, washed with saturated brine, and the organic phase was dried over anhydrous sodium sulfate, filtered and concentrated. The residue was purified by silica gel column chromatography to obtain compound 24g (50 mg, yield 47%). ESI-MS (m/z): 255.5 [M+H]+.

Step 7: Dissolve compound 24g (100 mg, 0.39 mmol) and 1e (100 mg, 0.39 mmol) in n-butanol (3 mL), add trifluoroacetic acid (134 mg, 1.18 mmol). The reaction solution was heated to 150° C. by microwave to react for 3 hours, and LCMS monitored that the reaction was complete. The reaction solution was concentrated, and the residue was purified by preparative HPLC to obtain compound 24 (43 mg, yield 23%). ESI-MS (m/z): 475.4 [M+H]+; 1HNMR (500 MHz, DMSO-d6) δ 8.65 (s, 1H), 8.23 (s, 1H), 7.90-7.84 (m, 3H), 7.52 (s, 1H), 7.37 (s, 1H), 6.14 (s, 1H), 5.48 (s, 2H), 4.47-4.36 (m, 2H), 4.17-4.14 (m, 1H), 3.57 (dd, J=10.0, 5.6 Hz, 1H), 3.46 (dd, J=9.8, 7.3 Hz, 1H), 3.30-3.26 (m, 6H).

Example 25

(R)-6-(methoxymethyl)-4,8-dimethyl-N-((1-((6-(trifluoromethyl)pyridin-3-yl)methyl)-1H-pyrazol-4-yl)methyl)-5,6-dihydro-4H-pyrrolo[3,2,1-de]pteridin-2-amine Compound 25 was prepared by the following steps:

25a

25b

-continued

25c

25d

25e

25f

25g

25h

-continued

25

Step 1: under nitrogen protection, SOCl$_2$ (2.26 g, 19.00 mmol, 1.38 mL) was dissolved in anhydrous dichloromethane (50 mL). After the reaction solution was cooled to −70° C., a solution of imidazole (3.98 g, 58.47 mmol) and triethylamine (2.96 g, 29.23 mmol, 4.05 mL) in anhydrous dichloromethane (10 mL) was added dropwise. The reaction is violently exothermic, and the internal temperature of the reaction solution is controlled below −40° C. After the dropwise addition, the reaction solution was re-cooled to −70° C. and stirred for 10 minutes, and then a solution of compound 25a (3.0 g, 14.62 mmol) in anhydrous dichloromethane (10 mL) was added dropwise. The reaction mixture was slowly warmed to room temperature and stirred overnight. The reaction solution was diluted with dichloromethane, 0.5M aqueous citric acid solution was added, and the organic phase was separated. The obtained organic phase was washed successively with saturated sodium bicarbonate solution and saturated brine, dried over anhydrous sodium sulfate, filtered and concentrated to obtain compound 25b (3.6 g), which was directly used in the next reaction.

Step 2: Dissolve compound 25b (3.6 g) obtained in the previous step in acetonitrile (50 mL), add ruthenium trichloride (99 mg, 0.47 mmol), and then add sodium periodate aqueous solution (4.10 g, 19.19 mmol, dissolved in 50 mL water). After the addition was complete, the reaction mixture was warmed to room temperature and stirred for 4 hours. The reaction solution was diluted with ethyl acetate, washed with saturated brine, and the organic phase was dried over anhydrous sodium sulfate, filtered and concentrated to obtain compound 25c (3.5 g, two-step reaction yield 46%). $^1$HNMR (500 MHz, DMSO-d6) δ 5.14-5.06 (m, 1H), 4.13-4.06 (m, 1H), 3.85-3.78 (m, 1H), 3.73-3.65 (m, 2H), 3.31 (s, 3H), 1.47 (s, 9H).

Step 3: Dissolve compound 19a (2.0 g, 10.64 mmol), 25c (3.70 g, 13.83 mmol) and 18-crown-6 (281 mg, 1.06 mmol) in dioxane (50 mL), add potassium carbonate (4.41 g, 31.91 mmol). The reaction system was heated to 80° C. to react for 16 hours, and the reaction was complete as monitored by LCMS. The reaction solution was diluted with ethyl acetate, washed with water and saturated brine respectively, the organic phase was dried over anhydrous sodium sulfate, filtered and concentrated to obtain compound 25d (3.8 g, crude product), which was directly used in the next reaction. ESI-MS (m/z): 375.4 [M+H]$^+$.

Step 4: Dissolve compound 25d (3.8 g) obtained in the previous step in dichloromethane (40 mL), add dioxane hydrochloride solution (4N, 12.66 mL), stir the reaction solution at room temperature for 16 hours. LCMS monitored that the reaction was complete. The reaction solution was concentrated to obtain the hydrochloride salt of compound 25e (3.0 g, crude product), which was directly used in the next reaction. ESI-MS (m/z): 275.5 [M+H]$^+$.

Step 5: Dissolve the hydrochloride salt of compound 25e (3.6 g, crude product) in a mixture of dioxane (50 mL) and N, N-dimethylformamide (5 mL), add N,N-diisopropyleth-ylamine (7.47 g, 57.77 mmol, 9.57 mL), the reaction solution was heated to 90° C. to react for 16 hours, and the reaction was complete by LCMS monitoring. The reaction solution was concentrated, and the residue was diluted with ethyl acetate, and washed successively with saturated ammonium chloride solution and saturated brine. The organic phase was dried over anhydrous sodium sulfate, filtered and concentrated. The residue was purified by silica gel column chromatography to obtain compound 25f (0.84 g). ESI-MS (m/z): 239.6 [M+H]$^+$.

Step 6: Dissolve compound 25f (150 mg, 0.62 mmol) in anhydrous N, N-dimethylformamide (2 mL), add NaH (75 mg, content 60%, 1.89 mmol) under ice-cooling, The reaction mixture was stirred for 30 minutes after which iodomethane (133 mg, 0.94 mmol) was added. The reaction solution was raised to room temperature, and after stirring for 3 hours, the reaction was complete as monitored by LCMS. The reaction solution was diluted with ethyl acetate, washed with saturated brine, and the organic phase was dried over anhydrous sodium sulfate, filtered and concentrated. The residue was purified by silica gel column chromatography to obtain compound 25g (130 mg, yield 81%). ESI-MS (m/z): 253.5 [M+H]$^+$.

Step 7: Under nitrogen protection, 25g of the compound (130 mg, 0.51 mmol) was dissolved in anhydrous tetrahydrofuran (3 mL), the reaction solution was cooled to –70° C., and n-butyllithium solution (2.5M, 0.82 mL) was added dropwise. After stirring for 30 minutes, iodomethane (292 mg, 2.06 mmol) was added. The reaction mixture was stirred at –70° C. for 1 hours and then slowly warmed to room temperature. The reaction solution was quenched with satu-rated ammonium chloride aqueous solution, diluted with ethyl acetate, and washed with water and saturated brine successively. The organic phase was dried over anhydrous sodium sulfate, filtered and concentrated to obtain com-pound 25h (100 mg, crude). ESI-MS (m/z): 267.4 [M+H]$^+$.

Step 8: Compound 25h (100 mg, crude product), com-pound 1e (124 mg, 0.48 mmol), Pd$_2$(dba)$_3$ (68 mg, 0.074 mmol), t-BuONa (108 mg, 1.12 mmol) and X-Phos (35 mg, 0.074 mmol) were dispersed in toluene (5 mL), and the reaction system was replaced with nitrogen and heated to 100° C. to react for 16 hours. The completion of the reaction was monitored by LCMS, the reaction solution was concen-trated, and the residue was purified by silica gel column chromatography to obtain a crude product, and then purified by Prep-HPLC to obtain compound 25 (13 mg). ESI-MS (m/z): 487.4 [M+H]$^+$; $^1$HNMR (500 MHz, DMSO-d6) δ 8.65 (s, 1H), 8.29 (br s, 1H), 7.88 (d, J=8.0 Hz, 1H), 7.84 (d, J=8.0 Hz, 1H), 7.78 (s, 1H), 7.45 (s, 1H), 6.33 (br s, 1H), 5.80 (s, 1H), 5.45 (s, 2H), 4.63 (s, 1H), 4.29 (d, J=6.0 Hz, 2H), 3.57 (s, 2H), 3.43 (dd, J=9.5, 7.0 Hz, 1H), 3.34-3.30 (m, 1H), 3.24 (s, 3H), 3.01 (s, 3H), 2.33 (s, 3H).

Example 26

8,8-difluoro-6-methyl-N-((1-((6-(trifluoromethyl) pyridin-3-yl)methyl)-1H-pyrazol-4-yl)methyl)-6,7,8, 9-tetrahydro-3,5,6,9a-tetraazabenzo[cd]azulene-4-amine Compound 26 was prepared by the following steps:

155

-continued

26e

1e

TFA

26

Step 1: Dissolve compound 19a (400 mg, 2.13 mmol) and triphenylphosphine (1.67 g, 6.38 mmol) in anhydrous tetra-hydrofuran (15 mL) at room temperature, and add N,N-diisopropylethylamine (1.37 g, 10.64 mmol) and diisopropyl azodicarboxylate (1.29 g, 6.38 mmol, 1.25 mL). After stir-ring for 30 minutes, a solution of compound 26a (898 mg, 4.26 mmol) in anhydrous tetrahydrofuran (5 mL) was con-tinued to be added dropwise. The reaction mixture was warmed up to 70° C. and reacted for 16 hours to terminate the reaction. The reaction solution was concentrated, and the residue was purified by silica gel column chromatography to obtain compound 26b (500 mg, yield 61%). ESI-MS (m/z): 325.4 [M−55]⁺.

Step 2: Dissolve compound 26b (500 mg, 1.31 mmol) in dichloromethane (5 mL), add dioxane hydrochloride solu-tion (4N, 1.64 mL), stir the reaction solution at room temperature for 16 hours, and monitor the complete reaction by LCMS. The reaction solution was filtered, the filter cake was collected, and dried under reduced pressure to obtain the hydrochloride salt of compound 26c (360 mg, yield 86%).

Step 3: Dissolve the hydrochloride salt of compound 26c (360 mg, 1.13 mmol) in a mixture of dioxane (5 mL) and N,N-dimethylformamide (1 mL), add N, N-diisopropylethyl-amine (732 mg, 5.67 mmol). The reaction solution was heated to 100° C. to react for 4 hours, and LCMS monitored that the reaction was complete. The reaction solution was concentrated, and the residue was diluted with ethyl acetate, and washed successively with saturated ammonium chloride solution and saturated brine. The organic phase was dried over anhydrous sodium sulfate, filtered and concentrated. The residue was purified by silica gel column chromatog-raphy to obtain white solid 26d (250 mg, yield 90%). ESI-MS (m/z): 245.5 [M+H]⁺.

Step 4: Dissolve compound 26d (300 mg, 1.23 mmol) in anhydrous N, N-dimethylformamide (5 mL), add NaH (122 mg, content 60%, 3.07 mmol) in batches under ice-cooling, the reaction mixture was stirred for 15 minutes and then iodomethane (261 mg, 1.84 mmol, 0.17 mL) was added. The reaction solution was raised to room temperature, and after stirring for 4 hours, the reaction was complete as monitored by LCMS. The reaction solution was diluted with ethyl acetate, washed with saturated brine, the organic phase was dried over anhydrous sodium sulfate, filtered and concen-trated to obtain compound 26e (290 mg, yield 91%). ESI-MS (m/z): 259.5 [M+H]⁺.

Step 5: Dissolve compound 26e (100 mg, 0.38 mmol) and 1e (148 mg, 0.57 mmol) in n-butanol (4 mL), add trifluo-roacetic acid (44 mg, 0.38 mmol). The reaction solution was heated by microwave to 150° C. to react for 6 hours, and LCMS monitored that the reaction was complete. The reac-tion solution was concentrated, and the residue was purified by preparative HPLC to obtain compound 26 (17 mg, yield 9%). ESI-MS (m/z): 479.5 [M+H]⁺; ¹HNMR (500 MHz, DMSO-d6) δ 8.64 (s, 1H), 7.90-7.80 (m, 3H), 7.52-7.40 (m, 2H), 6.26 (d, J=2.5 Hz, 1H), 5.46 (s, 2H), 4.73 (t, J=12.0 Hz, 2H), 4.37 (d, J=6.0 Hz, 2H), 4.17 (t, J=12.0 Hz, 2H), 3.26 (s, 3H).

Example 27

(R)-4,6-dimethyl-N-((1-((6-(trifluoromethyl)pyridin-3-yl)methyl)-1H-pyrazol-4-yl)methyl)-5,6-dihydro-4H-pyrrolo[3,2,1-de]pteridin-2-amine Replace (R)-1-(BOC-amino)-2-propanol methane-sulfonate in the first step in Example 19 with (S)-1-(BOC-amino)-2-propanol methanesulfonate 19b, compound 27 can be obtained by similar methods and reaction steps. ESI-MS (m/z): 443.6 [M+H]⁺; ¹HNMR (500 MHz, DMSO-d6) δ 12.19 (br s, 1H), 8.64 (s, 1H), 8.34 (br s, 1H), 7.92-7.83 (m, 3H), 7.53 (s, 1H), 7.44 (d, J=2.5 Hz, 1H), 6.20 (s, 1H), 5.49 (s, 2H), 4.44 (s, 2H), 4.29-4.06 (m, 3H), 3.22 (s, 3H), 1.29 (d, J=6.5 Hz, 3H).

Example 28

(R)—N-((1-((6-(trifluoromethyl)pyridin-3-yl)methyl)-1H-pyrazol-4-yl)methyl)-7a,8,10,11-tetra-hydro-7H-[1,4]oxazino[3,4-h]pyrrolo[3,2,1-de]pteri-din-2-amine Compound 28 was prepared by the following steps:

28a

19a

PPh₃, DIAD

28b

HCl

28c

1e

TFA

28

Step 1: Dissolve compound 19a (300 mg, 1.60 mmol) and triphenylphosphine (1.26 g, 4.79 mmol) in anhydrous tetrahydrofuran (10 mL) at room temperature, and add N,N-diisopropylethylamine (1.03 g, 7.98 mmol) and diisopropyl azodicarboxylate (967 mg, 4.79 mmol, 0.94 mL). After stirring for 30 minutes, a solution of compound 28a (866 mg, 3.99 mmol) in anhydrous tetrahydrofuran (5 mL) was continued to be added dropwise. The reaction mixture was warmed up to 70° C. and reacted for 16 hours to terminate the reaction. The reaction solution was concentrated, and the residue was purified by silica gel column chromatography to obtain compound 28b (200 mg, yield 32%). ESI-MS (m/z): 331.4 [M–55]⁺.

Step 2: Dissolve compound 28b (200 mg, 0.51 mmol) in dichloromethane (2 mL), add dioxane hydrochloride solution (4N, 1.29 mL), stir the reaction solution at room temperature for 16 hours, and monitor the complete reaction by LCMS. The reaction solution was concentrated to obtain compound 28c (100 mg, crude product), which was directly used in the next reaction. ESI-MS (m/z): 251.5 [M+H]⁺.

Step 3: Dissolve compound 28c (100 mg) and 1e (122 mg, 0.47 mmol) in n-butanol (4 mL), add trifluoroacetic acid (45 mg, 0.39 mmol), and heat the reaction solution to 150° C. to react for 5 hours, and LCMS monitored that the reaction was complete. The reaction solution was concentrated, and the residue was purified by preparative HPLC to obtain compound 28 (13 mg). ESI-MS (m/z): 471.5 [M+H]⁺; ¹HNMR (500 MHz, DMSO-d6) δ 12.19 (s, 1H), 8.63 (s, 1H), 8.36 (br s, 1H), 8.01-7.79 (m, 3H), 7.65-7.44 (m, 2H), 6.23 (s, 1H), 5.48 (s, 2H), 4.56-4.40 (m, 3H), 4.29-4.25 (m, 1H), 4.13-4.02 (m, 3H), 3.93-3.82 (m, 1H), 3.62-3.52 (m, 2H), 3.24-3.17 (m, 1H).

Example 59 (W284)

(S)-4,5-dimethyl-2-(((6-((6-(trifluoromethyl)pyridin-3-yl)methyl)pyridin-3-yl)methyl)amino)-4,5,9,10-tetrahydro-6H,8H-pyrido[3,2,1-de]pteridin-6-one Compound 59 was prepared by the following steps:

59a

HCl

EDCI, HOBt, DIPEA

59b

59c n-BuLi, THF, -78° C.

59d

NaBH₄

-continued

59e

CS₂, NaH, MeI
THF, 0° C.-r.t.

59f n-Bu₃SnH, AIBN
Toluene, r.t.-80° C.

59g

Zn(CN)₂, Pd₂(dba)₃,
S-Phos,
NMP, 150° C.,
microwave

59h

H₂, Ra—Ni
NH₄OH, MeOH

59i

1i

TsOH—H₂O,
n-BuOH, 160° C.,
microwave, 2 h

59

Step 1: Dissolve compound 59a (2 g, 12.69 mmol) and N-methyl-N-methoxyamine hydrochloride (1.86 g, 19.04 mmol) in dichloromethane (20 mL), add EDCI (3.65 g, 19.04 mmol), HOBt (2.57 g, 19.04 mmol) and N, N-diisopropylpropylamine (4.92 g, 38.08 mmol). The reaction was stirred at room temperature for 12 hours. LCMS monitored the completion of the reaction. The reaction solution was diluted with water and extracted with ethyl acetate. The organic phase was washed with saturated brine, dried over anhydrous sodium sulfate, filtered and concentrated. The residue was purified by silica gel column chromatography (petroleum ether/ethyl acetate=5/1) to obtain colorless oily liquid 59b (2.2 g, yield 86%). ESI-MS (m/z): 201.4 [M+H]⁺.

Step 2: Compound 59c (371 mg, 1.64 mmol) was dissolved in dry tetrahydrofuran (10 mL), and the reaction system was replaced with nitrogen and stirred at −78° C. for 5 minutes. n-butyllithium (0.72 mL, 2.5M, 1.79 mmol) was added dropwise into the reaction solution, and the reaction solution was stirred at −78° C. for 30 minutes. Subsequently, compound 59b (300 mg, 1.50 mmol, dissolved in 1 mL of dry tetrahydrofuran) was added to the reaction solution. The reaction solution was stirred at −78° C. for 2 hours. After the reaction system returned to room temperature, the reaction solution was quenched with saturated ammonium chloride aqueous solution and extracted with ethyl acetate. The organic phase was washed with saturated aqueous sodium chloride, dried over anhydrous sodium sulfate, filtered and concentrated. The residue was purified by silica gel column chromatography (petroleum ether/ethyl acetate=10/1) to obtain white solid compound 59d (80 mg, yield 19%). ESI-MS (m/z): 287.2 [M+H]⁺; H NMR (500 MHz, CDCl3) δ 9.43 (s, 1H), 8.68 (d, J=2.2 Hz, 1H), 8.61 (d, J=6.7 Hz, 1H), 8.20 (d, J=8.4 Hz, 1H), 7.94 (dd, J=8.4, 2.2 Hz, 1H), 7.83 (d, J=8.1 Hz, 1H).

Step 3: Dissolve compound 59d (200 mg, 0.70 mmol) in methanol (8 mL), slowly add sodium borohydride (40 mg, 1.05 mmol) at 0° C., and continue to stir the reaction solution at 0° C. for 4 hours. LCMS monitored the completion of the reaction. The reaction was quenched with saturated aqueous ammonium chloride, followed by extraction with ethyl acetate. The organic phase was washed with saturated aqueous sodium chloride, dried over anhydrous sodium sulfate, filtered and concentrated. The residue was purified by silica gel column chromatography (petroleum ether/ethyl acetate=5/1) to obtain compound 59e (201 mg, yield 99%). ESI-MS (m/z): 289.2 [M+H]⁺.

Step 4: Dissolve compound 59e (100 mg, 0.35 mmol) in dry tetrahydrofuran (5 mL), then add sodium hydride (24 mg, content 60%, 0.6 mmol) at 0° C., and the reaction solution was stirred for half an hour. Carbon disulfide (80 mg, 1.05 mmol) and methyl iodide (148 mg, 1.05 mmol) were then added sequentially, and the reaction was stirred at 0° C. for 2 hours. LCMS monitored the completion of the reaction. The reaction solution was quenched with an aqueous solution of saturated ammonium chloride at 0° C., and extracted with ethyl acetate. The organic phase was washed with saturated aqueous sodium chloride, dried over anhydrous sodium sulfate, filtered and concentrated. The residue was purified by silica gel column chromatography (petroleum ether/ethyl acetate=10/1) to obtain compound 59f (98 mg, yield 75%). ESI-MS (m/z): 379.1 [M+H]⁺.

Step 5: Dissolve compound 59f (98 mg, 0.26 mmol) and tributyltin hydride (150 mg, 0.52 mmol) in toluene (5 mL), add azobisisobutyronitrile (5 mg, 0.03 mmol). The reaction system was stirred at 80° C. for 12 hours after nitrogen replacement. LCMS monitored the completion of the reaction. The reaction liquid was added dropwise to ice water to quench, and extracted with ethyl acetate. The organic phase was washed with saturated aqueous sodium chloride, dried over anhydrous sodium sulfate, filtered and concentrated.

The residue was purified by silica gel column chromatography (petroleum ether/ethyl acetate=10/1) to obtain compound 59g (40 mg, yield 57%). ESI-MS (m/z): 273.2 [M+H]⁺.

Step 6: Dissolve compound 59g (40 mg, 0.15 mmol) in N-methylpyrrolidone (3 mL), add zinc cyanide (35 mg, 0.30 mmol), Pd₂(dba)₃ (27 mg, 0.03 mmol) and S-Phos (12 mg, 0.03 mmol), the reaction system was replaced with nitrogen and stirred at 150° C. for 2 hours under microwave conditions. LCMS monitored the completion of the reaction. The reaction solution was filtered through celite, and the filtrate was concentrated. The residue was purified by silica gel column chromatography (petroleum ether/ethyl acetate=10/1) to obtain white solid 59h (21 mg, yield 55%). ESI-MS (m/z): 264.4 [M+H]⁺.

Step 7: Dissolve compound 59h (21 mg, 0.08 mmol) in methanol (5 mL) and ammonia water (1 mL), add Raney Nickel (0.5 mL, aqueous suspension), and replace the reaction system with hydrogen, and then stir the reaction system at room temperature for 12 hours. LCMS monitored the completion of the reaction. The reaction solution was filtered through celite, and the filtrate was concentrated. The residue was purified by silica gel column chromatography (dichloromethane/methanol=5/1) to obtain compound 59i (20 mg, yield 94%). ESI-MS (m/z): 268.3 [M+H]⁺.

Step 8: Dissolve compound 59i (20 mg, 0.08 mmol) and compound 1i (13 mg, 0.05 mmol) in n-butanol (3 mL), add p-toluenesulfonic acid monohydrate (9 mg, 0.05 mmol), the reaction solution was stirred at 160° C. for 3 hours under microwave conditions. After the reaction solution was cooled to room temperature, the reaction solution was concentrated under reduced pressure, and the residue was purified by preparative HPLC to obtain compound 59 (9 mg, yield 25%) as a white solid. ESI-MS (m/z): 484.3 [M+H]⁺; ¹H NMR (500 MHz, DMSO-d6) δ 8.70 (s, 1H), 8.44 (s, 1H), 7.94 (d, J=7.8 Hz, 1H), 7.82 (s, 1H), 7.67 (dd, J=7.9, 1.6 Hz, 1H), 7.31 (d, J=7.9 Hz, 1H), 7.02 (br s, 1H), 4.43-4.30 (m, 2H), 4.19 (s, 2H), 4.10 (q, J=6.7 Hz, 1H), 4.02-3.97 (m, 1H), 3.31-3.22 (m, 3H), 2.90 (s, 3H), 1.93-1.87 (m, 1H), 1.83-1.74 (m, 1H), 1.21 (d, J=6.8 Hz, 3H).

According to the synthetic route and the synthetic method of the intermediate described in the above examples, the compounds of the following examples were obtained.

| Example | structure | analyze data |
|---|---|---|
| 61 | | ESI-MS (m/z): 392.4 [M + H]⁺; ¹H NMR (500 MHz, DMSO-d6) δ 7.78 (s, 1H), 7.46 (s, 1H), 7.46-7.35 (m, 2H), 7.29-7.22 (m, 1H), 7.08-7.03 (m, 1H), 6.14 (d, J = 2.6 Hz, 1H), 5.26 (s, 2H), 4.42-4.33 (m, 2H), 4.22-4.03 (m, 3H), 3.16 (s, 3H), 1.24 (d, J = 6.6 Hz, 3H). |
| 62 | | ESI-MS (m/z): 422.4 [M + H]⁺; ¹H NMR (500 MHz, DMSO-d6) δ 7.77 (s, 1H), 7.43 (s, 1H), 7.38 (s, 1H), 7.30-7.22 (m, 2H), 7.17-7.10 (m, 2H), 6.15 (s, 1H), 5.23 (s, 2H), 4.46-4.26 (m, 1H), 4.16-4.05 (m, 3H), 3.70-3.56 (m, 2H), 3.32 (s, 7H), 1.24 (d, J = 6.0 Hz, 3H). |
| 63 | | ESI-MS (m/z): 406.5 [M + H]⁺; ¹H NMR (500 MHz, DMSO-d6) δ 7.63 (s, 1H), 7.36 (s, 1H), 7.27-7.19 (m, 4H), 7.16-7.07 (m, 2H), 6.00 (d, J = 2.9 Hz, 1H), 5.85 (t, J = 6.0 Hz, 1H), 4.24 (dd, J = 6.0, 3.4 Hz, 2H), 4.20-4.08 (m, 2H), 3.90-3.83 (m, 1H), 3.10 (s, 3H), 2.35-2.16 (m, 2H), 1.13 (d, J = 6.8 Hz, 3H). |

-continued

| Example | structure | analyze data |
|---|---|---|
| 64 | | ESI-MS (m/z): 410.5 [M + H]⁺; ¹H NMR (500 MHz, DMSO-d6) δ 7.68 (s, 1H), 7.40 (s, 1H), 7.34-7.22 (m, 3H), 7.18-7.10 (m, 2H), 5.23 (s, 2H), 4.30 (d, J = 5.0 Hz, 2H), 4.08-4.00 (m, 1H), 3.96-3.89 (m, 2H), 3.05 (s, 3H), 1.23 (d, J = 6.4 Hz, 3H). |
| 65 | | ESI-MS (m/z): 406.6 [M + H]⁺; ¹H NMR (500 MHz, DMSO-d6) δ 8.21 (s, 1H), 7.66 (s, 1H), 7.39 (s, 1H), 7.27-7.20 (m, 2H), 7.16-7.07 (m, 2H), 6.97 (s, 1H), 5.21 (s, 2H), 4.32-4.23 (m, 1H), 4.05-3.98 (m, 1H), 3.94-3.82 (m, 2H), 3.02 (s, 3H), 2.05 (s, 3H), 1.19 (d, J = 6.5 Hz, 3H). |
| 66 | | ESI-MS (m/z): 406.5 [M + H]⁺; ¹H NMR (500 MHz, DMSO-d6) δ 12.38 (br s, 1H), 8.39 (s, 1H), 7.57 (s, 1H), 7.46 (s, 1H), 7.43 (d, J = 2.5 Hz, 1H), 7.16-7.10 (m, 2H), 7.05-6.98 (m, 2H), 6.20 (d, J = 2.4 Hz, 1H), 4.44-4.34 (m, 2H), 4.45-4.35 (m, 2H), 4.31-4.12 (m, 5H), 3.23 (s, 3H), 3.05 (t, J = 7.1 Hz, 2H), 1.29 (d, J = 6.5 Hz, 3H). |
| 67 | | ESI-MS (m/z): 386.5 [M + H]⁺; ¹H NMR (500 MHz, DMSO-d6) δ 7.44-7.34 (m, 4H), 7.31 (s, 1H), 7.12 (t, J = 7.4 Hz, 1H), 7.01-6.93 (m, 4H), 6.10 (s, 1H), 4.58-4.49 (m, 2H), 4.19 (dd, J = 12.5, 3.7 Hz, 1H), 4.08 (dd, J = 12.5, 2.6 Hz, 1H), 4.01 (br s, 1H), 3.13 (s, 3H), 1.25 (d, J = 6.5 Hz, 3H). |
| 68 | 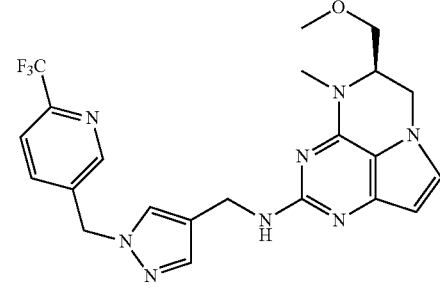 [SMILES: COC[C@H]1Cn2ccc3nc(NCc4cnn(Cc5ccc(C(F)(F)F)nc5)c4)nc(c32)N1C] | ESI-MS (m/z): 473.5 [M + H]⁺; ¹H NMR (500 MHz, DMSO-d6) δ 8.64 (s, 1H), 7.87 (d, J = 8.1 Hz, 1H), 7.83 (d, J = 8.1 Hz, 1H), 7.77 (s, 1H), 7.45 (s, 1H), 7.17 (d, J = 2.6 Hz, 1H), 6.25 (br s, 1H), 6.01 (d, J = 2.5 Hz, 1H), 5.44 (s, 2H), 4.28 (d, J = 5.6 Hz, 2H), 4.26-4.19 (m, 1H), 4.10-3.96 (m, 2H), 3.56-3.50 (m, 2H), 3.27 (s, 3H), 3.11 (s, 3H). |

-continued

| Example | structure | analyze data |
|---|---|---|
| 69 | | ESI-MS (m/z): 491.4 [M + H]⁺; ¹H NMR (500 MHz, DMSO-d6) δ 8.63 (s, 1H), 8.17 (s, 1H), 7.93-7.83 (m, 3H), 7.51 (s, 1H), 7.44 (s, 1H), 6.19 (s, 1H), 5.47 (s, 2H), 4.65-4.59 (m, 1H), 4.44-4.35 (m, 3H), 4.10-4.00 (m, 2H), 3.92-3.86 (m, 1H), 2.85-2.76 (m, 1H), 2.60-2.50 (m, 1H). |
| 70 | | ESI-MS (m/z): 511.5 [M + H]⁺; ¹H NMR (500 MHz, DMSO-d6) δ 8.64 (s, 1H), 8.17 (s, 1H), 7.89-7.82 (m, 2H), 7.77 (s, 1H), 7.44 (s, 1H), 7.27 (d, J = 2.1 Hz, 1H), 6.48 (br s, 1H), 6.06 (d, J = 2.1 Hz, 1H), 5.44 (s, 2H), 4.79-4.67 (m, 1H), 4.35-4.30 (m, 2H), 4.16-4.02 (m, 4H), 1.20 (d, J = 6.4 Hz, 2H). |
| 71 | | ESI-MS (m/z): 459.5 [M + H]⁺; ¹H NMR (500 MHz, DMSO-d6) δ 8.65 (s, 1H), 8.26 (s, 1H), 7.80-7.82 (m, 3H), 7.49 (s, 1H), 7.27 (s, 1H), 6.06 (d, J = 2.5 Hz, 1H), 5.46 (s, 2H), 4.39-4.31 (m, 3H), 4.12-4.04 (m, 1H), 3.88-3.80 (m, 1H), 3.67-3.60 (m, 1H), 3.42-3.33 (m, 1H), 3.20 (s, 3H). |
| 72 | | ESI-MS (m/z): 444.6 [M + H]⁺; ¹H NMR (500 MHz, DMSO-d6) δ 8.64 (s, 1H), 8.22 (s, 1H), 7.90-7.82 (m, 2H), 7.79 (s, 1H), 7.46 (s, 1H), 6.03 (s, 1H), 5.45 (s, 2H), 4.31 (d, J = 5.6 Hz, 2H), 4.17-4.11 (m, 1H), 4.05-3.96 (m, 1H), 3.95-3.86 (m, 1H), 3.05 (s, 3H), 1.21 (d, J = 6.5 Hz, 4H). |
| 73 | | ESI-MS (m/z): 446.6 [M + H]⁺; ¹H NMR (500 MHz, DMSO-d6) δ 8.64 (s, 1H), 8.16 (s, 1H), 7.90-7.82 (m, 2H), 7.80 (s, 1H), 7.46 (s, 1H), 7.21 (d, J = 2.3 Hz, 1H), 6.04 (d, J = 2.5 Hz, 1H), 5.45 (s, 2H), 4.31 (d, J = 5.7 Hz, 2H), 4.17-4.12 (m, 1H), 4.07-4.00 (m, 2H), 3.96-3.97 (m, 1H), 1.21 (d, J = 6.6 Hz, 3H). |

-continued

| Ex-am-ple | structure | analyze data |
|---|---|---|
| 74 | | ESI-MS (m/z): 400.6 [M + H]+; 1H NMR (500 MHz, DMSO-d6) δ 12.38 (br s, 1H), 8.29 (br s, 1H), 7.46-7.36 (m, 5H), 7.35-7.27 (m, 3H), 6.98 (d, J = 8.6 Hz, 2H), 6.17 (d, J = 2.4 Hz, 1H), 5.09 (s, 2H), 4.57-4.46 (m, 2H), 4.27-4.20 (m, 1H), 4.17-4.05 (m, 2H), 3.19 (s, 3H), 1.27 (d, J = 6.5 Hz, 3H). |
| 75 | | ESI-MS (m/z): 469.6 [M + H]+; 1H NMR (500 MHz, DMSO-d6) δ 8.63 (s, 1H), 7.91-7.83 (m, 2H), 7.80 (s, 1H), 7.47 (s, 1H), 7.23 (d, J = 2.5 Hz, 1H), 6.62 (br s, 1H), 6.05 (d, J = 2.5 Hz, 1H), 5.45 (s, 2H), 4.32 (d, J = 4.4 Hz, 2H), 4.25-4.10 (m, 2H), 3.16 (s, 3H), 3.06-3.02 (m, 1H), 0.95-0.83 (m, 1H), 0.76-0.57 (m, 2H), 0.56-0.40 (m, 1H), 0.34-0.22 (m, 1H). |
| 76 | | ESI-MS (m/z): 469.5 [M + H]+; 1H NMR (500 MHz, DMSO-d6) δ 12.24 (s, 1H), 8.63 (s, 1H), 7.96 (br s, 1H), 7.92-7.85 (m, 3H), 7.51 (s, 1H), 7.42 (d, J = 2.5 Hz, 1H), 6.22 (d, J = 2.5 Hzm 1H), 5.48 (s, 2H), 4.43 (d, J = 6.0 Hz, 2H), 4.13 (s, 2H), 3.70 (s, 2H), 3.25 (s, 3H), 0.82-0.65 (m, 4H). |
| 77 | | ESI-MS (m/z): 456.5 [M + H]+; 1H NMR (500 MHz, DMSO-d6) δ 8.64 (d, J = 2.0 Hz, 1H), 8.23 (s, 1H), 8.20 (s, 1H), 8.01-7.94 (m, 2H), 7.88 (d, J = 2.0 Hz, 1H), 7.31 (s, 1H), 7.20 (d, J = 8.4 Hz, 1H), 6.11 (d, J = 2.1 Hz, 1H), 4.53 (s, 2H), 4.21-4.05 (m, 2H), 4.01 (br s, 1H), 3.13 (s, 3H), 1.25 (d, J = 6.5 Hz, 3H). |
| 78 | | ESI-MS (m/z): 455.5 [M + H]+; 1H NMR (500 MHz, DMSO-d6) δ 8.53 (d, J = 2.2 Hz, 1H), 8.32 (br s, 1H), 8.17 (s, 1H), 7.90 (d, J = 8.7 Hz, 1H), 7.54-7.47 (m, 3H), 7.41 (s, 1H), 7.19 (d, J = 8.4 Hz, 2H), 6.18 (s, 1H), 4.67-4.55 (m, 2H), 4.26-4.07 (m, 3H), 3.18 (s, 3H), 1.28 (d, J = 6.5 Hz, 3H). |
| 79 | | ESI-MS (m/z): 437.5 [M + H]+; 1H NMR (500 MHz, DMSO-d6) δ 8.18 (s, 1H), 8.00 (br s, 1H), 7.74 (d, J = 8.5 Hz, 1H), 7.36 (s, 1H), 6.82 (d, J = 8.5 Hz, 1H), 6.15 (s, 1H), 4.56-4.44 (m, 2H), 4.43-4.31 (m, 2H), 4.20-4.02 (m, 5H), 3.97-3.90 (m, 2H), 3.17 (s, 3H), 1.26 (d, J = 6.0 Hz, 3H). |

-continued

| Ex-ample | structure | analyze data |
|---|---|---|
| 80 | 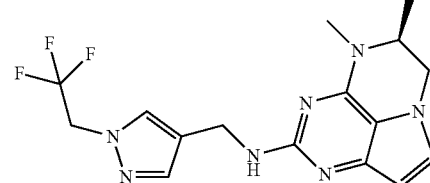 | ESI-MS (m/z): 366.5 [M + H]⁺; ¹H NMR (500 MHz, DMSO-d6) δ 12.60 (br s, 1H), 8.62 (s, 1H), 7.85 (s, 1H), 7.59 (s, 1H), 7.44 (d, J = 2.5 Hz, 1H), 6.19 (d, J = 2.5 Hz, 1H), 5.10 (q, J = 9.0 Hz, 2H), 4.54-4.42 (m, 2H), 4.30-4.10 (m, 3H), 3.25 (s, 3H), 1.30 (d, J = 7.0 Hz, 3H). |
| 81 | 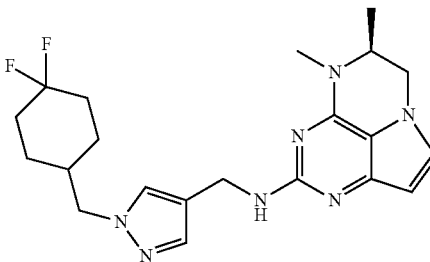 | ESI-MS (m/z): 394.5 [M + H]⁺; ¹H NMR (500 MHz, DMSO-d6) δ 8.33 (br s, 1H), 7.72 (s, 1H), 7.46 (s, 1H), 7.39 (s, 1H), 6.15 (s, 1H), 4.41 (br s, 2H), 4.25-4.04 (m, 5H), 3.21 (s, 3H), 2.26-2.15 (m, 2H), 2.00-1.89 (m, 2H), 1.27 (d, J = 6.5 Hz, 3H). |
| 82 | | ESI-MS (m/z): 375.6 [M + H]⁺; ¹H NMR (500 MHz, DMSO-d6) δ 8.23 (s, 2H), 7.83 (d, J = 8.5 Hz, 1H), 7.37 (s, 1H), 6.96 (d, J = 8.0 Hz, 1H), 6.15 (s, 1H), 4.97 (q, J = 9.1 Hz, 2H), 4.54 (br s, 2H), 4.21 (dd, J = 12.5, 3.7 Hz, 1H), 4.12 (dd, J = 12.7, 2.0 Hz, 1H), 4.07 (s, 1H), 3.17 (s, 3H), 1.26 (d, J = 6.5 Hz, 3H). |
| 83 | | ESI-MS (m/z): 416.6 [M + H]⁺; ¹HNMR (500 MHz, DMSO-d6) δ 7.57 (s, 1H), 7.38 (s, 1H), 7.16 (d, J = 2.7 Hz, 1H), 6.07 (t, J = 5.6 Hz, 1H), 6.01 (d, J = 2.6 Hz, 1H), 4.27 (d, J = 5.9 Hz, 2H), 4.13 (dd, J = 12.3, 3.8 Hz, 1H), 3.99 (dd, J = 12.3, 3.5 Hz, 1H), 3.95 (d, J = 7.1 Hz, 2H), 3.91-3.83 (m, 1H), 3.03 (s, 3H), 2.03-1.85 (m, 4H), 1.82-1.64 (m, 2H), 1.61-1.53 (m, 2H), 1.20 (d, J = 6.5 Hz, 4H). |
| 84 | | ESI-MS (m/z): 380.5 [M + H]⁺; ¹H NMR (500 MHz, DMSO-d6) δ 7.72 (s, 1H), 7.52 (s, 1H), 7.21 (d, J = 2.3 Hz, 1H), 6.05 (d, J = 2.5 Hz, 1H), 5.06 (q, J = 9.2 Hz, 2H), 4.33 (d, J = 6.0 Hz, 2H), 3.98 (s, 2H), 3.03 (s, 3H), 1.30 (s, 6H). |
| 85 | 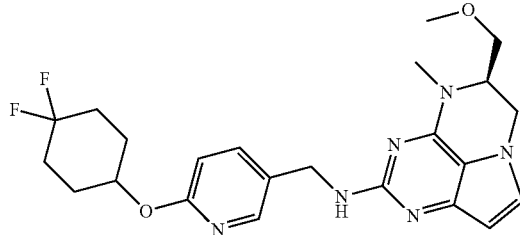 | ESI-MS (m/z): 459.5 [M + H]⁺; ¹H NMR (500 MHz, DMSO-d6) δ 8.26 (br s, 1H), 8.14 (s, 1H), 7.71 (d, J = 8.3 Hz, 1H), 7.25 (s, 1H), 6.75 (d, J = 8.4 Hz, 1H), 6.05 (s, 1H), 5.16 (br s, 1H), 4.48-4.38 (m, 2H), 4.32-4.25 (m, 1H), 4.12-4.00 (m, 2H), 3.57-3.50 (m, 1H), 3.43-3.35 (m, 1H), 3.27 (s, 3H), 3.17 (s, 3H), 2.10-1.88 (m, 6H), 1.87-1.75 (m, 2H). |

-continued

| Ex-ample | structure | analyze data |
|---|---|---|
| 86 | | ESI-MS (m/z): 393.5 [M + H]⁺; ¹H NMR (500 MHz, DMSO-d6) δ 8.74 (s, 1H), 8.18 (s, 1H), 8.00 (d, J = 8.1 Hz, 1H), 7.82 (d, J = 8.1 Hz, 1H), 7.17 (d, J = 2.8 Hz, 1H), 6.84 (t, J = 6.3 Hz, 1H), 5.99 (d, J = 2.7 Hz, 1H), 4.56 (d, J = 6.2 Hz, 2H), 4.28-4.18 (m, 1H), 4.07-4.02 (m, 1H), 4.00-3.93 (m, 1H), 3.55-3.48 (m, 2H), 3.28 (s, 3H), 3.12 (s, 3H). |
| 87 | | ESI-MS (m/z): 511.4 [M + H]⁺; ¹H NMR (500 MHz, DMSO-d6) δ 8.64 (d, J = 2.0 Hz, 1H), 8.22 (s, 1H), 7.87 (d, J = 8.1 Hz, 1H), 7.84 (dd, J = 8.1, 2.0 Hz, 1H), 7.79 (s, 1H), 7.46 (s, 1H), 7.23 (d, J = 2.8 Hz, 1H), 6.41 (d, J = 6.9 Hz, 1H), 6.06 (d, J = 2.8 Hz, 1H), 5.45 (s, 2H), 4.30 (d, J = 6.0 Hz, 2H), 4.25-4.17 (m, 2H), 4.14-4.07 (m, 1H), 3.08 (s, 3H), 2.70-2.59 (m, 1H). |
| 88 | | ESI-MS (m/z): 487.4 [M + H]⁺; ¹H NMR (500 MHz, DMSO-d6) δ 8.65 (s, 1H), 8.30-8.15 (m, 1H), 7.95-7.84 (m, 3H), 7.54 (s, 1H), 7.45 (d, J = 2.0 Hz, 1H), 6.15 (d, J = 2.4 Hz, 1H), 5.49 (s, 2H), 4.68 (q, J = 6.7 Hz, 1H), 4.47-4.38 (m, 2H), 3.96 (t, J = 6.1 Hz, 1H), 3.56-3.49 (m, 1H), 3.46-3.38 (m, 1H), 3.30 (s, 3H), 3.26 (s, 3H), 1.26 (d, J = 6.6 Hz, 2H). |
| 89 | | ESI-MS (m/z): 475.4 [M + H]⁺; ¹H NMR (500 MHz, DMSO-d6) δ 8.65 (s, 1H), 8.23 (br s, 1H), 7.93-7.84 (m, 3H), 7.52 (s, 1H), 7.37 (d, J = 2.0 Hz, 1H), 6.14 (d, J = 2.3 Hz, 1H), 5.48 (s, 2H), 4.47-4.36 (m, 2H), 4.22-4.14 (m, 1H), 3.61-3.55 (m, 1H), 3.50-3.43 (m, 1H), 3.27 (s, 3H), 3.25 (s, 3H). |
| 90 | | ESI-MS (m/z): 468.1 [M + H]⁺; ¹H NMR (500 MHz, DMSO-d6) δ 8.64 (s, 1H), 7.88-7.82 (m, 2H), 7.78 (s, 1H), 7.46 (s, 1H), 7.28 (d, J = 2.7 Hz, 1H), 6.31 (br s, 1H), 6.03 (d, J = 2.7 Hz, 1H), 5.44 (s, 2H), 4.30 (d, J = 5.0 Hz, 2H), 4.23 (d, J = 2.4 Hz, 1H), 3.68-3.62 (m, 1H), 3.333-3.26 (m, 2H), 2.71-2.65 (m, 1H), 1.38 (d, J = 6.4 Hz, 3H), 0.84-0.79 (m, 1H), 0.77-0.65 (m, 3H). |

Example 91 (W221)

(S)-4,5-dimethyl-2-(((6-((2-(trifluoromethyl)pyrimi-din-5-yl)oxo)pyridin-3-yl)methyl)amino)-4,5,910-tetrahydro-6H,8H-pyrido[3,2,1-de]pteridin-6-one Compound 91 was prepared by the following steps:

Step: 2-(trifluoromethyl)pyrimidin-5-ol 91a (1.0 g, 6.09 mmol), 6-fluoro-nicotinonitrile 91b (1.01 g, 7.31 mmol) and cesium carbonate (3.97 g, 12.19 mmol)) were dissolved in DMF (10 mL), and stirred overnight at 80° C. LCMS monitored the completion of the reaction. The reaction solution was diluted with ethyl acetate, washed with water and saturated brine successively, the organic phase was dried over anhydrous sodium sulfate, concentrated and purified by silica gel column chromatography (petroleum ether/ethyl acetate=5/1) to obtain a yellow oil 91c (1.3 g, 80% yield).

Step 2: Dissolve and disperse compound 91c (1.3 g, 4.88 mmol) and Raney Nickel (0.5 mL, aqueous suspension) in methanol (2 mL) and ammonia water (0.2 mL). Pump and exchange air with a hydrogen balloon and stir overnight at room temperature. The completion of the reaction was monitored by LCMS, the reaction solution was diluted with methanol, suction filtered through a celite filter layer, and the organic phase was concentrated to obtain a yellow oil 91d (700 mg, yield 53%). ESI-MS (m/z): 271.3 [M+H]$^+$.

Step 3: Dissolve compound 1i (150 mg, 593 umol), compound 91d (192 mg, 712 umol) and p-toluenesulfonic acid monohydrate (11 mg, 59 umol) in n-butanol (2 mL), and at 160° C. under the microwave conditions the reaction was carried out for 2 hours. LCMS monitored the completion of the reaction. The reaction solution was purified by reverse-phase preparative HPLC to obtain a white solid 91 (68 mg, yield 23%). ESI-MS (m/z): 487.4 [M+H]$^+$; $^1$H NMR (500 MHz, DMSO-d6) δ 9.03 (s, 2H), 8.12 (d, J=2.3 Hz, 1H), 7.92 (dd, J=8.4, 2.4 Hz, 1H), 7.22 (d, J=8.5 Hz, 1H), 7.05 (br s, 1H), 4.45-4.32 (m, 2H), 4.11 (q, J=6.8 Hz, 1H), 4.03-3.97 (m, 1H), 3.35-3.22 (m, 2H), 2.92 (s, 3H), 2.52-2.48 (m, 2H), 1.95-1.88 (m, 1H), 1.84-0.75 (m, 1H), 1.22 (d, J=6.8 Hz, 3H).

Example 92 (W232)

(S)-4,5-dimethyl-2-(((6-((3-(trifluoromethyl)-1H-pyrazol-1-yl)methyl)pyridin-3-yl)methyl)amino)-4,5,9,10-tetrahydro-6H,8H-pyrido[3,2,1-de]pteridin-6-one Compound 92 was prepared by the following steps:

-continued

92d

92

Step 1: Dissolve 3-(trifluoromethyl)pyrazole 92a (89 mg, 0.66 mmol) and 3-cyano-6-chloromethylpyridine 92b (100 mg, 0.66 mmol) in N, N-dimethylformamide (5 mL), and add potassium carbonate (181 mg, 1.31 mmol). The reaction solution was carried out at room temperature for 6 hours. LCMS monitored the completion of the reaction. The reaction solution was diluted with saturated aqueous sodium chloride and extracted with ethyl acetate. The organic phase was washed with saturated aqueous sodium chloride, dried over anhydrous sodium sulfate, filtered and concentrated. The residue was purified by silica gel column chromatography (petroleum ether/ethyl acetate=10/3) to obtain brown liquid compound 92c (142 mg, yield 86%). ESI-MS (m/z): 253.2 [M+H]$^+$.

Step 2: Dissolve compound 92c (142 mg, 0.56 mmol) in methanol (9 mL) and ammonia water (1 mL), add Raney Nickel (0.5 mL, aqueous suspension). The reaction system was replaced with hydrogen and stirred for 12 hours at room temperature. The reaction solution was filtered through celite, and the filtrate was concentrated. The residue was purified by silica gel column chromatography (dichloromethane/methanol=5/1) to obtain colorless oily liquid 92d (79 mg, yield 55%). ESI-MS (m/z): 257.3 [M+H]$^+$.

Step 3: Dissolve compound 92d (80 mg, 0.31 mmol) and compound 1i (53 mg, 0.21 mmol) in n-butanol (3 mL), add p-toluenesulfonic acid monohydrate (40 mg, 0.21 mmol), the reaction solution was stirred at 160° C. for 3 hours under microwave conditions. After the reaction solution was cooled to room temperature, the reaction solution was concentrated under reduced pressure, and the residue was purified by reverse-phase preparative HPLC to obtain compound 92 (19 mg, yield 13%) as a white solid. ESI-MS (m/z): 473.3 [M+H]$^+$; $^1$H NMR (500 MHz, DMSO-d6) δ 8.49 (d, J=1.7 Hz, 1H), 8.07 (d, J=1.2 Hz, 1H), 7.72 (dd, J=8.0, 2.1 Hz, 1H), 7.14 (d, J=8.0 Hz, 1H), 7.04 (t, J=5.7 Hz, 1H), 6.74 (d, J=2.2 Hz, 1H), 5.48 (s, 2H), 4.46-4.32 (m, 2H), 4.10 (q, J=6.8 Hz, 1H), 4.04-3.96 (m, 1H), 3.40-3.23 (m, 3H), 2.90 (s, 3H), 1.96-1.87 (m, 1H), 1.85-1.74 (m, 1H), 1.21 (d, J=6.8 Hz, 3H).

Example 93 (W223)

(S)-4,5-dimethyl-2-(((1-(4,4,4-trifluorobutyl)-1H-pyrazol-4-yl)methyl)amino)-4, 5,9,10-tetrahydro-6H,8H-pyrido[3,2,1-de]pteridin-6-one Compound 93 was prepared by the following steps:

13b

93a

93b

93c

-continued

93

Step 1: 1,1,1-trifluoro-4-iodobutane 93a (289 mg, 1.22 mmol), 4-(BOC-aminomethyl)pyrazole 13b (200 mg, 1.01 mmol), and cesium carbonate (660 mg, 2.03 mol) was dissolved in N, N-dimethylformamide (10 mL), and the reaction solution was stirred at room temperature for 12 hours. After the reaction, the reaction solution was filtered, and the filtrate was concentrated to obtain a crude product. The crude product was purified by silica gel column chromatography (petroleum ether/ethyl acetate=3/1) to obtain the target compound 93b (230 mg, yield 73%) as a white solid. ESI-MS (m/z): 308.4 [M+H]$^+$.

Step 2: Dissolve compound 93b (200 mg, 650 ummol) in dichloromethane (10 mL), add hydrochloric acid-dioxane solution (1M, 3.25 mL) to the above reaction solution, and the reaction solution was stirred at room temperature for 6 hours. After the reaction, the reaction solution was concentrated to obtain the target product 93c (134 mg) as a white solid, which was directly used in the next reaction. ESI-MS (m/z): 208.3 [M+H]$^+$.

Step 3: Compound 93c (103 mg, obtained from Step 2), 1i (126 mg, 0.5 mmol), and p-toluenesulfonic acid monohydrate (9 mg, 50 ummol) were dissolved in n-butanol (4 mL), and the reaction solution reacted at 160 degrees Celsius under microwave for 2 hours. After the reaction, the reaction solution was purified by reverse-phase preparative HPLC to obtain the target compound 93 (25 mg, two-step reaction yield 9%) as a white solid. ESI-MS (m/z): 424.3 [M+H]$^+$; $^1$H NMR (500 MHz, DMSO-d6) δ 7.58 (s, 1H), 7.37 (s, 1H), 6.60 (t, J=6.0 Hz, 1H), 4.26-4.17 (m, 2H), 4.10 (t, J=6.9 Hz, 3H), 4.04-3.99 (m, 1H), 3.30-3.23 (m, 2H), 2.95 (s, 3H), 2.54-2.49 (m, 2H), 2.23-2.12 (m, 2H), 1.95-1.91 (m, 2H), 1.82-1.78 (m, 1H), 1.22 (d, J=6.7 Hz, 3H).

Example 94 (W252)

(S)-4,5-dimethyl-2-((((6-((5-(trifluoromethyl)pyridin-2-yl)oxo)pyridin-3-yl)methyl)amino)-4,5,9,10-tetra-hydro-6H,8H-pyrido[3,2,1-de]pteridin-6-one Compound 94 was prepared by the following steps:

94b

94a

94c

94d

94

Step 1: Dissolve compound 94a (52 mg, 0.23 mmol) and 94b (25 mg, 0.21 mmol) in dimethyl sulfoxide (2 mL), add cuprous iodide (4 mg, 0.021 mol), anhydrous potassium phosphate (88 mg, 0.42 mol) and 2,2,6,6-tetramethyl-3,5-heptanedione (8 mg, 0.042 mol).

The reaction system was replaced with nitrogen and then heated to 100° C. and stirred for 2 hours. After the reaction was complete, water was added to quench the reaction, and the aqueous phase was extracted with ethyl acetate. The organic phases were combined, washed with saturated brine, dried over anhydrous sodium sulfate, filtered and concentrated. The residue was separated by silica gel column chromatography (petroleum ether/ethyl acetate=10/1) to obtain a white solid 94c (50 mg, yield 90%). ESI-MS (m/z): 266.4 [M+H]$^+$; $^1$H NMR (500 MHz, DMSO-d6) δ 8.79 (d, J=2.5 Hz, 1H), 8.77-8.73 (m, 1H), 8.49-8.44 (m, 1H), 8.41-8.38 (m, 1H), 7.50 (t, J=8.5 Hz, 2H).

Step 2: Dissolve compound 94c (50 mg, 0.19 mmol) in a mixed solution of methanol (10 mL) and ammonia water (1 mL), add Raney nickel (0.1 mL, aqueous suspension), and the mixture was stirred under hydrogen atmosphere at room temperature for 16 hours. After the reaction was complete, it was filtered with celite, the filter cake was washed with methanol, and the filtrate was concentrated to obtain a white solid 94d (45 mg, yield 88%). ESI-MS (m/z): 270.3 [M+H]$^+$.

Step 3: Dissolve compound 94d (45 mg, 0.17 mmol) and 1i (36 mg, 0.14 mmol) in 1, 4-dioxane (5 mL), add Pd$_2$(dba)$_3$ (15 mg, 0.017 mol), Sphos (14 mg, 0.034 mol) and cesium carbonate (109 mg, 0.34 mol). The reaction system was replaced with nitrogen and then heated to 100° C. and stirred for 16 hours. After the reaction solution was cooled to room temperature, the reaction solution was filtered through celite, and the filtrate was concentrated. The residue was purified by reverse phase preparative HPLC to give 94 (6 mg, yield 7%) as a white solid. ESI-MS (m/z): 486.3 [M+H]⁺; ¹H NMR (500 MHz, DMSO-d6) δ 8.61-8.59 (m, 1H), 8.29-8.23 (m, 2H), 7.92-7.86 (m, 1H), 7.31 (d, J=8.5 Hz, 1H), 7.17 (d, J=8.5 Hz, 1H), 7.13-7.05 (m, 1H), 4.49-4.35 (m, 2H), 4.17-4.08 (m, 1H), 4.05-3.98 (m, 1H), 3.29-3.24 (m, 1H), 2.94 (s, 3H), 2.55-2.50 (m, 2H), 1.97-1.88 (m, 1H), 1.85-1.73 (m, 1H), 1.23 (d, J=7.0 Hz, 3H).

Example 95 (W253)

(S)-2-(((6-(difluoro(6-(trifluoromethyl)pyridin-3-yl) methyl)pyridin-3-yl)methyl) amino)-4,5-dimethyl yl-4,5,9,10-tetrahydro-6H,8H-pyrido[3,2,1-de]pteridin-6-one Compound 95 was prepared by the following steps:

59d

95a

95b

-continued

1i

TsOH—H₂O, n-BuOH, 160° C., microwave, 2 h

95c

95

Step 1: Compound 59d (80 mg, 0.28 mmol) was dissolved in dichloromethane (2 mL), and diethylaminosulfur trifluoride (2.44 g, 15.14 mmol) was slowly added dropwise to the reaction system at 0° C. The reaction solution was stirred at 0° C. for 4 hours. LCMS monitored the completion of the reaction. The reaction solution was added dropwise into saturated aqueous sodium bicarbonate solution, and extracted with ethyl acetate. The organic phase was washed with saturated aqueous sodium chloride, dried over anhydrous sodium sulfate, filtered and concentrated. The residue was purified by silica gel column chromatography (petroleum ether/ethyl acetate=5/1) to obtain white solid 95a (83 mg, yield 96%). ESI-MS (m/z): 309.0 [M+H]⁺.

Step 2: Dissolve compound 95a (83 mg, 0.27 mmol) in N-methylpyrrolidone (3 mL), add zinc cyanide (63 mg, 0.54 mmol), Pd₂(dba)₃ (50 mg, 0.05 mmol) and S-Phos (22 mg, 0.05 mmol), the reaction system was replaced with nitrogen and stirred at 150° C. for 2 hours under microwave conditions. After the reaction solution was cooled to room temperature, it was filtered through celite, and the filtrate was concentrated. The residue was purified by silica gel column chromatography (petroleum ether/ethyl acetate=10/1) to obtain white solid 95b (66 mg, yield 82%). ESI-MS (m/z): 300.1 [M+H]⁺.

Step 3: Dissolve compound 95b (66 mg, 0.22 mmol) in methanol (5 mL) and ammonia water (1 mL), add Raney Nickel (0.5 mL, aqueous suspension), and replace the reaction system with hydrogen at room temperature Stir for 12 hours. The reaction solution was filtered through celite, and the filtrate was concentrated. The residue was purified by silica gel column chromatography (dichloromethane/methanol=10/1) to obtain colorless oily liquid 95c (66 mg, yield 99%). ESI-MS (m/z): 304.2 [M+H]⁺.

Step 4: Dissolve compound 95c (66 mg, 0.22 mmol) and compound 1i (37 mg, 0.15 mmol) in n-butanol (3 mL), add p-toluenesulfonic acid monohydrate (25 mg, 0.15 mmol). The reaction solution was stirred at 160° C. for 3 hours under microwave conditions. After the reaction solution was cooled to room temperature, the reaction solution was concentrated under reduced pressure, and the residue was purified by reverse-phase preparative HPLC to obtain compound 95 (8 mg, yield 9%) as a white solid. ESI-MS (m/z): 520.3

[M+H]⁺; ¹H NMR (500 MHz, DMSO-d6) δ 9.01 (s, 1H), 8.59 (s, 1H), 8.31 (d, J=7.7 Hz, 1H), 8.06 (d, J=8.2 Hz, 1H), 7.97 (d, J=9.4 Hz, 1H), 7.90 (d, J=8.1 Hz, 1H), 7.13 (t, J=5.8 Hz, 1H), 4.52-4.38 (m, 2H), 4.11 (q, J=6.7 Hz, 1H), 4.04-3.96 (m, 1H), 3.31-3.24 (m, 1H), 2.89 (s, 3H), 2.52-2.47 (m, 2H), 1.95-1.86 (m, 1H), 1.83-1.73 (m, 1H), 1.21 (d, J=6.8 Hz, 3H).

Example 96 (W256)

(S)-2-(((6-(4-fluorobenzyl)pyridin-3-yl)methyl)amino)-4,5-dimethyl-4,5,9,10-tetrahydro-6H,8H-pyrido[3,2,1-de]pteridin-6-one Compound 96 was prepared by the following steps:

96

Step 1: Compound 96a (1.0 g, 7.0 mmol), Boc₂O (2.29 g, 10.52 mmol) and N, N-diisopropylethylamine (1.81 g, 14.03 mmol, 2.44 mL) were dissolved in dichloromethane (10 mL). The reaction solution was stirred overnight at room temperature. LCMS monitored the completion of the reaction. The reaction solution was diluted with dichloromethane, washed with water, saturated ammonium chloride solution, and saturated aqueous sodium bicarbonate solution successively, the organic phase was dried over anhydrous sodium sulfate, filtered and concentrated to obtain a colorless oil 96b (1.6 g, yield 94%). ESI-MS (m/z): 243.3 [M+H]⁺.

Step 2: Compound 96b (200 mg, 824 umol), 4-fluorobenzylboronic acid pinacol ester 96c (194 mg, 824 umol), Pd(t-Bu₃P)₂ (42 mg, 82 umol) and potassium carbonate (227 mg, 1.65 mmol) were dispersed in 1, 4-dioxane (5 mL) and water (0.5 mL). The reaction system was heated to 100° C. and stirred overnight after replacing nitrogen. LCMS monitored the completion of the reaction. The reaction solution was diluted with ethyl acetate, washed with water and saturated brine successively, the organic phase was dried over anhydrous sodium sulfate, filtered and concentrated, and then purified by silica gel column chromatography (petroleum ether/ethyl acetate=2/1) to obtain a yellow oil Compound 96d (180 mg, yield 69%). ESI-MS (m/z): 317.5 [M+H]⁺.

Step 3: Dissolve compound 96d (180 mg, 568 umol) and 1, 4-dioxane hydrochloride solution (4M, 0.5 mL) in dichloromethane (2 mL), and stir overnight at room temperature. LCMS monitored the completion of the reaction. The reaction solution was concentrated to obtain yellow solid 96e (140 mg, yield 97%). ESI-MS (m/z): 217.5 [M+H]⁺.

Step 4: Dissolve compound 1i (50 mg, 197 umol), compound 96e (64 mg, 296 umol) and p-toluenesulfonic acid monohydrate (4 mg, 19 umol) in n-butanol (2 mL), and at 160° C. under the microwave conditions the reaction was carried out for 2 hours. LCMS monitored the completion of the reaction. The reaction solution was purified by reverse-phase preparative HPLC to obtain a white solid 95 (28 mg, yield 33%). ESI-MS (m/z): 433.5 [M+H]⁺; ¹H NMR (500 MHz, DMSO-d6) δ 8.44 (d, J=2.2 Hz, 1H), 7.64 (dd, J=8.0, 2.2 Hz, 1H), 7.28 (dd, J=8.3, 5.6 Hz, 2H), 7.20 (d, J=7.9 Hz, 1H), 7.09 (t, J=8.8 Hz, 2H), 7.02 (s, 1H), 4.42-4.31 (m, 2H), 4.11 (q, J=6.8 Hz, 1H), 4.03-3.97 (m, 3H), 3.28-3.24 (m, 1H), 2.92 (s, 3H), 2.55-2.48 (m, 2H), 1.94-1.87 (m, 1H), 1.83-1.76 (m, 1H), 1.22 (d, J=6.8 Hz, 3H).

Example 97 (W312)

(S)-2-(((6-((2-cyclopropylpyrimidin-5-yl)oxo)pyri-
din-3-yl)methyl)amino)-4,5-dimethyl-4,5,9,10-tetra-
hydro-6H,8H-pyrido[3,2,1-de]pteridin-6-one Compound 97 was prepared by the following steps:

-continued

Step 1: Dissolve compound 97a (800 mg, 6.13 mmol), compound 97b (748 mg, 6.13 mmol) and cesium carbonate (2.40 g, 7.35 mmol) in N, N-dimethylformamide (15 mL). The reaction solution was stirred at room temperature for 12 hours. After the reaction, the reaction solution was filtered, and the filtrate was concentrated to obtain a crude product. The crude product was purified by silica gel column chromatography (petroleum ether/ethyl acetate=3/1) to obtain the target compound 97c (950 mg, yield 66%). ESI-MS (m/z): 233.2 [M+H]$^+$.

Step 2: Intermediate 97c (500 mg, 2.15 mmol), cyclopropylboronic acid (923 mg, 10.75 mmol), 1, 1-bis (diphenylphosphine) dioxonium palladium dichloride (314 mg, 429 ummol) and potassium carbonate (549 mg, 4.30 mmol) were dissolved in a mixed solution of 1,4-dioxane (10 mL) and water (2 mL), and the reaction system was replaced with nitrogen and heated to 100° C. to react for 4 hours. After the reaction, the reaction solution was filtered with diatomaceous earth, and the filtrate was concentrated to obtain a crude product. The crude product was purified by silica gel column chromatography (petroleum ether/ethyl acetate=3/1) to obtain the target compound 97d (290 mg, yield 56%). ESI-MS (m/z): 239.4 [M+H]$^+$.

Step 3: Dissolve intermediate 97d (100 mg, 419 ummol) and Raney Nickel (0.1 mL, aqueous suspension) in a mixed solution of methanol (10 mL) and ammonia (1 mL), and the reaction solution was stirred at room temperature under hydrogen atmosphere for 12 hours. After the reaction, the reaction solution was filtered, and the filtrate was concentrated to obtain the crude product 97e (101 mg), which was directly used in the next reaction. ESI-MS (m/z): 243.5 [M+H]$^+$.

Step 4: Intermediate 97e (101 mg, obtained from Step 3), Intermediate 1i (106 mg, 419 umol) and p-toluenesulfonic acid monohydrate (8 mg, 42 umol) were dissolved in n-butanol (4 mL). The reaction solution reacted at 160° C. under microwave for 2 hours. After the reaction, the reaction solution was purified by reverse-phase preparative HPLC to obtain the target product 97 (34 mg, two-step reaction yield 17%). ESI-MS (m/z): 459.5 [M+H]$^+$; $^1$H NMR (500 MHz, DMSO-d6) δ 8.55 (s, 2H), 8.06 (d, J=2.5 Hz, 1H), 7.85 (dd, J=8.0, 2.5 Hz, 1H), 7.10 (d, J=8.5 Hz, 1H), 7.01 (br s, 1H), 4.40-4.30 (m, 2H), 4.11 (q, J=7.0 Hz, 1H), 4.03-3.98 (m, 1H), 3.30-3.25 (m, 2H), 2.93 (s, 3H), 2.53-2.48 (m, 2H), 2.26-2.21 (m, 1H), 1.93-1.78 (m, 2H), 1.23 (d, J=7.0 Hz, 3H), 1.07-0.96 (m, 4H).

Example 98 (W188)

(S)-2-(((6-((4,4-difluorocyclohexyl)oxo)pyridin-3-yl)methyl)amino)-4,5-dimethyl-4,5,9,10-tetrahydro-6H,8H-pyrido[3,2,1-de]pteridin-6-one Replace the 3,3-difluorocyclobutan-1-ol 12a in the first step in Example 12 with 4,4-difluorocyclohexane-1-ol, and use similar methods and reaction steps to obtain compound 98. ESI-MS (m/z): 459.2 [M+H]⁺; ¹H NMR (500 MHz, DMSO-d6) δ 8.09 (d, J=2.3 Hz, 1H), 7.66 (dd, J=8.6, 2.4 Hz, 1H), 6.98 (br s, 1H), 6.74 (d, J=8.4 Hz, 1H), 5.15 (br s, 1H), 4.40-4.24 (m, 2H), 4.11 (q, J=6.7 Hz, 1H), 4.06-3.98 (m, 1H), 3.32-3.24 (m, 1H), 2.94 (s, 3H), 2.55-2.48 (m, 2H), 2.10-1.72 (m, 10H), 1.22 (d, J=6.7 Hz, 3H).

Example 99 (W193)

(S)-4,5-dimethyl-2-(((6-((5-(trifluoromethyl)pyridin-3-yl)oxo)pyridin-3-yl)methyl)amino)-4,5,9,10-tetra-hydro-6H,8H-pyrido[3,2,1-de]pteridin-6-one Compound 99 was prepared by the following steps:

-continued

Step 1: Dissolve 5-(trifluoromethyl)pyridin-3-ol 99a (500 mg, 3.07 mmol) and 6-chloro-3-cyanopyridine 99b (509 mg, 3.68 mmol) in N, N-dimethylformamide (10 mL), and add cesium carbonate (2.0 g, 6.14 mmol). The reaction solution was stirred overnight at 80° C. LCMS monitored the completion of the reaction. The reaction solution was diluted with ethyl acetate, washed with water and saturated brine successively, the organic phase was dried over anhydrous sodium sulfate, concentrated by filtration, and the residue was purified by silica gel column chromatography (petroleum ether/ethyl acetate=5/1) to obtain colorless oil 99c (600 mg, 73% yield). ESI-MS (m/z): 266.0 [M+H]⁺.

Step 2: Dissolve intermediate 99c (550 mg, 2.07 mmol) in methanol (2 mL), add Raney nickel (0.5 mL, aqueous suspension) and ammonia water (0.2 mL) successively. The system was ventilated by hydrogen balloon and stirred overnight under the condition of hydrogen balloon. The completion of the reaction was monitored by LCMS. The reaction solution was diluted with methanol and filtered with suction. The filtrate was concentrated and purified by silica gel column chromatography (dichloromethane/metha-nol=10/1) to obtain a white solid 99d (400 mg, yield 71%). ESI-MS (m/z): 270.3 [M+H]⁺.

Step 3: Dissolve compound 1i (50 mg, 197 umol), compound 99d (79 mg, 296 umol) and p-toluenesulfonic acid monohydrate (4 mg, 19 umol) in n-butanol (2 mL). The reaction was carried out at 160° C. under microwave for 2 hours. LCMS monitored the completion of the reaction. The reaction solution was purified by reverse-phase preparative HPLC to obtain a white solid 99 (19 mg, yield 20%). ESI-MS (m/z): 486.3 [M+H]⁺; ¹H NMR (500 MHz, DMSO-d6) δ 8.83 (d, J=1.8 Hz, 1H), 8.76 (d, J=2.6 Hz, 1H), 8.15-8.08 (m, 2H), 7.88 (dd, J=8.4, 2.4 Hz, 1H), 7.15 (d, J=8.4 Hz, 1H), 7.04 (br s, 1H), 4.46-4.32 (m, 2H), 4.11 (q, J=6.7 Hz, 1H), 4.07-3.99 (m, 1H), 3.31-3.24 (m, 1H), 2.93 (s, 3H), 2.55-2.51 (m, 2H), 1.96-1.88 (m, 1H), 1.87-1.73 (m, 1H), 1.22 (d, J=6.8 Hz, 3H).

Example 100 (W239)

(S)-4,5-dimethyl-2-(((6-((2-(trifluoromethyl)pyridin-4-yl)oxo)pyridin-3-yl)methyl)amino)-4,5,9,10-tetra-hydro-6H,8H-pyrido[3,2,1-de]pteridin-6-one Using 2-(trifluoromethyl)pyridin-4-ol instead of 5-(trif-luoromethyl)pyridin-3-ol 99a in the first step in Example 99, compound 100 can be obtained with similar methods and reaction steps. ESI-MS (m/z): 486.3 [M+H]$^+$; $^1$HNMR (500 MHz, DMSO-d6) δ 8.71 (d, J=5.6 Hz, 1H), 8.24 (d, J=2.4 Hz, 1H), 7.93 (dd, J=8.4, 2.4 Hz, 1H), 7.63 (d, J=2.3 Hz, 1H), 7.42 (dd, J=5.6, 2.3 Hz, 1H), 7.20 (d, J=8.3 Hz, 1H), 7.07 (t, J=6.2 Hz, 1H), 4.47-4.36 (m, 2H), 4.12 (q, J=6.8 Hz, 1H), 4.05-3.98 (m, 1H), 3.29-3.24 (m, 1H), 2.93 (s, 3H), 2.55-2.49 (m, 2H), 1.96-1.88 (m, 1H), 1.85-1.77 (m, 1H), 1.23 (d, J=6.7 Hz, 3H).

Example 101 (W213)

(S)-4,5-dimethyl-2-((4-((6-(trifluoromethyl)pyridin-3-yl)oxo)benzyl)amino)-4,5, 9, 10-tetrahydro-6H, 8H-pyrido[3,2,1-de]pteridin-6-one Replace 5-(trifluoromethyl)pyridin-3-ol 99a and 6-chloro-3-cyanopyridine 99b in the first step in Example 99 with 4-hydroxybenzonitrile and 5-fluoro-2-(trifluoromethyl) pyridine, compound 101 can be obtained by using similar methods and reaction steps. ESI-MS (m/z): 485.3 [M+H]$^+$; $^1$H NMR (500 MHz, DMSO-d6) δ 8.52 (d, J=2.8 Hz, 1H), 7.90-7.85 (m, 1H), 7.50-7.45 (m, 1H), 7.44-7.39 (m, 2H), 7.18-7.11 (m, 2H), 7.10-7.01 (m, 1H), 4.50-4.35 (m, 2H), 4.15-4.10 (m, 1H), 4.06-3.97 (m, 1H), 3.31-3.23 (m, 1H), 2.93 (s, 3H), 2.55-2.49 (m, 2H), 1.98-1.87 (m, 1H), 1.86-1.74 (in, 1H), 1.23 (d, J=6.4 Hz, 3H).

Example 102 (W214)

(S)-4,5-dimethyl-2-(((6-((1-(2,2,2-trifluoroethyl)piperidin-4-yl)oxo)pyridin-3-yl) methyl)amino)-4,5,9,10-tetrahydro-6H,8H-pyrido[3,2,1-de]pteridin-6-one Compound 102 was prepared by the following steps:

-continued

102e

1i

TsOH—H₂O,
n-BuOH, 160° C.,
microwave, 2 h

102

Step 1: Dissolve compound 102a (500 mg, 2.48 mmol) in N, N-dimethylformamide (8 mL), add sodium hydride (105 mg, content 60%, 2.62 mmol) at 0° C., and the reaction solution was stirred for half an hour. Compound 99b (344 mg, 2.48 mmol) was added to the reaction solution, and the reaction solution continued to be stirred at 0° C. for 2 hours. LCMS monitored the completion of the reaction. The reaction solution was quenched with saturated aqueous ammonium chloride and extracted with ethyl acetate. The organic phase was washed with saturated brine, dried over anhydrous sodium sulfate, filtered and concentrated. The residue was purified by silica gel column chromatography (petroleum ether/ethyl acetate=5/1) to obtain white solid 102b (606 mg, yield 81%). ESI-MS (m/z): 304.3 [M+H]⁺.

Step 2: Compound 102b (606 mg, 2.0 mmol) was dissolved in dioxane hydrochloride (4M, 5 mL), and the reaction solution was stirred at room temperature for 1 hour. LCMS monitored the completion of the reaction. The reaction solution was concentrated to obtain the crude product of compound 102c, which was directly used in the next reaction. ESI-MS (m/z): 204.5 [M+H]⁺.

Step 3: Dissolve the crude compound 102c obtained in the previous step in N, N-dimethylformamide (5 mL), add potassium carbonate (502 mg, 3.63 mmol) and trifluoroethyl trifluoromethanesulfonate (280 mg, 1.21 mmol), and the reaction solution was stirred at room temperature for 12 hours. LCMS monitored the completion of the reaction. The reaction solution was diluted with saturated brine and extracted with ethyl acetate. The organic phase was washed with saturated brine, dried over anhydrous sodium sulfate, filtered and concentrated to obtain the crude compound 102d, which was directly used in the next reaction. ESI-MS (m/z): 286.4 [M+H]⁺.

Step 4: Dissolve the 102d crude product obtained in the previous step in methanol (9 mL) and ammonia water (1 mL), add Raney Nickel (0.5 mL, aqueous suspension), and stir the reaction system at room temperature for 12 hours after replacing hydrogen. LCMS monitored the completion of the reaction. The reaction solution was filtered through celite, and the filtrate was concentrated. The residue was purified by silica gel column chromatography (dichloromethane/methanol=5/1) to obtain yellow oily liquid 102e (171 mg, yield 29% in three steps). ESI-MS (m/z): 290.4 [M+H]⁺.

Step 5: Dissolve compound 102e (160 mg, 0.55 mmol) and compound 1i (94 mg, 0.37 mmol) in n-butanol (4 mL), add p-toluenesulfonic acid monohydrate (71 mg, 0.37 mmol), and the reaction solution was stirred at 160° C. for 3 hours under microwave conditions. After the reaction solution was cooled to room temperature, the reaction solution was concentrated under reduced pressure, and the residue was purified by reverse-phase preparative HPLC to obtain compound 102 (20 mg, yield 7%) as a white solid. ESI-MS (m/z): 506.3 [M+H]⁺; ¹H NMR (400 MHz, DMSO) δ 8.11-8.06 (m, 1H), 7.68-7.62 (m, 1H), 6.99 (br s, 1H), 6.75-6.68 (m, 1H), 5.21-4.92 (m, 1H), 4.75-4.65 (m, 1.5H), 4.38-4.22 (m, 2H), 4.11 (q, J=6.8 Hz, 1H), 4.06-3.97 (m, 1H), 3.76-3.66 (m, 1.5H), 3.32-3.22 (m, 2H), 3.21-3.13 (m, 1H), 2.93 (s, 3H), 2.88-2.79 (m, 1H), 2.60-2.50 (m, 2H), 2.00-1.88 (m, 3H), 1.84-1.73 (m, 1H), 1.70-1.50 (m, 2H), 1.22 (d, J=6.8 Hz, 3H).

Example 103 (W195)

(S)-4,5-dimethyl-2-(((5-methyl-6-((6-(trifluorom-ethyl)pyridin-3-yl)oxo)pyridin-3-yl)methyl)amino)-4,5,9,10-tetrahydro-6H,8H-pyrido[3,2,1-de]pteridin-6-one Replace 5-(trifluoromethyl)pyridine-3-ol 99a and 6-chloro-3-cyanopyridine 99b in the first step in Example 99 with 6-(trifluoromethyl)pyridine-3-ol and 6-chloro-5-methyl-3-cyanopyridine, compound 103 can be obtained by using similar methods and reaction steps. ESI-MS (m/z): 500.2 [M+H]⁺; ¹HNMR (500 MHz, DMSO-d6) δ 8.61 (d, J=2.5 Hz, 1H), 7.95 (d, J=8.6 Hz, 1H), 7.92 (d, J=1.5 Hz, 1H), 7.83 (dd, J=8.6, 2.5 Hz, 1H), 7.75 (d, J=1.5 Hz, 1H), 7.02 (t, J=5.6 Hz, 1H), 4.40-4.29 (m, 2H), 4.11 (q, J=6.7 Hz, 1H), 4.04-3.98 (m, 1H), 3.29-3.22 (m, 1H), 2.93 (s, 3H), 2.55-2.49 (m, 2H), 2.30 (s, 3H), 1.93-1.86 (m, 1H), 1.82-1.77 (m, 1H), 1.22 (d, J=6.8 Hz, 3H).

Example 104 (W198)

4-Methyl-2-(((6-((6-(trifluoromethyl)pyridin-3-yl)oxo)pyridin-3-yl)methyl)amino)-4,5,9,10-tetrahydro-6H,8H-pyrido[3,2,1-de]pteridin-6-one Compound 104 was prepared by the following steps:

104

Step 1: Dissolve 2,4-dichloropyrido[3,2-d]pyrimidine 1f (0.70 g, 3.50 mmol) and glycine methyl ester hydrochloride 104a (0.66 g, 5.25 mmol) in THF (10 mL), and add N, N-diisopropylethylamine (1.36 g, 10.50 mmol, 1.83 mL). The reaction solution was stirred overnight at room temperature. The completion of the reaction was monitored by LCMS. The reaction solution was concentrated, and the residue was purified by silica gel column chromatography (petroleum ether/ethyl acetate=1/1) to obtain yellow oil 104b (0.70 g, yield 79%). ESI-MS (m/z): 275.3 [M+Na]+.

Step 2: Dissolve compound 104b (0.70 g, 2.77 mmol) in tetrahydrofuran (30 mL), add aqueous hydrochloric acid (6M, 0.46 mL) and platinum dioxide (62 mg, 0.28 mmol). The reaction system was replaced with hydrogen by using a hydrogen balloon and stirred under the pressure of hydrogen balloon at room temperature for 48 hours. The reaction was complete as monitored by LCMS. The reaction solution was diluted with methanol, filtered, and the filtrate was concentrated and purified by silica gel column chromatography (dichloromethane/methanol=10/1) to obtain gray solid 104c (0.35 g, yield 56%). ESI-MS (m/z): 225.5 [M+H]+.

Step 3: Dissolve compound 104c (100 mg, 0.45 mmol) and iodomethane (94 mg, 0.67 mmol) in acetonitrile (2 mL), add cesium carbonate (290 mg, 0.89 mmol), and at 50° C. the reaction was carried out for 2 hours. LCMS monitored the completion of the reaction. The reaction solution was diluted with dichloromethane, filtered, and the filtrate was concentrated and purified by silica gel column chromatography (dichloromethane/methanol=20/1) to obtain a yellow solid 104d (80 mg, yield 75%). ESI-MS (m/z): 239.5 [M+H]+.

Step 4: Dissolve compound 104d (50 mg, 209 umol), compound 11d (67 mg, 251 umol) and p-toluenesulfonic acid monohydrate (4 mg, 21 umol) in n-butanol (2 mL). The reaction was carried out at 160° C. under microwave for 2 hours. LCMS monitored the completion of the reaction. The reaction solution was purified by reverse-phase preparative HPLC to obtain a white solid 104 (40 mg, yield 40%). ESI-MS (m/z): 472.2 [M+H]+; 1H NMR (500 MHz, DMSO-d6) δ 8.63 (d, J=2.7 Hz, 1H), 8.12 (d, J=2.5 Hz, 1H), 7.97 (d, J=8.6 Hz, 1H), 7.89 (dd, J=8.5, 2.6 Hz, 1H), 7.85 (dd, J=8.5, 2.6 Hz, 1H), 7.17 (dd, J=8.4, 0.7 Hz, 1H), 7.03 (br s, 1H), 4.37 (d, J=6.4 Hz, 2H), 4.00 (s, 2H), 3.73-3.62 (m, 2H), 2.91 (s, 3H), 2.53-2.47 (m, 2H), 1.89-1.78 (m, 2H).

Example 105 (W199)

(S)-5-methyl-4-(methyl-d3)-2-(((6-((6-(trifluorom-ethyl)pyridin-3-yl)oxo)pyridin-3-yl) methyl)amino)-4,5,9,10-tetrahydro-6H,8H-pyrido[3,2,1-de]pteridin-6-one Compound 105 was prepared by the following steps:

105b

-continued

105c

105d

105

Step 1: Dissolve 2,4-dichloropyrido[3,2-d]pyrimidine 1f (2.0 g, 3.5 mmol) and L-alanine methyl ester hydrochloride 105a (1.81 g, 13.0 mmol) in tetrahydrofuran (20 mL), add N,N-diisopropylethylamine (3.88 g, 30.0 mmol, 5.22 mL), and stir the reaction solution overnight at room temperature. The completion of the reaction was monitored by LCMS. The reaction solution was concentrated, and the residue was purified by silica gel column chromatography (petroleum ether/ethyl acetate=1/1) to obtain yellow oil 105b (2.5 g, yield 93%). ESI-MS (m/z): 267.3 [M+H]$^+$.

Step 2: Dissolve compound 105b (2.5 g, 9.37 mmol) in tetrahydrofuran (30 mL), add aqueous hydrochloric acid (6M, 1.56 mL) and platinum dioxide (212 mg, 0.94 mmol), and replace the reaction system with hydrogen by using a hydrogen balloon. The reaction solution was stirred at room temperature under hydrogen balloon pressure for 48 hours, and LCMS monitored the completion of the reaction. The reaction solution was diluted with methanol, filtered, and the filtrate was concentrated and purified by silica gel column chromatography (dichloromethane/methanol=10/1) to obtain gray solid 105c (0.8 g, yield 35%). ESI-MS (m/z): 239.5 [M+H]$^+$.

Step 3: Dissolve compound 105c (100 mg, 0.42 mmol) and deuterated iodomethane (121 mg, 0.84 mmol) in acetonitrile (10 mL), add cesium carbonate (273 mg, 0.84 mmol), at 50° C. the reaction was carried out for 2 hours. LCMS monitored the completion of the reaction. The reaction solution was diluted with dichloromethane, filtered, and the filtrate was concentrated and purified by silica gel column chromatography (dichloromethane/methanol=20/1) to obtain a white solid 105d (80 mg, yield 74%). ESI-MS (m/z): 256.3 [M+H]$^+$.

Step 4: Dissolve compound 105d (50 mg, 195 umol), compound 11d (63 mg, 234 umol) and p-toluenesulfonic acid monohydrate (4 mg, 19 umol) in n-butanol (2 mL). The reaction was carried out at 160° C. under microwave for 2 hours. LCMS monitored the completion of the reaction. The reaction solution was purified by reverse-phase preparative HPLC to obtain a white solid 105 (33 mg, yield 34%). MS (ESI): m/z 489.2 [M+H]$^+$; $^1$H NMR (500 MHz, DMSO-d6) δ 8.63 (d, J=2.6 Hz, 1H), 8.12 (d, J=2.4 Hz, 1H), 7.97 (d, J=8.6 Hz, 1H), 7.89 (dd, J=8.5, 2.6 Hz, 1H), 7.85 (dd, J=8.5, 2.6 Hz, 1H), 7.17 (d, J=8.4 Hz, 1H), 7.06 (br s, 1H), 4.45-4.31 (m, 2H), 4.11 (q, J=6.8 Hz, 1H), 4.04-3.96 (m, 1H), 3.30-3.22 (m, 1H), 2.62-2.50 (m, 2H), 1.96-1.87 (m, 1H), 1.84-1.73 (m, 1H), 1.22 (d, J=6.8 Hz, 3H).

Example 106 (W190)

(S)-5-(methoxymethyl)-4-methyl-2-(((6-((6-(trifluoromethyl)pyridin-3-yl)oxo)pyridin-3-yl)methyl) amino)-4,5,9,10-tetrahydro-6H,8H-pyrido[3,2,1-de] pteridin-6-one Compound 106 was prepared by the following steps:

1f

106a

106b

-continued

106c

MeI, Cs₂CO₃ →

106d

11d

TsOH—H₂O,
n-BuOH, 160° C., microwave, 2 h →

106

Step 1: 2,4-dichloropyrido[3,2-d]pyrimidine 1f (2 g, 10.00 mmol) and O-methyl-L-serine methyl ester hydrochloride 106a (2.45 g, 15.00 mmol) were dissolved in tetrahydrofuran (20 mL), N, N-diisopropylethylamine (3.88 g, 30.00 mmol, 5.22 mL) was added, and the reaction solution was stirred overnight at room temperature. The completion of the reaction was monitored by LCMS. The reaction solution was concentrated, and the residue was purified by silica gel column chromatography (petroleum ether/ethyl acetate=1/1) to obtain yellow oil 106b (2.5 g, yield 84%). ESI-MS (m/z): 297.2 [M+H]⁺.

Step 2: Dissolve compound 106b (2.5 g, 8.43 mmol) in tetrahydrofuran (30 mL), add aqueous hydrochloric acid (6N, 1.40 mL) and platinum dioxide (191 mg, 0.84 mmol), and replace the reaction system with hydrogen by using a hydrogen balloon. The reaction solution was stirred at room temperature under hydrogen balloon pressure for 48 hours, and LCMS monitored the completion of the reaction. The reaction solution was diluted with methanol, filtered through celite, and the filtrate was concentrated and purified by silica gel column chromatography (dichloromethane/methanol=10/1) to obtain a gray solid 106c (2.0 g, yield 88%). ESI-MS (m/z): 269.3 [M+H]⁺.

Step 3: Dissolve compound 106c (500 mg, 1.86 mmol) and iodomethane (343 mg, 2.42 mmol) in acetonitrile (10 mL), add cesium carbonate (1.21 g, 372 mmol), and at 50° C. the reaction was carried out for 2 hours. LCMS monitored the completion of the reaction. The reaction solution was diluted with dichloromethane, filtered, and the filtrate was concentrated and purified by silica gel column chromatography (dichloromethane/methanol=20/1) to obtain a white solid 106d (350 mg, yield 66%). ESI-MS (m/z): 283.3 [M+H]⁺.

Step 4: Dissolve compound 106d (50 mg, 176 umol), compound 11d (71 mg, 265 umol) and p-toluenesulfonic acid monohydrate (3 mg, 17 umol) in n-butanol (2 mL). The reaction was carried out at 160° C. under microwave for 2 hours. LCMS monitored the completion of the reaction. The reaction solution was purified by reverse-phase preparative HPLC to obtain a white solid 106 (6 mg, yield 7%). ESI-MS (m/z): 516.2 [M+H]⁺; ¹H NMR (500 MHz, DMSO-d6) δ 8.63 (d, J=2.7 Hz, 1H), 8.13 (d, J=2.4 Hz, 1H), 7.97 (d, J=8.6 Hz, 1H), 7.89 (dd, J=8.5, 2.6 Hz, 2H), 7.85 (dd, J=8.5, 2.6 Hz, 2H), 7.17 (d, J=8.4 Hz, 1H), 6.99 (br s, 1H), 4.45-4.32 (m, 2H), 4.22 (t, J=2.8 Hz, 1H), 4.02-3.95 (m, 1H), 3.71-3.60 (m, 2H), 3.40-3.30 (m, 1H), 3.15 (s, 3H), 2.96 (s, 3H), 2.55-2.47 (m, 2H), 1.88 (d, J=7.6 Hz, 1H), 1.74 (s, 1H).

Example 107 (W192)

(S)-5-(hydroxymethyl)-4-methyl-2-(((6-((6-(trifluo-romethyl)pyridin-3-yl)oxo)pyridin-3-yl)methyl) amino)-4,5,9,10-tetrahydro-6H,8H-pyrido[3,2,1-de] pteridin-6-one Compound 107 was prepared by the following steps:

106d

BBr₃ →

107a

11d

TsOH—H₂O, n-BuOH, 160° C., microwave, 2 h →

-continued

107

Step 1: Dissolve 106d (250 mg, 0.88 mmol) in dichloromethane (2 mL), then add boron tribromide (2.21 g, 8.84 mmol, 0.85 mL) dropwise at 0° C., and after the addition is complete, place at 0° C. to react for two hours. LCMS monitored the completion of the reaction. The reaction solution was carefully quenched with sodium bicarbonate solution, extracted with dichloromethane, the organic phase was washed with saturated brine, dried over anhydrous sodium sulfate, concentrated by filtration, and the residue was subjected to silica gel column chromatography (dichloromethane/methanol=10/1) for purification to obtain 107a as a white solid (100 mg, 42% yield). ESI-MS (m/z): 269.3 [M+H]$^+$.

Step 2: Dissolve compound 107a (30 mg, 111 umol), compound 11d (45 mg, 167 umol) and p-toluenesulfonic acid monohydrate (2 mg, 11 umol) in n-butanol (2 mL). The reaction was carried out at 160° C. under microwave for 2 hours. LCMS monitored the completion of the reaction. The reaction solution was purified by reverse-phase preparative HPLC to obtain a white solid 107 (9 mg, yield 17%). ESI-MS (m/z): 501.6 [M+H]$^+$; $^1$H NMR (500 MHz, DMSO-d6) δ 8.64 (d, J=2.6 Hz, 1H), 8.27 (s, 1H), 8.13 (d, J=2.5 Hz, 1H), 7.97 (d, J=8.6 Hz, 1H), 7.89 (dd, J=8.6, 2.5 Hz, 2H), 7.86 (dd, J=8.6, 2.5 Hz, 2H), 7.17 (d, J=8.4 Hz, 1H), 6.95 (br s, 1H), 4.44-4.30 (m, 2H), 4.08-3.97 (m, 2H), 3.76-3.65 (m, 2H), 3.40-3.30 (m, 1H), 2.96 (s, 3H), 2.52-2.47 (m, 2H), 1.92-1.86 (m, 1H), 1.83-1.72 (s, 1H).

Example 108 (W207)

(S)-5-(hydroxymethyl)-4-(methyl-d3)-2-(((6-((6-(trifluoromethyl)pyridin-3-yl)oxo)pyridine-3-yl)
methyl)amino)-4,5,9,10-tetrahydro-6H,8H-pyrido[3,
2,1-de]pteridin-6-one Compound 108 was prepared by the following steps:

106c

108a

11d

108b

108

Step 1: Dissolve compound 106c (200 mg, 0.74 mmol) and deuteroiodomethane (215 mg, 1.49 mmol) in acetonitrile (5 mL), add cesium carbonate (485 mg, 1.49 mmol), and at 50° C. the reaction was carried out for 2 hours. LCMS monitored the completion of the reaction. The reaction solution was diluted with dichloromethane, filtered, and the filtrate was concentrated and purified by silica gel column chromatography (dichloromethane/methanol=20/1) to obtain a yellow solid 108a (200 mg, yield 94%). ESI-MS (m/z): 286.3 [M+H]$^+$.

Step 2: 108a (200 mg, 0.87 mmol) was dissolved in dichloromethane (2 mL), and boron tribromide (2.19 g, 8.75 mmol, 0.84 mL) was added dropwise at 0° C., and after the addition was completed, at 0° C. the reaction was carried out for two hours. LCMS monitored the completion of the reaction. The reaction solution was carefully quenched with sodium bicarbonate solution, extracted with dichloromethane, the combined organic phases were dried over anhydrous sodium sulfate, concentrated by filtration, and the residue was purified by silica gel column chromatography (dichloromethane/methanol=10/1) to obtain white solid 108b (150 mg, 75% yield). ESI-MS (m/z): 272.3 [M+H]$^+$.

Step 3: Dissolve compound 108b (50 mg, 184 umol), compound 11d (59 mg, 220 umol) and p-toluenesulfonic acid monohydrate (3.5 mg, 18 umol) in n-butanol (2 mL). The reaction was carried out at 160° C. under microwave for 2 hours. LCMS monitored the completion of the reaction. The reaction solution was purified by reverse-phase preparative HPLC to obtain a white solid 108 (41 mg, yield 44%). ESI-MS (m/z): 505.4 [M+H]$^+$; $^1$H NMR (500 MHz, DMSO-d6) δ 8.64 (d, J=2.7 Hz, 1H), 8.15 (d, J=2.4 Hz, 1H), 7.97 (d, J=8.6 Hz, 1H), 7.92 (dd, J=8.4, 2.5 Hz, 1H), 7.87 (dd, J=8.5, 2.7 Hz, 1H), 7.19 (d, J=8.4 Hz, 1H), 5.07 (br s, 1H), 4.52-4.37 (m, 2H), 4.14 (s, 1H), 4.07-4.00 (m, 1H), 3.80-3.68 (m, 2H), 3.35-3.29 (m, 1H), 2.56-2.50 (m, 2H), 1.97-1.88 (m, 1H), 1.82-1.71 (m, 1H).\

Example 109 (W220)

(S)-5-((R)-1-hydroxyethyl)-4-methyl-2-(((6-((6-(trif-luoromethyl)pyridin-3-yl)oxo)pyridine-3-yl)methyl) amino)-4,5,9,10-tetrahydro-6H,8H-pyrido[3,2,1-de] pteridin-6-one Compound 109 was prepared by the following steps:

-continued

Step 1: Dissolve 2,4-dichloropyrido[3,2-d]pyrimidine 1f (1.0 g, 5.0 mmol) and L-threonine methyl ester hydrochloride 109a (1.10 g, 6.5 mmol) in tetrahydrofuran (10 mL), add N, N-diisopropylethylamine (1.94 g, 15.0 mmol, 2.61 mL), and stir the reaction solution overnight at room temperature. The completion of the reaction was monitored by LCMS. The reaction solution was concentrated, and the residue was purified by silica gel column chromatography (petroleum ether/ethyl acetate=1/1) to obtain yellow oil 109b (1.3 g, yield 87%). ESI-MS (m/z): 297.3 [M+H]$^+$.

Step 2: Dissolve compound 109b (1.3 g, 4.38 mmol) in tetrahydrofuran (20 mL), add aqueous hydrochloric acid (6M, 0.73 mL) and platinum dioxide (99 mg, 0.44 mmol), and replace the reaction system with hydrogen by using a hydrogen balloon. The reaction solution was stirred at room temperature under hydrogen balloon pressure for 48 hours, and LCMS monitored the completion of the reaction. The reaction solution was diluted with methanol, filtered through celite, and the filtrate was concentrated and purified by silica gel column chromatography (dichloromethane/methanol=10/1) to obtain a gray solid 109c (0.4 g, yield 33%). ESI-MS (m/z): 269.3 [M+H]$^+$.

Step 3: Dissolve compound 109c (150 mg, 0.56 mmol) and iodomethane (118 mg, 0.84 mmol) in acetonitrile (3 mL), add cesium carbonate (363 mg, 1.12 mmol), and at 50° C. the reaction was carried out for 2 hours. LCMS monitored the completion of the reaction. The reaction solution was diluted with dichloromethane, filtered, and the filtrate was concentrated and purified by silica gel column chromatography (dichloromethane/methanol=10/1) to obtain a white solid 109d (100 mg, yield 63%). ESI-MS (m/z): 283.4 [M+H]$^+$.

Step 4: Dissolve compound 109d (50 mg, 176 umol), compound 11d (57 mg, 212 umol) and p-toluenesulfonic acid monohydrate (3.3 mg, 17 umol) in n-butanol (2 mL). The reaction was carried out at 160° C. under microwave for 2 hours. LCMS monitored the completion of the reaction. The reaction solution was purified by reverse-phase preparative HPLC to obtain a white solid 109 (40 mg, yield 44%). ESI-MS (m/z): 516.3 [M+H]$^+$; $^1$H NMR (400 MHz, DMSO-d6) δ 8.64 (d, J=2.6 Hz, 1H), 8.19 (s, 1H), 8.13 (d, J=2.4 Hz, 1H), 7.97 (d, J=8.6 Hz, 1H), 7.89 (dd, J=8.5, 2.5 Hz, 1H), 7.86 (dd, J=8.5, 2.5 Hz, 2H), 7.17 (d, J=8.4 Hz, 1H), 7.02 (t, J=6.4 Hz, 1H), 4.93 (br s, 1H), 4.47-4.27 (m, 2H), 4.17-4.06 (m, 1H), 3.93-3.83 (m, 2H), 3.17-3.10 (m, 1H), 3.07 (s, 3H), 2.52-247 (m, 2H), 1.98-1.88 (m, 1H), 1.82-1.68 (m, 1H), 1.09 (d, J=6.2 Hz, 3H).

Example 110 (W231)

(S)-5-((S)-1-hydroxyethyl)-4-methyl-2-(((6-((6-(trifluoromethyl)pyridin-3-yl)oxo)pyridine-3-yl)methyl)amino)-4,5,9,10-tetrahydro-6H,8H-pyrido[3,2,1-de]pteridin-6-one Compound 110 was prepared by the following steps:

1f

110b

-continued

110c

110d

110

Step 1: Dissolve 2,4-dichloropyrido[3,2-d]pyrimidine 1f (3.0 g, 15.0 mmol) and L-allothreonine methyl ester hydrochloride 110a (3.31 g, 19.5 mmol) in dichloromethane (30 mL), add N, N-diisopropylethylamine (5.82 g, 45.0 mmol, 7.84 mL), and stir the reaction solution overnight at room temperature. The completion of the reaction was monitored by LCMS. The reaction solution was concentrated, and the residue was purified by silica gel column chromatography (petroleum ether/ethyl acetate=1/1) to obtain yellow oil 110b (3.8 g, yield 85%). ESI-MS (m/z): 297.3 [M+H]$^+$.

Step 2: Dissolve compound 110b (1.5 g, 5.06 mmol) in tetrahydrofuran (20 mL), add aqueous hydrochloric acid (6N, 0.84 mL) and platinum dioxide (114.80 mg, 0.51 mmol), and replace the reaction system with hydrogen by using a hydrogen balloon. The reaction solution was stirred at room temperature under hydrogen balloon pressure for 48 hours, and LCMS monitored the completion of the reaction. The reaction solution was diluted with methanol, filtered, and the filtrate was concentrated and purified by silica gel column chromatography (dichloromethane/methanol=10/1) to obtain gray solid 110c (0.5 g, yield 36%). ESI-MS (m/z): 269.5 [M+H]$^+$.

Step 3: Dissolve compound 110c (100 mg, 0.37 mmol) and iodomethane (79 mg, 0.56 mmol) in acetonitrile (3 mL), add cesium carbonate (242 mg, 0.74 mmol), and at 50° C. the reaction was carried out for 2 hours. LCMS monitored the completion of the reaction. The reaction solution was diluted with dichloromethane, filtered, and the filtrate was concentrated and purified by silica gel column chromatography (dichloromethane/methanol=10/1) to obtain a white solid 110d (80 mg, yield 76%). ESI-MS (m/z): 283.3 [M+H]$^+$.

Step 4: Dissolve compound 110d (50 mg, 176 umol), compound 11d (57 mg, 212 umol) and p-toluenesulfonic acid monohydrate (3.3 mg, 17 umol) in n-butanol (2 mL). The reaction was carried out at 160° C. under microwave for 2 hours. LCMS monitored the completion of the reaction. The reaction solution was purified by reverse-phase preparative HPLC to obtain a white solid 110 (44 mg, yield 48%). ESI-MS (m/z): 516.4 [M+H]$^+$; $^1$H NMR (500 MHz, DMSO-d6) δ 8.65 (d, J=2.7 Hz, 1H), 8.17-8.13 (m, 1H), 7.98 (d, J=8.6 Hz, 1H), 7.92 (dd, J=8.4, 2.5 Hz, 1H), 7.87 (dd, J=8.6, 2.7 Hz, 1H), 7.19 (d, J=8.3 Hz, 1H), 7.10-6.90 (m, 1H), 5.05 (d, J=4.8 Hz, 1H), 4.52-4.34 (m, 2H), 4.16-4.02 (m, 3H), 3.25-3.17 (m, 1H), 3.05 (s, 3H), 2.55-2.47 (m, 2H), 1.99-1.90 (m, 1H), 1.80-1.70 (m, 1H), 1.04 (d, J=6.4 Hz, 3H).

Example 111 (W241)

(S)-2-(((6-((6-(trifluoromethyl)pyridin-3-yl)oxo)pyridin-3-yl)methyl)amino)-5,6, 8a,9, 10,11-hexahydro-4H,8H-pyrido[3,2,1-de]pyrrolo[2,1-h]pteridin-8-one Compound 111 was prepared by the following steps:

-continued

111

Step 1: Dissolve 2,4-dichloropyrido[3,2-d]pyrimidine 1f (1.00 g, 5.00 mmol) and L-proline methyl ester hydrochloride 111a (1.08 g, 6.50 mmol) in tetrahydrofuran (10 mL), add N, N-diisopropylethylamine (1.94 g, 15.00 mmol, 2.61 mL), and stir the reaction solution overnight at room temperature. The completion of the reaction was monitored by LCMS, the reaction solution was concentrated, and the residue was purified by silica gel column chromatography (petroleum ether/ethyl acetate=1/1) to obtain a yellow solid 111b (1.20 g, yield 82%). ESI-MS (m/z): 293.2 [M+H]$^+$.

Step 2: Dissolve compound 111b (1.20 g, 4.10 mmol) in tetrahydrofuran (20 mL), add aqueous hydrochloric acid (6N, 0.70 mL) and platinum dioxide (94 mg, 0.41 mmol), and replace the reaction system with hydrogen by using a hydrogen balloon. The reaction solution was stirred at room temperature under hydrogen balloon pressure for 48 hours, and LCMS monitored the completion of the reaction. The reaction solution was diluted with methanol, filtered, and the filtrate was concentrated and purified by silica gel column chromatography (dichloromethane/methanol=20/1) to obtain a yellow solid 111c (0.60 g, yield 55%). ESI-MS (m/z): 265.3 [M+H]$^+$.

Step 3: Dissolve compound 111c (50 mg, 188 umol), compound 11d (67 mg, 251 umol) and p-toluenesulfonic acid monohydrate (3.6 mg, 18 umol) in n-butanol (2 mL). The reaction was carried out at 160° C. under microwave for 2 hours. LCMS monitored the completion of the reaction. The reaction solution was purified by reverse-phase preparative HPLC to obtain white solid 111 (15 mg, yield 16%). ESI-MS (m/z): 498.3 [M+H]$^+$; $^1$H NMR (500 MHz, DMSO-d6) δ 8.64 (d, J=2.6 Hz, 1H), 8.13 (d, J=2.3 Hz, 1H), 7.98 (d, J=8.6 Hz, 1H), 7.90 (dd, J=8.5, 2.6 Hz, 1H), 7.86 (dd, J=8.5, 2.6 Hz, 2H), 7.17 (d, J=8.4 Hz, 1H), 7.06 (t, J=6.4 Hz, 1H), 4.44-4.32 (m, 2H), 4.14-4.04 (m, 2H), 3.62-3.54 (m, 1H), 3.49-3.40 (m, 1H), 3.25-3.16 (m, 1H), 2.52-2.47 (m, 2H), 2.26-2.20 (m, 1H), 2.00-1.75 (m, 5H).

Example 112 (W242)

(8aS, 10S)-10-hydroxyl-2-(((6-((6-(trifluoromethyl)pyridin-3-yl)oxo)pyridin-3-yl)methyl)amino)-5,6,8a,9,10,11-hexahydro-4H,8H-pyrido[3,2,1-de]pyrrolo[2,1-h]pteridin-8-one Compound 112 was prepared by the following steps:

112a

DIPEA, THF

1f

H₂, PtO₂

HCl, THF

112b

11d

TsOH—H₂O, n-BuOH, 160° C., microwave, 2 h

112c

112

Step: 2,4-dichloropyrido[3,2-d]pyrimidine 1f (1.0 g, 5.0 mmol) and cis-4-hydroxy-L-proline methyl ester hydrochloride 112a (943 mg, 6.50 mmol) were dissolved in tetrahydrofuran (10 mL), N, N-diisopropylethylamine (1.94 g, 15.0 mmol, 2.61 mL) was added, and the reaction solution was stirred overnight at room temperature. The completion of the reaction was monitored by LCMS, the reaction solution was concentrated, and the residue was purified by silica gel column chromatography (petroleum ether/ethyl acetate=1/1) to obtain a yellow solid 112b (1.3 g, yield 84%). ESI-MS (m/z): 309.2 [M+H]⁺.

Step 2: Dissolve compound 112b (1.3 g, 4.21 mmol) in tetrahydrofuran (10 mL), add aqueous hydrochloric acid (6N, 0.70 mL) and platinum dioxide (95 mg, 0.42 mmol), and replace the reaction system with hydrogen by using a hydrogen balloon. The reaction solution was stirred at room temperature under hydrogen balloon pressure for 48 hours, and LCMS monitored the completion of the reaction. The reaction solution was diluted with methanol, filtered, and the filtrate was concentrated and purified by silica gel column chromatography (dichloromethane/methanol=20/1) to obtain a white solid 112c (0.80 g, yield 67%). ESI-MS (m/z): 281.3 [M+H]⁺.

Step 3: Dissolve compound 112c (50 mg, 178 umol), compound 11d (57 mg, 213 umol) and p-toluenesulfonic acid monohydrate (3.4 mg, 17 umol) in n-butanol (2 mL). The reaction was carried out at 160° C. under microwave for 2 hours. LCMS monitored the completion of the reaction. The reaction solution was purified by reverse-phase preparative HPLC to obtain a white solid 112 (23 mg, yield 25%). ESI-MS (m/z): 514.3 [M+H]⁺; ¹H NMR (500 MHz, DMSO-d6) δ 8.64 (d, J=2.6 Hz, 1H), 8.13 (d, J=2.3 Hz, 1H), 7.97 (d, J=8.6 Hz, 1H), 7.89 (dd, J=8.5, 2.6 Hz, 1H), 7.86 (dd, J=8.5, 2.6 Hz, 2H), 7.17 (d, J=8.4 Hz, 1H), 7.06 (t, J=4.3 Hz, 1H), 5.14 (br s, 1H), 4.45-4.29 (m, 4H), 4.15-4.08 (m, 1H), 3.80-3.70 (m, 1H), 3.54-3.40 (m, 2H), 3.25-3.17 (m, 1H), 2.50-2.39 (m, 1H), 2.15-2.09 (m, 1H), 2.04-1.89 (m, 2H), 1.86-1.77 (m, 1H).

Example 113 (W247)

(S)-5-((S)-1-methoxyethyl)-4-methyl-2-(((6-((6-(trifluoromethyl)pyridin-3-yl)oxo)pyridin-3-yl)methyl)amino)-4,5,9,10-tetrahydro-6H,8H-pyrido[3,2,1-de]pteridin-6-one Compound 113 was prepared by the following steps:

MeI, Cs₂CO₃

Ag₂CO₃, Cs₂CO₃

110c

11d

TsOH—H₂O, n-BuOH, 160° C., microwave, 2 h

113a

-continued

113

Step 1: Dissolve compound 110c (100 mg, 0.37 mmol) in tetrahydrofuran (2 mL), add silver carbonate (431 mg, 1.86 mmol), cesium carbonate (242 mg, 0.74 mmol) and iodomethane (158 mg, 1.12 mmol, 69 uL), and stir the reaction solution at 60° C. under nitrogen protection for 16 hours. The completion of the reaction was monitored by LCMS. The reaction solution was diluted with methanol, filtered, and the filtrate was concentrated and purified by silica gel column chromatography (dichloromethane/methanol=20/1) to obtain yellow oil 113a (60 mg, yield 54%). ESI-MS (m/z): 297.3 [M+H]⁺.

Step 2: Dissolve compound 113a (60 mg, 202 umol), compound 11d (65 mg, 242 umol) and p-toluenesulfonic acid monohydrate (3.8 mg, 20 umol) in n-butanol (2 mL). The reaction was carried out at 160° C. under microwave for 2 hours. LCMS monitored the completion of the reaction. The reaction solution was purified by reverse-phase preparative HPLC to obtain a white solid 113 (23 mg, yield 21%). ESI-MS (m/z): 530.3 [M+H]⁺; ¹H NMR (500 MHz, DMSO-d6) δ 8.64 (d, J=2.7 Hz, 1H), 8.14 (d, J=2.5 Hz, 1H), 7.97 (d, J=8.5 Hz, 1H), 7.91 (dd, J=8.4, 2.5 Hz, 1H), 7.86 (dd, J=8.6, 2.7 Hz, 1H), 7.18 (d, J=8.4 Hz, 1H), 7.01 (br s, 1H), 4.39 (d, J=6.2 Hz, 2H), 4.31 (d, J=1.9 Hz, 1H), 4.12-4.03 (m, 1H), 3.75-3.68 (m, 1H), 3.30-3.21 (m, 1H), 3.20 (s, 3H), 3.02 (s, 3H), 2.52-2.47 (m, 2H), 1.96-1.89 (m, 1H), 1.80-1.70 (m, 1H), 1.00 (d, J=6.4 Hz, 3H).

Example 114 (W243)

(S)-5-((R)-1-methoxyethyl)-4-methyl-2-(((6-((6-(trifluoromethyl)pyridin-3-yl)oxo)pyridin-3-yl)methyl)amino)-4,5,9,10-tetrahydro-6H,8H-pyrido[3,2,1-de]pteridin-6-one Compound 114 can be obtained by replacing 110c in the first step in Example 113 with intermediate 109c and using similar methods and reaction steps. ESI-MS (m/z): 530.3 [M+H]⁺; ¹HNMR (500 MHz, DMSO-d6) δ 8.64 (d, J=2.6 Hz, 1H), 8.15 (d, J=2.3 Hz, 1H), 7.97 (d, J=8.6 Hz, 1H), 7.92 (dd, J=8.4, 2.5 Hz, 1H), 7.87 (dd, J=8.6, 2.7 Hz, 1H), 7.18

(d, J=8.4 Hz, 1H), 7.06 (br s, 1H), 4.45-4.33 (m, 2H), 4.17-4.10 (m, 1H), 4.07 (d, J=4.8 Hz, 1H), 3.60-3.51 (m, 1H), 3.20-3.11 (m, 4H), 3.07 (s, 3H), 2.55-2.49 (m, 2H), 2.02-1.93 (m, 1H), 1.81-1.69 (m, 1H), 1.08 (d, J=6.4 Hz, 3H).

Example 115 (W244)

(S)-4-(2-methoxyethyl)-5-methyl-2-(((6-((6-(trifluoromethyl)pyridin-3-yl)oxo)pyridine-3-yl)methyl)amino)-4,5,9,10-tetrahydro-6H,8H-pyrido[3,2,1-de]pteridin-6-one Compound 115 was prepared by the following steps:

105c

115a

115

Step 1: Sodium hydride (84 mg, content 60%, 2.10 mmol) was dissolved in dry DMF (1 mL), and compound 105c (100 mg, 0.42 mmol, dissolved in 1 mL DMF) was added at 0° C. The reaction solution continued to be stirred at 0° C. for 1 hour under nitrogen protection. Then 1-bromoethyl methyl ether (117 mg, 0.84 mmol) was added, and the reaction solution was stirred at 0° C. for 2 hours. The completion of the reaction was monitored by TLC. After being quenched by adding water, the reaction solution was extracted by adding ethyl acetate (2*20 mL), and the organic phase was dried over anhydrous sodium sulfate, filtered and concentrated. The residue was purified by silica gel column chromatography (ethyl acetate/petroleum ether=1/1 to 4/1) to obtain yellow solid 115a (95 mg, yield 76%). ESI-MS (m/z): 297.3 [M+H]$^+$.

Step 4: Compound 115a (90 mg, 0.30 mmol), compound 11d (81 mg, 0.30 mol) and p-toluenesulfonic acid monohydrate (5.7 mg, 0.03 mol) were dissolved in n-butanol (3 mL). The reaction was carried out at 160° C. under microwave for 3 hours. LCMS monitored the completion of the reaction. The reaction solution was purified by reverse-phase preparative HPLC to obtain a white solid 115 (23 mg, yield 15%). ESI-MS (m/z): 530.2 [M+H]$^+$; $^1$H NMR (500 MHz, DMSO-d6) δ 8.63 (d, J=2.7 Hz, 1H), 8.11 (d, J=2.5 Hz, 1H), 7.97 (d, J=8.6 Hz, 1H), 7.90-7.83 (m, 2H), 7.18 (d, J=8.4 Hz, 1H), 7.08 (br s, 1H), 4.48-4.28 (m, 2H), 4.16 (q, J=6.7 Hz, 1H), 4.09-3.98 (m, 2H), 3.30-3.15 (m, 5H), 2.55-2.50 (m, 2H), 1.99-1.89 (m, 1H), 1.84-1.75 (m, 1H), 1.23 (d, J=6.8 Hz, 3H).

Example 116 (W249)

(S)-4-ethyl-5-methyl-2-(((6-((6-(trifluoromethyl) pyridin-3-yl)oxo)pyridin-3-yl)methyl)amino)-4,5,9, 10-tetrahydro-6H,8H-pyrido[3,2,1-de]pteridin-6-one Compound 116 can be obtained by replacing deuterated methyl iodide in the third step in Example 105 with iodoethane, and using a similar method and reaction steps. ESI-MS (m/z): 499.9 [M+H]$^+$; $^1$H NMR (500 MHz, DMSO-d6) δ 8.63 (d, J=2.6 Hz, 1H), 8.12 (d, J=2.3 Hz, 1H), 7.98 (d, J=8.6 Hz, 1H), 7.92-7.83 (m, 2H), 7.18 (d, J=8.4 Hz, 1H), 7.06 (br s, 1H), 4.45-4.31 (m, 2H), 4.16 (q, J=6.7 Hz, 1H), 4.06-3.99 (m, 1H), 3.89-3.77 (m, 1H), 3.32-3.25 (m, 2H), 3.15-3.07 (m, 1H), 2.00-1.90 (m, 1H), 1.86-1.74 (m, 1H), 1.25 (d, J=6.7 Hz, 3H), 1.06 (t, J=7.1 Hz, 3H).

Example 117 (W237)

(S)-5-isopropyl-4-methyl-2-(((6-((6-(trifluoromethyl)pyridin-3-yl)oxo)pyridin-3-yl)methyl) amino)-4,5,9,10-tetrahydro-6H,8H-pyrido[3,2,1-de]pteridin-6-one Compound 117 can be obtained by replacing O-methyl-L-serine methyl ester hydrochloride 106a in the first step in Example 106 with L-valine methyl ester hydrochloride, and using a similar method and reaction steps. ESI-MS (m/z): 514.5 [M+H]$^+$; $^1$HNMR (500 MHz, DMSO-d6) δ 8.64 (d, J=2.6 Hz, 1H), 8.14 (d, J=2.4 Hz, 1H), 7.98 (d, J=8.5 Hz, 1H), 7.91 (dd, J=8.5, 3.0 Hz, 1H), 7.86 (dd, J=8.5, 3.0 Hz, 1H), 7.18 (d, J=8.3 Hz, 1H), 7.02 (br s, 1H), 4.45-4.33 (m, 2H), 4.18-4.12 (m, 1H), 3.99 (d, J=3.8 Hz, 1H), 3.22-3.15 (m, 1H), 3.01 (s, 3H), 2.55-2.49 (m, 2H), 2.18-2.13 (m, 1H), 2.01-1.93 (m, 1H), 1.80-1.69 (m, 1H), 0.94 (d, J=7.0 Hz, 3H), 0.75 (d, J=6.9 Hz, 3H).

Example 118 (W279)

(S)-4-ethyl-5-isopropyl-2-(((6-((6-(trifluoromethyl) pyridin-3-yl)oxo)pyridin-3-yl)methyl) amino)-4,5,9, 10-tetrahydro-6H,8H-pyrido[3,2,1-de]pteridin-6-one O-methyl-L-serine methyl ester hydrochloride 106a in the first step in Example 106 was replaced with L-valine methyl ester hydrochloride, and then methyl iodide in the third step was replaced with ethyl iodide. Compound 118 can be obtained by similar method and reaction steps. ESI-MS (m/z): 526.4 [M+H]$^+$; $^1$H NMR (500 MHz, DMSO-d6) δ 8.61 (d, J=2.2 Hz, 1H), 8.11 (d, J=1.6 Hz, 1H), 7.96 (d, J=8.6 Hz, 1H), 7.88 (dd, J=8.4, 2.0 Hz, 1H), 7.83 (dd, J=8.6, 2.1 Hz, 1H), 7.17 (d, J=8.4 Hz, 1H), 7.01 (br s, 1H), 4.47-4.31 (m, 2H), 4.17-4.11 (m, 1H), 4.06-3.95 (m, 2H), 3.35-3.26 (m, 2H), 3.21-3.15 (m, 1H), 3.10-3.00 (m, 1H), 2.09-2.01 (m, 1H), 1.99-1.93 (m, 1H), 1.76-1.67 (m, 1H), 1.02 (t, J=6.7 Hz, 3H), 0.93 (d, J=6.9 Hz, 3H), 0.74 (d, J=6.8 Hz, 3H).

Example 119 (W255)

(S)-5-ethyl-4-methyl-2-(((6-((6-(trifluoromethyl) pyridin-3-yl)oxo)pyridin-3-yl)methyl)amino)-4,5,9, 10-tetrahydro-6H,8H-pyrido[3,2,1-de]pteridin-6-one Compound 119 can be obtained by replacing O-methyl-L-serine methyl ester hydrochloride 106a in the first step in Example 106 with L-2-aminobutyric acid methyl ester hydrochloride, and using a similar method and reaction steps. ESI-MS (m/z): 500.0 [M+H]⁺; ¹H NMR (500 MHz, DMSO-d6) δ 8.62 (d, J=2.6 Hz, 1H), 8.12 (d, J=2.3 Hz, 1H), 7.96 (d, J=8.5 Hz, 1H), 7.89 (dd, J=8.5, 2.5 Hz, 2H), 7.85 (dd, J=8.5, 2.5 Hz, 2H), 7.16 (d, J=8.4 Hz, 1H), 7.00 (t, J=6.3 Hz, 1H), 4.43-4.31 (m, 2H), 4.15-4.10 (m, 1H), 4.07-4.00 (m, 1H), 3.30-3.25 (m, 1H), 2.94 (s, 3H), 2.55-2.49 (m, 2H), 1.99-1.89 (m, 1H), 1.85-1.70 (m, 3H), 0.68 (t, J=7.4 Hz, 3H).

Example 120 (W265)

(S)-5-cyclopropyl-4-methyl-2-(((6-((6-(trifluorom-ethyl)pyridin-3-yl)oxo)pyridin-3-yl)methyl) amino-4,5,9,10-tetrahydro-6H,8H-pyrido[3,2,1-de]pteridin-6-one Compound 120 can be obtained by replacing O-methyl-L-serine methyl ester hydrochloride 106a in the first step in Example 106 with L-cyclopropylglycine methyl ester hydrochloride, and using a similar method and reaction steps. ESI-MS (m/z): 512.4 [M+H]⁺; ¹H NMR (500 MHz, DMSO-d6) δ 8.62 (d, J=2.5 Hz, 1H), 8.13 (d, J=2.3 Hz, 1H), 7.96 (d, J=8.6 Hz, 1H), 7.90 (dd, J=8.5, 2.4 Hz, 1H), 7.85 (dd, J=8.7, 2.6 Hz, 1H), 7.17 (d, J=8.4 Hz, 1H), 7.07 (br s, 1H), 4.46-4.29 (m, 2H), 4.14-4.06 (m, 1H), 3.47 (d, J=8.7 Hz, 1H), 3.20-3.12 (m, 1H), 3.01 (s, 3H), 2.54-2.49 (m, 2H), 2.00-1.90 (m, 1H), 1.84-1.72 (m, 1H), 0.93-0.83 (m, 1H), 0.56-0.47 (m, 2H), 0.45-0.31 (m, 2H).

Example 121 (W266)

(S)-4-ethyl-5-((S)-1-hydroxyethyl)-2-(((6-((6-(trif-luoromethyl)pyridin-3-yl)oxo)pyridine-3-yl)methyl) amino)-4,5,9,10-tetrahydro-6H,8H-pyrido[3,2,1-de] pteridin-6-one Compound 121 was prepared by the following steps:

Step 1: Dissolve compound 110c (230 mg, 0.86 mmol) in acetonitrile (5 mL), add cesium carbonate (557 mg, 1.71 mmol) and ethyl iodide (200 mg, 1.28 mmol), and the reaction solution was stirred at 50° C. for 12 hours. The reaction solution was diluted with saturated brine and extracted with ethyl acetate. The organic phase was dried over anhydrous sodium sulfate, filtered and concentrated. The residue was purified by silica gel column chromatog-raphy (petroleum ether/ethyl acetate=2/1) to obtain com-pound 121a (265 mg, yield 70%). ESI-MS (m/z): 297.2 [M+H]⁺.

Step 2: Dissolve compound 11d (65 mg, 0.24 mmol) and compound 121a (48 mg, 0.16 mmol) in n-butanol (5 mL), add p-toluenesulfonic acid monohydrate (28 mg, 0.16 mmol), and the reaction solution was stirred at 160° C. for 3 hours under microwave conditions. After the reaction solution was cooled to room temperature, the reaction solu-tion was concentrated under reduced pressure, and the residue was purified by reverse-phase preparative HPLC to obtain compound 119 (8 mg, yield 6%) as a white solid. ESI-MS (m/z): 530.5 [M+H]⁺; ¹H NMR (500 MHz, DMSO-d6) δ 8.62 (d, J=2.2 Hz, 1H), 8.12 (d, J=1.6 Hz, 1H), 7.96 (d, J=8.6 Hz, 1H), 7.89 (dd, J=8.4, 2.0 Hz, 1H), 7.84 (dd, J=8.6, 2.1 Hz, 1H), 7.17 (d, J=8.4 Hz, 1H), 6.94 (br s, 1H), 5.01 (d, J=4.8 Hz, 1H), 4.49-4.27 (m, 2H), 4.13-4.05 (m, 2H), 4.04-3.95 (m, 2H), 3.24-3.14 (m, 2H), 2.50-2.43 (m, 2H), 1.95-1.87 (m, 1H), 1.79-1.66 (m, 1H), 1.06-0.99 (m, 6H).

213

214

Example 122 (W272)

(S)-5-(2-hydroxypropan-2-yl)-4-methyl-2-(((6-((6-(trifluoromethyl)pyridin-3-yl) oxo)pyridine-3-yl)methyl)amino)-4,5,9,10-tetrahydro-6H,8H-pyrido[3,2,1-de]pteridin-6-one Example 124 (W278)

(S)-2-(((6-((6-(trifluoromethyl)pyridin-3-yl)oxo)pyridin-3-yl)methyl)amino)-5,6, 8a,9, 11,12-Hexahydro-4H,8H-[1,4]oxazino[3,4-h]pyrido[3,2,1-de]pteridin-8-one Replace O-methyl-L-serine methyl ester hydrochloride 106a in the first step in Example 106 with (S)-2-amino-3-hydroxyl-3-methylbutyric acid methyl ester hydrochloride, and use a similar method and reaction steps, compound 122 can be obtained. ESI-MS (m/z): 530.3 [M+H]$^+$; $^1$H NMR (500 MHz, DMSO-d6) δ 8.60 (d, J=3.0 Hz, 1H), 8.11 (d, J=2.0 Hz, 1H), 7.96-7.92 (m, 1H), 7.91-7.87 (m, 1H), 7.85-7.80 (m, 1H), 7.16-7.12 (m, 1H), 7.01-6.94 (m, 1H), 4.68 (s, 1H), 4.46-4.30 (m, 2H), 4.17-4.11 (m, 1H), 3.86 (s, 1H), 3.09 (s, 3H), 3.08-3.03 (m, 1H), 2.58-2.52 (m, 2H), 2.00-1.89 (m, 1H), 1.77-1.66 (m, 1H), 1.15 (s, 3H), 0.91 (s, 3H).

Compound 124 can be obtained by replacing the L-proline methyl ester hydrochloride 111a in the first step in Example 111 with (S)-methyl 3-morpholinecarboxylate hydrochloride, and using a similar method and reaction steps. ESI-MS (m/z): 514.3 [M+H]$^+$; $^1$H NMR (500 MHz, DMSO-d6) δ 8.62 (d, J=2.5 Hz, 1H), 8.12 (d, J=2.3 Hz, 1H), 7.96 (d, J=8.6 Hz, 1H), 7.88 (dd, J=8.4, 2.5 Hz, 2H), 7.85 (dd, J=8.4, 2.5 Hz, 2H), 7.16 (d, J=8.5 Hz, 1H), 7.13 (br s, 1H), 4.38 (d, J=6.3 Hz, 2H), 4.24-4.19 (m, 1H), 4.13-4.09 (m, 2H), 3.90-3.85 (m, 2H), 3.48-3.37 (m, 3H), 2.86-2.76 (m, 1H), 2.55-2.48 (m, 2H), 1.93-1.75 (m, 2H).

Example 123 (W276)

(8aS, 9S)-9-hydroxyl-2-(((6-((6-(trifluoromethyl)pyridin-3-yl)oxo)pyridin-3-yl)methyl)amino)-5,6,8a,9,10,11-hexahydro-4H,8H-pyrido[3,2,1-de]pyrrolo[2,1-h]pteridin-8-one Example 125 (W281)

(S)-4-ethyl-5-((R)-1-hydroxyethyl)-2-(((6-((6-(trifluoromethyl)pyridin-3-yl)oxo) pyridine-3-yl)methyl)amino)-4,5,9,10-tetrahydro-6H,8H-pyrido[3,2,1-de]pteridin-6-one Replace cis-4-hydroxyl-L-proline 112a in the first step in Example 112 with trans-3-hydroxyl-L-proline methyl ester hydrochloride, and use similar methods and reaction steps to obtain Compound 123. ESI-MS (m/z): 514.3 [M+H]$^+$; $^1$H NMR (500 MHz, DMSO-d6) δ 8.62 (d, J=2.5 Hz, 1H), 8.11 (d, J=2.3 Hz, 1H), 7.96 (d, J=8.6 Hz, 1H), 7.88 (dd, J=8.5, 2.5 Hz, 2H), 7.85 (dd, J=8.5, 2.5 Hz, 2H), 7.15 (d, J=8.4 Hz, 1H), 7.05 (t, J=6.3 Hz, 1H), 5.27 (d, J=5.0 Hz, 1H), 4.43-4.32 (m, 3H), 4.15-4.06 (m, 1H), 3.74 (d, J=6.4 Hz, 1H), 3.65-3.55 (m, 1H), 3.46-3.35 (m, 1H), 3.24-3.13 (m, 1H), 2.52-2.45 (m, 2H), 2.13-2.04 (m, 1H), 1.99-1.87 (m, 1H), 1.85-1.67 (m, 2H).

Compound 125 can be obtained by replacing 110c in the first step in Example 121 with intermediate 109c and using similar methods and reaction steps. ESI-MS (m/z): 530.4 [M+H]$^+$; $^1$H NMR (500 MHz, DMSO-d6) δ 8.62 (d, J=2.5 Hz, 1H), 8.12 (d, J=2.5 Hz, 1H), 7.96 (d, J=8.5 Hz, 1H), 7.89 (dd, J=8.0, 2.0 Hz, 1H), 7.84 (dd, J=9.0, 2.5 Hz, 1H), 7.17 (d, J=8.5 Hz, 1H), 6.99 (br s, 1H), 4.87 (d, J=5.5 Hz, 1H), 4.50-4.40 (m, 1H), 4.36-4.28 (m, 1H), 4.20-4.10 (m, 2H), 3.92 (d, J=4.5 Hz, 1H), 3.86-3.77 (m, 1H), 3.18-3.05 (m, 2H), 2.55-2.43 (m, 2H), 2.00-1.90 (m, 1H), 1.80-1.70 (m, 1H), 1.05 (d, J=6.5 Hz, 3H), 0.99 (t, J=7.5 Hz, 1H).

Example 126 (W308)

(R)-5-((S)-1-fluoroethyl)-4-methyl-2-(((6-((6-(trif-luoromethyl)pyridin-3-yl)oxo) pyridine-3-yl)methyl) amino)-4,5,9,10-tetrahydro-6H,8H-pyrido[3,2,1-de] pteridin-6-one Compound 126 was prepared by the following steps:

109

126

Step 1: Compound 109 (30 mg, 58 umol) was dissolved in dichloromethane (2 mL), and diethylaminosulfur trifluoride (19 mg, 116 umol) was added under an ice bath at 0° C., and the mixture was stirred at 0° C. for 2 hours. After the reaction was complete, water was added to quench the reaction, and the aqueous phase was extracted with ethyl acetate. The organic phases were combined, washed with saturated brine, dried over anhydrous sodium sulfate, filtered and concentrated. The residue was separated by reverse preparative HPLC to obtain compound 126 (4.5 mg, yield 15%) as a white solid. ESI-MS (m/z): 518.3 [M+H]$^+$; $^1$H NMR (500 MHz, DMSO-d6) δ 8.62 (d, J=2.6 Hz, 1H), 8.12 (d, J=2.3 Hz, 1H), 7.96 (d, J=8.6 Hz, 1H), 7.88 (dd, J=8.5, 2.5 Hz, 1H), 7.85 (dd, J=8.5, 2.5 Hz, 1H), 7.16 (d, J=8.4 Hz, 1H), 7.08 (br s, 1H), 5.16-4.96 (m, 1H), 4.45-4.31 (m, 3H), 4.13-4.05 (m, 1H), 3.31-3.20 (m, 1H), 3.02 (s, 3H), 2.55-2.47 (m, 2H), 1.97-1.89 (m, 1H), 1.80-1.68 (m, 1H), 1.30-1.20 (m, 3H).

Example 127 (W280)

(S)-4-methyl-5-phenyl-2-(((6-((6-(trifluoromethyl) pyridin-3-yl)oxo)pyridin-3-yl) methyl)amino)-4,5,9, 10-tetrahydro-6H,8H-pyrido[3,2,1-de]pteridin-6-one Compound 127 can be obtained by replacing the O-methyl-L-serine methyl ester hydrochloride 106a in the first step in Example 106 with L-phenylglycine methyl ester hydrochloride, and using similar methods and reaction steps. ESI-MS (m/z): 548.3 [M+H]$^+$; $^1$H NMR (500 MHz, DMSO-d6) δ 8.63 (d, J=2.6 Hz, 1H), 8.14 (d, J=2.3 Hz, 1H), 7.96 (d, J=8.6 Hz, 1H), 7.91 (dd, J=8.3, 2.4 Hz, 1H), 7.85 (dd, J=8.6, 2.6 Hz, 1H), 7.40-7.29 (m, 3H), 7.25-7.15 (m, 3H), 7.12 (br s, 1H), 5.19 (s, 1H), 4.47-4.35 (m, 2H), 4.06-3.99 (m, 1H), 3.40-3.30 (m, 1H), 2.83 (s, 3H), 2.60-2.50 (m, 2H), 1.98-1.91 (m, 1H), 1.84-1.72 (m, 1H).

Example 128 (W263)

(S)-4,5-dimethyl-2-(((6-((1-methyl-3-(trifluorom-ethyl)-1H-pyrazol-5-yl)oxo)pyridine-3-yl)methyl) amino)-4,5,9,10-tetrahydro-6H,8H-pyrido[3,2,1-de] pteridin-6-one By replacing 5-(trifluoromethyl)pyridin-3-ol 99a in the first step in Example 99 with 5-hydroxy-1-methyl-3-trifluo-romethyl-1H-pyrazole, and using similar methods and reaction steps, compound 128 can be obtained. ESI-MS (m/z): 489.3 [M+H]$^+$; $^1$H NMR (500 MHz, DMSO-d6) δ 8.15 (d, J=2.3 Hz, 1H), 7.90 (dd, J=8.4, 2.3 Hz, 1H), 7.18 (d, J=8.4 Hz, 1H), 7.05 (t, J=5.5 Hz, 1H), 6.53 (s, 1H), 4.47-4.31 (m, 2H), 4.10 (q, J=6.8 Hz, 1H), 4.05-3.96 (m, 1H), 3.69 (s, 3H), 3.30-3.23 (m, 1H), 2.92 (s, 3H), 2.52-2.47 (m, 2H), 1.95-1.85 (m, 1H), 1.83-1.72 (m, 1H), 1.22 (d, J=6.8 Hz, 3H).

Example 129 (W369)

(S)-4,5-dimethyl-2-((((6-((1-methyl-5-(trifluorom-
ethyl)-1H-pyrazol-3-yl)oxo)pyridine-3-yl)methyl)
amino)-4,5,9,10-tetrahydro-6H,8H-pyrido[3,2,1-de]
pteridin-6-one By replacing 5-(trifluoromethyl)pyridin-3-ol 99a in the first step in Example 99 with 3-hydroxy-1-methyl-5-trifluo-romethyl-1H-pyrazole, and using similar methods and reaction steps, compound 129 can be obtained. ESI-MS (m/z): 489.3 [M+H]$^+$; $^1$H NMR (500 MHz, DMSO-d6) δ 8.13 (d, J=2.3 Hz, 1H), 7.84 (dd, J=8.4, 2.4 Hz, 1H), 7.08-7.02 (m, 2H), 6.71 (s, 1H), 4.43-4.31 (m, 2H), 4.12 (q, J=6.8 Hz, 1H), 4.05-3.99 (m, 1H), 3.89 (s, 3H), 3.33-3.23 (m, 2H), 2.94 (s, 3H), 2.01-1.90 (m, 1H), 1.86-1.73 (m, 1H), 1.24 (d, J=6.7 Hz, 3H).

Example 130 (W354)

(S)-2-(((6-((1-cyclopropyl-3-(trifluoromethyl)-1H-
pyrazol-5-yl)oxo)pyridin-3-yl) methyl)amino)-4,5-
dimethyl-4,5,9,10-tetrahydro-6H,8H-pyrido[3,2,1-
de]pteridin-6-one Compound 130 was prepared by the following steps:

-continued

97b

Cs$_2$CO$_3$, THF, 80° C.

130c

130d

H$_2$, Raney Ni

NH$_3$—H$_2$O, MeOH

130d

1i

TsOH—H$_2$O, n-BuOH,
160° C., microwave, 3 h

130

Step 1: Ethyl trifluoroacetoacetate 130a (1.7 g, 9.21 mmol) and cyclopropylhydrazine hydrochloride 130b (1.0 g, 9.21 mmol) were dissolved in 20 mL of ethanol, and the reaction was carried out overnight at 80° C. The reaction solution was concentrated, the residue was slurried with petroleum ether, and filtered to obtain brown solid compound 130c (800 mg, yield 45%). ESI-MS (m/z): 193.2 [M+H]$^+$.

Step 2: Dissolve compound 130c (300 mg, 1.56 mmol) and compound 97b (229 mg, 1.87 mmol) in 10 mL of acetonitrile, add cesium carbonate (763 mg, 2.34 mmol). The reaction was carried out overnight at room temperature, and LCMS monitored that the reaction of raw materials was complete. The reaction solution was diluted with ethyl acetate, washed with water and saturated brine respectively, the organic phase was dried over anhydrous sodium sulfate, concentrated by filtration, and the residue was purified by silica gel column chromatography to obtain compound 130d as a colorless oil (350 mg, yield 76%). ESI-MS (m/z): 295.3 [M+H]$^+$.

Step 3: Dissolve compound 130d (350 mg, 1.19 mmol) in 30 mL of methanol, add Raney nickel (0.5 mL, aqueous suspension), 3 mL of ammonia water, and the reaction was carried out overnight at room temperature under a hydrogen atmosphere, and LCMS monitored that the reaction of raw materials was complete. The reaction solution was filtered with celite, the filter cake was washed with methanol, and the filtrate was concentrated to obtain compound 130e (350 mg, yield 98%) as a light gray oil. ESI-MS (m/z): 299.1 [M+H]$^+$.

Step 4: Dissolve compound 1i (50 mg, 0.2 mmol) and compound 130e (77 mg, 0.25 mmol) in n-butanol (2 mL), add p-toluenesulfonic acid monohydrate (3.7 mg, 0.02 mmol), the reaction was carried out at 160° C. for 3 hours under microwave conditions, and LCMS monitored that the reaction of the raw materials was complete. The reaction solution was directly purified by reverse preparative HPLC to obtain compound 130 (45 mg, yield 44%) as a white solid. ESI-MS (m/z): 515.4 [M+H]$^+$; $^1$H NMR (500 MHz, DMSO-d6) δ 12.92 (br s, 1H), 8.23 (d, J=2.3 Hz, 1H), 7.97 (dd, J=8.4, 2.4 Hz, 1H), 7.26 (d, J=8.4 Hz, 1H), 6.55 (s, 1H), 4.62-4.51 (m, 2H), 4.32 (q, J=6.9 Hz, 1H), 4.04-3.94 (m, 1H), 3.48 (dt, J=7.4, 3.8 Hz, 1H), 3.33-3.28 (m, 1H), 3.06 (s, 3H), 2.64 (t, J=6.3 Hz, 2H), 2.03-1.94 (m, 1H), 1.90-1.78 (m, 1H), 1.37 (d, J=6.9 Hz, 3H), 1.07-1.02 (m, 2H), 0.99-0.86 (m, 2H).

Example 131 (W366)

(S)-4,5-dimethyl-2-((((6-((6-(trifluoromethyl)pyridin-3-yl)thio)pyridin-3-yl)methyl)amino)-4,5,9,10-tetra-hydro-6H,8H-pyrido[3,2,1-de]pteridin-6-one Substitute 5-(trifluoromethyl)pyridin-3-ol 99a in the first step in Example 99 with 6-trifluoromethyl-pyridine-3-thiol, and use similar methods and reaction steps to obtain compound 131. ESI-MS (m/z): 501.7 [M+H]$^+$; $^1$HNMR (500 MHz, DMSO-d6) δ 8.79 (s, 1H), 8.41 (d, J=2.2 Hz, 1H), 8.18 (d, J=8.2 Hz, 1H), 7.94 (d, J=8.2 Hz, 1H), 7.72 (dd, J=8.2, 2.2 Hz, 1H), 7.36 (d, J=8.2 Hz, 1H), 7.05 (t, J=6.4 Hz, 1H), 4.46-4.31 (m, 2H), 4.11 (q, J=7.0 Hz, 2H), 4.04-3.98 (m, 1H), 3.32-3.23 (m, 2H), 2.91 (s, 3H), 2.56-2.47 (m, 2H), 1.97-1.89 (m, 1H), 1.86-1.74 (m, 1H), 1.23 (d, J=6.7 Hz, 3H).

Example 132 (W383)

(S)-5-((methoxy-d3)methyl)-4-(methyl-d3)-2-(((6-((2-(trifluoromethyl)pyrimidin-5-yl) oxo)pyridin-3-yl)methyl)amino)-4,5,9,10-tetrahydro-6H,8H-pyrido [3,2,1-de]pteridin-6-one Compound 132 was prepared by the following steps:

106c

CD$_3$I, Cs$_2$CO$_3$

132a

BBr$_3$

132b

CD$_3$I, Ag$_2$O

-continued

132c

132

Step 1: Compound 106c (1.0 g, 3.72 mmol) and cesium carbonate (2.43 g, 7.44 mmol) were dissolved in acetonitrile (10 mL), and deuteroiodomethane (701 mg, 4.84 mmol) was added. The reaction solution was stirred at room temperature for 12 hours. The reaction solution was diluted with water and extracted with ethyl acetate. The organic phase was washed with saturated aqueous sodium chloride, dried over anhydrous sodium sulfate, filtered and concentrated to obtain yellow solid 132a (693 mg, yield 65%). ESI-MS (m/z): 286.3 [M+H]$^+$.

Step 2: Compound 132a (200 mg, 0.7 mmol) was dissolved in dichloromethane (10 mL), and boron tribromide (876 mg, 3.5 mmol) was slowly added dropwise at 0° C. The reaction solution was stirred and reacted for 2 hours at 0° C. The reaction solution was slowly added dropwise to saturated aqueous sodium bicarbonate solution to quench the reaction, and extracted with ethyl acetate. The organic phase was washed with saturated aqueous sodium chloride, dried over anhydrous sodium sulfate, filtered and concentrated to obtain compound 132b (108 mg, yield 58%). ESI-MS (m/z): 272.4 [M+H]$^+$.

Step 3: Dissolve compound 132b (108 mg, 0.4 mmol) in acetonitrile (8 mL), add silver oxide (461 mg, 1.99 mmol) and deuteroiodomethane (115 mg, 0.8 mmol). The reaction solution was stirred and reacted at 50° C. for 12 hours. The reaction solution was filtered through celite, and the filtrate was concentrated. The residue was purified by silica gel column chromatography (dichloromethane/methanol=10/1) to obtain yellow liquid 132c (68 mg, yield 59%). ESI-MS (m/z): 289.4 [M+H]$^+$.

Step 4: Dissolve compound 91d (100 mg, 0.38 mmol) and compound 132c (68 mg, 0.24 mmol) in n-butanol (3 mL), add p-toluenesulfonic acid monohydrate (40 mg, 0.24 mmol). The reaction solution was stirred at 160° C. for 3 hours under microwave conditions. After the reaction solution was cooled to room temperature, the reaction solution was concentrated under reduced pressure, and the residue was purified by reverse-phase preparative HPLC to obtain compound 140 (21 mg, yield 10%) as a white solid. ESI-MS (m/z): 523.3 [M+H]$^+$; $^1$H NMR (500 MHz, DMSO-d6) δ 9.04 (s, 2H), 8.14 (s, 1H), 7.93 (d, J=8.3 Hz, 1H), 7.23 (d, J=8.4 Hz, 1H), 6.99 (s, 1H), 4.45-4.31 (m, 2H), 4.22 (s, 1H), 4.01-3.92 (m, 1H), 3.70-3.60 (m, 2H), 3.40-3.30 (m, 1H), 2.54-2.47 (m, 2H), 1.95-1.84 (m, 1H), 1.78-1.68 (m, 1H).

Example 133 (W377)

(S)-5-(hydroxymethyl)-4,5-dimethyl-2-(((6-((6-(trif-luoromethyl)pyridin-3-yl)oxo)pyridine-3-yl)methyl)amino)-4,5,9,10-tetrahydro-6H,8H-pyrido[3,2,1-de]pteridin-6-one Compound 133 was prepared by the following steps:

1f

133b

133c

-continued

11d

TsOH—H₂O, n-BuOH, 160° C.,
microwave, 3 h

133d

133

Step 1: 2,4-dichloropyrido[3,2-d]pyrimidine 1f (4.0 g, 20.0 mmol) and 2-methyl-L-serine methyl ester hydrochloride 133a (4.07 g, 24.0 mmol) were dissolved in dichloromethane (30 mL), N, N-diisopropylethylamine (7.75 g, 59.99 mmol, 10.45 mL) was added. The reaction solution was stirred overnight at room temperature. The completion of the reaction was monitored by LCMS. The reaction solution was diluted with dichloromethane, washed with water and saturated brine, and the organic phase was dried over anhydrous sodium sulfate, filtered and concentrated to obtain a white solid 133b (5.0 g, yield 84%). ESI-MS (m/z): 297.3 [M+H]⁺.

Step 2: Dissolve compound 133b (5.0 g, 16.85 mmol) in tetrahydrofuran (50 mL), add aqueous hydrochloric acid (6M, 5.62 mL) and platinum dioxide (382 mg, 1.69 mmol), and replace the reaction system with hydrogen by using a hydrogen balloon. The reaction solution was stirred at room temperature under hydrogen balloon pressure for 48 hours, and LCMS monitored the completion of the reaction. The reaction solution was diluted with methanol, filtered, and the filtrate was concentrated to obtain white solid 133c (4.0 g, yield 88%). ESI-MS (m/z): 269.3 [M+H]⁺.

Step 3: Dissolve compound 133c (1.5 g, 5.58 mmol) and iodomethane (1.58 g, 11.16 mmol) in acetonitrile (5 mL), add cesium carbonate (3.64 g, 11.16 mmol). The reaction mixture was stirred at room temperature for 48 hours. LCMS monitored the completion of the reaction. The reaction solution was diluted with ethyl acetate, filtered and washed with water and saturated brine respectively, the organic phase was dried over anhydrous sodium sulfate, filtered and concentrated. The residue was purified by silica gel column chromatography (dichloromethane/methanol=10/1) to obtain yellow solid 133d (1.1 g, yield 69%). ESI-MS (m/z): 283.3 [M+H]⁺.

Step 4: Dissolve compound 133d (50 mg, 176 umol), compound 11d (62 mg, 229 umol) and p-toluenesulfonic acid monohydrate (3.3 mg, 17 umol) in n-butanol (2 mL). The reaction was carried out at 160° C. under microwave for 3 hours. LCMS monitored the completion of the reaction. The reaction solution was purified by reverse-phase preparative HPLC to obtain a white solid 133 (38 mg, yield 41%).

ESI-MS (m/z): 516.3 [M+H]⁺; ¹H NMR (500 MHz, DMSO-d6) δ 8.64 (d, J=2.6 Hz, 1H), 8.14 (d, J=2.3 Hz, 1H), 7.97 (d, J=8.6 Hz, 1H), 7.91 (dd, J=8.5, 2.5 Hz, 2H), 7.87 (dd, J=8.5, 2.5 Hz, 2H), 7.18 (d, J=8.4 Hz, 1H), 6.92 (t, J=7.5 Hz, 1H), 5.06 (t, J=5.5 Hz, 1H), 4.47-4.32 (m, 2H), 3.80-3.70 (m, 2H), 3.69-3.61 (m, 1H), 3.60-3.52 (m, 1H), 2.96 (s, 3H), 2.54-2.48 (m, 2H), 1.92-1.75 (m, 2H), 1.34 (s, 3H).

Example 134 (W380)

(S)-5-(hydroxymethyl)-4,5-dimethyl-2-(((2-((6-(trif-luoromethyl)pyridin-3-yl)oxo)pyrimidine-5-Base)
methyl)amino)-4,5,9,10-tetrahydro-6H,8H-pyrido[3,
2,1-de]pteridin-6-one Compound 134 was prepared by the following steps:

134a

NaBH₃CN,
HOAc

134b

Boc₂O, Et₃N
DCM, 0° C. to rt

134c

11a t-BuOK, NMP

-continued

134d

134e

133d

TsOH—H₂O, n-BuOH,
microwave, 160° C.

134

Step 1: Dissolve 2-chloropyrimidine-5-carbaldehyde 134a (800 mg, 5.61 mmol) in tetrahydrofuran (20 mL), add acetic acid (0.5 mL) and 2, 4-dimethoxybenzylamine to the reaction solution in turn (985 mg, 5.89 mmol), reacted for 4 hours, after the aldehyde 134a was completely converted to imine, then added sodium cyanoborohydride (1.06 g, 16.84 mmol) and reacted overnight. The completion of the reaction was monitored by LCMS, then water was added to quench the reaction, extracted with ethyl acetate, the organic phases were combined and washed with saturated brine, dried over anhydrous sodium sulfate, and the organic phase was filtered and concentrated to obtain compound 134b. Compound 134b was used directly in the next reaction. ESI-MS (m/z): 294.3 [M+H]⁺.

Step 2: The above product 134b was dissolved in dichloromethane (15 mL), triethylamine (1.21 mL, 8.71 mmol) was added to the reaction solution, and di-tert-butyl dicarbonate (800 mg, 5.61 mmol) was added at. After reacting at room temperature for 30 minutes, LCMS monitored the end of the reaction. The reaction was quenched by adding water, extracted with dichloromethane, the organic phases were combined and washed with saturated brine, dried over anhydrous sodium sulfate, concentrated by filtration, and the residue was purified by silica gel column chromatography (petroleum ether/ethyl acetate=3/1) to obtain yellow oily liquid 134c (720 mg, two-step reaction yield 32%). ESI-MS (m/z): 394.2 [M+H]⁺.

Step 3: Dissolve 5-hydroxy-2-trifluoromethylpyridine 11a (328 mg, 2.01 mmol) and potassium tert-butoxide (308 mg, 2.74 mmol) in N-methylpyrrolidone (10 mL), and after the reaction solution was stirred at room temperature for one hour, compound 134c (720 mg, 1.83 mmol) was added thereto, and the reaction was continued at 80° C. for 24 hours. The end of reaction was monitored by LCMS, and then water was added to quench the reaction, extracted with ethyl acetate, the organic phases were combined and washed with saturated brine, dried over anhydrous sodium sulfate, concentrated by filtration, and the residue was purified by silica gel column chromatography (petroleum ether/ethyl acetate=3/1) to obtain yellow oily liquid 134d (638 mg, yield 67%). ESI-MS (m/z): 521.4 [M+H]⁺.

Step 4: 134d (638 mg, 1.23 mmol) was dissolved in trifluoroacetic acid (5 mL), and the reaction solution was stirred at room temperature for 30 minutes. The completion of the reaction was monitored by LCMS, and then trifluoroacetic acid was distilled off under reduced pressure, the pH was adjusted to 8 by adding 1 N aqueous sodium hydroxide solution, extracted with ethyl acetate, the organic phases were combined and washed with saturated brine, dried over anhydrous sodium sulfate, and reduced pressure The organic phase was concentrated and purified by silica gel column chromatography (petroleum ether/ethyl acetate=3/1) to obtain yellow oily liquid 134e (145 mg, yield 43%). ESI-MS (m/z): 271.4 [M+H]⁺.

Step 5: Dissolve compound 133d (45 mg, 159.16 umol), compound 134e (52 mg, 191 umol) and p-toluenesulfonic acid monohydrate (3 mg, 16 umol) in n-butanol (3 mL). The reaction was carried out at 160° C. under microwave for 3 hours. LCMS monitored the completion of the reaction. The reaction solution was purified by reverse-phase preparative HPLC to obtain a white solid 134 (27 mg, yield 33%). ESI-MS (m/z): 517.5 [M+H]⁺; ¹H NMR (500 MHz, DMSO-d₆) δ 8.74 (s, 1H), 8.65 (s, 2H), 8.02 (s, 2H), 6.94 (t, J=6.1 Hz, 1H), 5.06 (t, J=5.5 Hz, 1H), 4.36 (d, J=6.2 Hz, 2H), 3.77-3.71 (m, 1H), 3.69 (dd, J=11.3, 5.7 Hz, 1H), 3.65-3.59 (m, 1H), 3.55 (dd, J=11.4, 5.4 Hz, 1H), 2.96 (s, 3H), 2.49-2.44 (m, 2H), 1.89-1.77 (m, 2H), 1.34 (s, 3H).

Example 135 (W382)

(S)-5-(hydroxymethyl)-2-(((6-(2-(5-methoxy-3-(trifluoromethyl)-1H-pyrazol-1-yl)ethoxy)pyridin-3-yl)methyl)amino)-4,5-dimethyl-4,5,9,10-tetrahydro-6H, 8H-pyrido[3,2,1-de]pteridine-6-one

Example 136 (W381)

(S)-5-(hydroxymethyl)-2-(((6-(2-(5-methoxy-4-methyl-3-(trifluoromethyl)-1H-pyrazole-1-Base) ethoxy) pyridin-3-yl) methyl) amino)-4,5-dimethyl-4,5,9,10-tetrahydro-6H,8H-pyrido[3,2,1-Des]pteridin-6-one Compounds 135 and 136 were prepared by the following steps:

130a

135a

EtOH, 80° C.

135cb

91b

Cs₂CO₃, THF, 80° C.

-continued

135c $\xrightarrow{\text{MeI, NaH}}$

135d

+

135d'

$\xrightarrow[\substack{\text{NH}_3\text{—H}_2\text{O,} \\ \text{MeOH, rt}}]{\text{H}_2, \text{Raney Ni}}$ 135e

+

135e'

133d $\xrightarrow[\substack{\text{TsOH—H}_2\text{O, n-BuOH,} \\ \text{microwave, 160° C.}}]{}$

135

+

136

Step 1: Ethyl trifluoroacetoacetate 130a (508 mg, 6.68 mmol) and 135a (1.23 g, 6.68 mmol) were dissolved in ethanol (15 mL), and the reaction solution was stirred at 80° C. for 16 hours. LCMS monitored that the reaction was complete, and then ethanol was distilled off under reduced pressure, then water and ethyl acetate were added for extraction, the organic phases were combined and washed with saturated brine, dried over anhydrous sodium sulfate, the organic phase was concentrated under reduced pressure and passed through silica gel column chromatography (petroleum ether)/ethyl acetate=3/1) to obtain white solid 135b (778 mg, yield 59%). ESI-MS (m/z): 197.5 [M+H]+.

Step 2: Add compound 135b (678 mg, 3.46 mmol), 6-fluoro-nicotinonitrile 91b (422 mg, 3.46 mmol) and cesium carbonate (2.25 g, 6.91 mmol) into N, N-dimethylformamide (20 mL), react at 80° C. for 5 hours. After the end of the reaction was monitored by LCMS, N, N-dimethylformamide was distilled off under reduced pressure, then extracted with water and ethyl acetate, the organic phases were combined and washed with saturated brine, dried over anhydrous sodium sulfate, filtered and concentrated to obtain a white solid 135c (443 mg, yield 43%). ESI-MS (m/z): 299.3 [M+H]+.

Step 3: Add sodium hydride (59 mg, 1.48 mmol, content 60%) to a solution of compound 135c (221 mg, 0.74 mmol) in tetrahydrofuran (10 mL) at 0° C. under nitrogen atmosphere. The reaction solution was stirred at room temperature for one hour, and then iodomethane (210 mg, 1.48 mmol) was added thereto at 0° C., and stirring was continued at room temperature for 24 hours. LCMS monitored that the reaction was complete, and then ice water was added to quench the reaction, extracted with ethyl acetate, the organic phases were combined and washed with saturated brine, dried over anhydrous sodium sulfate, the organic phase was concentrated under reduced pressure and passed through silica gel column chromatography (petroleum ether:ethyl acetate esters=5:1) purification to obtain a colorless oily liquid mixture of 135d and 135d' (100 mg, 135d to 135d' about 4:1). ESI-MS (m/z): 313.3 & 327.3 [M+H]+.

Step 4: Dissolve the mixture of compounds 135d and 135d' (100 mg) in methanol (10 mL), add ammonia water (1 mL) and Raney nickel (0.1 mL, aqueous suspension) to the reaction system in turn, and replace hydrogen by using a hydrogen balloon. The reaction was carried out for 3 hours under a hydrogen atmosphere at room temperature, and the reaction was complete as monitored by LCMS. The reaction solution was diluted with methanol, filtered with suction, and the filtrate was concentrated to obtain a mixture of brown oily liquid 135e and 135e' (81 mg, 135e to 135e' about 4:1). ESI-MS (m/z): 317.3 & 331.4 [M+H]+.

Step 5: Dissolve compound 133d (50 mg, 177 umol), a mixture of compounds 135e and 135e' (81 mg) and p-toluenesulfonic acid monohydrate (3.3 mg, 18 umol) in n-butanol (3 mL), and reacted for 3 hours under the condition of microwave at 160° C. LCMS monitored the completion of the reaction. The reaction solution was purified by reverse-phase preparative HPLC to obtain white solid 135 (27 mg, yield 23%) and by-product white solid 136.

Compound 135: ESI-MS (m/z): 563.3 [M+H]+; 1H NMR (500 MHz, DMSO-d6) δ 8.08 (d, J=2.3 Hz, 1H), 7.65 (dd, J=8.4, 2.4 Hz, 1H), 6.86-6.78 (m, 1H), 6.68 (d, J=8.5 Hz, 1H), 6.19 (s, 1H), 5.05 (t, J=5.5 Hz, 1H), 4.53 (t, J=5.4 Hz, 2H), 4.37-4.28 (m, 4H), 3.85 (s, 3H), 3.78-3.68 (m, 2H), 3.67-3.58 (m, 1H), 3.55 (dd, J=11.2, 5.3 Hz, 1H), 2.96 (s, 3H), 2.50-2.44 (m, 2H), 1.89-1.78 (m, 2H), 1.33 (s, 3H).

Compound 136: ESI-MS (m/z): 577.4 [M+H]+; H NMR (500 MHz, DMSO-d6) δ 8.09 (d, J=2.3 Hz, 1H), 7.66 (dd, J=8.5, 2.4 Hz, 1H), 6.82 (t, J=5.7 Hz, 1H), 6.70 (d, J=8.5 Hz, 1H), 5.05 (t, J=5.5 Hz, 1H), 4.54 (t, J=5.3 Hz, 2H), 4.38-4.29 (m, 4H), 3.90 (s, 3H), 3.76-3.67 (m, 2H), 3.65-3.59 (m, 1H), 3.55 (dd, J=11.3, 5.4 Hz, 1H), 2.96 (s, 3H), 2.49-2.42 (m, 2H), 2.03 (s, 3H), 1.88-1.76 (m, 2H), 1.33 (s, 3H).

Example 137 (W335)

(S)-2-((((6-((6-cyclopropylpyridin-3-yl)oxo)pyridin-3-yl)methyl)amino)-4,5-dimethyl-4,5,9,10-tetra-hydro-6H,8H-pyrido[3,2,1-de]pteridin-6-one Compound 137 can be obtained by substituting 6-bromopyridin-3-ol for 2-chloro-5-hydroxypyrimidine 97a in the first step in Example 97, and using a similar method and reaction steps. ESI-MS (m/z): 458.5 [M+H]+; 1H NMR (500 MHz, DMSO-d6) δ 8.21 (d, J=2.5 Hz, 1H), 8.05 (d, J=2.5 Hz, 1H), 7.81 (dd, J=8.5, 2.5 Hz, 1H), 7.43 (dd, J=8.0, 2.5 Hz, 1H), 7.32 (d, J=8.5 Hz, 1H), 7.05-6.98 (m, 2H), 4.39-4.29 (m, 2H), 4.11 (q, J=6.8 Hz, 1H), 4.04-3.98 (m, 1H), 3.32-3.22 (m, 1H), 2.92 (s, 3H), 2.55-2.47 (m, 2H), 2.14-2.09 (m, 1H), 1.95-1.90 (m, 1H), 1.82-1.75 (m, 1H), 1.22 (d, J=6.8 Hz, 3H), 0.96-0.85 (m, 4H).

Example 138 (W271)

(S)-4,5-dimethyl-2-(((6-(4-(trifluoromethyl)benzyl)pyridin-3-yl)methyl)amino)-4,5,9, 10-tetrahydro-6H, 8H-pyrido[3,2,1-de]pteridin-6-one Compound 138 can be obtained by replacing 4-fluorobenzylboronic acid pinacol ester 96c in the second step of Example 96 with 4-trifluoromethylbenzylboronic acid pinacol ester, and using a similar method and reaction steps. ESI-MS (m/z): 483.5 [M+H]+; 1HNMR (500 MHz, DMSO-d6) δ 8.43 (d, J=2.2 Hz, 1H), 7.65 (d, J=2.5 Hz, 1H), 7.62 (d, J=7.9 Hz, 2H), 7.46 (d, J=7.9 Hz, 2H), 7.24 (d, J=8.0 Hz, 1H), 7.00 (br s, 1H), 4.40-4.32 (m, 2H), 4.13 (s, 2H), 4.09 (q, J=6.7 Hz, 1H), 4.02-3.97 (m, 1H), 3.35-3.25 (m, 2H), 2.90 (s, 3H), 2.55-2.45 (m, 2H), 1.92-1.85 (m, 1H), 1.82-1.72 (m, 1H), 1.20 (d, J=6.8 Hz, 3H).

Example 139 (W268)

(S)-5-(hydroxymethyl)-4-methyl-2-(((6-((2-(trifluo-romethyl)pyrimidin-5-yl)oxo) pyridin-3-yl)methanol Base)amino)-4,5,9,10-tetrahydro-6H,8H-pyrido[3,2,1-de]pteridin-6-one Compound 139 can be obtained by substituting intermediate 91d for 11d in the second step of Example 107. ESI-MS (m/z): 503.1 [M+H]⁺; ¹H NMR (500 MHz, DMSO-d6) δ 9.04 (s, 2H), 8.23 (s, 1H), 8.13 (d, J=2.3 Hz, 1H), 7.93 (dd, J=8.4, 2.4 Hz, 1H), 7.22 (d, J=8.4 Hz, 1H), 6.94 (t, J=6.4 Hz, 1H), 4.45-4.29 (m, 2H), 4.07-3.98 (m, 2H), 3.75-3.67 (m, 2H), 3.35-3.30 (m, 1H), 2.96 (s, 3H), 2.52-2.46 (m, 2H), 1.92-1.84 (m, 1H), 1.82-1.71 (m, 1H).

Example 140 (W376)

(S)-5-(hydroxymethyl)-4,5-dimethyl-2-(((6-((2-(trif-luoromethyl)pyrimidin-5-yl) oxo)pyridine-3-Base) methyl)amino)-4,5,9,10-tetrahydro-6H,8H-pyrido[3,2,1-de]pteridin-6-one Compound 140 can be obtained by replacing 11d in the fourth step in Example 133 with intermediate 91d and using a similar method and reaction steps. ESI-MS (m/z): 517.3 [M+H]⁺; ¹H NMR (500 MHz, DMSO-d6) δ 9.06 (s, 2H), 8.19 (d, J=2.3 Hz, 1H), 7.97 (dd, J=8.5, 2.3 Hz, 1H), 7.28 (d, J=8.4 Hz, 1H), 5.26 (br s, 1H), 4.50 (d, J=5.9 Hz, 2H), 3.87-3.78 (m, 1H), 3.73-3.68 (m, 1H), 3.65-3.54 (m, 2H), 3.05 (s, 3H), 2.58-2.49 (m, 2H), 1.95-1.80 (m, 2H), 1.41 (s, 3H).

Example 141 (W261)

(S)-5-((S)-1-hydroxyethyl)-4-(methyl-d3)-2-(((6-((6-(trifluoromethyl)pyridin-3-yl)Oxo)pyridin-3-yl) methyl)amino)-4,5,9,10-tetrahydro-6H,8H-pyrido[3,2,1-de]pteridin-6-one Starting from intermediate 110c, methyl iodide in the fourth step in Example 110 is replaced by deuterated methyl iodide to obtain compound 141. ESI-MS (m/z): 519.3 [M+H]⁺; ¹H NMR (500 MHz, DMSO-d6) δ 8.62 (d, J=2.5 Hz, 1H), 8.11 (d, J=2.0 Hz, 1H), 7.95 (d, J=9.0 Hz, 1H), 7.89 (dd, J=8.5, 2.5 Hz, 1H), 7.85 (dd, J=8.5, 2.5 Hz, 1H), 7.16 (d, J=8.5 Hz, 1H), 6.93 (br s, H), 4.43-4.32 (m, 2H), 4.11-4.02 (m, 3H), 3.26-3.17 (m, 2H), 2.53-2.45 (m, 2H), 1.94-1.85 (m, 1H), 1.80-1.70 (m, 1H), 1.00 (d, J=6.4 Hz, 3H).

Example 142 (W257)

(S)-5-((S)-1-hydroxyethyl)-4-methyl-2-(((6-((2-(trif-luoromethyl)pyrimidin-5-yl) oxo)pyridine-3-yl) methyl)amino)-4,5,9,10-tetrahydro-6H,8H-pyrido[3,2,1-de]pteridin-6-one Compound 142 can be obtained by replacing 11d in the fourth step in Example 110 with intermediate 91d. ESI-MS (m/z): 517.4 [M+H]⁺; ¹H NMR (500 MHz, DMSO-d6) δ 9.03 (s, 2H), 8.13 (d, J=2.3 Hz, 1H), 7.93 (dd, J=8.4, 2.4 Hz, 1H), 7.22 (d, J=8.4 Hz, 1H), 6.95 (t, J=6.1 Hz, 1H), 4.99 (d, J=4.9 Hz, 1H), 4.44-4.32 (m, 2H), 4.12-4.01 (m, 3H), 3.25-3.15 (m, 1H), 3.02 (s, 3H), 2.52-2.46 (m, 2H), 1.95-1.86 (m, 1H), 1.80-1.67 (m, 1H), 1.00 (d, J=6.4 Hz, 3H).

According to the synthetic route and the synthetic method of the intermediate described in the above examples, the compounds of the following examples were obtained.

| Example | structure | analyze data |
|---|---|---|
| 143 (W277) | | ESI-MS (m/z): 506.3 [M + H]⁺; ¹H NMR (500 MHz, DMSO-d6) δ 9.04 (s, 2H), 8.13 (d, J = 2.2 Hz, 1H), 7.93 (dd, J = 8.5, 2.3 Hz, 1H), 7.22 (d, J = 8.4 Hz, 1H), 6.93 (t, J = 6.5 Hz, 1H), 4.96 (t, J = 5.6 Hz, 1H), 4.45-4.32 (m, 2H), 4.06-3.97 (m, 2H), 3.77-3.64 (m, 2H), 3.36-3.27 (m, 1H), 2.52-2.46 (m, 2H), 1.92-1.84 (m, 1H), 1.82-1.69 (m, 1H). |
| 144 (W290) | | ESI-MS (m/z): 517.3 [M + H]⁺; ¹H NMR (500 MHz, DMSO-d6) δ 9.03 (s, 2H), 8.11 (d, J = 2.3 Hz, 1H), 7.91 (dd, J = 8.5, 2.3 Hz, 1H), 7.22 (d, J = 8.4 Hz, 1H), 6.95 (br s, 1H), 4.95 (t, J = 5.0 Hz, 1H), 4.45-4.29 (m, 2H), 4.10-4.07 (m, 1H), 4.07-3.98 (m, 1H), 3.94-3.85 (m, 1H), 3.73-3.65 (m, 2H), 3.17-3.08 (m, 1H), 2.52-2.46 (m, 2H), 1.94-1.85 (m, 1H), 1.81-1.70 (m, 1H), 1.04 (t, J = 7.0 Hz, 3H). |
| 145 (W331) | | ESI-MS (m/z): 531.1 [M + H]⁺; ¹H NMR (500 MHz, DMSO-d6) δ 9.04 (s, 2H), 8.14 (d, J = 2.5 Hz, 1H), 7.93 (dd, J = 8.5, 2.5 Hz, 1H), 7.23 (d, J = 8.5 Hz, 1H), 7.00 (t, J = 6.0 Hz, 1H), 4.71 (s, 1H), 4.50-4.32 (m, 2H), 4.20-4.12 (m, 1H), 3.88 (s, 1H), 3.11 (s, 3H), 3.10-3.04 (m, 1H), 2.52-2.47 (m, 2H), 2.01-1.92 (m, 1H), 1.80-1.68 (m, 1H), 1.17 (s, 3H), 0.94 (s, 3H). |
| 146 (W273) | | ESI-MS (m/z): 487.5 [M + H]⁺; ¹HNMR (500 MHz, DMSO-d6) δ 8.49 (d, J = 2.1 Hz, 1H), 8.07 (d, J = 2.2 Hz, 1H), 7.72 (dd, J = 8.0, 2.2 Hz, 1H), 7.14 (d, J = 7.9 Hz, 1H), 7.00 (t, J = 5.9 Hz, 1H), 6.74 (d, J = 2.3 Hz, 1H), 5.49 (s, 2H), 4.43-4.34 (m, 2H), 4.14-4.10 (m, 1H), 4.08-4.01 (m, 1H), 3.35-3.24 (m, 2H), 2.92 (s, 3H), 2.52-2.46 (m, 2H), 1.95-1.87 (m, 1H), 1.84-1.69 (m, 3H), 0.68 (t, J = 7.4 Hz, 3H). |
| 147 (W274) | | ESI-MS (m/z): 503.4 [M + H]⁺; ¹HNMR (500 MHz, DMSO-d6) δ 8.50 (d, J = 2.1 Hz, 1H), 8.07 (s, 1H), 7.73 (dd, J = 8.0, 2.5 Hz, 1H), 7.13 (d, J = 7.9 Hz, 1H), 6.98 (t, J = 6.2 Hz, 1H), 6.74 (d, J = 2.3 Hz, 1H), 5.49 (s, 2H), 4.89 (d, J = 5.3 Hz, 1H), 4.51-4.31 (m, 2H), 4.12-4.06 (m, 1H), 3.90-3.86 (m, 2H), 3.17-3.10 (m, 1H), 3.05 (s, 3H), 2.53-2.46 (m, 2H), 1.95-1.89 (m, 1H), 1.80-1.70 (m, 1H), 1.08 (d, J = 5.9 Hz, 3H). |
| 148 (W250) | | ESI-MS (m/z): 500.1 [M + H]⁺; ¹H NMR (500 MHz, DMSO-d6) δ 8.50 (s, 1H), 8.08 (s, 1H), 7.73 (dd, J = 7.9, 1.8 Hz, 1H), 7.15 (d, J = 8.0 Hz, 1H), 7.01 (t, J = 6.1 Hz, 1H), 6.75 (d, J = 2.1 Hz, 1H), 5.49 (s, 2H), 4.46-4.34 (m, 2H), 4.18-4.10 (m, 1H), 3.97 (d, J = 3.7 Hz, 1H), 3.22-3.14 (m, 1H), 2.98 (s, 3H), 2.52-2.47 (m, 2H), 2.18-2.10 (m, 1H), 1.99-1.92 (m, 1H), 1.78-1.67 (m, 1H), 0.92 (d, J = 6.9 Hz, 3H), 0.74 (d, J = 6.9 Hz, 3H). |

-continued

| Example | structure | analyze data |
|---|---|---|
| 149 (W285) | | ESI-MS (m/z): 518.3 [M + H]⁺; ¹H NMR (500 MHz, DMSO-d6) δ 8.62 (d, J = 2.6 Hz, 1H), 8.13 (d, J = 2.3 Hz, 1H), 7.96 (d, J = 8.6 Hz, 1H), 7.90 (dd, J = 8.5, 2.4 Hz, 1H), 7.85 (dd, J = 8.6, 2.6 Hz, 1H), 7.16 (d, J = 8.4 Hz, 1H), 7.11 (t, J = 6.8 Hz, 1H), 4.96-4.80 (m, 1H), 4.46-4.24 (m, 3H), 4.16-4.09 (m, 1H), 3.22-3.13 (m, 1H), 3.08 (s, 3H), 2.54-2.48 (m, 2H), 2.00-1.90 (m, 1H), 1.80-1.68 (m, 1H), 1.35-1.25 (m, 3H). |
| 150 (W301) | | ESI-MS (m/z): 505.2 [M + H]⁺; ¹H NMR (500 MHz, DMSO-d6) δ 9.03 (s, 2H), 8.13 (d, J = 2.5 Hz, 1H), 7.92 (dd, J = 8.5, 2.5 Hz, 1H), 7.22 (d, J = 8.5 Hz, 1H), 7.07 (br s, 1H), 4.87-4.59 (m, 2H), 4.46-4.30 (m, 3H), 4.06-3.95 (m, 1H), 3.47-3.40 (m, 1H), 3.00 (s, 3H), 2.55-2.50 (m, 2H), 1.95-1.85 (m, 1H), 1.81-1.69 (m, 1H). |
| 151 (W332) | | ESI-MS (m/z): 530.3 [M + H]+; 1H NMR (500 MHz, DMSO-d6) δ 9.04 (s, 2H), 8.14 (d, J = 2.0 Hz, 1H), 7.98-7.91 (m, 1H), 7.23 (d, J = 8.5 Hz, 1H), 7.15-7.10 (m, 1H), 4.45-4.35 (m, 2H), 4.30 (d, J = 14.5 Hz, 1H), 4.20-4.14 (m, 1H), 3.17-3.10 (m, 1H), 3.08 (d, J = 2.5 Hz, 3H), 2.55-2.52 (m, 2H), 2.01-1.94 (m, 1H), 1.79-1.70 (m, 1H), 1.39 (d, J = 23.0 Hz, 3H), 1.17 (d, J = 23.0 Hz, 3H). |
| 152 (W336) | | ESI-MS (m/z): 503.2 [M + H]⁺; ¹H NMR (500 MHz, DMSO-d6) δ 8.16 (d, J = 2.4 Hz, 1H), 7.90 (dd, J = 8.4, 2.4 Hz, 1H), 7.20 (d, J = 8.4 Hz, 1H), 7.07 (br s, 1H), 6.53 (s, 1H), 4.47-4.30 (m, 2H), 4.11 (q, J = 6.8 Hz, 1H), 4.08-3.97 (m, 3H), 3.30-3.23 (m, 1H), 2.92 (s, 3H), 2.55-2.47 (m, 2H), 1.96-1.87 (m, 1H), 1.85-1.74 (m, 1H), 1.30 (t, J = 7.3 Hz, 3H), 1.22 (d, J = 6.8 Hz, 3H). |
| 153 (W293) | | ESI-MS (m/z): 503.2 [M + H]⁺; ¹H NMR (500 MHz, DMSO-d6) δ 8.13 (d, J = 2.0 Hz, 1H), 7.87 (dd, J = 8.5, 2.5 Hz, 1H), 7.18 (d, J = 8.5 Hz, 1H), 7.04 (br s, 1H), 6.51 (s, 1H), 4.43-4.28 (m, 2H), 4.14 (q, J = 6.5 Hz, 1H), 4.02-3.96 (m, 1H), 3.85-3.76 (m, 1H), 3.68 (s, 3H), 3.32-3.24 (m, 1H), 3.12-3.05 (m, 1H), 2.56-2.47 (m, 2H), 1.95-1.87 (m, 1H), 1.83-1.73 (m, 1H), 1.22 (d, J = 6.5 Hz, 3H), 1.02 (t, J = 6.5 Hz, 3H). |
| 154 (W258) | | ESI-MS (m/z): 517.3 [M + H]⁺; ¹H NMR (500 MHz, DMSO-d6) δ 9.05 (s, 2H), 8.15 (d, J = 2.3 Hz, 1H), 7.94 (dd, J = 8.5, 2.4 Hz, 1H), 7.24 (d, J = 8.4 Hz, 1H), 7.00 (br s, 1H), 4.46-4.32 (m, 2H), 4.23 (t, J = 2.8 Hz, 1H), 4.02-3.94 (m, 1H), 3.71-3.61 (m, 2H), 3.42-3.32 (m, 1H), 3.17 (s, 3H), 2.98 (s, 3H), 2.52-2.46 (m, 2H), 1.94-1.86 (m, 1H), 1.81-1.70 (s, 1H). |

-continued

| Example | structure | analyze data |
|---------|-----------|--------------|
| 155 (W347) | | ESI-MS (m/z): 531.2 [M + H]$^+$; $^1$HNMR (500 MHz, DMSO-d6) δ 9.05 (s, 2H), 8.14 (d, J = 2.4 Hz, 1H), 7.94 (dd, J = 8.4, 2.4 Hz, 1H), 7.24 (d, J = 8.3 Hz, 1H), 7.00 (br s, 1H), 4.39 (d, J = 6.4 Hz, 2H), 4.20 (t, J = 2.9 Hz, 1H), 4.05-3.98 (m, 1H), 3.74-3.63 (m, 2H), 3.35-3.28 (m, 2H), 2.98 (s, 3H), 2.55-2.48 (m, 2H), 1.94-1.88 (m, 1H), 1.77-1.69 (m, 1H), 0.90 (t, J = 7.0 Hz, 3H). |
| 156 (W264) | | ESI-MS (m/z): 531.3 [M + H]$^+$; $^1$H NMR (500 MHz, DMSO-d6) δ 9.03 (s, 2H), 8.13 (d, J = 2.3 Hz, 1H), 7.93 (dd, J = 8.4, 2.4 Hz, 1H), 7.22 (d, J = 8.4 Hz, 1H), 7.04 (t, J = 6.0 Hz, 1H), 4.46-4.32 (m, 2H), 4.17-4.09 (m, 1H), 4.05 (d, J = 4.8 Hz, 1H), 3.58-3.50 (m, 1H), 3.18-3.10 (m, 4H), 3.05 (s, 3H), 2.54-2.48 (m, 2H), 2.00-1.92 (m, 1H), 1.78-1.68 (m, 1H), 1.06 (d, J = 6.4 Hz, 3H). |
| 157 (W262) | | ESI-MS (m/z): 499.1 [M + H]$^+$; $^1$H NMR (500 MHz, DMSO-d6) δ 9.03 (s, 2H), 8.12 (d, J = 2.3 Hz, 1H), 7.92 (dd, J = 8.5, 2.3 Hz, 1H), 7.22 (d, J = 8.4 Hz, 1H), 7.05 (t, J = 6.3 Hz, 1H), 4.45-4.34 (m, 2H), 4.12-4.02 (m, 2H), 3.60-3.53 (m, 1H), 3.46-3.39 (m, 1H), 3.26-3.16 (m, 1H), 2.52-2.45 (m, 2H), 2.25-2.15 (m, 1H), 2.00-1.70 (m, 5H). |
| 158 (W275) | | ESI-MS (m/z): 515.3 [M + H]$^+$; $^1$H NMR (500 MHz, DMSO-d6) δ 9.03 (s, 2H), 8.12 (d, J = 2.3 Hz, 1H), 7.91 (dd, J = 8.4, 2.3 Hz, 1H), 7.22 (d, J = 8.4 Hz, 1H), 7.07 (t, J = 6.2 Hz, 1H), 5.27 (d, J = 5.0 Hz, 1H), 4.43-4.32 (m, 3H), 4.12-4.05 (m, 1H), 3.74 (d, J = 6.5 Hz, 1H), 3.66-3.54 (m, 1H), 3.43-3.35 (m, 1H), 3.21-3.15 (m, 1H), 2.52-2.46 (m, 2H), 2.13-2.05 (m, 1H), 1.97-1.90 (m, 1H), 1.86-1.67 (m, 2H). |
| 159 (W259) | | ESI-MS (m/z): 515.3 [M + H]$^+$; $^1$HNMR (500 MHz, DMSO-d6) δ 9.05 (s, 2H), 8.14 (d, J = 2.3 Hz, 1H), 7.94 (dd, J = 8.5, 2.4 Hz, 1H), 7.24 (d, J = 8.4 Hz, 1H), 7.03 (br s, 1H), 4.46-4.34 (m, 2H), 4.18-4.12 (m, 1H), 3.99 (d, J = 3.8 Hz, 1H), 3.21-3.15 (m, 1H), 3.01 (s, 3H), 2.55-2.47 (m, 2H), 2.21-2.14 (m, 1H), 2.02-1.93 (m, 1H), 1.80-1.69 (m, 1H), 0.94 (d, J = 7.0 Hz, 3H), 0.76 (d, J = 6.9 Hz, 3H). |
| 160 (W362) | | ESI-MS (m/z): 529.4 [M + H]$^+$; $^1$H NMR (500 MHz, DMSO-d6) δ 9.03 (s, 2H), 8.14 (d, J = 2.4 Hz, 1H), 7.94 (dd, J = 8.4, 2.4 Hz, 1H), 7.23 (d, J = 8.4 Hz, 1H), 7.05 (t, J = 6.1 Hz, 1H), 4.47-4.33 (m, 2H), 4.24-4.16 (m, 1H), 3.82 (s, 1H), 3.35-3.30 (m, 1H), 3.10 (s, 3H), 3.09-3.03 (m, 1H), 2.55-2.45 (m, 2H), 2.04-1.95 (m, 1H), 1.78-1.66 (m, 1H), 0.87 (s, 9H). |

-continued

| Example | structure | analyze data |
|---------|-----------|--------------|
| 161 (W269) | | ESI-MS (m/z): 501.7 [M + H]⁺; ¹H NMR (500 MHz, DMSO-d6) δ 9.03 (s, 2H), 8.12 (d, J = 2.4 Hz, 1H), 7.92 (dd, J = 8.4, 2.4 Hz, 1H), 7.22 (d, J = 8.4 Hz, 1H), 7.01 (br s, 1H), 4.44-4.30 (m, 2H), 4.15-4.10 (m, 1H), 4.07-4.00 (m, 1H), 3.32-3.27 (m, 1H), 2.94 (s, 3H), 2.52-2.46 (m, 2H), 1.95-1.88 (m, 1H), 1.85-1.71 (m, 3H), 0.68 (t, J = 7.4 Hz, 3H). |
| 162 (W270) | | ESI-MS (m/z): 504.4 [M + H]⁺; ¹H NMR (500 MHz, DMSO-d6) δ 9.03 (s, 2H), 8.12 (d, J = 2.2 Hz, 1H), 7.92 (dd, J = 8.4, 2.3 Hz, 1H), 7.22 (d, J = 8.4 Hz, 1H), 7.01 (br s, 1H), 4.46-4.32 (m, 2H), 4.12 (dd, J = 5.8, 3.6 Hz, 1H), 4.08-4.00 (m, 1H), 3.32-3.28 (m, 1H), 2.52-2.47 (m, 2H), 1.96-1.88 (m, 1H), 1.84-1.70 (m, 3H), 0.69 (t, J = 7.4 Hz, 3H). |
| 163 (W325) | | ESI-MS (m/z): 539.4 [M + H]⁺; ¹H NMR (500 MHz, DMSO-d6) δ 8.63 (d, J = 2.6 Hz, 1H), 8.13 (d, J = 2.4 Hz, 1H), 7.96 (d, J = 8.6 Hz, 1H), 7.90 (dd, J = 8.4, 2.4 Hz, 1H), 7.86 (dd, J = 8.6, 2.7 Hz, 1H), 7.17 (d, J = 8.4 Hz, 1H), 7.08 (br s, 1H), 6.19-5.89 (m, 1H), 4.44-4.28 (m, 3H), 4.05-3.97 (m, 1H), 3.37-3.33 (m, 1H), 2.53-2.47 (m, 2H), 2.37-2.25 (m, 2H), 1.95-1.77 (m, 2H). |
| 164 (W326) | | ESI-MS (m/z): 540.3 [M + H]⁺; ¹H NMR (500 MHz, DMSO-d6) δ 9.04 (s, 2H), 8.13 (d, J = 2.4 Hz, 1H), 7.93 (dd, J = 8.4, 2.4 Hz, 1H), 7.23 (d, J = 8.4 Hz, 1H), 7.09 (br s, 1H), 6.19-5.86 (m, 1H), 4.46-4.30 (m, 3H), 4.05-3.96 (m, 1H), 3.36-3.30 (m, 1H), 2.53-2.47 (m, 2H), 2.39-2.21 (m, 2H), 1.96-1.74 (m, 2H). |
| 165 (W286) | | ESI-MS (m/z): 516.3 [M + H]⁺; ¹H NMR (500 MHz, DMSO-d6) δ 9.03 (s, 2H), 8.13 (d, J = 2.2 Hz, 1H), 7.93 (dd, J = 8.3, 2.3 Hz, 1H), 7.23 (d, J = 8.4 Hz, 1H), 7.08 (t, J = 6.3 Hz, 1H), 4.49-4.33 (m, 2H), 4.13-4.06 (m, 1H), 3.47 (d, J = 8.7 Hz, 1H), 3.21-3.12 (m, 1H), 2.53-2.47 (m, 2H), 2.00-1.91 (m, 1H), 1.85-1.72 (m, 1H), 0.93-0.82 (m, 1H), 0.57-0.48 (m, 2H), 0.45-0.30 (m, 2H). |
| 166 (W287) | | ESI-MS (m/z): 527.3 [M + H]⁺; ¹H NMR (500 MHz, DMSO-d6) δ 9.02 (s, 2H), 8.12 (d, J = 2.3 Hz, 1H), 7.91 (dd, J = 8.5, 2.4 Hz, 1H), 7.23 (d, J = 8.4 Hz, 1H), 7.07 (br s, 1H), 4.47-4.32 (m, 2H), 4.5-4.08 (m, 1H), 3.92-3.84 (m, 1H), 3.57 (d, J = 8.4 Hz, 1H), 3.27-3.20 (m, 1H), 3.19-3.11 (m, 1H), 2.55-2.49 (m, 2H), 2.03-1.94 (m, 1H), 1.84-1.73 (m, 1H), 1.08 (t, J = 7.0 Hz, 3H), 0.96-0.88 (m, 1H), 0.55-0.33 (m, 4H). |

-continued

| Exam-ple | structure | analyze data |
|---|---|---|
| 167 (W289) | | ESI-MS (m/z): 513.4 [M + H]⁺; ¹H NMR (500 MHz, DMSO-d6) δ 9.03 (s, 2H), 8.13 (d, J = 2.3 Hz, 1H), 7.93 (dd, J = 8.4, 2.3 Hz, 1H), 7.23 (d, J = 8.5 Hz, 1H), 7.08 (br s, 1H), 4.50-4.32 (m, 2H), 4.14-4.06 (m, 1H), 3.47 (d, J = 8.8 Hz, 1H), 3.22-3.13 (m, 1H), 3.01 (s, 3H), 2.53-2.47 (m, 2H), 2.02-1.93 (m, 1H), 1.85-1.72 (m, 1H), 0.94-0.83 (m, 1H), 0.56-0.48 (m, 2H), 0.45-0.30 (m, 2H). |
| 168 (W298) | | ESI-MS (m/z): 500.0 [M + H]⁺; ¹H NMR (500 MHz, DMSO-d6) δ 9.01 (s, 2H), 8.10 (d, J = 2.3 Hz, 1H), 7.90 (dd, J = 8.4, 2.4 Hz, 1H), 7.22 (d, J = 8.4 Hz, 1H), 7.03 (br s, 1H), 4.45-4.30 (m, 2H), 4.14 (q, J = 6.7 Hz, 1H), 4.04-3.93 (m, 1H), 3.86-3.76 (m, 1H), 3.30-3.20 (m, 1H), 3.16-3.03 (m, 1H), 1.98-1.88 (m, 1H), 1.82-1.71 (m, 1H), 1.22 (d, J = 6.7 Hz, 3H), 1.04 (t, J = 7.1 Hz, 3H). |
| 169 (W294) | | ESI-MS (m/z): 518.3 [M + H]⁺; ¹H NMR (500 MHz, DMSO-d6) δ 8.61 (s, 1H), 8.09 (s, 1H), 7.95 (d, J = 8.5 Hz, 1H), 7.86 (dd, J = 8.5, 2.5 Hz, 1H), 7.82 (dd, J = 8.5, 2.5 Hz, 1H), 7.15 (d, J = 8.4 Hz, 1H), 7.11 (br s, 1H), 4.62-4.29 (m, 4H), 4.20-3.97 (m, 3H), 3.29-3.20 (m, 1H), 2.55-2.50 (m, 2H), 1.98-1.89 (m, 1H), 1.86-1.71 (m, 1H), 1.22 (d, J = 6.7 Hz, 3H). |
| 170 (W368) | | ESI-MS (m/z): 515.3 [M + H]⁺; ¹H NMR (500 MHz, DMSO-d6) δ 9.02 (s, 2H), 8.12 (d, J = 2.3 Hz, 1H), 7.92 (dd, J = 8.5, 2.3 Hz, 1H), 7.24 (d, J = 8.5 Hz, 1H), 7.07 (br s, 1H), 4.49-4.35 (m, 3H), 4.18 (q, J = 7.0 Hz, 1H), 4.12-4.07 (m, 1H), 3.16-3.08 (m, 1H), 2.57-2.49 (m, 2H), 2.04-1.93 (m, 1H), 1.84-1.70 (m, 1H), 1.28-1.14 (m, 9H). |
| 171 (W367) | | ESI-MS (m/z): 513.3 [M + H]⁺; ¹H NMR (500 MHz, DMSO-d6) δ 9.04 (s, 2H), 8.15 (d, J = 2.3 Hz, 1H), 7.96 (dd, J = 8.5, 2.3 Hz, 1H), 7.24 (d, J = 8.4 Hz, 1H), 7.12 (br s, 1H), 4.55-4.31 (m, 2H), 4.11-3.99 (m, 2H), 3.28-3.16 (m, 1H), 2.63-2.52 (m, 3H), 1.96-1.74 (m, 2H), 1.23 (d, J = 6.8 Hz, 3H), 0.94-0.85 (m, 1H), 0.73-0.57 (m, 2H), 0.50-0.40 (m, 1H). |
| 172 (W305) | | ESI-MS (m/z): 549.4 [M + H]⁺; ¹H NMR (500 MHz, DMSO-d6) δ 9.04 (s, 2H), 8.14 (d, J = 2.2 Hz, 1H), 7.94 (dd, J = 8.5, 2.3 Hz, 1H), 7.40-7.30 (m, 3H), 7.24 (d, J = 8.4 Hz, 1H), 7.21-7.05 (m, 3H), 5.20 (s, 1H), 4.50-4.34 (m, 2H), 4.05-3.96 (m, 1H), 3.37-3.32 (m, 1H), 2.84 (s, 3H), 2.56 (t, J = 6.4 Hz, 2H), 2.00-1.90 (m, 1H), 1.84-1.73 (m, 1H). |

-continued

| Example | structure | analyze data |
|---------|-----------|--------------|
| 173 (W313) | | ESI-MS (m/z): 567.3 [M + H]+; 1H NMR (500 MHz, DMSO-d6) δ 9.03 (s, 2H), 8.13 (d, J = 2.3 Hz, 1H), 7.93 (dd, J = 8.5, 2.3 Hz, 1H), 7.28-7.10 (m, 6H), 5.22 (s, 1H), 4.50-4.34 (m, 2H), 4.04-3.95 (m, 1H), 3.37-3.30 (m, 1H), 2.82 (s, 3H), 2.55 (t, J = 6.2 Hz, 2H), 1.96-1.89 (m, 1H), 1.85-1.73 (m, 1H). |
| 174 (W314) | | ESI-MS (m/z): 567.3 [M + H]+; 1H NMR (500 MHz, DMSO-d6) δ 9.03 (s, 2H), 8.13 (d, J = 2.3 Hz, 1H), 7.93 (dd, J = 8.5, 2.3 Hz, 1H), 7.40 (q, J = 7.4 Hz, 1H), 7.23 (d, J = 8.4 Hz, 1H), 7.21-7.13 (m, 2H), 7.10-6.94 (m, 2H), 5.26 (s, 1H), 4.48-4.32 (m, 2H), 4.03-3.94 (m, 1H), 3.37-3.30 (m, 1H), 2.84 (s, 3H), 2.55 (t, J = 6.4 Hz, 3H), 1.96-1.89 (m, 1H), 1.85-1.74 (s, 1H). |
| 175 (W327) | | ESI-MS (m/z): 499.0 [M + H]+; 1H NMR (500 MHz, DMSO-d6) δ 9.03 (s, 2H), 8.11 (d, J = 2.3 Hz, 1H), 7.91 (dd, J = 8.4, 2.4 Hz, 1H), 7.22 (d, J = 8.4 Hz, 1H), 7.05 (t, J = 6.0 Hz, 1H), 4.37 (d, J = 6.3 Hz, 2H), 3.70-3.61 (m, 2H), 2.73 (s, 3H), 2.55-2.49 (m, 2H), 1.86-1.78 (m, 2H), 1.35-1.28 (m, 2H), 1.19-1.09 (m, 2H). |
| 176 (W296) | | ESI-MS (m/z): 500.1 [M + H]+; 1H NMR (500 MHz, DMSO-d6) δ 8.63 (d, J = 2.6 Hz, 1H), 8.13 (d, J = 2.3 Hz, 1H), 7.97 (d, J = 8.6 Hz, 1H), 7.89 (dd, J = 8.5, 2.5 Hz, 1H), 7.86 (dd, J = 8.5, 2.5 Hz, 1H), 7.17 (d, J = 8.4 Hz, 1H), 7.05 (br s, 1H), 4.39 (d, J = 6.3 Hz, 2H), 3.71-3.65 (m, 2H), 2.96 (s, 3H), 2.55-2.48 (m, 2H), 1.91-1.83 (m, 2H), 1.38 (s, 6H). |
| 177 (W297) | | ESI-MS (m/z): 500.0 [M + H]+; 1H NMR (500 MHz, DMSO-d6) δ 9.04 (s, 2H), 8.13 (d, J = 2.2 Hz, 1H), 7.93 (dd, J = 8.3, 2.3 Hz, 1H), 7.24 (d, J = 8.4 Hz, 1H), 7.06 (br s, 1H), 4.39 (d, J = 6.3 Hz, 2H), 3.66 (t, J = 5.7 Hz, 2H), 2.96 (s, 3H), 2.60-2.52 (m, 2H), 1.92-1.82 (m, 2H), 1.38 (s, 6H). |
| 178 (W333) | | ESI-MS (m/z): 520.4 [M + H]+; 1H NMR (500 MHz, DMSO-d6) δ 9.04 (s, 2H), 8.14 (d, J = 2.4 Hz, 1H), 7.93 (d, J = 8.4 Hz, 1H), 7.23 (d, J = 8.3 Hz, 1H), 7.00 (br s, 1H), 4.46-4.32 (m, 2H), 4.22 (t, J = 2.8 Hz, 1H), 4.02-3.92 (m, 1H), 3.71-3.60 (m, 2H), 3.40-3.32 (m, 1H), 3.16 (s, 3H), 2.49-2.35 (m, 2H), 1.94-1.83 (m, 1H), 1.80-1.68 (m, 1H). |

-continued

| Example | structure | analyze data |
|---|---|---|
| 179 (W375) | | ESI-MS (m/z): 530.4 [M + H]+; 1H NMR (500 MHz, DMSO-d6) δ 8.64 (d, J = 2.6 Hz, 1H), 8.14 (d, J = 2.3 Hz, 1H), 7.97 (d, J = 8.6 Hz, 1H), 7.90 (dd, J = 8.5, 2.5 Hz, 1H), 7.87 (dd, J = 9.0, 3.0 Hz, 1H), 7.18 (d, J = 8.4 Hz, 1H), 6.98 (br s, 1H), 4.38 (d, J = 6.3 Hz, 2H), 3.76-3.61 (m, 3H), 3.56 (d, J = 10.0 Hz, 1H), 3.32-3.26 (m, 1H), 3.18 (s, 3H), 2.96 (s, 3H), 2.55-2.47 (m, 2H), 1.90-1.77 (m, 2H), 1.35 (s, 3H). |
| 180 (W386) | | ESI-MS (m/z): 531.1 [M + H]+; 1H NMR (500 MHz, DMSO-d6) δ 9.05 (s, 2H), 8.14 (d, J = 2.3 Hz, 1H), 7.94 (dd, J = 8.4, 2.4 Hz, 1H), 7.24 (d, J = 8.4 Hz, 1H), 6.99 (br s, 1H), 4.39 (d, J = 6.3 Hz, 2H), 3.75-3.62 (m, 3H), 3.56 (d, J = 10.1 Hz, 1H), 3.18 (s, 3H), 2.96 (s, 3H), 2.55-2.47 (m, 2H), 1.89-1.78 (m, 2H), 1.35 (s, 3H). |
| 181 (W396) | | ESI-MS (m/z): 537.4 [M + H]+; 1H NMR (500 MHz, DMSO) δ 9.04 (s, 2H), 8.13 (s, 1H), 7.93 (dd, J = 8.4, 1.5 Hz, 1H), 7.23 (d, J = 8.4 Hz, 1H), 6.98 (br s, 1H), 4.38 (d, J = 6.2 Hz, 2H), 3.73-3.61 (m, 3H), 3.54 (d, J = 10.1 Hz, 1H), 2.52-2.43 (m, 2H), 1.86-1.76 (m, 2H), 1.33 (s, 3H). |
| 182 (W395) | | ESI-MS (m/z): 536.3 [M + H]+; 1H NMR (500 MHz, DMSO) δ 8.63 (d, J = 1.7 Hz, 1H), 8.13 (s, 1H), 7.96 (d, J = 8.6 Hz, 1H), 7.90 (d, J = 8.4 Hz, 1H), 7.86 (dd, J = 8.5, 1.6 Hz, 1H), 7.17 (d, J = 8.4 Hz, 1H), 6.97 (br s, 1H), 4.37 (d, J = 6.2 Hz, 2H), 3.73-3.62 (m, 3H), 3.54 (d, J = 10.1 Hz, 1H), 2.52-2.46 (m, 2H), 1.86-1.78 (m, 2H), 1.33 (s, 3H). |
| 183 (W309) | | ESI-MS (m/z): 535.2 [M + H]+; 1H NMR (500 MHz, DMSO-d6) δ 9.03 (s, 2H), 8.14 (d, J = 2.3 Hz, 1H), 7.92 (dd, J = 8.6, 2.4 Hz, 1H), 7.34-7.19 (m, 2H), 4.49 (dd, J = 10.4, 7.1 Hz, 1H), 4.37 (d, J = 6.3 Hz, 2H), 4.14-4.00 (m, 2H), 3.81-3.67 (m, 1H), 3.27-3.18 (m, 1H), 2.75-2.59 (m, 2H), 2.53-2.47 (m, 2H), 2.01-1.91 (m, 1H), 1.86-1.73 (m, 1H). |

-continued

| Example | structure | analyze data |
|---------|-----------|--------------|
| 184 (W282) | | ESI-MS (m/z): 540.3 [M + H]+; 1H NMR (500 MHz, DMSO-d6) δ 8.62 (d, J = 2.5 Hz, 1H), 8.13 (d, J = 2.3 Hz, 1H), 7.96 (d, J = 8.6 Hz, 1H), 7.87 (dd, J = 8.5, 2.4 Hz, 1H), 7.84 (dd, J = 8.5, 2.4 Hz, 1H), 7.30 (br s, 1H), 7.17 (d, J = 8.4 Hz, 1H), 5.26 (q, J = 7.5 Hz, 1H), 4.47-4.32 (m, 2H), 4.18-4.12 (m, 1H), 3.28-3.22 (m, 1H), 3.09 (s, 3H), 2.60-2.55 (m, 2H), 2.05-1.95 (m, 1H), 1.83-1.70 (m, 1H). |
| 185 (W310) | | ESI-MS (m/z): 540.5 [M + H]+; 1H NMR (500 MHz, DMSO-d6) δ 8.62 (d, J = 2.5 Hz, 1H), 8.13 (d, J = 2.2 Hz, 1H), 7.96 (d, J = 8.6 Hz, 1H), 7.87 (dd, J = 8.5, 2.4 Hz, 1H), 7.84 (dd, J = 8.5, 2.4 Hz, 1H), 7.30 (br s, 1H), 7.17 (d, J = 8.4 Hz, 1H), 5.27 (q, J = 7.5 Hz, 1H), 4.47-4.32 (m, 2H), 4.18-4.12 (m, 1H), 3.28-3.22 (m, 1H), 3.09 (s, 3H), 2.60-2.55 (m, 2H), 2.05-1.95 (m, 1H), 1.83-1.70 (m, 1H). Retention time on chiral column = 1.47 min (AD-H column, CO2:EtOH (0.05% DEA) = 70:30) |
| 186 (W311) | | ESI-MS (m/z): 540.5 [M + H]+; 1H NMR (500 MHz, DMSO-d6) δ 8.62 (d, J = 2.5 Hz, 1H), 8.13 (d, J = 2.2 Hz, 1H), 7.96 (d, J = 8.6 Hz, 1H), 7.87 (dd, J =8.5, 2.4 Hz, 1H), 7.84 (dd, J = 8.5, 2.4 Hz, 1H), 7.30 (br s, 1H), 7.17 (d, J = 8.4 Hz, 1H), 5.27 (q, J = 7.5 Hz, 1H), 4.47-4.32 (m, 2H), 4.18-4.12 (m, 1H), 3.28-3.22 (m, 1H), 3.09 (s, 3H), 2.60-2.55 (m, 2H), 2.05-1.95 (m, 1H), 1.83-1.70 (m, 1H). Retention time on chiral column Retention time on chiral column = 1.77 min (AD-H column, CO2:EtOH (0.05% DEA) = 70:30) |
| 187 (W315) | | ESI-MS (m/z): 544.5 [M + H]+; 1H NMR (500 MHz, DMSO-d6) δ 9.04 (s, 2H), 8.14 (d, J = 2.3 Hz, 1H), 7.93 (dd, J = 8.4, 2.4 Hz, 1H), 7.33 (br s, 1H), 7.24 (d, J = 8.5 Hz, 1H), 5.28 (q, J = 7.5 Hz, 1H), 4.50-4.33 (m, 2H), 4.22-4.13 (m, 1H), 3.30-3.23 (m, 1H), 2.65-2.54 (m, 2H), 2.04-1.95 (m, 1H), 1.84-1.71 (m, 1H). |
| 188 (W316) | | ESI-MS (m/z): 555.3 [M + H]+; 1HNMR (500 MHz, DMSO-d6) δ 9.02 (s, 2H), 8.12 (d, J = 2.4 Hz, 1H), 7.91 (dd, J = 8.4, 2.4 Hz, 1H), 7.33 (br s, 1H), 7.23 (d, J = 8.4 Hz, 1H), 5.31 (q, J = 7.5 Hz, 1H), 4.50-4.40 (m, 1H), 4.38-4.31 (m, 1H), 4.23-4.14 (m, 1H), 4.12-4.02 (m, 1H), 3.29-3.20 (m, 1H), 3.20-3.10 (m, 1H), 2.58-2.52 (m, 2H), 2.06-1.93 (m, 1H), 1.81-1.67 (m, 1H), 1.05 (br s, 3H). |
| 189 (W306) | | ESI-MS (m/z): 554.4 [M + H]+; 1H NMR (500 MHz, DMSO-d6) δ 8.63 (d, J = 2.5 Hz, 1H), 8.13 (d, J = 2.3 Hz, 1H), 7.96 (d, J = 8.6 Hz, 1H), 7.87 (dd, J = 8.4, 2.4 Hz, 1H), 7.85 (dd, J = 8.4, 2.4 Hz, 1H), 7.17 (d, J = 8.4 Hz, 1H), 7.09 (br s, 1H), 4.58-4.52 (m, 1H), 4.44-4.32 (m, 2H), 4.03-3.95 (m, 1H), 3.43-3.35 (m, 1H), 2.97 (s, 3H), 2.96-2.85 (m, 1H), 2.82-2.70 (m, 1H), 2.55-2.50 (m, 1H), 1.96-1.87 (m, 1H), 1.80-1.70 (m, 1H). |

-continued

| Example | structure | analyze data |
|---------|-----------|--------------|
| 109 (W317) | | ESI-MS (m/z): 554.3 [M + H]+; 1H NMR (500 MHz, DMSO-d6) δ 8.63 (d, J = 2.7 Hz, 1H), 8.13 (d, J = 3.7 Hz, 1H), 7.96 (d, J = 8.6 Hz, 1H), 7.87 (dd, J = 8.5, 2.5 Hz, 1H), 7.85 (dd, J = 8.5, 2.5 Hz, 1H), 7.17 (d, J = 8.5 Hz, 1H), 7.08 (br s, 1H), 4.58-4.52 (m, 1H), 4.44-4.32 (m, 2H), 4.03-3.95 (m, 1H), 3.43-3.35 (m, 1H), 2.97 (s, 3H), 2.96-2.85 (m, 1H), 2.82-2.70 (m, 1H), 2.55-2.50 (m, 2H), 1.96-1.87 (m, 1H), 1.80-1.70 (m, 1H). |
| 191 (W318) | | ESI-MS (m/z): 554.4 [M + H]+; 1H NMR (500 MHz, DMSO-d6) δ 8.63 (d, J = 2.7 Hz, 1H), 8.13 (d, J = 2.4 Hz, 1H), 7.96 (d, J = 8.5 Hz, 1H), 7.87 (dd, J = 8.5, 2.6 Hz, 1H), 7.85 (dd, J = 8.5, 2.6 Hz, 1H), 7.16 (d, J = 8.4 Hz, 1H), 7.09 (br s, 1H), 4.58-4.52 (m, 1H), 4.44-4.32 (m, 2H), 4.03-3.95 (m, 1H), 3.43-3.35 (m, 1H), 2.97 (s, 3H), 2.96-2.85 (m, 1H), 2.82-2.70 (m, 1H), 2.55-2.50 (m, 2H), 1.96-1.87 (m, 1H), 1.80-1.70 (m, 1H). |
| 192 (W324) | | ESI-MS (m/z): 558.3 [M + H]+; 1H NMR (500 MHz, DMSO-d6) δ 9.04 (s, 2H), 8.13 (d, J = 2.3 Hz, 1H), 7.92 (dd, J = 8.4, 2.4 Hz, 1H), 7.23 (d, J = 8.0 Hz, 1H), 7.10 (br s, 1H), 4.57-4.52 (m, 1H), 4.43-4.34 (m, 2H), 4.02-3.95 (m, 1H), 3.40-3.34 (m, 1H), 2.98-2.86 (m, 1H), 2.82-2.70 (m, 1H), 2.55-2.50 (m, 2H), 1.96-1.87 (m, 1H), 1.80-1.70 (m, 1H). |
| 193 (W342) | | ESI-MS (m/z): 558.4 [M + H]+; 1H NMR (500 MHz, DMSO-d6) δ 9.04 (s, 2H), 8.13 (d, J = 2.4 Hz, 1H), 7.92 (dd, J = 8.4, 2.4 Hz, 1H), 7.23 (d, J = 8.4 Hz, 1H), 7.10 (d, J = 6.9 Hz, 1H), 4.55 (dd, J = 5.6, 3.5 Hz, 1H), 4.47-4.34 (m, 2H), 4.05-3.96 (m, 1H), 3.42-3.35 (m, 1H), 2.99-2.88 (m, 1H), 2.83-2.70 (m, 1H), 2.55-2.47 (m, 2H), 1.99-1.88 (m, 1H), 1.83-1.70 (m, 1H). Retention time on chiral column = 2.04 min (AD-H column, CO2:EtOH (0.05% DEA) = 60:40) |
| 194 (W341) | | ESI-MS (m/z): 558.3 [M + H]+; 1H NMR (500 MHz, DMSO-d6) δ 9.04 (s, 2H), 8.13 (d, J = 2.4 Hz, 1H), 7.92 (dd, J = 8.4, 2.4 Hz, 1H), 7.23 (d, J = 8.5 Hz, 1H), 7.10 (s, 1H), 4.55 (dd, J = 5.7, 3.5 Hz, 1H), 4.45-4.32 (m, 2H), 4.03-3.94 (m, 1H), 3.40-3.35 (m, 1H), 2.99-2.85 (m, 1H), 2.81-2.70 (m, 1H), 2.55-2.49 (m, 2H), 1.95-1.88 (m, 1H), 1.83-1.63 (m, 1H). Retention time on chiral column = 1.63 min (AD-H column, CO2:EtOH (0.05% DEA) = 60:40) |
| 195 (W323) | | ESI-MS (m/z): 557.3 [M + H]+; 1H NMR (500 MHz, DMSO-d6) δ 8.63 (d, J = 2.7 Hz, 1H), 8.13 (d, J = 2.4 Hz, 1H), 7.96 (d, J = 8.6 Hz, 1H), 7.90 (dd, J = 8.4, 2.6 Hz, 1H), 7.90 (dd, J = 8.4, 2.6 Hz, 1H), 7.85 (dd, J = 8.4, 2.6 Hz, 1H), 7.19-7.15 (m, 1H), 7.09 (br s, 1H), 4.57-4.52 (m, 1H), 4.44-4.32 (m, 2H), 4.02-3.95 (m, 1H), 3.41-3.32 (m, 1H), 2.97-2.86 (m, 1H), 2.82-2.69 (m, 1H), 2.56-2.50 (m, 2H), 1.96-1.88 (m, 1H), 1.80-1.70 (m, 1H). |

-continued

| Example | structure | analyze data |
|---|---|---|
| 196 (W344) | | ESI-MS (m/z): 557.4 [M + H]$^+$; $^1$H NMR (500 MHz, DMSO-d6) δ 8.63 (d, J = 2.7 Hz, 1H), 8.13 (d, J = 2.0 Hz, 1H), 7.96 (d, J = 8.6 Hz, 1H), 7.90 (dd, J = 8.4, 2.6 Hz, 1H), 7.90 (dd, J = 8.4, 2.6 Hz, 1H), 7.85 (dd, J = 8.4, 2.6 Hz, 1H), 7.19-7.15 (m, 1H), 7.09 (br s, 1H), 4.57-4.52 (m, 1H), 4.44-4.32 (m, 2H), 4.02-3.95 (m, 1H), 3.41-3.32 (m, 1H), 2.97-2.86 (m, 1H), 2.82-2.69 (m, 1H), 2.56-2.50 (m, 2H), 1.96-1.88 (m, 1H), 1.80-1.70 (m, 1H). Retention time on chiral column = 2.43 min (AD-H column, CO$_2$:EtOH (0.05% DEA) = 60:40) |
| 197 (W343) | | ESI-MS (m/z): 557.4 [M + H]$^+$; $^1$H NMR (500 MHz, DMSO-d6) δ 8.63 (d, J = 2.7 Hz, 1H), 8.13 (d, J = 2.4 Hz, 1H), 7.96 (d, J = 8.6 Hz, 1H), 7.90 (dd, J = 8.4, 2.6 Hz, 1H), 7.90 (dd, J = 8.4, 2.6 Hz, 1H), 7.85 (dd, J = 8.4, 2.6 Hz, 1H), 7.19-7.15 (m, 1H), 7.09 (br s, 1H), 4.57-4.52 (m, 1H), 4.44-4.32 (m, 2H), 4.02-3.95 (m, 1H), 3.41-3.32 (m, 1H), 2.97-2.86 (m, 1H), 2.82-2.69 (m, 1H), 2.56-2.50 (m, 2H), 1.96-1.88 (m, 1H), 1.80-1.70 (m, 1H). Retention time on chiral column = 1.69 min (AD-H column, CO$_2$:EtOH (0.05% DEA) = 60:40) |
| 198 (W307) | | ESI-MS (m/z): 555.4 [M + H]$^+$; $^1$H NMR (500 MHz, DMSO-d6) δ 9.04 (s, 2H), 8.13 (d, J = 2.2 Hz, 1H), 7.92 (dd, J = 8.4, 2.4 Hz, 1H), 7.23 (d, J = 8.4 Hz, 1H), 7.11 (br s, 1H), 4.58-4.52 (m, 1H), 4.45-4.32 (m, 2H), 4.03-3.96 (m, 1H), 3.40-3.34 (m, 1H), 2.97 (s, 3H), 2.96-2.85 (m, 1H), 2.80-2.70 (m, 1H), 2.55-2.50 (m, 2H), 1.96-1.87 (m, 1H), 1.80-1.70 (m, 1H). |
| 199 (W319) | | ESI-MS (m/z): 555.4 [M + H]$^+$; $^1$H NMR (500 MHz, DMSO-d6) δ 9.04 (s, 2H), 8.26 (br s, 1H), 8.22 (d, J = 2.4 Hz, 1H), 8.00 (dd, J = 8.5, 2.5 Hz, 1H), 7.29 (d, J = 8.4 Hz, 1H), 4.81-4.77 (m, 1H), 4.63-4.56 (m, 2H), 4.03-3.96 (m, 1H), 3.45-3.34 (m, 1H), 3.25-3.10 (m, 4H), 2.98-2.85 (m, 1H), 2.80-2.63 (m, 1H), 2.06-1.95 (m, 1H), 1.85-1.70 (m, 1H). Retention time on chiral column = 1.92 min (AD-H column, CO$_2$:EtOH (0.05% DEA) = 60:40) |
| 200 (W320) | | ESI-MS (m/z): 555.3 [M + H]$^+$; $^1$H NMR (500 MHz, DMSO-d6) δ 9.04 (s, 2H), 8.30-8.15 (m, 2H), 7.99 (dd, J = 8.4 ,2.4 Hz, 1H), 7.29 (d, J = 8.4 Hz, 1H), 4.84-4.76 (m, 1H), 4.65-4.55 (m, 2H), 4.05-3.98 (m, 1H), 3.45-3.30 (m, 1H), 3.25-3.10 (m, 4H), 2.97-2.88 (m, 1H), 2.78-2.63 (m, 2H), 2.05-1.95 (m, 1H), 1.84-1.72 (m, 1H). Retention time on chiral column = 3.23 min (AD-H column, CO$_2$:EtOH (0.05% DEA) = 60:40) |

| Example | structure | analyze data |
|---|---|---|
| 201 (W360) | | ESI-MS (m/z): 536.3 [M + H]+; 1HNMR (500 MHz, DMSO-d6) δ 8.17 (d, J = 2.3 Hz, 1H), 7.91 (dd, J = 8.4, 2.4 Hz, 1H), 7.19 (d, J = 8.5 Hz, 1H), 6.98 (t, J = 5.4 Hz, 1H), 6.52 (s, 1H), 4.44-4.32 (m, 2H), 4.24-4.19 (m, 1H), 4.04 (q, J = 7.3 Hz, 2H), 4.00-3.93 (m, 1H), 3.69-3.61 (m, 2H), 3.40-3.30 (m, 2H), 3.15 (s, 3H), 2.49-2.35 (m, 2H), 1.93-1.85 (m, 1H), 1.78-1.69 (m, 1H), 1.30 (t, J = 7.3 Hz, 3H). |
| 202 (W361) | | ESI-MS (m/z): 532.6 [M + H]+; 1H NMR (500 MHz, DMSO-d6) δ 8.17 (d, J = 2.3 Hz, 1H), 7.91 (dd, J = 8.5, 2.4 Hz, 1H), 7.19 (d, J = 8.5 Hz, 1H), 6.99 (t, J = 5.9 Hz, 2H), 6.52 (s, 1H), 4.44-4.31 (m, 2H), 4.22 (t, J = 2.8 Hz, 1H), 4.04 (q, J = 7.2 Hz, 2H), 4.01-3.94 (m, 1H), 3.69-3.60 (m, 2H), 3.39-3.28 (m, 2H), 3.15 (s, 3H), 2.96 (s, 3H), 2.49-2.35 (m, 2H), 1.95-1.84 (m, 1H), 1.80-1.68 (m, 1H), 1.30 (t, J = 7.3 Hz, 3H). |
| 203 (W372) | | ESI-MS (m/z): 545.4 [M + H]+; 1H NMR (500 MHz, DMSO-d6) δ 8.16 (d, J = 2.3 Hz, 1H), 7.91 (dd, J = 8.4, 2.4 Hz, 1H), 7.20 (d, J = 8.4 Hz, 1H), 6.92 (br s, 1H), 6.53 (s, 1H), 5.05 (t, J = 5.5 Hz, 1H), 4.43-4.35 (m, 2H), 3.77-3.72 (m, 2H), 3.71-3.64 (m, 1H), 3.63-3.58 (m, 1H), 3.55-3.45 (m, 1H), 2.95 (s, 3H), 2.51-2.44 (m, 2H), 1.86-1.75 (m, 2H), 1.33 (s, 3H), 1.04-1.00 (m, 2H), 0.96-0.88 (m, 2H). |
| 204 (W374) | | ESI-MS (m/z): 532.3 [M + H]+; 1H NMR (500 MHz, DMSO-d6) δ 8.16 (d, J = 2.3 Hz, 1H), 7.91 (dd, J = 8.5, 2.4 Hz, 1H), 7.19 (d, J = 8.4 Hz, 1H), 6.98-6.86 (m, 1H), 6.53 (s, 1H), 5.05 (t, J = 5.5 Hz, 1H), 4.44-4.29 (m, 2H), 4.04 (q, J = 7.3 Hz, 2H), 3.77-3.67 (m, 2H), 3.65-3.58 (m, 1H), 3.56-3.51 (m, 1H), 2.95 (s, 3H), 2.48-2.36 (m, 2H), 1.86-1.78 (m, 2H), 1.33 (s, 3H), 1.30 (t, J = 7.3 Hz, 3H). |
| 205 (W379) | | ESI-MS (m/z): 531.2 [M + H]+; 1H NMR (500 MHz, DMSO-d6) δ 8.17 (d, J = 2.3 Hz, 1H), 7.91 (dd, J = 8.4, 2.4 Hz, 1H), 7.20 (d, J = 8.4 Hz, 1H), 6.94 (t, J = 6.2 Hz, 1H), 6.53 (s, 1H), 4.97 (t, J = 5.6 Hz, 1H), 4.47-4.28 (m, 2H), 4.10-3.96 (m, 2H), 3.79-3.67 (m, 2H), 3.49-3.44 (m, 1H), 2.96 (s, 3H), 2.52-2.45 (m, 2H), 1.96-1.85 (m, 1H), 1.82-1.70 (m, 1H), 1.05-1.00 (m, 2H), 0.95-0.88 (m, 2H). |
| 206 (W388) | | ESI-MS (m/z): 545.3 [M + H]+; 1H NMR (500 MHz, DMSO-d6) δ 8.16 (s, 1H), 7.91 (d, J = 8.7 Hz, 1H), 7.20 (d, J = 8.4 Hz, 1H), 6.96 (br s, 1H), 6.53 (s, 1H), 5.00 (s, 1H), 4.46-4.32 (m, 2H), 4.13-4.04 (m, 3H), 3.46 (br s, 1H), 3.26-3.18 (m, 1H), 3.02 (s, 3H), 2.55-2.47 (m, 2H), 1.96-1.88 (m, 1H), 1.81-1.69 (m, 1H), 1.09-0.98 (m, 5H), 0.96-0.89 (m, 2H). |

-continued

| Example | structure | analyze data |
|---------|-----------|--------------|
| 207 (W357) | | ESI-MS (m/z): 528.4 [M + H]⁺; ¹H NMR (500 MHz, DMSO-d6) δ 8.64 (d, J = 2.6 Hz, 1H), 8.13 (s, 1H), 7.98 (d, J = 8.6 Hz, 1H), 7.90 (d, J = 8.5 Hz, 1H), 7.86 (dd, J = 8.5, 2.5 Hz, 1H), 7.18 (d, J = 8.4 Hz, 1H), 7.09 (br s, 1H), 4.39 (d, J = 6.3 Hz, 2H), 4.15-4.00 (m, 3H), 3.80-3.60 (m, 3H), 2.98 (s, 3H), 2.56-2.49 (m, 2H), 2.47-2.40 (m, 1H), 2.24-2.14 (m, 1H), 1.94-1.83 (m, 2H). |
| 208 (W404) | | ESI-MS (m/z): 528.4 [M + H]⁺; ¹H NMR (500 MHz, DMSO-d6) δ 8.64 (d, J = 2.5 Hz, 1H), 8.14 (d, J = 2.3 Hz, 1H), 7.97 (d, J = 8.6 Hz, 1H), 7.89 (dd, J = 8.5, 2.4 Hz, 1H), 7.86 (dd, J = 8.5, 2.4 Hz, 1H), 7.18 (d, J = 8.4 Hz, 1H), 7.07 (t, J = 5.8 Hz, 1H), 4.40 (d, J = 6.3 Hz, 2H), 4.14-4.00 (m, 3H), 3.82-3.61 (m, 3H), 2.98 (s, 3H), 2.58-2.50 (m, 2H), 2.47-2.42 (m, 1H), 2.24-2.15 (m, 1H), 1.93-1.84 (m, 2H). Retention time on chiral column = 5.17 min (AD-H column, CO₂:MeOH (0.05% DEA) = 50:50) |
| 209 (W405) | | ESI-MS (m/z): 528.4 [M + H]⁺; H NMR (500 MHz, DMSO-d6) δ 8.64 (d, J = 2.5 Hz, 1H), 8.13 (d, J = 2.3 Hz, 1H), 7.97 (d, J = 8.6 Hz, 1H), 7.89 (dd, J = 8.5, 2.4 Hz, 1H), 7.86 (dd, J = 8.5, 2.4 Hz, 1H), 7.18 (d, J = 8.4 Hz, 1H), 7.07 (t, J = 5.4 Hz, 1H), 4.40 (d, J = 6.3 Hz, 2H), 4.14-3.99 (m, 3H), 3.85-3.63 (m, 3H), 2.98 (s, 3H), 2.57-2.52 (m, 2H), 2.48-2.41 (m, 1H), 2.23-2.15 (m, 1H), 1.93-1.84 (m, 2H). Retention time on chiral column = 8.97 min (AD-H column, CO₂:MeOH (0.05% DEA) = 50:50) |
| 210 (W371) | | ESI-MS (m/z): 531.2 [M + H]⁺; ¹H NMR (500 MHz, DMSO-d6) δ 9.04 (s, 2H), 8.13 (d, J = 2.3 Hz, 1H), 7.93 (dd, J = 8.3, 2.4 Hz, 1H), 7.23 (d, J = 8.4 Hz, 1H), 7.00 (br s, 1H), 4.47-4.33 (m, 2H), 4.22-4.17 (m, 1H), 4.06-3.97 (m, 1H), 3.30-3.21 (m, 2H), 320-3.12 (m, 1H), 3.00 (s, 3H), 2.94 (s, 3H), 2.52-2.47 (m, 2H), 2.06-1.98 (m, 1H), 1.95-1.85 (m, 2H), 1.83-1.72 (m, 1H). |
| 211 (W390, P1) | | ESI-MS (m/z): 531.1 [M + H]⁺; ¹H NMR (500 MHz, DMSO-d6) δ 9.04 (s, 2H), 8.13 (d, J = 2.3 Hz, 1H), 7.93 (dd, J = 8.4, 2.3 Hz, 1H), 7.23 (d, J = 8.4 Hz, 1H), 7.00 (br s, 1H), 4.46-4.35 (m, 2H), 4.22-4.17 (m, 1H), 4.05-3.98 (m, 1H), 3.30-3.21 (m, 2H), 3.20-3.12 (m, 1H), 3.00 (s, 3H), 2.94 (s, 3H), 2.54-2.48 (m, 2H), 2.06-1.99 (m, 1H), 1.96-1.87 (m, 2H), 1.83-1.71 (m, 1H). Retention time on chiral column = 2.67 min (AD-H column, CO₂:EtOH (0.05% DEA) = 60:40) |

-continued

| Example | structure | analyze data |
|---------|-----------|--------------|
| 212 (W389, P2) | | ESI-MS (m/z): 531.1 [M + H]$^+$; $^1$H NMR (500 MHz, DMSO-d6) δ 9.04 (s, 2H), 8.14 (s, 1H), 7.93 (d, J = 8.5 Hz, 1H), 7.23 (d, J = 8.5 Hz, 1H), 7.01 (br s, 1H), 4.46-4.34 (m, 2H), 4.22-4.14 (m, 1H), 4.04-3.96 (m, 1H), 3.30-3.20 (m, 2H), 3.19-3.12 (m, 1H), 3.00 (s, 3H), 2.94 (s, 3H), 2.55-2.48 (m, 2H), 2.06-1.97 (m, 1H), 1.96-1.85 (m, 2H), 1.82-1.72 (m, 1H). Retention time on chiral column = 3.82 min (AD-H column, CO$_2$:EtOH (0.05% DEA) = 60:40) |
| 213 (W355) | | ESI-MS (m/z): 530.4 [M + H]$^+$; $^1$H NMR (500 MHz, DMSO-d6) δ 8.62 (d, J = 2.6 Hz, 1H), 8.13 (d, J = 2.3 Hz, 1H), 7.96 (d, J = 8.7 Hz 1H), 7.87 (dd, J = 8.7, 2.5 Hz, 1H), 7.85 (dd, J = 8.7, 2.5 Hz, 1H), 7.17 (d, J = 8.4 Hz, 1H), 7.00 (br s, 1H), 4.44-4.34 (m, 2H), 4.21-4.16 (m, 1H), 4.04-3.97 (m, 1H), 3.30-3.21 (m, 2H), 3.20-3.12 (m, 1H), 3.00 (s, 3H), 2.94 (s, 3H), 2.54-2.48 (m, 2H), 2.06-1.97 (m, 1H), 1.95-1.85 (m, 2H), 1.83-1.72 (s, 1H). |
| 214 (W392, P1) | | ESI-MS (m/z): 530.4 [M + H]$^+$; $^1$H NMR (500 MHz, DMSO-d6) δ 8.63 (d, J = 2.5 Hz, 1H), 8.13 (d, J = 2.3 Hz, 1H), 7.97 (d, J = 8.6 Hz, 1H), 7.87 (dd, J = 8.5, 2.5 Hz, 1H), 7.85 (dd, J = 8.5, 2.5 Hz, 1H), 7.17 (d, J = 8.4 Hz, 1H), 7.00 (br s, 1H), 4.46-4.34 (m, 2H), 4.21-4.16 (m, 1H), 4.06-3.98 (m, 1H), 3.30-3.21 (m, 2H), 3.20-3.10 (m, 1H), 3.00 (s, 3H), 2.94 (s, 3H), 2.54-2.48 (m, 2H), 2.06-1.97 (m, 1H), 1.95-1.84 (m, 2H), 1.82-1.71 (m, 1H). Retention time on chiral column = 2.80 min (AD-H column, CO$_2$:EtOH (0.05% DEA) = 60:40) |
| 215 (W391, P2) | | ESI-MS (m/z): 530.4 [M + H]$^+$; $^1$H NMR (500 MHz, DMSO-d6) δ 8.63 (d, J = 2.6 Hz, 1H), 8.13 (d, J = 2.3 Hz, 1H), 7.97 (d, J = 8.6 Hz, 1H), 7.88 (dd, J = 8.5, 2.5 Hz, 1H), 7.85 (dd, J = 8.5, 2.5 Hz, 1H), 7.17 (d, J = 8.4 Hz, 1H), 7.00 (t, J = 6.3 Hz, 1H), 4.46-4.34 (m, 2H), 4.21-4.16 (m, 1H), 4.06-3.98 (m, 1H), 3.30-3.21 (m, 2H), 3.20-3.10 (m, 1H), 3.00 (s, 3H), 2.94 (s, 3H), 2.54-2.48 (m, 2H), 2.06-1.97 (m, 1H), 1.95-1.84 (m, 2H), 1.82-1.71 (m, 1H). Retention time on chiral column = 5.93 min (AD-H column, CO$_2$:EtOH (0.05% DEA) = 60:40) |
| 216 (W352) | | ESI-MS (m/z): 542.4 [M + H]$^+$; $^1$HNMR (500 MHz, DMSO-d6) δ 8.64 (d, J = 2.5 Hz, 1H), 8.33 (br s, 1H), 8.13 (d, J = 2.5 Hz, 1H), 7.98 (d, J = 8.6 Hz, 1H), 7.90 (dd, J = 8.5, 2.5 Hz, 1H), 7.86 (dd, J = 8.5, 2.5 Hz, 1H), 7.18 (d, J = 8.4 Hz, 1H), 7.13 (br s, 1H), 4.40 (d, J = 6.3 Hz, 2H), 3.83-3.76 (m, 4H), 3.65 (t, J = 5.7 Hz, 2H), 3.02 (s, 3H), 2.60-2.52 (m, 2H), 1.98-1.84 (m, 4H), 1.75-1.70 (m, 2H). |

-continued

| Example | structure | analyze data |
|---------|-----------|--------------|
| 217 (W359) | | ESI-MS (m/z): 543.3 [M + H]⁺; ¹HNMR (500 MHz, DMSO-d6) δ 9.05 (s, 2H), 8.15 (d, J = 2.0 Hz, 1H), 7.95 (dd, J = 8.5, 2.0 Hz, 1H), 7.25 (d, J = 8.5 Hz, 1H), 4.44 (d, J = 6.2 Hz, 2H), 3.94-3.75 (m, 4H), 3.70-3.56 (m, 2H), 3.04 (s, 3H), 2.58 (t, J = 6.5 Hz, 2H), 2.00-1.84 (m, 4H), 1.78-1.68 (m, 2H). |
| 218 (W339) | | ESI-MS (m/z): 557.6 [M + H]⁺; ¹HNMR (500 MHz, DMSO-d6) δ 9.05 (s, 2H), 8.14 (d, J = 2.3 Hz, 1H), 7.94 (dd, J = 8.4, 2.4 Hz, 1H), 7.24 (d, J = 8.4 Hz, 1H), 7.05 (br s, 1H), 4.46-4.33 (m, 2H), 4.20-4.13 (m, 1H), 4.01 (d, J = 4.3 Hz, 1H), 3.85-3.74 (m, 2H), 3.35-3.30 (m, 1H), 3.25-3.13 (m, 3H), 3.03 (s, 3H), 2.10-2.04 (m, 1H), 2.02-1.93 (m, 1H), 1.83-1.72 (m, 1H), 1.51-1.43 (m, 2H), 1.31-1.24 (m, 1H), 1.22-1.13 (m, 1H). |
| 219 (W338) | | ESI-MS (m/z): 556.5 [M + H]⁺; ¹HNMR (500 MHz, DMSO-d6) δ 8.64 (d, J = 2.7 Hz, 1H), 8.14 (d, J = 2.4 Hz, 1H), 7.98 (d, J = 8.5 Hz, 1H), 7.90 (dd, J = 8.5, 2.5 Hz, 2H), 7.86 (dd, J = 8.5, 2.5 Hz, 2H), 7.18 (d, J = 8.4 Hz, 1H), 7.05 (br s, 1H), 4.46-4.32 (m, 2H), 4.21-4.13 (m, 1H), 4.00 (d, J = 4.3 Hz, 1H), 3.85-3.74 (m, 2H), 3.25-3.13 (m, 3H), 3.03 (s, 3H), 2.53-2.47 (m, 2H), 2.11-2.04 (m, 1H), 2.02-1.94 (m, 1H), 1.83-1.71 (m, 1H), 1.52-1.40 (m, 2H), 1.31-1.24 (m, 1H), 1.22-1.10 (m, 1H). |
| 220 (W398) | | ESI-MS (m/z): 519.3 [M + H]⁺; ¹HNMR (500 MHz, DMSO-d6) δ 8.63 (d, J = 2.5 Hz, 1H), 8.13 (d, J = 2.3 Hz, 1H), 7.96 (d, J = 8.6 Hz, 1H), 7.88 (dd, J = 8.5, 2.4 Hz, 1H), 7.85 (dd, J = 8.5, 2.4 Hz, 1H), 7.17 (d, J = 8.4 Hz, 1H), 6.89 (br s, 1H), 5.04 (t, J = 5.5 Hz, 1H), 4.45-4.36 (m, 2H), 3.77-3.66 (m, 2H), 3.65-3.58 (m, 1H), 3.54 (dd, J = 11.3, 5.4 Hz, 1H), 2.53-2.47 (m, 2H), 1.89-1.76 (m, 2H), 1.33 (s, 3H). |
| 221 (W399) | | ESI-MS (m/z): 520.3 [M + H]⁺; ¹HNMR (500 MHz, DMSO-d6) δ 9.04 (s, 2H), 8.14 (d, J = 2.3 Hz, 1H), 7.93 (dd, J = 8.4, 2.3 Hz, 1H), 7.23 (d, J = 8.4 Hz, 1H), 6.91 (br s, 1H), 5.04 (d, J = 5.3 Hz, 1H), 4.45-4.32 (m, 2H), 3.77-3.67 (m, 2H), 3.66-3.59 (m, 1H), 3.54 (dd, J = 11.5, 4.6 Hz, 1H), 2.53-2.47 (m, 2H), 1.87-1.75 (m, 2H), 1.33 (s, 3H). |
| 222 (W402) | | ESI-MS (m/z): 505.3 [M + H]⁺; ¹HNMR (500 MHz, DMSO-d6) δ 8.17 (d, J = 2.3 Hz, 1H), 7.92 (dd, J = 8.4, 2.4 Hz, 1H), 7.20 (d, J = 8.4 Hz, 1H), 6.95 (t, J = 6.4 Hz, 1H), 6.56 (s, 1H), 4.98 (t, J = 5.5 Hz, 1H), 4.47-4.30 (m, 2H), 4.13-3.97 (m, 2H), 3.79-3.64 (m, 5H), 2.97 (s, 3H), 2.51-2.44 (m, 2H), 1.95-1.70 (m, 2H). |

-continued

| Example | structure | analyze data |
|---|---|---|
| 223 (W403) | | ESI-MS (m/z): 519.3 [M + H]⁺; ¹H NMR (500 MHz, DMSO-d6) δ 8.17 (d, J = 2.3 Hz, 1H), 7.92 (dd, J = 8.4, 2.4 Hz, 1H), 7.20 (d, J = 8.4 Hz, 1H), 6.93 (t, J = 6.3 Hz, 1H), 6.56 (s, 1H), 5.07 (br s, 1H), 4.46-4.33 (m, 2H), 3.80-3.67 (m, 5H), 3.66-3.50 (m, 2H), 2.96 (s, 3H), 2.51-2.46 (m, 2H), 1.83 (q, J = 6.4 Hz, 2H), 1.34 (s, 3H). |
| 224 (W406) | | ESI-MS (m/z): 529.3 [M + H]⁺; ¹HNMR (500 MHz, DMSO-d6) δ 9.05 (s, 2H), 8.14 (d, J = 2.3 Hz, 1H), 7.94 (dd, J = 8.5, 2.3 Hz, 1H), 7.24 (d, J = 8.4 Hz, 1H), 7.08 (t, J = 6.3 Hz, 1H), 4.41 (d, J = 6.3 Hz, 2H), 4.11-4.00 (m, 3H), 3.80-3.62 (m, 3H), 2.98 (s, 3H), 2.57-2.50 (m, 2H), 2.47-2.40 (m, 1H), 2.23-2.15 (m, 1H), 1.93-1.85 (m, 2H). Retention time on chiral column = 5.88 min (AD-H column, CO₂:MeOH (0.05% DEA) = 50:50) |
| 225 (W407) | | ESI-MS (m/z): 529.3 [M + H]⁺; ¹HNMR (500 MHz, DMSO-d6) δ 9.05 (s, 2H), 8.14 (d, J = 2.3 Hz, 1H), 7.94 (dd, J = 8.4, 2.3 Hz, 1H), 7.24 (d, J = 8.4 Hz, 1H), 7.08 (t, J = 6.2 Hz, 1H), 4.41 (d, J = 6.3 Hz, 2H), 4.13-4.01 (m, 3H), 3.80-3.62 (m, 3H), 2.98 (s, 3H), 2.58-2.50 (m, 2H), 2.47-2.41 (m, 1H), 2.23-2.16 (m, 1H), 1.92-1.85 (m, 2H). Retention time on chiral column = 9.43 min (AD-H column, CO₂:MeOH (0.05% DEA) = 50:50) |
| 226 (W411) | | ESI-MS (m/z): 501.4 [M + H]⁺; ¹H NMR (500 MHz, DMSO-d6) δ 9.04 (s, 2H), 8.13 (d, J = 2.0 Hz, 1H), 7.93 (dd, J = 8.5, 2.5 Hz, 1H), 7.23 (d, J = 8.5 Hz, 1H), 6.94 (br s, 1H), 4.46-4.32 (m, 2H), 4.08-3.96 (m, 2H), 3.35-3.38 (m, 1H), 2.97 (s, 3H), 2.94 (d, J = 3.5 Hz, 2H), 2.53-2.47 (m, 2H), 2.02-1.97 (m, 1H), 1.93-1.80 (m, 1H). |
| 227 (W412) | | ESI-MS (m/z): 500.5 [M + H]⁺; ¹H NMR (500 MHz, DMSO-d6) δ 8.64 (d, J = 2.5 Hz, 1H), 8.14 (d, J = 2.3 Hz, 1H), 7.97 (d, J = 8.5 Hz, 1H), 7.91 (dd, J = 8.5, 2.5 Hz, 1H), 7.86 (dd, J = 8.5, 2.5 Hz, 1H), 7.18 (d, J = 8.5 Hz, 1H), 6.94 (t, J = 6.5 Hz, 1H), 4.46-4.32 (m, 2H), 4.06-3.98 (m, 2H), 3.37-3.30 (m, 1H), 2.98 (s, 3H), 2.95 (d, J = 3.6 Hz, 2H), 2.52-2.45 (m, 2H), 1.93-1.86 (m, 1H), 1.85-1.75 (m, 1H). |
| 228 (W413) | | ESI-MS (m/z): 544.3 [M + H]⁺; ¹H NMR (500 MHz, DMSO-d6) δ 9.06 (s, 2H), 8.12 (d, J = 2.5 Hz, 1H), 7.94 (dd, J = 8.5, 2.3 Hz, 1H), 7.87-7.82 (m, 1H), 7.23 (d, J = 8.5 Hz, 1H), 6.97 (t, J = 6.5 Hz, 1H), 4.39 (d, J = 6.0 Hz, 2H), 4.13-4.05 (m, 2H), 3.68-3.61 (m, 1H), 3.27-3.18 (m, 2H), 2.98 (s, 3H), 2.52-2.46 (m, 2H), 1.95-1.83 (m, 2H), 1.48 (s, 3H). |

-continued

| Example | structure | analyze data |
|---|---|---|
| 229 (W414) | | ESI-MS (m/z): 515.3 [M + H]⁺; ¹H NMR (500 MHz, DMSO-d6) δ 8.64 (s, 1H), 8.14 (s, 1H), 7.98 (d, J = 9.0 Hz, 1H), 7.90 (dd, J = 8.5, 2.5 Hz, 1H), 7.86 (dd, J = 8.5, 2.5 Hz, 1H), 7.18 (d, J = 8.5 Hz, 1H), 6.97 (br s, 1H), 4.45-4.33 (m, 2H), 4.11 (t, J = 3.5 Hz, 1H), 4.02-3.98 (m, 1H), 3.33-3.26 (m, 1H), 2.97 (s, 3H), 2.90-2.83 (m, 2H), 2.52-2.46 (m, 2H), 2.17 (s, 3H), 1.95-1.86 (m, 1H), 1.85-1.76 (m, 2H). |
| 230 (W415) | | ESI-MS (m/z): 501.8 [M + H]⁺; ¹H NMR (500 MHz, DMSO-d6) δ 7.70 (s, 1H), 7.42 (s, 1H), 6.68 (t, J = 7.0 Hz, 1H), 6.54 (s, 1H), 5.53 (s, 2H), 4.32-4.18 (m, 2H), 4.17-4.07 (m, 1H), 4.08-4.00 (m, 1H), 3.73-3.63 (m, 1H), 3.32-3.26 (m, 1H), 2.95 (s, 3H), 2.00-1.89 (m, 1H), 1.86-1.76 (m, 0H), 1.23 (d, J = 6.9 Hz, 3H), 1.11-0.96 (m, 4H). |
| 231 (W417) | | ESI-MS (m/z): 516.3 [M + H]⁺; ¹H NMR (500 MHz, DMSO-d6) δ 8.02 (s, 1H), 7.84 (d, J = 8.3 Hz, 1H), 7.77 (d, J = 7.8 Hz, 1H), 7.55 (d, J = 7.9 Hz, 1H), 7.09 (d, J = 8.4 Hz, 1H), 7.02 (t, J = 5.4 Hz, 1H), 4.40-4.28 (m, 2H), 4.11 (q, J = 6.7 Hz, 1H), 4.04-3.97 (m, 1H), 3.81 (s, 3H), 3.31-3.24 (m, 1H), 2.92 (s, 3H), 2.56-2.49 (s, 2H), 1.95-1.87 (m, 1H), 1.83-1.75 (m, 1H), 1.22 (d, J = 6.8 Hz, 3H). |
| 232 (W418) | | ESI-MS (m/z): 546.3 [M + H]⁺; ¹H NMR (500 MHz, DMSO-d6) δ 8.02 (s, 1H), 7.84 (d, J = 8.6 Hz, 1H), 7.77 (d, J = 7.8 Hz, 1H), 7.55 (d, J = 7.9 Hz, 1H), 7.09 (d, J = 8.4 Hz, 1H), 6.88 (t, J = 5.9 Hz, 1H), 5.04 (t, J = 5.4 Hz, 1H), 4.40-4.30 (m, 2H), 3.83 (s, 3H), 3.77-3.66 (m, 2H), 3.65-3.58 (m, 1H), 3.57-3.52 (m, 1H), 2.95 (s, 3H), 2.52-2.46 (m, 2H), 1.87-1.77 (m, 2H), 1.33 (s, 3H). |
| 233 (W419) | | ESI-MS (m/z): 573.3 [M + H]⁺; ¹H NMR (500 MHz, DMSO-d6) δ 8.12 (d, J = 2.2 Hz, 1H), 7.91 (dd, J = 8.4, 2.3 Hz, 1H), 7.19 (d, J = 8.4 Hz, 1H), 7.05 (br s, 1H), 5.09 (t, J = 5.5 Hz, 1H), 4.47-4.33 (m, 2H), 3.88 (q, J = 7.3 Hz, 2H), 3.78-3.72 (m, 1H), 3.71-3.66 (m, 1H), 3.65-3.59 (m, 1H), 3.58-3.52 (m, 1H), 2.95 (s, 3H), 2.52-2.48 (m, 2H), 1.90-1.77 (m, 2H), 1.48-1.38 (m, 1H), 1.34 (s, 3H), 1.23 (t, J = 7.2 Hz, 3H), 0.64-0.56 (m, 2H), 0.43-0.36 (m, 2H). |
| 234 (W420) | | ESI-MS (m/z): 575.3 [M + H]⁺; ¹H NMR (500 MHz, DMSO-d6) δ 8.20 (d, J = 2.2 Hz, 1H), 7.95 (dd, J = 8.4, 2.4 Hz, 1H), 7.24 (d, J = 8.4 Hz, 1H), 5.20 (br s, 1H), 5.05-4.96 (m, 1H), 4.55-4.42 (m, 2H), 3.98 (q, J = 7.5 Hz, 1H), 3.94-3.89 (m, 1H), 3.87-3.83 (m, 1H), 3.82-3.75 (m, 2H), 3.72-3.67 (m, 1H), 3.65-3.55 (m, 3H), 3.01 (s, 3H), 2.60-2.50 (m, 2H), 2.31-2.22 (m, 1H), 1.93-1.79 (m, 2H), 1.38 (s, 3H). |

-continued

| Example | structure | analyze data |
|---------|-----------|--------------|
| 235 (W422) | | ESI-MS (m/z): 519.3 [M + H]⁺; ¹H NMR (500 MHz, DMSO-d6) δ 8.17 (d, J = 2.2 Hz, 1H), 7.92 (dd, J = 8.5, 2.4 Hz, 1H), 7.20 (d, J = 8.4 Hz, 1H), 6.96 (t, J = 6.2 Hz, 12H), 6.55 (s, 1H), 5.01 (d, J = 4.9 Hz, 1H), 4.46-4.32 (m, 2H), 4.13-4.02 (m, 3H), 3.71 (s, 3H), 3.25-3.18 (m, 1H), 3.03 (s, 3H), 2.53-2.46 (m, 2H), 1.97-1.89 (m, 1H), 1.82-1.70 (m, 1H), 1.01 (d, J = 6.4, Hz, 3H). |
| 236 (W424) | | ESI-MS (m/z): 516.3 [M + H]⁺; ¹H NMR (500 MHz, DMSO-d6) δ 9.04 (s, 2H), 8.13 (s, 1H), 7.93 (dd, J = 8.5, 2.5 Hz, 1H), 7.23 (d, J = 8.5 Hz, 1H), 6.97 (t, J = 6.5 Hz, 1H), 4.45-4.31 (m, 2H), 4.10 (t, J = 4.0 Hz, 1H), 4.03-3.97 (m, 1H), 3.35-3.27 (m, 1H), 2.97 (s, 3H), 2.84 (d, J = 4.0 Hz, 2H), 2.53-2.47 (m, 2H), 2.16 (s, 3H), 1.93-1.84 (m, 1H), 1.82-1.72 (m, 1H). |
| 237 (W425) | | ESI-MS (m/z): 549.3 [M + H]⁺; ¹H NMR (500 MHz, DMSO-d6) δ 8.17 (d, J = 2.3 Hz, 1H), 7.90 (dd, J = 8.5, 2.3 Hz, 1H), 7.17 (d, J = 8.4 Hz, 1H), 6.92 (t, J = 6.0 Hz, 2H), 6.53 (s, 1H), 5.05 (t, J = 5.5 Hz, 1H), 4.89 (t, J = 5.5 Hz, 1H), 4.43-4.34 (m, 2H), 4.07 (t, J = 5.8 Hz, 2H), 3.77-3.66 (m, 4H), 3.65-3.59 (m, 1H), 3.58-3.52 (m, 1H), 2.95 (s, 3H), 2.52-2.45 (m, 2H), 1.88-1.77 (m, 2H), 1.33 (s, 3H). |
| 238 (W426) | | ESI-MS (m/z): 511.3 [M + H]⁺; ¹H NMR (500 MHz, DMSO-d6) δ 8.79 (d, J = 1.9 Hz, 1H), 8.41 (d, J = 2.2 Hz, 1H), 8.36 (d, J = 2.1 Hz, 1H), 8.10-8.03 (m, 2H), 7.08 (t, J = 6.2 Hz, 1H), 4.47-4.34 (m, 2H), 4.13 (q, J = 6.7 Hz, 1H), 4.07-3.97 (m, 1H), 3.33-3.26 (m, 1H), 2.94 (s, 3H), 2.53-2.46 (m, 2H), 1.99-1.89 (m, 1H), 1.86-1.73 (m, 1H), 1.24 (d, J = 6.8 Hz, 3H). |
| 239 (W427) | | ESI-MS (m/z): 530.3 [M + H]⁺; ¹H NMR (500 MHz, DMSO-d6) δ 8.64 (s, 1H), 8.14 (s, 1H), 7.97 (d, J = 8.6 Hz, 1H), 7.91 (d, J = 8.5 Hz, 1H), 7.84 (d, J = 8.5 Hz, 1H), 7.18 (d, J = 8.4 Hz, 1H), 6.90 (t, J = 6.5 Hz, 1H), 5.08 (br s, 1H), 4.45-4.32 (m, 2H), 3.97-3.89 (m, 2H), 3.33-3.27 (m, 1H), 3.03 (s, 3H), 2.56-2.47 (m, 2H), 1.92-1.73 (m, 2H), 1.54 (s, 3H), 1.01 (d, J = 6.3 Hz, 3H). |
| 240 (W428) | | ESI-MS (m/z): 531.0 [M + H]⁺; ¹H NMR (500 MHz, DMSO-d6) δ 9.04 (s, 2H), 8.13 (d, J = 2.4 Hz, 1H), 7.93 (dd, J = 8.4, 2.4 Hz, 1H), 7.23 (d, J = 8.4 Hz, 1H), 6.91 (t, J = 6.5 Hz, 1H), 5.07 (br s, 1H), 4.45-4.32 (m, 2H), 3.96-3.87 (m, 2H), 3.45-3.36 (m, 1H), 3.03 (s, 3H), 2.51-2.46 (m, 2H), 1.90-1.73 (m, 2H), 1.53 (s, 3H), 1.00 (d, J = 6.4 Hz, 3H). |

-continued

| Example | structure | analyze data |
|---|---|---|
| 241 (W431) | | ESI-MS (m/z): 508.3 [M + H]$^+$; $^1$H NMR (500 MHz, DMSO-d6) δ 8.17 (d, J = 2.1 Hz, 1H), 7.92 (dd, J = 9.0, 1.5 Hz, 1H), 7.20 (d, J = 8.4 Hz, 1H), 6.95 (br s, 1H), 6.56 (s, 1H), 4.98 (br s, 1H), 4.46-4.31 (m, 2H), 4.08-3.97 (m, 2H), 3.78-3.66 (m, 2H), 2.97 (s, 3H), 2.53-2.46 (m, 2H), 1.94-1.86 (m, 1H), 1.82-1.71 (m, 1H). |

Biological Screening and Results of Wnt Pathway Inhibitors

Test Example 1: Construction of Colo205-LUC-TCF/LEF-M1 Reporter Cell Line

Colo205 cell line (Cell Bank of Chinese Academy of Sciences, Cat #TCHu102) was purchased from the Cell Bank of Chinese Academy of Sciences. After expansion and subculture, in the exponential growth phase of the cells, transfection with lipo3000 liposome transfection with TCF/LEF transcription factors Driven luciferase reporter plasmid (Promega). during the exponential growth phase, luciferase reporter plasmid (Promega) driven by TCF/LEF transcription factor was transfected by lipo3000 liposome transfection. The plasmid carries a resistance gene for resistance screening. Transfection was carried out in 10 cm culture dishes using conventional complete medium without resistance. After 2 days, the medium with resistance was replaced, and the culture was continued. After that, the resistant medium was replaced every 2 days, and the suspended cells were discarded. The original medium was centrifuged to remove cells and debris and retained as an adaptive medium. When the cells covered the culture dish, the cells were digested, counted, and passaged in a 96-well plate, so that the average number of cells contained in each well was 1.5/well, and the adaptive medium was used for passage. The rest of the cells were frozen. After subculture, culture for 4 hours to allow the cells to adhere to the wall, and then observe the number of cells in each well under a microscope. Wells with only 1 cell per well were labeled as monoclonal wells. Afterwards, normal culture was performed, and the culture medium was replaced every 2 days, and observed. There are holes where the monoclonal cells continue to grow in the early stage, and they are labeled twice, and can be replaced with normal resistant medium. When a monoclonal well was overgrown with a 96-well plate, it is digested and passaged to a 24-well culture plate. After the 24-well plate is overgrown, it is passaged to a 96-well plate and a 6-well plate. The cells in a 96-well plate are at least 6 wells, of which 3 wells were added with known Wnt inhibitors, and the other 3 wells were not treated. After 24 hours, the cells in the 96-well plate were added with a fluorescence detection reagent to detect the fluorescence intensity. Cell lines with fluorescent expression when not treated and decreased fluorescent light after inhibition were selected and further cultured. The Colo205-LUC-TCF/LEF-M1 cell line is one of the cell lines screened above. Its growth curve, cell shape, and cell growth state are similar to those of the original Colo205 cells, and the ratio of the fluorescent signals of the inhibitor-treated and untreated cells is the largest among all cell lines, and the ratio can reach 4-5 times when inhibited at 4 hours, which was completely suitable for the screening of Wnt inhibitors in the later stage.

Test Example 2: Detection of Compound's Inhibitory Ability on Colo205-LUC-TCF/LEF M1 Reporter Cell Line The Colo205-LUC-TCF/LEF M1 cell line is a reporter tool cell stably transfected with the pGL4.49-LUC2-TCF/LEF vector. The β-catenin Wnt pathway is continuously activated. After adding the inhibitor, the Wnt pathway is inhibited. The expression of firefly luciferase regulated by the/LEF cis-element decreased, and after adding the detection substrate, the detected light signal decreased accordingly, so as to detect the inhibitory effect of the compound.

To a 96-well cell culture plate, add 100 uL of the compound with a maximum concentration of 20 uM to each well, and make a 3-fold serial dilution of the compound concentration. Then 10,000 colo205 cells stably transfected with the reporter gene and 100 uL medium were inoculated into each well, and corresponding positive and negative control wells were made at the same time. Put the cells in a 5% CO2 incubator and incubate at 37° C. for 4 hours. After 4 hours, remove the culture medium, add 100 uL of reagent (Promega) containing the corresponding firefly luciferase substrate to each well, and measure the activity of luciferase reporter gene. Luminescence intensity was read with SpectraMax in full wavelength mode. The light signal intensity of cells treated only with DMSO was used as a positive control, and the light signal intensity of wells without cells was used as a negative control, and the concentration of IC50 of each compound was calculated. Colo 205 reporter gene detection data are summarized in Table 1.

TABLE 1

| compound | Colo205-LUC-TCF/LEF reporter IC$_{50}$ (nM) | compound | Colo205-LUC-TCF/LEF reporter IC$_{50}$ (nM) |
|---|---|---|---|
| 1 | 83 | 6 | 57 |
| 11 | 61 | 13 | 30 |
| 15 | 53 | 19 | 9 |
| 20 | 93 | 21 | 30 |
| 22 | 10 | 23 | 11 |
| 24 | 13 | 25 | 19 |
| 26 | 19 | 27 | 26 |
| 28 | 27 | 61 (W2) | 2 |
| 62 (W13) | 14 | 63 (W22) | 23 |
| 64 (W23) | 41 | 65 (W32) | 20 |
| 66 (W43) | 11 | 67 (W46) | 34 |
| 68 (W49) | 12 | 69 (W50) | 21 |
| 70 (W55) | 12 | 71 (W56) | 20 |

TABLE 1-continued

| compound | Colo205-LUC-TCF/LEF reporter IC$_{50}$ (nM) | compound | Colo205-LUC-TCF/LEF reporter IC$_{50}$ (nM) |
|---|---|---|---|
| 72 (W57) | 7 | 73 (W85) | 24 |
| 74 (W69) | 10 | 75 (W77) | 15 |
| 76 (W83) | 67 | 77 (W86) | 8 |
| 78 (W87) | 28 | 79 (W95) | 20 |
| 80 (W104) | 10 | 81 (W105) | 17 |
| 82 (W107) | 6 | 83 (W116) | 10 |
| 84 (W123) | 17 | 85 (W132) | 7 |
| 86 (W135) | 38 | 87 (W136) | 7 |
| 88 (W140) | 22 | 89 (W150) | 13 |
| 90 (W152) | 24 | 91 (W221) | 28 |
| 99 (W193) | 27 | 100 (W239) | 50 |
| 101 (W213) | 47 | 103 (W195) | 36 |
| 105 (W199) | 31 | 106 (W190) | 54 |
| 111 (W241) | 21 | 113 (W247) | 31 |
| 114 (W243) | 27 | 116 (W249) | 30 |
| 117 (W237) | 4 | 118 (W279) | 5 |
| 119 (W255) | 7 | 120 (W265) | 15 |
| 126 (W308) | 10 | 127 (W280) | 20 |
| 128 (W263) | 19 | 130 (W354) | <0.5 |
| 132 (W383) | 42 | 133 (W377) | 58 |
| 138 (W271) | 25 | 146 (W273) | 34 |
| 148 (W250) | 31 | 149 (W285) | 16 |
| 150 (W301) | 25 | 151 (W332) | 50 |
| 152 (W336) | 4 | 153 (W293) | 15 |
| 154 (W258) | 30 | 155 (W347) | 77 |
| 156 (W264) | 39 | 157 (W262) | 24 |
| 159 (W259) | 2 | 160 (W362) | 3 |
| 161 (W269) | 9 | 162 (W270) | 11 |
| 163 (W325) | 16 | 164 (W326) | 26 |
| 165 (W286) | 14 | 166 (W287) | 23 |
| 167 (W289) | 12 | 168 (W298) | 26 |
| 170 (W368) | 17 | 172 (W305) | 20 |
| 175 (W327) | 28 | 176 (W296) | 20 |
| 177 (W297) | 21 | 178 (W333) | 39 |
| 179 (W375) | 23 | 180 (W386) | 23 |
| 181 (W396) | 18 | 182 (W395) | 7 |
| 185 (W310) | 69 | 189 (W306) | 17 |
| 190 (W317) | 11 | 192 (W324) | 23 |
| 193 (W342) | 4 | 195 (W323) | 22 |
| 196 (W344) | 7 | 198 (W307) | 17 |

TABLE 1-continued

| compound | Colo205-LUC-TCF/LEF reporter IC$_{50}$ (nM) | compound | Colo205-LUC-TCF/LEF reporter IC$_{50}$ (nM) |
|---|---|---|---|
| 199 (W319) | 9 | 201 (W360) | 6 |
| 202 (W361) | 4 | 203 (W372) | 21 |
| 204 (W374) | 25 | 205 (W379) | 37 |
| 206 (W388) | 24 | 211 (W390) | 43 |
| 213 (W355) | 69 | 218 (W339) | 30 |
| 219 (W338) | 31 | 223 (W403) | 59 |
| 231 (W417) | <0.5 | 232 (W418) | 5.5 |
| 238 (W426) | 27.3 | 239 (W427) | 36 |
| 240 (W428) | 16.6 | 241 (W431) | 9.3 |

Test Example 3: Proliferation Inhibition Test of Compounds on Wnt Mutant Cell Lines (Colo205 and DU4475) and Non-Wnt Mutant Cell Lines (Hela and RKO)

The cell lines used in the experiment are Colo205 and DU4475 cell lines whose Wnt pathway is continuously activated and whose proliferation is Wnt pathway-dependent; while the BELA and RKO cell lines, whose Wnt pathway is not activated under normal circumstances and the proliferation is independent of Wnt pathway, as control cell lines. It is Judged that the inhibitory effect of the compound of the present invention on Wnt-dependent proliferation is not caused by other non-specific toxicity.

Treat the Colo205, Du4475, HELA and RKO cell lines cultured in their respective mediums in the logarithmic growth phase, collect the cells and prepare a uniform cell suspension of known concentration, and then add it to the 96-well cell culture plate Cell suspension, so that each well contains 1000 cells. Put it into a 5% CO2 incubator and incubate at 37° C. for 20-24 h. On the second day, the fully dissolved, 3-fold serially diluted compound was added to each cell culture well, so that the final maximum concentration in the cell culture well was 20 uM, and the culture was continued for 96 hours. In this test, Promega's cell viability detection test is used for detection. The more the cells proliferate, the stronger the final signal intensity will be. The detection instrument is SpectraMax, full wavelength mode. The wells only added with DMSO were used as positive control wells, and the wells that were not inoculated with cells were used as negative control wells. The IC50 values of each compound for the proliferation inhibition of Wnt sustained activation or proliferation-dependent cells, and for Wnt-inactive or proliferation-independent cells were calculated. The IC50 value of cell proliferation inhibition was used to evaluate the inhibitory effect of the compound on the Wnt pathway and the toxic effect on normal cells (Table 2).

TABLE 2

| compound | Antiproliferative IC$_{50}$ (nM) | | | |
|---|---|---|---|---|
| | Colo205 | DU4475 | Hela | RKO |
| 2 | ND | ND | ND | ND |
| 6 | 46 | 59 | >10000 | >10000 |

TABLE 2-continued

| compound | Colo205 | DU4475 | Hela | RKO |
|---|---|---|---|---|
| 8 | ND | ND | ND | ND |
| 9 | ND | ND | ND | ND |
| 10 | ND | ND | ND | ND |
| 11 | 32 | 37 | >10000 | >10000 |
| 12 | ND | ND | ND | ND |
| 13 | 17 | 18 | 6422 | 3756 |
| 14 | ND | ND | ND | ND |
| 15 | 41 | 44 | >10000 | >10000 |
| 16 | ND | ND | ND | ND |
| 17 | ND | ND | ND | ND |
| 18 | ND | ND | ND | ND |
| 19 | 8 | 9 | >10000 | >10000 |
| 21 | 97 | 73 | >10000 | 3033 |
| 22 | 22 | 19 | >10000 | 5425 |
| 23 | 16 | 15 | >10000 | 3383 |
| 24 | 9 | 9.7 | >10000 | >10000 |
| 25 | 44 | 50 | >10000 | >10000 |
| 26 | 35 | 28 | >10000 | >10000 |
| 27 | 76 | 37 | >10000 | 4431 |
| 28 | 29 | 34 | >10000 | >10000 |
| 61 (W2) | 5.5 | 11.8 | 4172 | 3435 |
| 62 (W13) | 13.3 | 13.5 | 7205 | 6539 |
| 63 (W22) | 14.6 | 36.3 | 2593 | 3044 |
| 64 (W23) | ND | ND | ND | ND |
| 65 (W32) | 43.5 | 41.7 | 3489 | 1718 |
| 66 (W43) | ND | ND | ND | ND |
| 67 (W46) | 60.4 | 62.5 | 1090 | 1185 |
| 68 (W49) | 8.2 | 12.8 | >10000 | >10000 |
| 69 (W50) | ND | ND | ND | ND |
| 70 (W55) | 13.1 | 13.1 | 1411 | 1732 |
| 71 (W56) | 13.5 | 16.7 | >10000 | >10000 |
| 72 (W57) | 4.8 | 2.8 | >10000 | 3227 |
| 73 (W85) | ND | ND | ND | ND |
| 74 (W69) | 39 | 46 | 5511 | 1692 |
| 75 (W77) | 9.2 | 6.7 | 3857 | 4260 |
| 76 (W83) | ND | ND | ND | ND |
| 77 (W86) | 4.7 | 5.1 | 2923 | 4010 |
| 78 (W87) | 27.8 | 26.3 | 914 | 1417 |
| 79 (W95) | 43.9 | 23.7 | 3674 | 6893 |
| 80 (W104) | 24.6 | 27.5 | >10000 | >10000 |
| 81 (W105) | 33.4 | 19.3 | >10000 | >10000 |
| 82 (W107) | 12.4 | 11 | 1443 | 1830 |
| 83 (W116) | 5.1 | 5.1 | 4903 | 7470 |
| 84 (W123) | 41 | 36 | 4761 | 5535 |
| 85 (W132) | 8.3 | 11.6 | ND | 5501 |
| 86 (W135) | 79 | ND | >10000 | >10000 |
| 87 (W136) | 6.7 | 5.4 | 2924 | 3980 |
| 88 (W140) | ND | ND | >10000 | >10000 |
| 89 (W150) | 9 | 9.7 | >10000 | >10000 |
| 90 (W152) | 42 | 37 | >10000 | 5656 |
| 91 (W221) | 31 | 24 | >10000 | >10000 |
| 92 (W232) | 81 | 80 | >10000 | >10000 |
| 93 (W223) | 89 | 79 | >10000 | >10000 |
| 98 (W188) | 31 | 31 | ND | >10000 |
| 99 (W193) | 12 | 21 | >10000 | >10000 |
| 100 (W239) | 59 | 52 | >10000 | >10000 |
| 101 (W213) | 86 | 73 | 6982 | 3928 |
| 103 (W195) | 19 | 11 | ND | >10000 |
| 105 (W199) | 21 | 31 | >10000 | >10000 |
| 106 (W190) | 30 | 46 | >10000 | >10000 |
| 111 (W241) | 20 | 37 | >10000 | >10000 |
| 113 (W247) | 48 | 64 | ND | >10000 |
| 114 (W243) | 23 | 20 | >10000 | >10000 |
| 116 (W249) | 36 | 46 | ND | >10000 |
| 117 (W237) | 3.4 | 8.2 | >10000 | >10000 |
| 118 (W279) | 8.5 | 6.5 | ND | >10000 |
| 119 (W255) | 7.5 | 2.3 | ND | >10000 |
| 120 (W265) | 7.8 | 0.5 | ND | >10000 |
| 122 (W272) | 87 | 58 | ND | >10000 |
| 124 (W278) | 152 | 51 | ND | >10000 |
| 126 (W308) | 9.1 | <0.5 | ND | >10000 |
| 127 (W280) | 21 | 42 | ND | >10000 |
| 128 (W263) | 18.6 | 4.1 | ND | >10000 |
| 130 (W354) | <0.5 | ND | ND | >10000 |
| 132 (W383) | 25 | ND | ND | >10000 |
| 133 (W377) | 35 | ND | ND | >10000 |

TABLE 2-continued

| compound | Colo205 | DU4475 | Hela | RKO |
|---|---|---|---|---|
| 137 (W335) | 138 | ND | ND | >10000 |
| 138 (W271) | 48 | 40 | ND | >10000 |
| 140 (W376) | 49 | ND | ND | >10000 |
| 145 (W331) | 43 | 53 | ND | >10000 |
| 146 (W273) | 31 | 18 | ND | >10000 |
| 148 (W250) | 27 | 13 | ND | >10000 |
| 149 (W285) | 15 | 2.9 | ND | >10000 |
| 150 (W301) | 24 | 12 | ND | >10000 |
| 151 (W332) | 11 | 13 | ND | >10000 |
| 152 (W336) | 2.7 | ND | ND | >10000 |
| 153 (W293) | 21 | 3.9 | ND | >10000 |
| 154 (W258) | 37 | 30 | ND | >10000 |
| 155 (W347) | 88 | ND | ND | >10000 |
| 156 (W264) | 27 | 13 | ND | >10000 |
| 157 (W262) | 31 | 18 | ND | >10000 |
| 159 (W259) | 4.6 | <0.5 | ND | >10000 |
| 160 (W362) | <0.5 | ND | ND | 7150 |
| 161 (W269) | 4.6 | <0.5 | ND | >10000 |
| 162 (W270) | 4.9 | <0.5 | ND | >10000 |
| 163 (W325) | 5 | 4.7 | ND | >10000 |
| 164 (W326) | 5 | 5 | ND | >10000 |
| 165 (W286) | 12 | 0.6 | ND | >10000 |
| 166 (W287) | 16 | 4.8 | ND | 4822 |
| 167 (W289) | 6 | 0.6 | ND | >10000 |
| 168 (W298) | 29 | 11 | ND | >10000 |
| 170 (W368) | 7 | ND | ND | >10000 |
| 172 (W305) | 17.4 | 5.8 | ND | >10000 |
| 174 (W314) | 66 | 37 | ND | >10000 |
| 176 (W296) | 5.6 | 3.8 | ND | >10000 |
| 177 (W297) | 16.1 | 1.2 | ND | >10000 |
| 178 (W333) | 19.2 | 13.7 | ND | >10000 |
| 179 (W375) | ND | ND | ND | >10000 |
| 180 (W386) | 14.6 | ND | ND | >10000 |
| 181 (W396) | 11.9 | ND | ND | >10000 |
| 182 (W395) | 10.9 | ND | ND | >10000 |
| 185 (W310) | 63 | 99 | ND | >10000 |
| 189 (W306) | 8.5 | ND | ND | >10000 |
| 190 (W317) | 7.9 | <0.5 | ND | >10000 |
| 192 (W324) | 3.2 | ND | ND | >10000 |
| 193 (W342) | 1.4 | <0.5 | ND | >10000 |
| 195 (W323) | 2.1 | ND | ND | >10000 |
| 196 (W344) | 1.4 | <0.5 | ND | >10000 |
| 198 (W307) | 8.8 | ND | ND | >10000 |
| 199 (W319) | 6.9 | <0.5 | ND | >10000 |
| 201 (W360) | 3.6 | ND | ND | >10000 |
| 202 (W361) | 5 | ND | ND | >10000 |
| 203 (W372) | 9.3 | ND | ND | >10000 |
| 204 (W374) | 9.6 | ND | ND | >10000 |
| 205 (W379) | 14.8 | ND | ND | >10000 |
| 206 (W388) | 10 | ND | ND | >10000 |
| 207 (W357) | 84 | ND | ND | >10000 |
| 209 (W405) | 30 | ND | ND | >10000 |
| 210 (W371) | 60 | ND | ND | >10000 |
| 211 (W390) | 23 | ND | ND | >10000 |
| 213 (W355) | 53 | ND | ND | >10000 |
| 214 (W392) | 34 | ND | ND | >10000 |
| 215 (W391) | 53 | ND | ND | >10000 |
| 216 (W352) | 39 | ND | ND | >10000 |
| 217 (W359) | 57 | ND | ND | >10000 |
| 218 (W339) | 17 | ND | ND | >10000 |
| 219 (W338) | 10 | ND | ND | >10000 |
| 220 (W398) | 48 | ND | ND | >10000 |
| 221 (W399) | 43 | ND | ND | >10000 |
| 222 (W402) | 61 | ND | ND | >10000 |
| 223 (W403) | 35 | ND | ND | >10000 |
| 224 (W406) | 63 | ND | ND | >10000 |
| 225 (W407) | 57 | ND | ND | >10000 |
| 230 (W415) | 42 | ND | ND | >10000 |
| 231 (W417) | 1.6 | ND | ND | >10000 |
| 232 (W418) | 4.0 | ND | ND | >10000 |
| 233 (W419) | 52 | ND | ND | >10000 |
| 234 (W420) | 51 | ND | ND | >10000 |
| 238 (W426) | 24.6 | ND | ND | >10000 |
| 239 (W427) | 28.3 | ND | ND | >10000 |

Antiproliferative IC$_{50}$ (nM)

TABLE 2-continued

| | Antiproliferative IC$_{50}$ (nM) | | | |
|---|---|---|---|---|
| compound | Colo205 | DU4475 | Hela | RKO |
| 240 (W428) | 11.1 | ND | ND | >10000 |
| 241 (W431) | 11.5 | ND | ND | >10000 |

Test Example 4: Proliferation Inhibitory Test of Compounds on NCI-1H929 and HepG2 Cell Lines The cell lines used in the test are NCI-H929 and HepG2 cell lines whose Wnt pathway is continuously activated and whose proliferation is Wnt pathway-dependent; the inhibitory effect of the compound of the present invention on Wnt-dependent proliferation is judged.

Treat the NCI-H929 and HepG2 cell lines cultured in their respective mediums in the logarithmic growth phase, collect the cells and prepare a uniform cell suspension of known concentration, and then add the cell suspension to the 96-well cell culture plate solution so that each well contains 4000 cells. Put it into a 500 CO2 incubator and incubate at 37° C. for 20-24 h. On the second day, the fully dissolved, 3-fold serially diluted compound was added to each cell culture well, so that the final maximum concentration in the cell culture well was 20 uM, and the culture was continued for 96 hours. In this test, Promega's cell viability detection test is used for detection. The more the cells proliferate, the stronger the final signal intensity will be. The detection instrument is SpectraMax, full wavelength mode. The wells only added with DMSO were used as positive control wells, and the wells that were not inoculated with cells were used as negative control wells. The IC50 values of each compound for the proliferation inhibition of Wnt sustained activation or proliferation-dependent cells, and for Wnt-inactive or proliferation-independent cells were calculated. The IC50 value of cell proliferation inhibition was used to evaluate the inhibitory effect of the compound on the Wnt pathway and the toxic effect on normal cells (Table 3).

| | Antiproliferative IC$_{50}$ (nM) | |
|---|---|---|
| compound | NCI-H929 | HepG2 |
| 11 (W176) | 55 | ND |
| 68 (W49) | ND | 4.4 |
| 80 (W104) | ND | 9.3 |
| 82 (W107) | ND | 1.0 |
| 91 (W221) | 65 | 35 |
| 103 (W195) | ND | 68 |
| 105 (W199) | 45 | 44 |
| 111 (W241) | 94 | 40 |
| 114 (W243) | 60 | 37 |
| 116 (W249) | 17 | 69 |
| 117 (W237) | 27 | 3.1 |
| 118 (W279) | 83 | 16 |
| 119 (W255) | 28 | 5.4 |
| 120 (W265) | 55 | 18 |
| 126 (W308) | 39 | 2.7 |
| 127 (W280) | 75 | 42 |
| 128 (W263) | 78 | 27 |
| 130 (W354) | 19 | <0.5 |
| 146 (W273) | 87 | 81 |
| 149 (W285) | 41 | 11 |
| 150 (W301) | 62 | 19 |
| 151 (W332) | 26 | 9.8 |
| 152 (W336) | 36 | 4.4 |
| 153 (W293) | 37 | 19 |
| 160 (W362) | 48 | 3.5 |
| 161 (W269) | 22 | 16 |

-continued

| | Antiproliferative IC$_{50}$ (nM) | |
|---|---|---|
| compound | NCI-H929 | HepG2 |
| 162 (W270) | 22 | 16 |
| 163 (W325) | 31 | 7 |
| 164 (W326) | 26 | 7.5 |
| 165 (W286) | 31 | 11 |
| 166 (W287) | 31 | 21 |
| 167 (W289) | 28 | 6.8 |
| 168 (W298) | 68 | 35 |
| 170 (W368) | 94 | 31 |
| 172 (W305) | 89 | 26 |
| 176 (W296) | 40 | 27 |
| 177 (W297) | 56 | 25 |
| 178 (W333) | 60 | 23 |
| 179 (W375) | 45 | 11 |
| 180 (W386) | 82 | 40 |
| 181 (W396) | 25 | 81 |
| 182 (W395) | ND | 24 |
| 189 (W306) | ND | 3.5 |
| 190 (W317) | 6.4 | 2.1 |
| 192 (W324) | 12 | 4 |
| 193 (W342) | 24 | 1.2 |
| 195 (W323) | 19 | 4 |
| 196 (W344) | 54 | 1.2 |
| 198 (W307) | ND | 2.3 |
| 199 (W319) | 28 | 2 |
| 201 (W360) | 51 | 14 |
| 202 (W361) | 50 | 10 |
| 203 (W372) | 95 | 8.2 |
| 204 (W374) | 60 | 12 |
| 205 (W379) | 67 | 5.6 |
| 206 (W388) | 90 | 49 |
| 214 (W392) | 82 | 9.6 |
| 230 (W415) | ND | 50.8 |
| 231 (W417) | ND | <0.5 |
| 232 (W418) | ND | <0.5 |
| 234 (W420) | ND | 66.2 |
| 238 (W426) | ND | 25.8 |

Test Example 5: The Tumor Growth Inhibition Test of Compound 11 on the NCI-H929 Mouse Xenograft Model In this study, human myeloma cell NCI-H929 SCID xenograft model was used to evaluate the anti-tumor activity of compound 11 in vivo.

Female SCID were subcutaneously inoculated with human myeloma cells NCI-H929 to establish the NCI-H929 SCID xenograft model. After the tumor grew to an average tumor volume of about 80 mm$^3$, the tumor-bearing mice were randomly divided into two groups according to the tumor volume: the solvent-treated control group and the 30 mg/kg compound 11 group. Compound 11 was administered orally, once a day, and the administration cycle was 21 days. The tumor volume was measured every other day, and the body weight and tumor volume were measured on Day 21 (Table 4 and FIG. 1).

TABLE 4

The effect of compound 11 on the tumor size of animals in the NCI-H929
SCID xenograft tumor model

| group | number of animals | Treatment programs | tumor volume (mm³, MeanSEM) Day 0 | Day 21 | RTV Day 21 | % T/C$_{RTV}$ Day 21 | % TGItv Day 21 | Tumor weight (g) Day 21 | % TGI$_{TW}$ Day 21 |
|---|---|---|---|---|---|---|---|---|---|
| 1 | 10 | Vehicle, PO, QD × 21 | 84.86 ± 5.32 | 1718.12 ± 67.77 | 20.70 ± 1.06 | / | / | 2.017 ± 0.137 | / |
| 2 | 10 | Compound 11, 30 mg/kg, PO, QD × 21 | 85.23 ± 5.35 | 27.1 ± 5.13*** | 0.33 ± 0.06*** | 1.59 | 98.42 | 0.023 ± 0.005*** | 98.86 |

***P < 0.001 compared with the negative control group.

The invention claimed is:

1. A compound having a structure represented by formula I or a pharmaceutically acceptable salt, an isotopic derivative, end a stereoisomer thereof for inhibiting Wnt pathway activity:

(I)

wherein: — — — means existence or non-existence;

$R_1$ represents $C_1$-$C_6$ alkyl, $C_3$-$C_6$ cycloalkyl, $C_6$-$C_{10}$ aryl, 5-10 membered heteroaryl, and said $R_1$ can be optionally substituted by 0, 1, 2, 3 substituents selected from hydrogen, halogen, ($C_1$-$C_6$)alkyl, $OR^a$, halogenated ($C_1$-$C_6$) alkyl, ($C_3$-$C_6$) cycloalkyl, halogenated ($C_3$-$C_6$) cycloalkyl, cyano, $SR^a$, halogenated ($C_1$-$C_6$) alkoxy, halo ($C_3$-$C_6$) cycloalkoxy, halo ($C_1$-$C_6$) alkylthio, ($C_3$-$C_6$) cycloalkyloxy, ($C_3$-$C_6$) cycloalkylthio, halo ($C_3$-$C_6$) cycloalkylthio;

X represents —$(CR^aR^{a'})_m$—, —$(CR^aR^{a'})_m$ O$(CR^aR^{a'})_n$-, —$(CR^aR^{a'})_m$ S$(R^aR^{a'})_n$;

$C_y$ represents $C_6$-$C_{10}$ aryl or 5-10 membered heteroaryl, and it can be optionally substituted by 0, 1, 2, 3 substituents selected from: hydrogen, halogen, —$OR^a$, ($C_1$-$C_6$) alkyl, halo ($C_1$-$C_6$) alkyl, ($C_3$-$C_6$) cycloalkyl, cyano, hydroxyl ($C_1$-$C_6$) alkyl;

$R_2$ represents hydrogen, ($C_1$-$C_6$) alkyl, halo ($C_1$-$C_6$) alkyl, ($C_3$-$C_6$) cycloalkyl, hydroxyl ($C_1$-$C_6$) alkyl;

$R_3$ and $R_{3'}$ independently represent hydrogen, halogen, $OR^a$, ($C_1$-$C_6$) alkyl, ($C_3$-$C_6$) cycloalkyl, hydroxyl ($C_1$-$C_6$ alkyl), ($C_1$-$C_6$) alkoxy ($C_1$-$C_6$) alkyl;

alternatively, $R_3$ and $R_{3'}$ form a 3-6 membered saturated or unsaturated ring together with the carbon atom connected to them, and the ring can also optionally contain 1 or 2 heteroatoms selected from O, S, and N; and the ring can also be optionally substituted by 0, 1, 2 halogens, hydroxyl, $C_1$-$C_6$ alkyl;

alternatively, $R_2$, $R_3$ or $R_{2'}$, $R_3$ form a 4-6 membered saturated or unsaturated ring together with the atoms connected to them, the ring may optionally contain 1 or 2 heteroatoms selected from O, S, and N; and the ring can also be optionally substituted by 0, 1, 2 halogens, hydroxyl, $C_1$-$C_6$ alkyl;

$R_4$ and $R_{4'}$ independently represent hydrogen, $C_1$-$C_6$ alkyl, $C_3$-$C_6$ cycloalkyl, hydroxyl ($C_1$-$C_6$ alkyl), halogenated ($C_1$-$C_6$ alkyl), ($C_1$-$C_6$) alkoxy ($C_1$-$C_6$) alkyl;

alternatively, $R_4$ and $R_{4'}$ together form =O;

$R^T$ and $R^{T'}$ each independently represent hydrogen, $C_1$-$C_6$ alkyl, halogenated ($C_1$-$C_6$ alkyl), hydroxyl $C_1$-$C_6$ alkyl, $C_3$-$C_6$ cycloalkyl, halogen, —$OR^a$;

alternatively, $R^T$ and $R^{T'}$ together form a 3-6 membered ring with the atom connected to them;

wherein, when — — — represents absence, A represents ($CR^LR^{L'})_p$, wherein $R^L$ and $R^{L'}$ each independently represent hydrogen, $C_1$-$C_6$ alkyl, halo ($C_1$-$C_6$ alkyl), hydroxyl ($C_1$-$C_6$ alkyl), $C_3$-$C_6$ cycloalkyl, halogen, $OR^a$, or $R^L$ and $R^{L'}$ together form a 3-6 membered ring with the carbon atom connected to them, and the ring can optionally contain 0, 1, 2 heteroatoms selected from O, S, N, and the ring can also be optionally substituted by 0, 1, 2 halogens, hydroxyl;

wherein, when — — — represents existence, A represents $CR^H$, wherein $R^H$ means hydrogen, $C_1$-$C_6$ alkyl, halogenated ($C_1$-$C_6$ alkyl), hydroxyl ($C_1$-$C_6$ alkyl), $C_3$-$C_6$ cycloalkyl, halogen, $OR^a$;

wherein, $R^a$, $R^{a'}$ independently represent hydrogen and $C_1$-$C_6$ alkyl;

wherein, m, n, and p each independently represent 0, 1, 2.

2. The compound or pharmaceutically acceptable salt, isotopic derivative, or stereoisomer as claimed in claim 1, wherein X represents —O—, —$CH_2$—, —$OCH_2$ or —$CH_2CH_2$—.

3. The compound or pharmaceutically acceptable salt, isotopic derivative, or stereoisomer as claimed in claim 1, wherein $C_y$ represents pyrazolyl, pyridyl, pyrazinyl, pyrimidinyl, imidazolyl, phenyl substituted by 0, 1, and 2 substituents selected from ($C_1$-$C_6$) alkyl, ($C_3$-$C_6$) cycloalkyl, halogenated ($C_1$-$C_6$ alkyl), —$OR^a$, halogen, cyano hydroxy ($C_1$-$C_6$) alkyl; wherein, $R^a$, $R^{a'}$ each independently represent hydrogen and $C_1$-$C_6$ alkyl.

4. The compound or pharmaceutically acceptable salt, isotopic derivative, or stereoisomer as claimed in claim 1, wherein $R_1$ represents ($C_1$-$C_6$) alkyl, ($C_3$-$C_6$) cycloalkyl, ($C_6$-$C_{10}$) aryl, (5-10) membered heteroaryl, which are optionally substituted by 0, 1, 2 substituents selected from halogen, $OR^a$, ($C_1$-$C_6$) alkyl, halogenated ($C_1$-$C_6$ alkyl); wherein, $R^a$ represents hydrogen and $C_1$-$C_6$ alkyl.

5. The compound or pharmaceutically acceptable salt, isotopic derivative, or stereoisomer as claimed in claim 1, wherein $R_2$ represents hydrogen or ($C_1$-$C_6$) alkyl.

6. The compound or pharmaceutically acceptable salt, isotopic derivative, or stereoisomer as claimed in claim 1, wherein $R_3$ and $R_{3'}$ each independently represent hydrogen or ($C_1$-$C_6$) alkyl.

7. The compound or pharmaceutically acceptable salt, isotopic derivative, or stereoisomer as claimed in claim 1, wherein $R_4$ and $R_{4'}$ form =O together.

8. The compound or pharmaceutically acceptable salt, isotopic derivative, or stereoisomer as claimed in claim 1, selected from the group consisting of:

| serial number | Compound structure | serial number | Compound structure |
|---|---|---|---|
| 1 (W1 64) | | 2 (W1 79) | |
| 3 (W1 66) | | 4 (W1 69) | |
| 5 (W1 71) | | 6 (W1 72) | |
| 7 (W1 74) | | 8 (W1 75) | |

-continued

| serial number | Compound structure | serial number | Compound structure |
|---|---|---|---|
| 9 (W1 76) | | 10 (W1 77) | |
| 11 (W1 78) | | 12 (180) | |
| 13 (W1 81) | | 14 (W1 82) | |
| 15 (W1 83) | | 16 (W1 84) | |

-continued

| serial number | Compound structure | serial number | Compound structure |
|---|---|---|---|
| 17 (W1 85) | | 18 (W1 86) | |
| 19 (W7 5) | | 20 (W1 59) | |
| 21 (W1 55) | | 22 (W1 54) | |

-continued

| serial number | Compound structure | serial number | Compound structure |
|---|---|---|---|
| 23 (W153) | | 24 (W150) | |
| 25 (W148) | | 26 (W110) | |
| 27 (W64) | | 28 (W94) | |

-continued

| serial number | Compound structure | serial number | Compound structure |
|---|---|---|---|
| 29 | | 30 | |
| 31 | | 32 | |
| 33 | | 34 | |

-continued

| serial number | Compound structure | serial number | Compound structure |
|---|---|---|---|
| 35 | | 36 | |
| 37 | | 38 | |
| 39 | | 40 | |

-continued

| serial number | Compound structure | serial number | Compound structure |
|---|---|---|---|
| 41 | | 42 | |
| 43 | | 44 | |
| 45 | | 46 | |

-continued

| serial number | Compound structure | serial number | Compound structure |
|---|---|---|---|
| 47 | | 48 | |
| 49 | | 50 | |
| 51 | | 52 | |

-continued

| serial number | Compound structure | serial number | Compound structure |
|---|---|---|---|
| 53 | | 54 | |
| 55 | | 56 | |
| 57 | | 58 | |

-continued

| serial number | Compound structure | serial number | Compound structure |
|---|---|---|---|
| 59 | | 60 | |
| 61 (W2) | | 62 (W1 3) | |
| 63 (W2 2) | | 64 (W2 3) | |

-continued

| serial number | Compound structure | serial number | Compound structure |
|---|---|---|---|
| 65 (W32) | | 66 (W43) | |
| 67 (W46) | | 68 (W49) | |
| 69 (W50) | | 70 (W55) | |

-continued

| serial number | Compound structure | serial number | Compound structure |
|---|---|---|---|
| 71 (W5 6) | | 72 (W5 7) | |
| 73 (W8 5) | | 74 (W6 9) | |
| 75 (W7 7) | | 76 (W8 3) | |

-continued

| serial number | Compound structure | serial number | Compound structure |
|---|---|---|---|
| 77 (W86) | | 78 (W87) | |
| 79 (W95) | | 80 (W104) | |
| 81 (W105) | | 82 (W107) | |
| 83 (W116) | | 84 (W123) | |

-continued

| serial number | Compound structure | serial number | Compound structure |
|---|---|---|---|
| 85 (W1 32) | | 86 (W1 35) | |
| 87 (W1 36) | | 88 (W1 40) | |
| 89 (W1 50) | | 90 (W1 52) | |

-continued

| serial number | Compound structure | serial number | Compound structure |
|---|---|---|---|
| 91 (W2 21) | | 92 (W2 32) | |
| 93 (W2 23) | | 94 (W2 52) | |
| 95 (W2 53) | | 96 (W2 56) | |
| 97 (W3 12) | | 98 (W1 88) | |

-continued

| serial number | Compound structure | serial number | Compound structure |
|---|---|---|---|
| 99 (W1 93) | | 100 (W2 39) | |
| 101 (W2 13) | | 102 (W2 14) | |
| 103 (W1 95) | | 104 (W1 98) | |
| 105 (W1 99) | | 106 (W1 90) | |

-continued

| serial number | Compound structure | serial number | Compound structure |
|---|---|---|---|
| 107 (W192) | | 108 (W207) | |
| 109 (W220) | | 110 (W231) | |
| 111 (W241) | | 112 (W242) | |
| 113 (W247) | | 114 (W243) | |

-continued

| serial number | Compound structure | serial number | Compound structure |
|---|---|---|---|
| 115 (W2 44) | | 116 (W2 49) | |
| 117 (W2 37) | | 118 (W2 79) | |
| 119 (W2 55) | | 120 (W2 65) | |
| 121 (W2 66) | | 122 (W2 72) | |

-continued

| serial number | Compound structure | serial number | Compound structure |
|---|---|---|---|

| 123 (W2 76) | | 124 (W2 78) | |
| 125 (W2 81) | | 126 (W3 08) | |
| 127 (W2 80) | | 128 (W2 63) | |
| 129 (W3 69) | | 130 (W3 54) | |

-continued

| serial number | Compound structure | serial number | Compound structure |
|---|---|---|---|
| 131 (W3 66) | | 132 (W3 83) | |
| 133 (W3 77) | | 134 (W3 80) | |
| 135 (W3 82) | | 136 (W3 81) | |

-continued

| serial number | Compound structure | serial number | Compound structure |
|---|---|---|---|
| 137 (W3 35) | | 138 (W2 71) | |
| 139 (W2 68) | | 140 (W3 76) | |
| 141 (W2 61) | | 142 (W2 57) | |
| 143 (W2 77) | | 144 (W2 90) | |

-continued

| serial number | Compound structure | serial number | Compound structure |
|---|---|---|---|
| 145 (W3 31) | | 146 (W2 73) | |
| 147 (W2 74) | | 148 (W2 50) | |
| 149 (W2 85) | | 150 (W3 01) | |
| 151 (W3 32) | | 152 (W3 36) | |

-continued

| serial number | Compound structure | serial number | Compound structure |
|---|---|---|---|
| 153 (W2 93) | | 154 (W2 58) | |
| 155 (W3 47) | | 156 (W2 64) | |
| 157 (W2 62) | | 158 (W2 75) | |

-continued

| serial number | Compound structure | serial number | Compound structure |
|---|---|---|---|
| 159 (W2 59) | | 160 (W3 62) | |
| 161 (W2 69) | | 162 (W2 70) | |
| 163 (W3 25) | | 164 (W3 26) | |
| 165 (W2 86) | | 166 (W2 87) | |

-continued

| serial number | Compound structure | serial number | Compound structure |
|---|---|---|---|
| 167 (W289) | | 168 (W298) | |
| 169 (W294) | | 170 (W368) | |
| 171 (W367) | | 172 (W305) | |

-continued

| serial number | Compound structure | serial number | Compound structure |
|---|---|---|---|
| 173 (W3 13) | | 174 (W3 14) | |
| 175 (W3 27) | | 176 (W2 96) | |
| 177 (W2 97) | | 178 (W3 33) | |

-continued

| serial number | Compound structure | serial number | Compound structure |
|---|---|---|---|
| 179 (W3 75) | | 180 (W3 86) | |
| 181 (W3 96) | | 182 (W3 95) | |
| 183 (W3 09) | | 184 (W2 82) | |

-continued

| serial number | Compound structure | serial number | Compound structure |
|---|---|---|---|
| 185 (W3 10) | | 186 (W3 11) | |
| 187 (W3 15) | | 188 (W3 16) | |
| 189 (W3 06) | | 190 (W3 17) | |
| 191 (W3 18) | | 192 (W3 24) | |

-continued

| serial number | Compound structure | serial number | Compound structure |
|---|---|---|---|
| 193 (W3 42) | | 194 (W3 41) | |
| 195 (W3 23) | | 196 (W3 44) | |
| 197 (W3 43) | | 198 (W3 07) | |
| 199 (W3 19) | | 200 (W3 20) | |

-continued

| serial number | Compound structure | serial number | Compound structure |
|---|---|---|---|
| 201 (W3 60) | | 202 (W3 61) | |
| 203 (W3 72) | | 204 (W3 74) | |
| 205 (W3 79) | | 206 (W3 88) | |
| 207 (W3 57) | | 208 (W) | |

-continued

| serial number | Compound structure | serial number | Compound structure |
|---|---|---|---|
| 209 (W) | | 210 (W3 71) | |
| 211 (W3 90) | | 212 (W3 89) | |
| 213 (W3 55) | | 214 (W3 92) | |

-continued

| serial number | Compound structure | serial number | Compound structure |
|---|---|---|---|
| 215 (W3 91) | | 216 (W3 52) | |
| 217 (W3 59) | | 218 (W3 39) | |
| 219 (W3 38) | | 220 (W3 98) | |

-continued

| serial number | Compound structure | serial number | Compound structure |
|---|---|---|---|
| 221 (W399) | | 222 (W402) | |
| 223 (W403) | | 224 (W406) | |
| 225 (W407) | | 226 (W411) | |
| 227 (W412) | | 228 (W413) | |

-continued

| serial number | Compound structure | serial number | Compound structure |
|---|---|---|---|
| 229 (W4 14) | | 230 (W4 15) | |
| 231 (W4 17) | | 232 (W4 18) | |
| 233 (W4 19) | | 234 (W4 20) | |

-continued

| serial number | Compound structure | serial number | Compound structure |
| --- | --- | --- | --- |
| 235 (W4 22) | | 236 (W4 24) | |
| 237 (W4 25) | | 238 (W4 26) | |
| 239 (W4 27) | | 240 (W4 28) | |
| 241 (W4 31) | | 242 | |

-continued

| serial number | Compound structure | serial number | Compound structure |
|---|---|---|---|
| 243 | | 244 | |
| 245 | | 246 | |
| 247 | | 248 | |

-continued

| serial number | Compound structure | serial number | Compound structure |
|---|---|---|---|
| 249 | | 250 | |
| 251 | | 252 | |
| 253 | | 254 | |
| 255 | | 256 | |

-continued

| serial number | Compound structure | serial number | Compound structure |
|---|---|---|---|
| 257 | | 258 | |
| 259 | | 260 | |
| 261 | | 262 | |

-continued

| serial number | Compound structure | serial number | Compound structure |
|---|---|---|---|
| 263 | | 264 | |
| 265 | | 266 | |

-continued

| serial number | Compound structure |
|---|---|
| 268 | |

| serial number | Compound structure |
|---|---|
| 267 | |
| 269 | |

9. A pharmaceutical composition, comprising the compound or pharmaceutically acceptable salt according to claim 1.

10. A method for preventing and/or treating cancer, tumor, inflammatory diseases, autoimmune diseases or immune-mediated diseases, comprising administering the compound or pharmaceutically acceptable salt, isotopic derivative, or stereoisomer as claimed in claim 1 to a subject in need thereof.

* * * * *